(12) United States Patent
Watanabe et al.

(10) Patent No.: US 10,460,879 B2
(45) Date of Patent: Oct. 29, 2019

(54) PHOTOELECTRIC CONVERSION ELEMENT, DYE-SENSITIZED SOLAR CELL, METAL COMPLEX DYE, DYE SOLUTION, DYE-ADSORBED ELECTRODE, AND METHOD FOR PRODUCING DYE-SENSITIZED SOLAR CELL

(71) Applicant: FUJIFILM Corporation, Tokyo (JP)

(72) Inventors: Kousuke Watanabe, Kanagawa (JP); Yukio Tani, Kanagawa (JP); Kouitsu Sasaki, Kanagawa (JP); Hirotaka Satou, Kanagawa (JP); Kazuhiro Tsuna, Kanagawa (JP); Katsumi Kobayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 720 days.

(21) Appl. No.: 14/713,341

(22) Filed: May 15, 2015

(65) Prior Publication Data
US 2015/0248969 A1 Sep. 3, 2015

Related U.S. Application Data

(63) Continuation of application No. PCT/JP2013/080883, filed on Nov. 15, 2013.

(30) Foreign Application Priority Data

Nov. 16, 2012 (JP) ................... 2012-252700
Nov. 16, 2012 (JP) ................... 2012-252701
(Continued)

(51) Int. Cl.
*H01G 9/20* (2006.01)
*C07D 401/14* (2006.01)
(Continued)

(52) U.S. Cl.
CPC ......... *H01G 9/2059* (2013.01); *C07D 213/55* (2013.01); *C07D 213/57* (2013.01);
(Continued)

(58) Field of Classification Search
CPC .... Y02E 10/549; Y02E 10/542; Y02P 70/521; H01G 9/2059; H01G 9/20–2095; H01L 51/0086
(Continued)

(56) References Cited

U.S. PATENT DOCUMENTS 6,245,988 B1 * 6/2001 Gratzel .................. C07F 9/587
                                                    136/252
2005/0081911 A1 * 4/2005 Islam .................. C07F 15/0053
                                                    136/263
(Continued)

FOREIGN PATENT DOCUMENTS

CN 1359901 A 7/2002
EP 2036955 A1 3/2009
(Continued)

OTHER PUBLICATIONS

Zakeeruddin et al., "Molecular Engineering of Photosensitizers for Nanocrystalline Solar Cells: Synthesis and Characterization of Ru Dyes Based on Phosphonated Terpyridines", Inorg. Chem., 1997, vol. 36, No. 25, pp. 5937-5946.
(Continued)

*Primary Examiner* — Eli S Mekhlin
*Assistant Examiner* — Dujuan A Horton
(74) *Attorney, Agent, or Firm* — Sughrue Mion, PLLC

(57) ABSTRACT

A photoelectric conversion element, having a photoconductor layer containing semiconductor fine particles carrying a metal complex dye of Formula (I); a metal complex dye, a dye solution, a dye-adsorbed electrode, a dye-sensitized solar cell, and a method for producing the solar cell:

$$M(LA)(LD)(LX)_{mX}(CI)_{mY} \quad \text{Formula (I)}$$

M represents a metal ion, LA represents a ligand of Formula (AL), LD represents a bidentate or tridentate ligand, at least
(Continued)

one of coordinating atoms being an anion; LX represents a monodentate ligand; CI represents a counter ion; mX is 0 or 1; mY is 0 to 3;

Formula (AL)

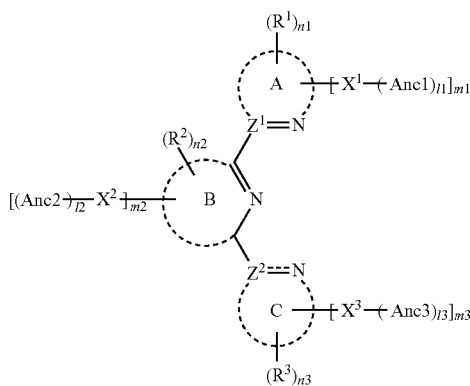

Rings A to C represent a heterocycle; $Z^1$ and $Z^2$ represent a carbon or nitrogen atom; Anc1 to Anc3 represent an acidic group; $X^1$ to $X^3$ represent a single bond or linking group; $R^1$ to $R^3$ represent a substituent; l1, l3, l2, m1, m3, m2, n1, n2, and n3 each are an integer.

27 Claims, 18 Drawing Sheets

(30) Foreign Application Priority Data

| Mar. 25, 2013 | (JP) | 2013-062895 |
| Jun. 19, 2013 | (JP) | 2013-129046 |
| Jul. 19, 2013 | (JP) | 2013-151149 |
| Sep. 30, 2013 | (JP) | 2013-205533 |
| Nov. 13, 2013 | (JP) | 2013-235218 |

(51) Int. Cl.

| C07D 409/14 | (2006.01) |
| C07D 495/04 | (2006.01) |
| C07D 213/55 | (2006.01) |
| C07D 213/57 | (2006.01) |
| C09B 57/10 | (2006.01) |
| C07F 15/00 | (2006.01) |
| H01L 51/00 | (2006.01) |
| C09B 19/00 | (2006.01) |
| C09B 21/00 | (2006.01) |
| C09B 23/01 | (2006.01) |
| C09B 23/10 | (2006.01) |
| C09B 57/00 | (2006.01) |
| C09B 69/00 | (2006.01) |

(52) U.S. Cl.
CPC ......... *C07D 401/14* (2013.01); *C07D 409/14* (2013.01); *C07D 495/04* (2013.01); *C07F 15/0046* (2013.01); *C07F 15/0053* (2013.01); *C09B 19/00* (2013.01); *C09B 21/00* (2013.01); *C09B 23/005* (2013.01); *C09B 23/0058* (2013.01); *C09B 23/105* (2013.01); *C09B 57/00* (2013.01); *C09B 57/008* (2013.01); *C09B 57/10* (2013.01); *C09B 69/008* (2013.01); *H01L 51/0086* (2013.01); *H01G 9/2031* (2013.01); *Y02E 10/542* (2013.01); *Y02E 10/549* (2013.01); *Y02P 70/521* (2015.11)

(58) Field of Classification Search
USPC ........................................... 136/256; 438/82
See application file for complete search history.

(56) References Cited

U.S. PATENT DOCUMENTS

| 2010/0101643 A1 | 4/2010 | Takahashi et al. |
| 2010/0258175 A1 | 10/2010 | Chi et al. |
| 2011/0155238 A1* | 6/2011 | Shen ..................... C07F 15/002 136/256 |
| 2012/0073660 A1 | 3/2012 | Chi et al. |

FOREIGN PATENT DOCUMENTS

| JP | 2002-105346 A | 4/2002 |
| JP | 2008-187162 A | 8/2008 |
| JP | 2008-222747 A | 9/2008 |
| JP | 2008-266639 A | 11/2008 |
| JP | 2011-502187 A | 1/2011 |
| JP | 2012-53983 A | 3/2012 |
| JP | 2012-216496 A | 11/2012 |
| TW | 201144293 A1 | 12/2011 |
| WO | 98/50393 A1 | 11/1998 |
| WO | 2009/055183 A2 | 4/2009 |
| WO | 2011/152603 A1 | 12/2011 |
| WO | 2012/017869 A1 | 2/2012 |
| WO | 2013/047615 A1 | 4/2013 |
| WO | 2013/088898 A1 | 6/2013 |
| WO | 2013/137221 A1 | 9/2013 |

OTHER PUBLICATIONS

Houarner-Rassin et al., "Synthesis and photoelectrochemical properties of ruthenium bisterpyridine sensitizers functionalized with a thienyl phosphoric acid moiety", Journal of Photochemistry and Photobiology A: Chemistry 192, 2007, pp. 56-65.
Communication dated Nov. 18, 2015, issued by the European Patent Office in corresponding European Application No. 13855922.4.
Adewale O. Adeloye, et al., "A High Molar Extinction Coefficient Bisterpyridyl Homoleptic Ru(II) Complex with trans-2-Methyl-2-butenoic Acid Functionality: Potential Dye for Dye-Sensitized Solar Cells", International Journal of Molecular Sciences, Mar. 14, 2012, pp. 3511-3526, vol. 13.
Frederik C. Krebs, et al., "Dye sensitized photovoltaic cells: Attaching conjugated polymers to zwitterionic ruthenium dyes", Solar Energy Materials & Solar Cells, 2006, pp. 142-165, vol. 90, No. 2.
S. Altobello, et al., "Sensitization of $TiO_2$ with ruthenium complexes containing boronic acid functions", Journal of Photochemistry and Photobiology, A: Chemistry, 2004, pp. 91-98, vol. 166.
International Search Report for PCT/JP2013/080883 dated Dec. 17, 2013 [PCT/ISA/210].
Communication dated Nov. 29, 2016, from the Intellectual Property Office of Taiwan in corresponding application No. 102141558.

* cited by examiner

{Fig. 1}
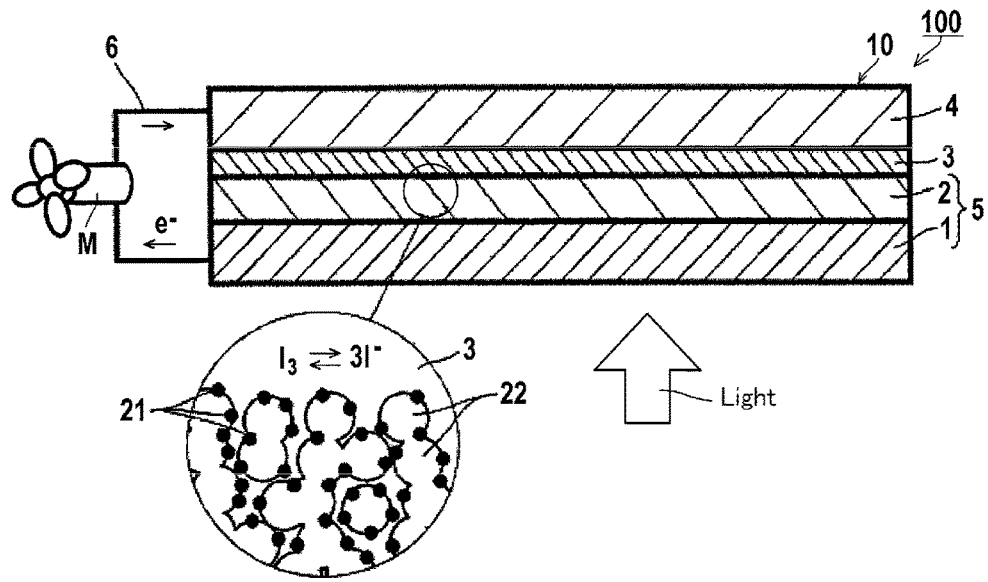
{Fig. 2}
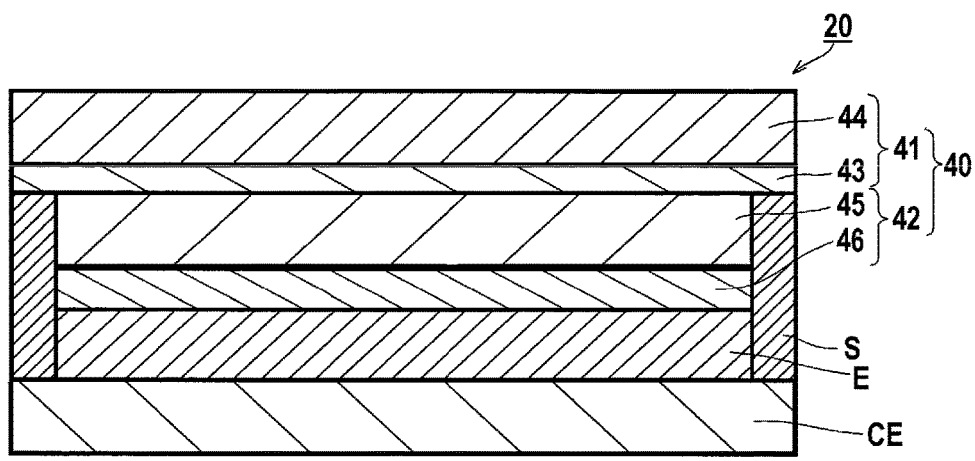

{Fig. 3}
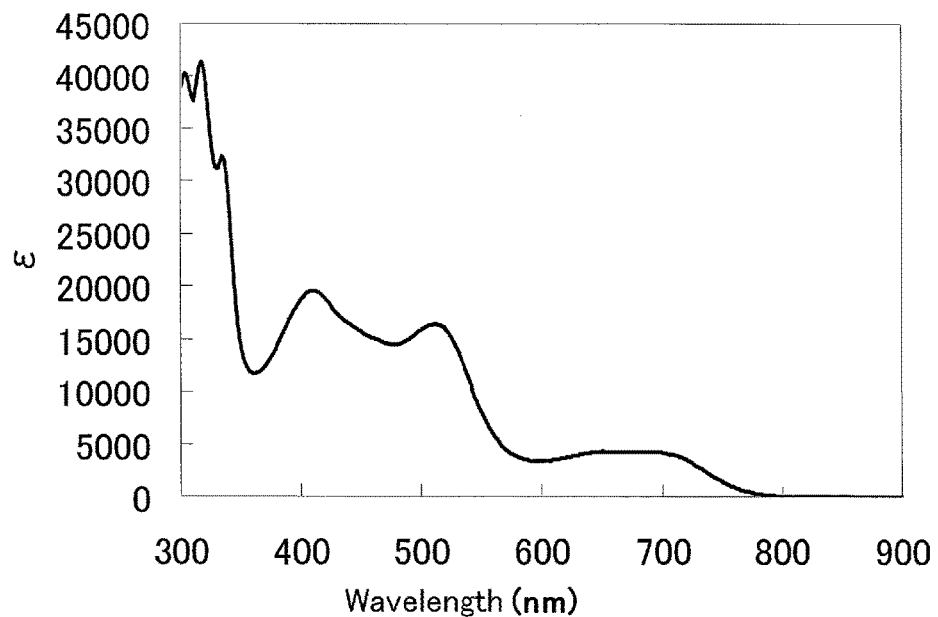
{Fig. 4}
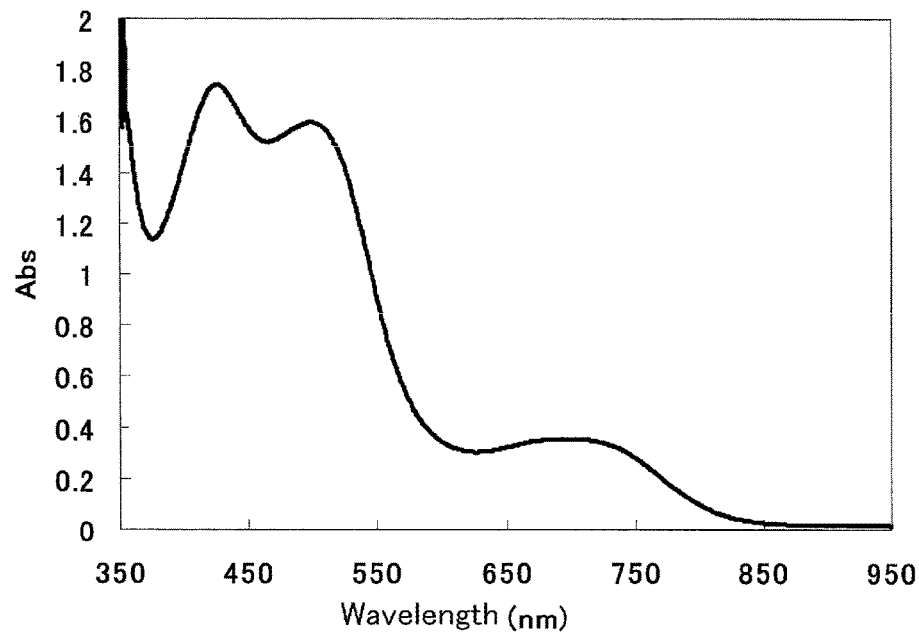

{Fig. 5}
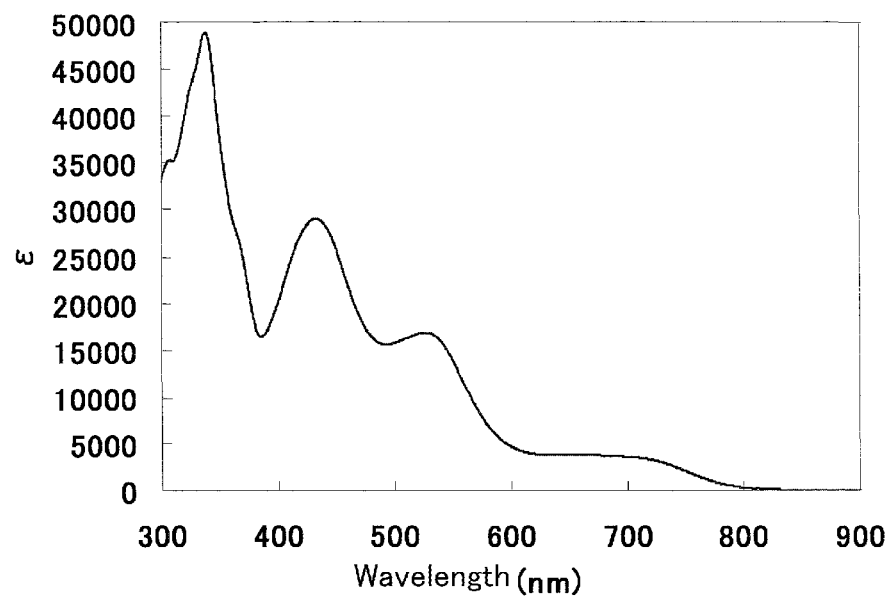
{Fig. 6}
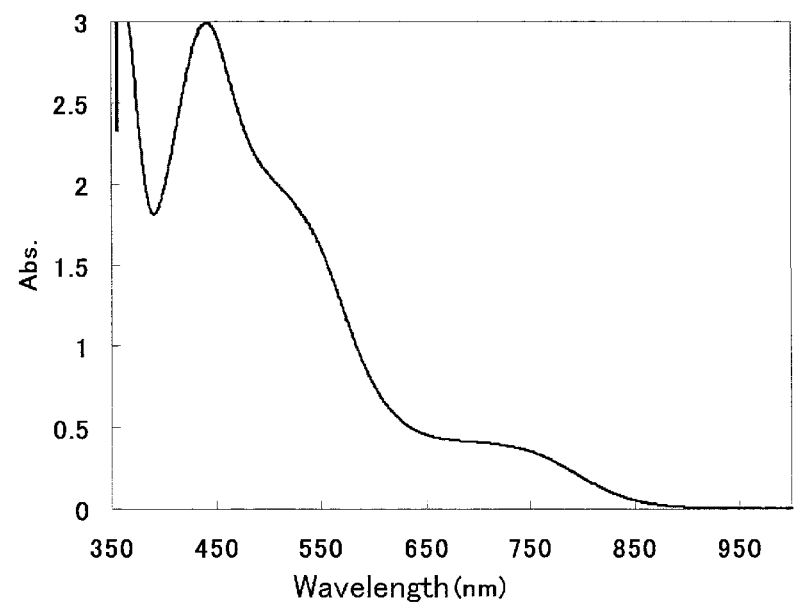

{Fig. 7}
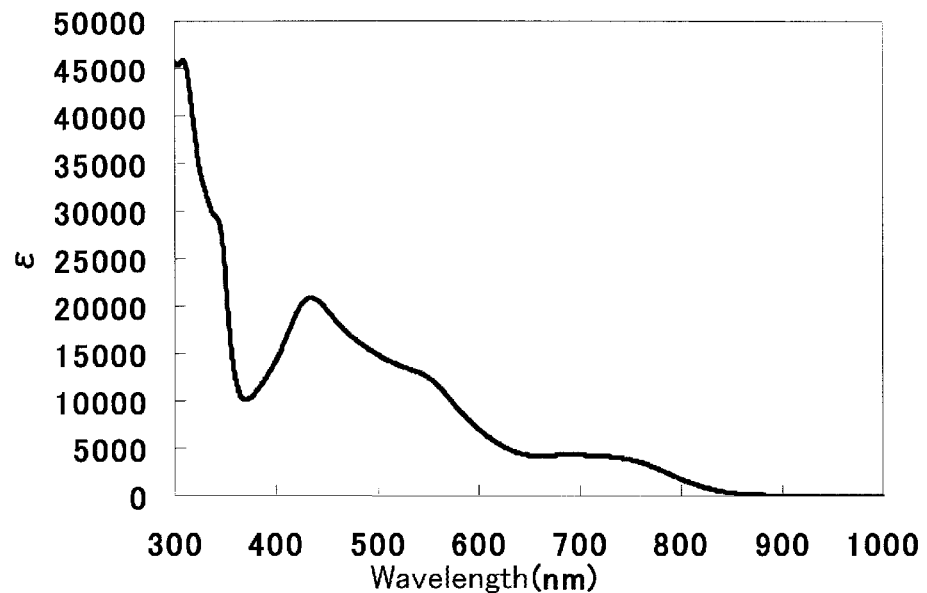
{Fig. 8}
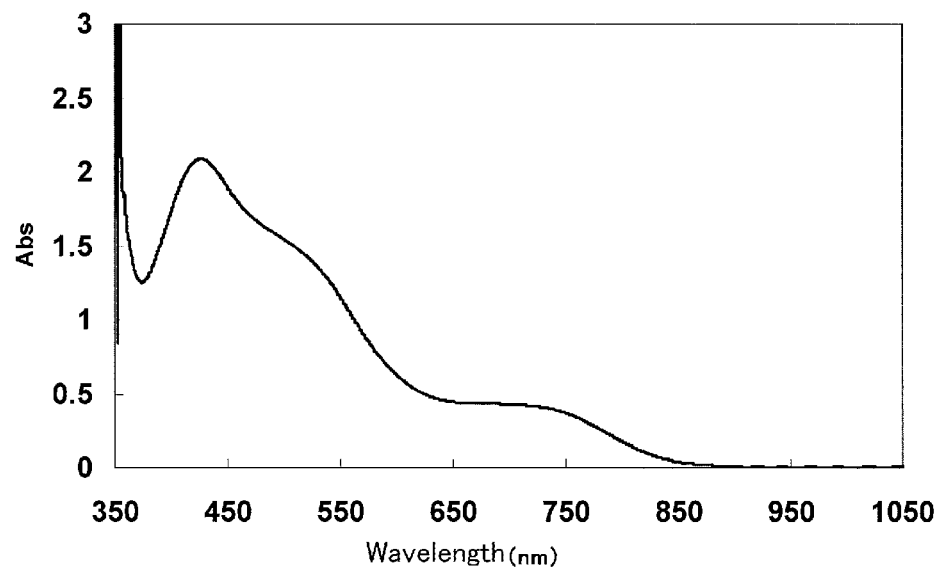

{Fig. 9}
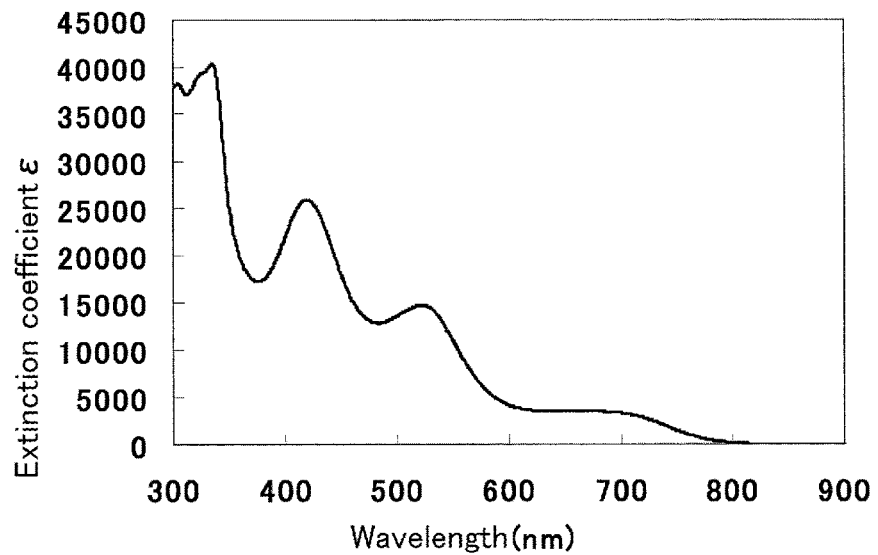
{Fig. 10}
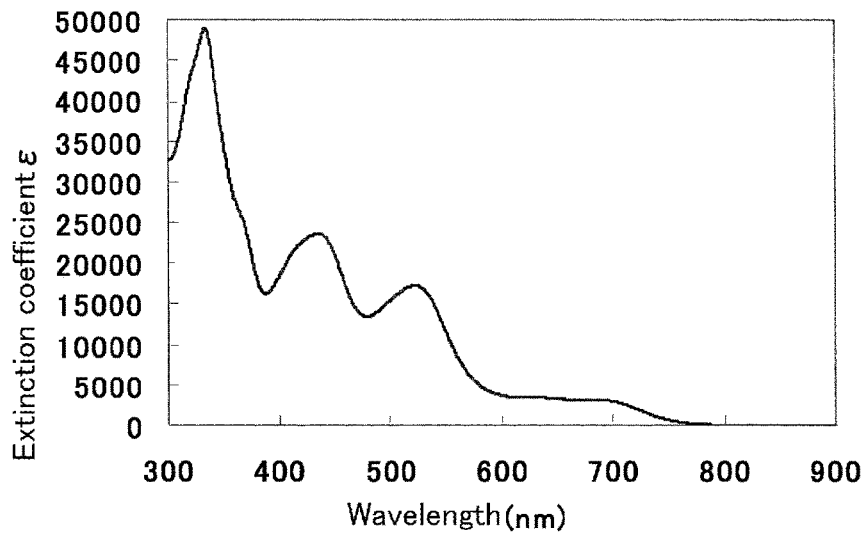

{Fig. 11}
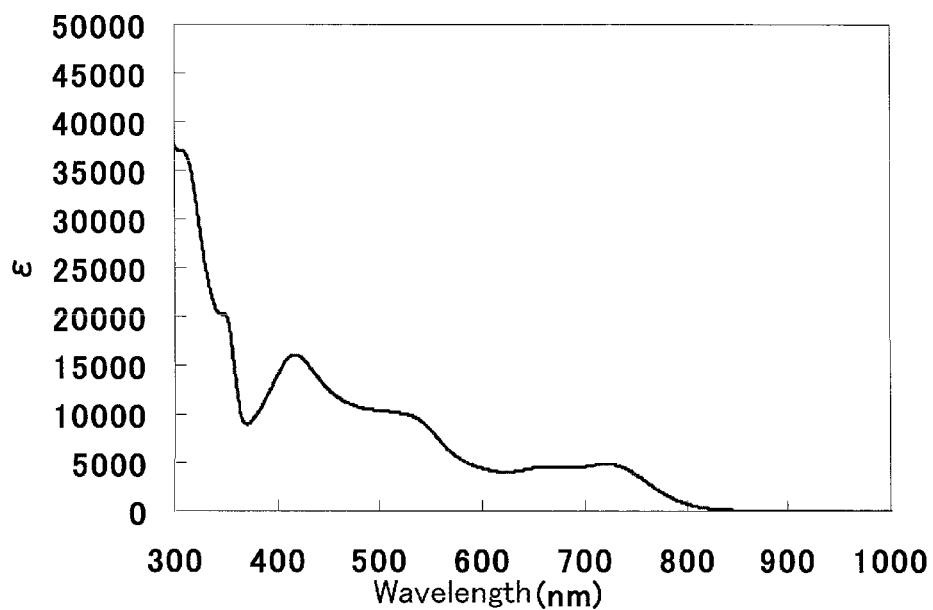
{Fig. 12}
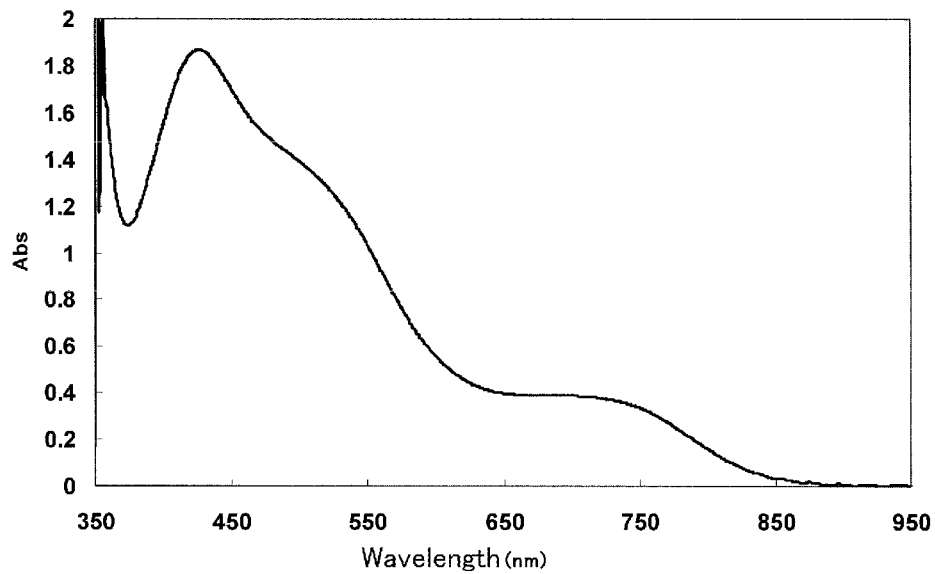

{Fig. 13}
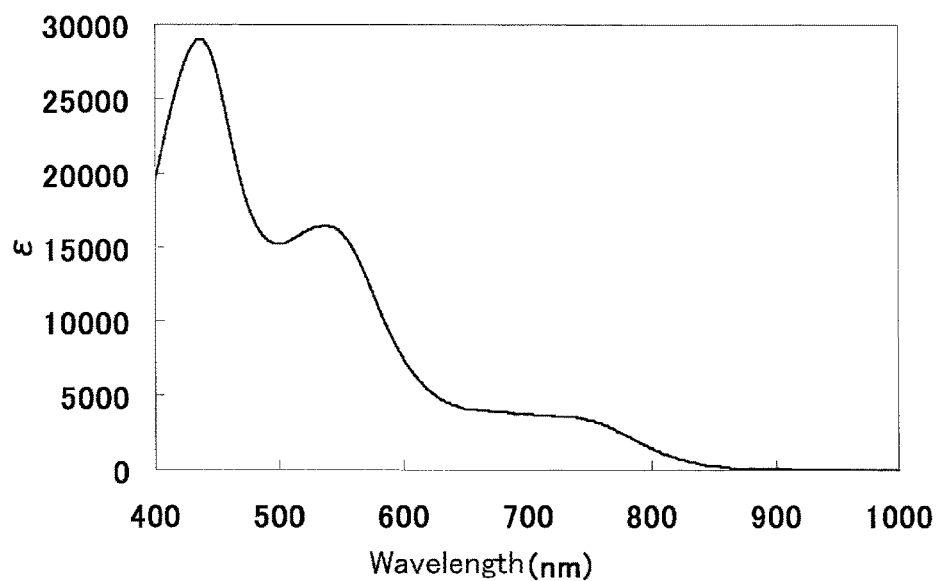
{Fig. 14}
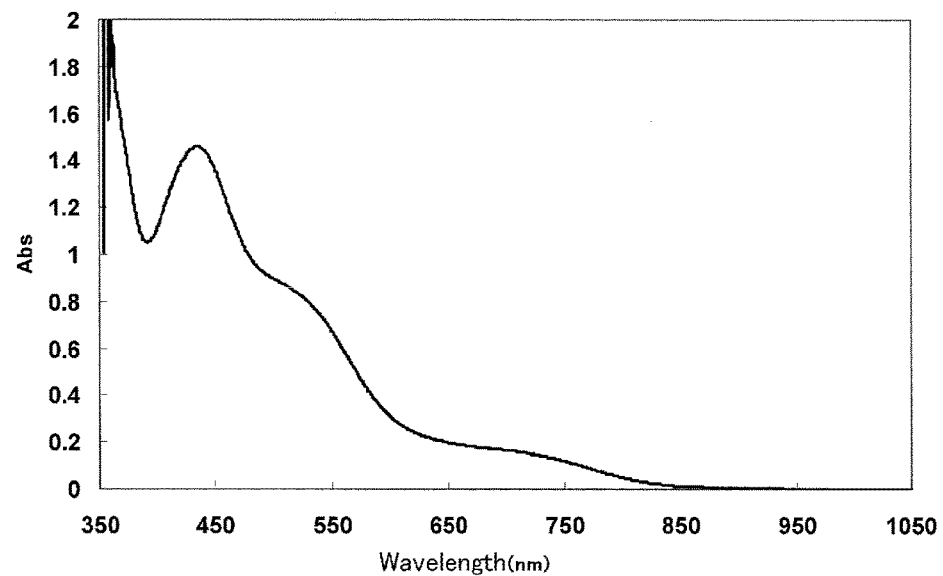

{Fig. 15}
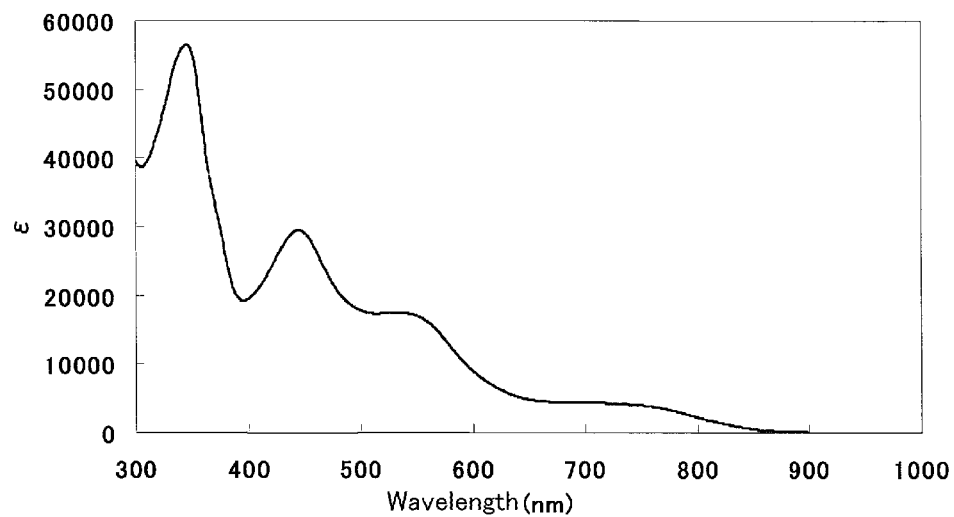
{Fig. 16}
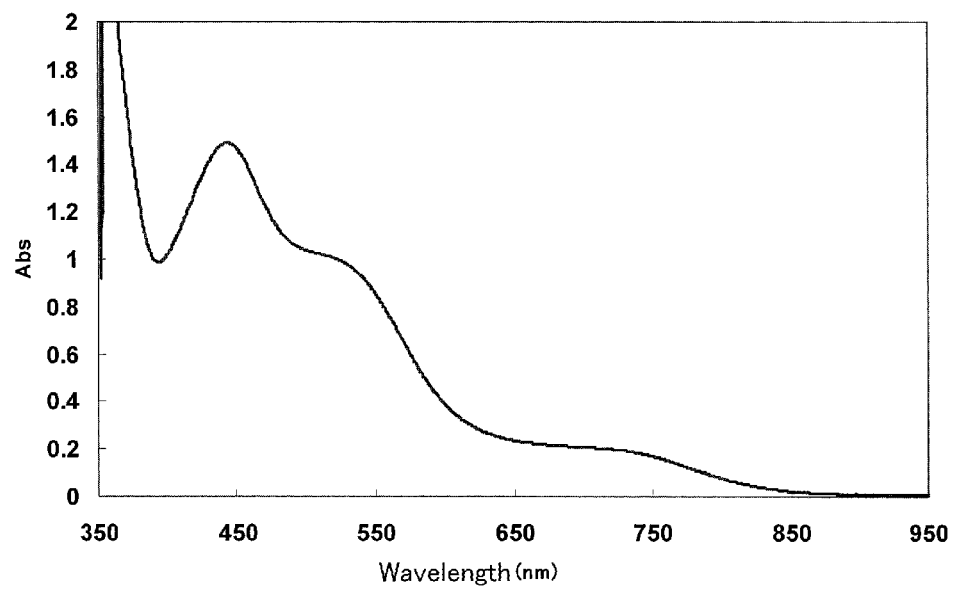

{Fig. 17}
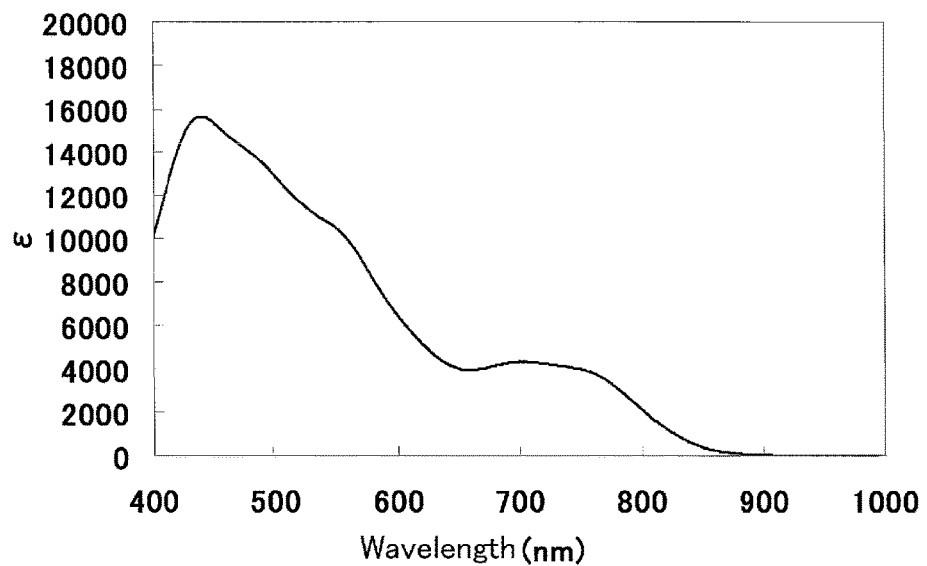
{Fig. 18}
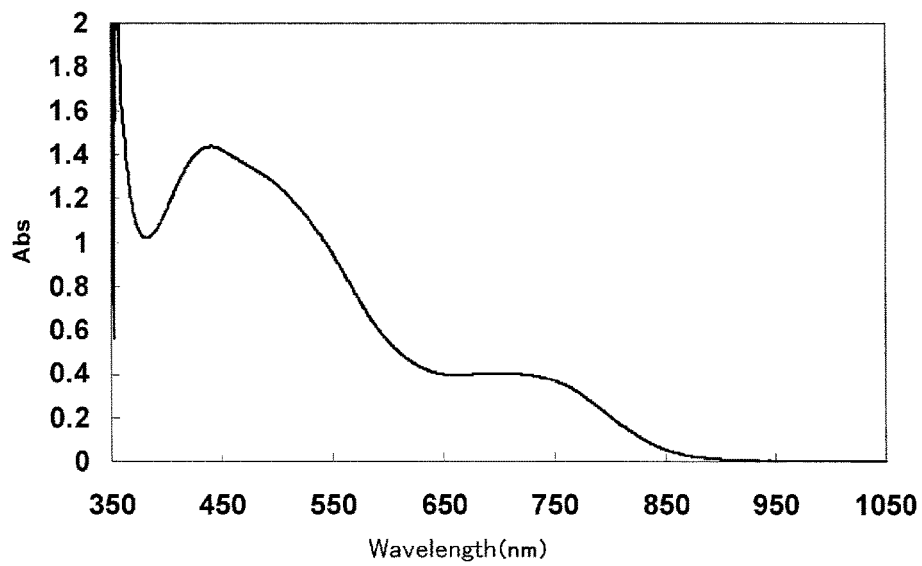

{Fig. 19}
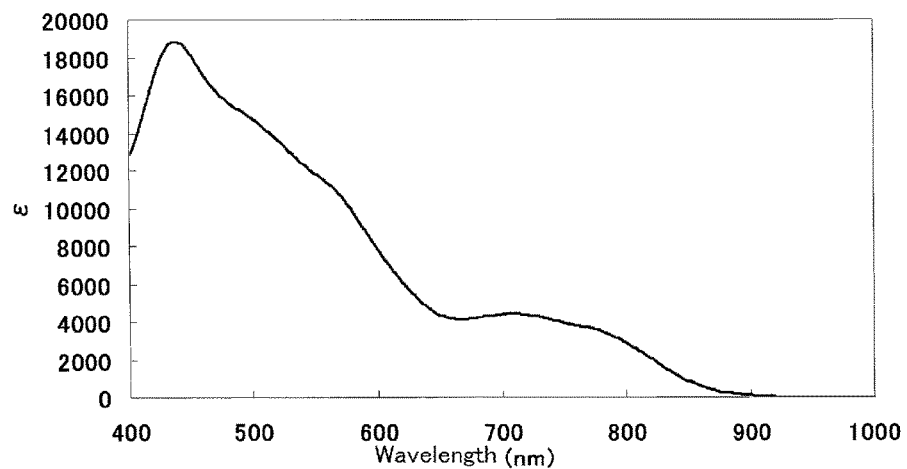
{Fig. 20}
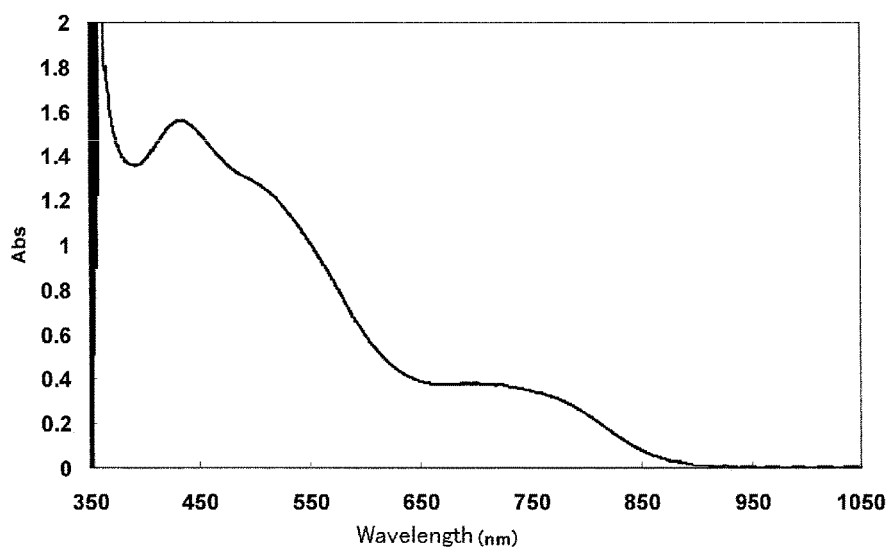

{Fig. 21}
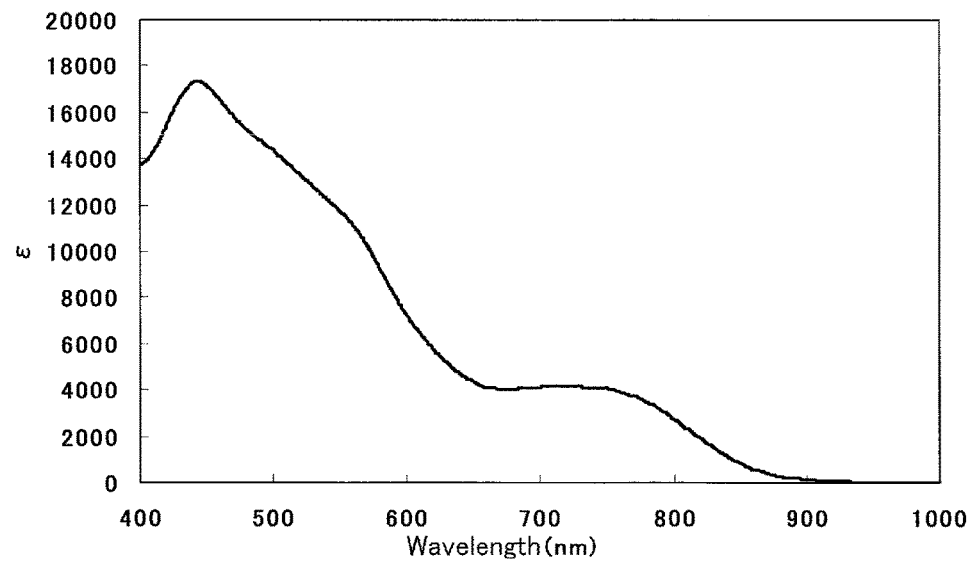
{Fig. 22}
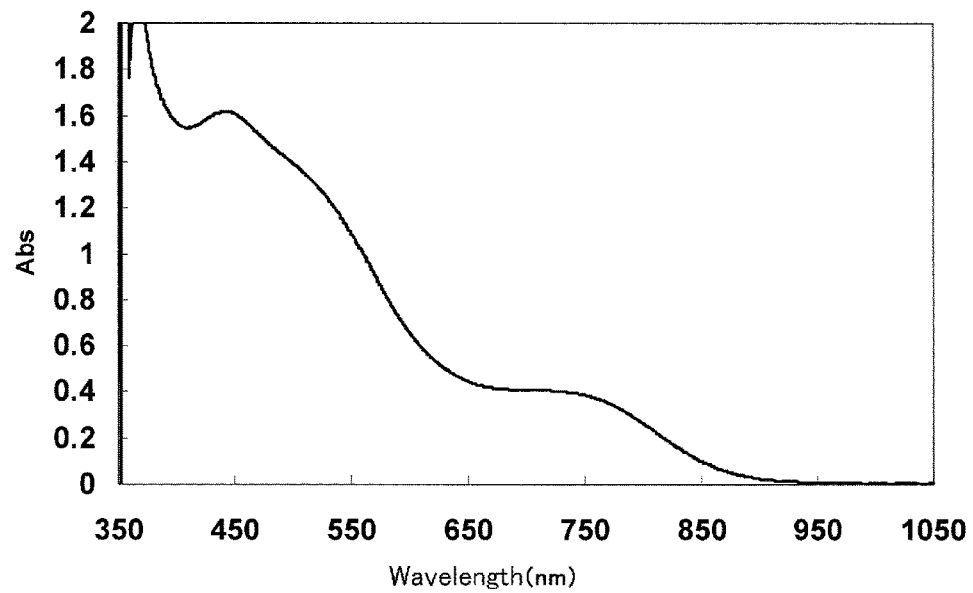

{Fig. 23}
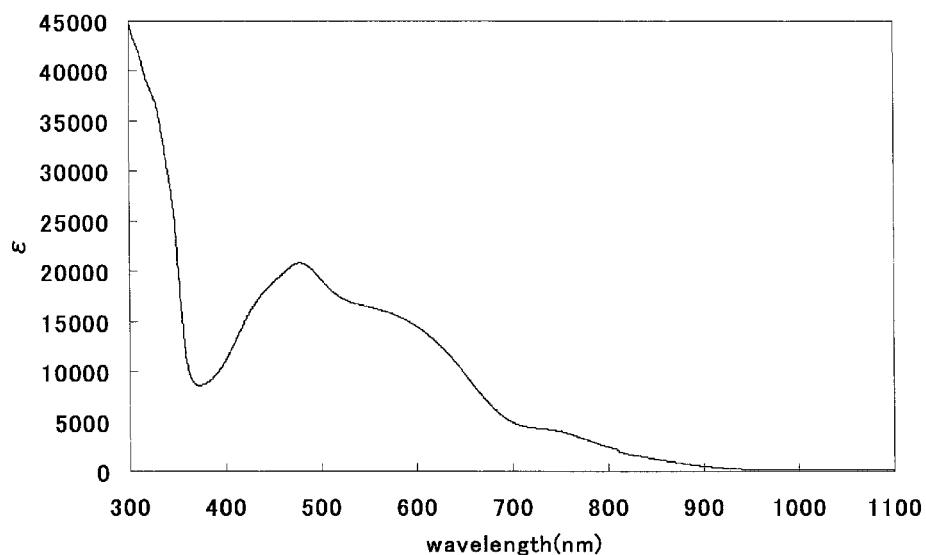
{Fig. 24}
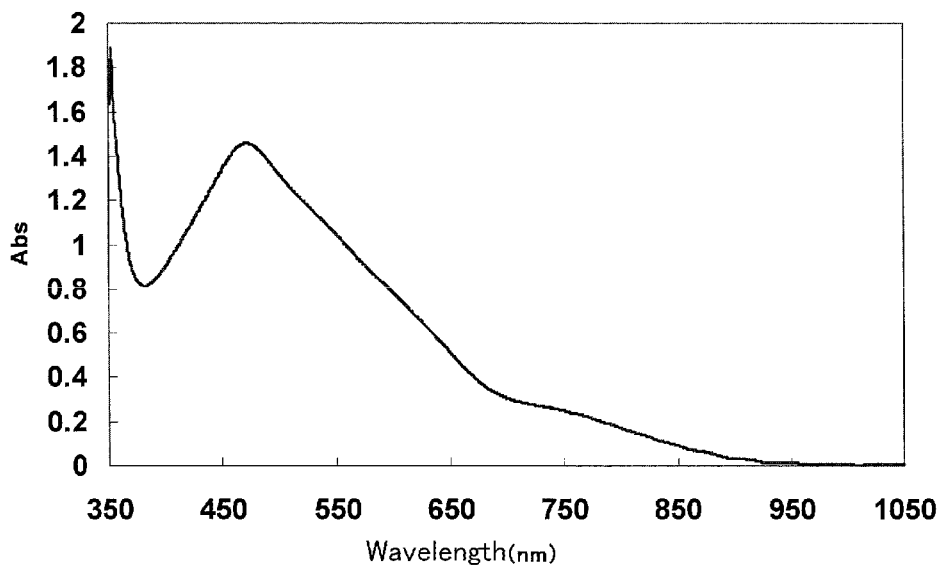

{Fig. 25}
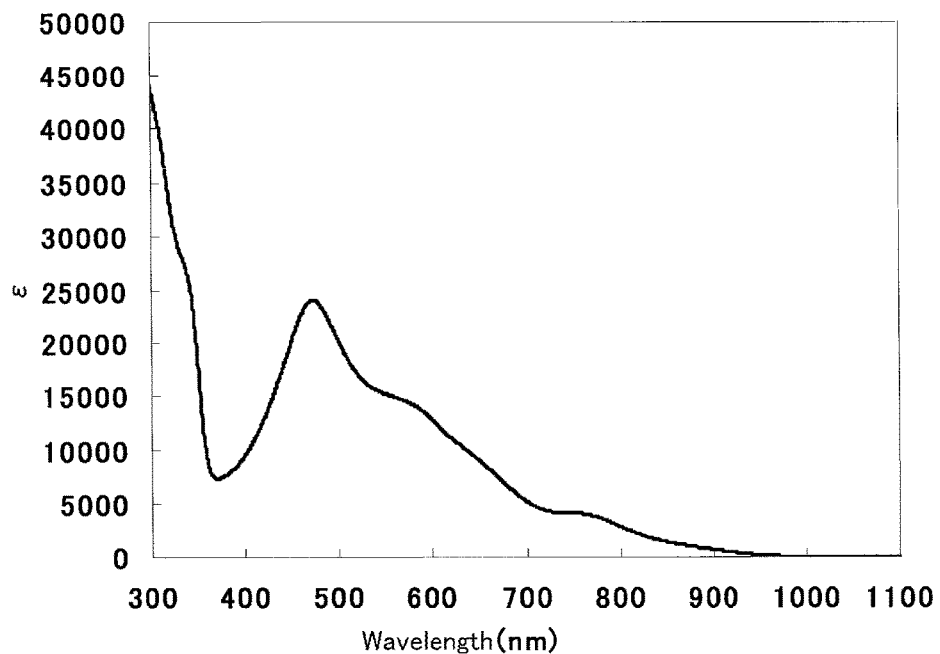
{Fig. 26}
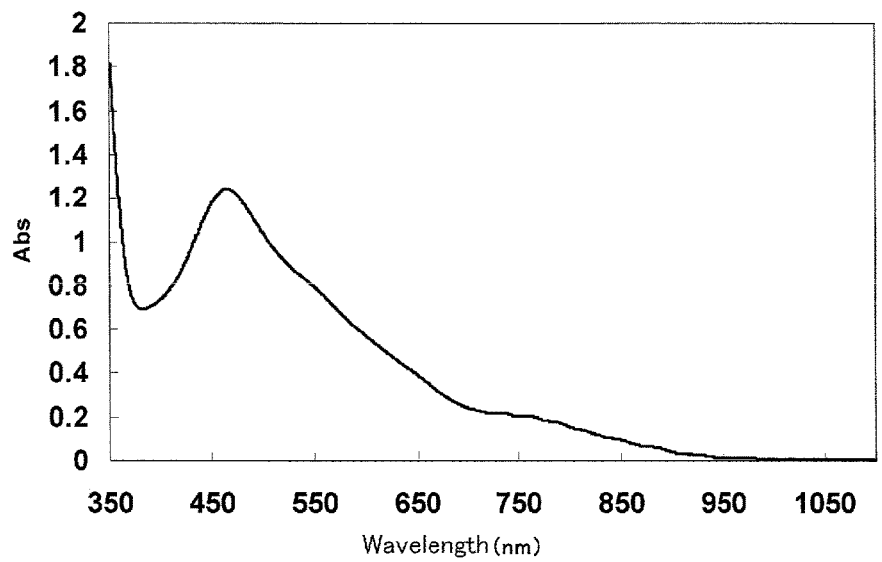

{Fig. 27}
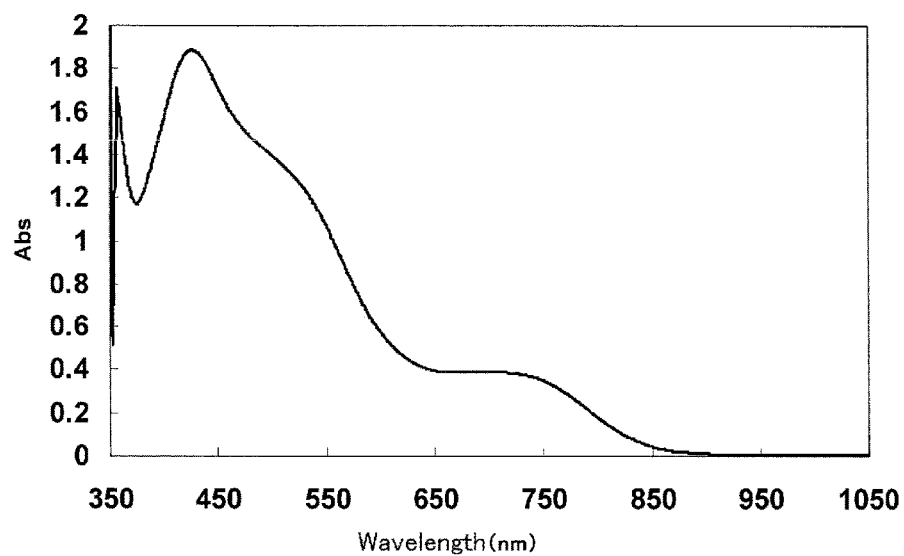
{Fig. 28}
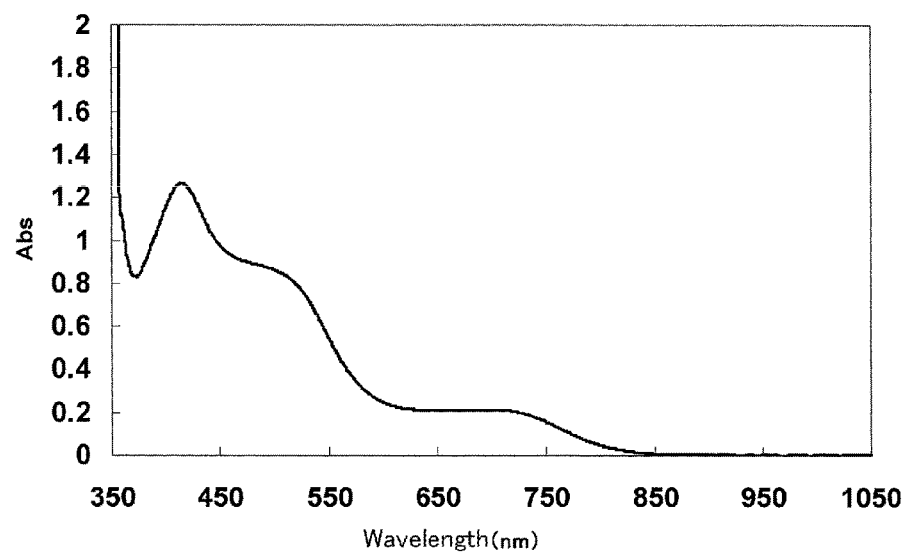

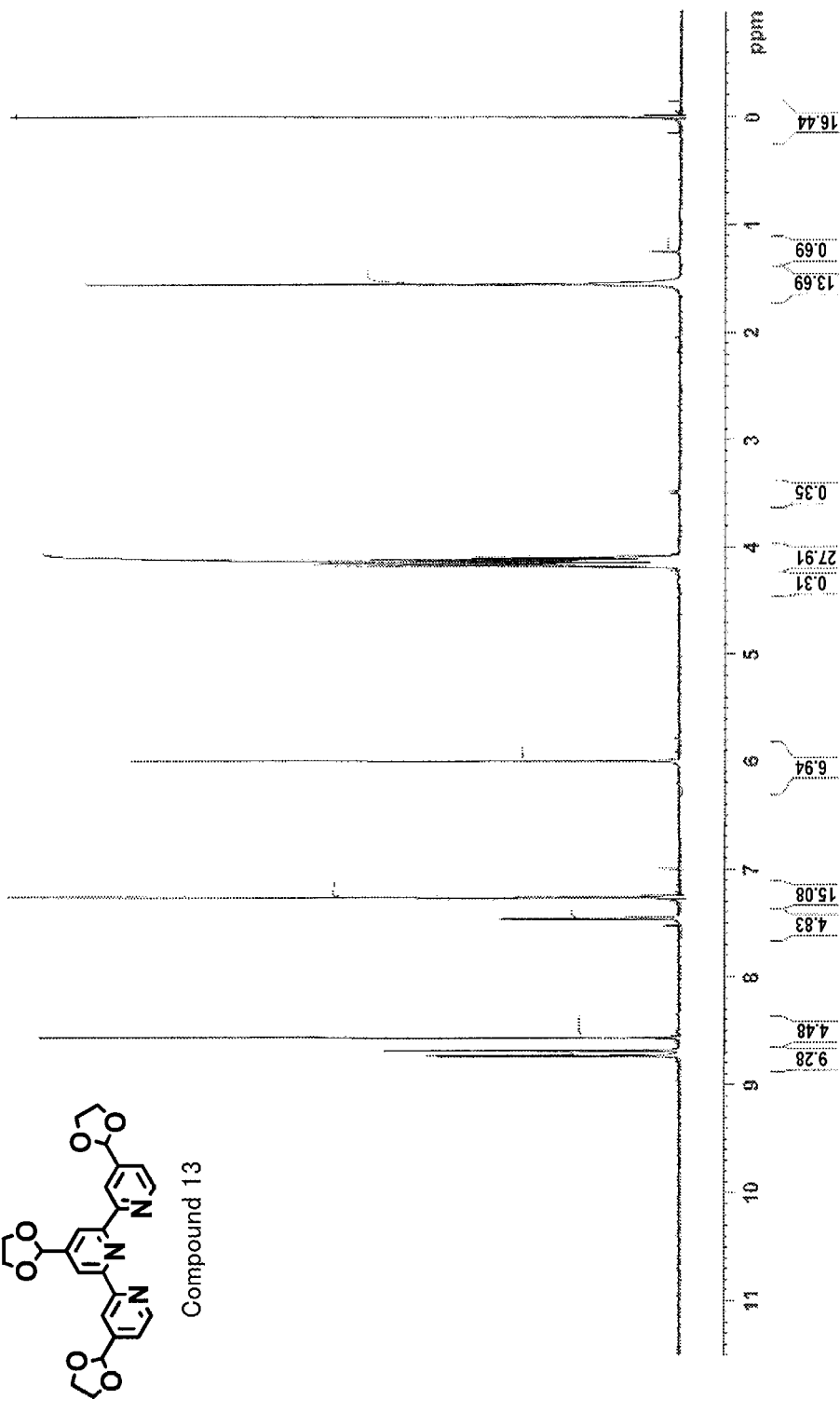
{Fig. 29}

{Fig. 30}
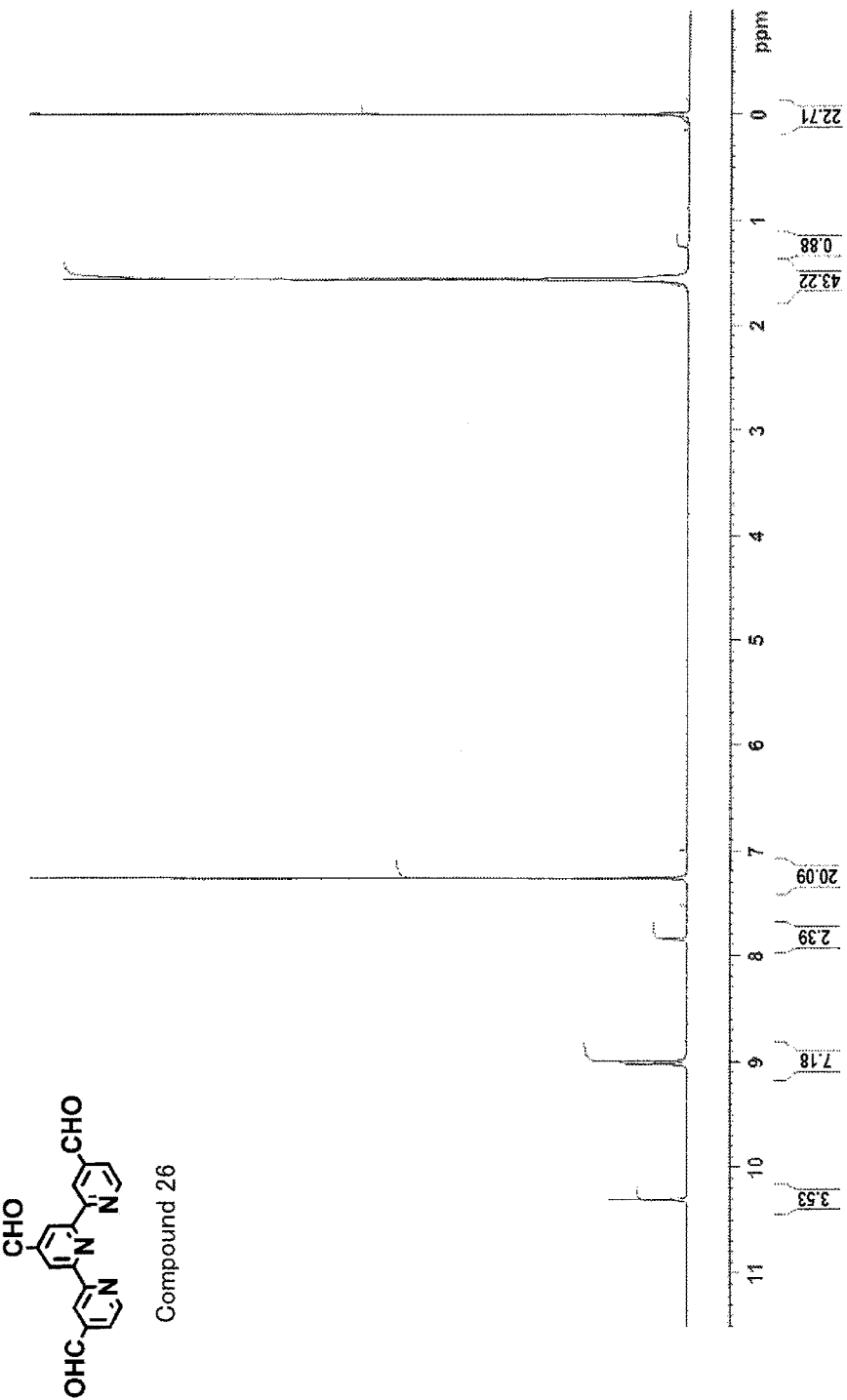

{Fig. 31}
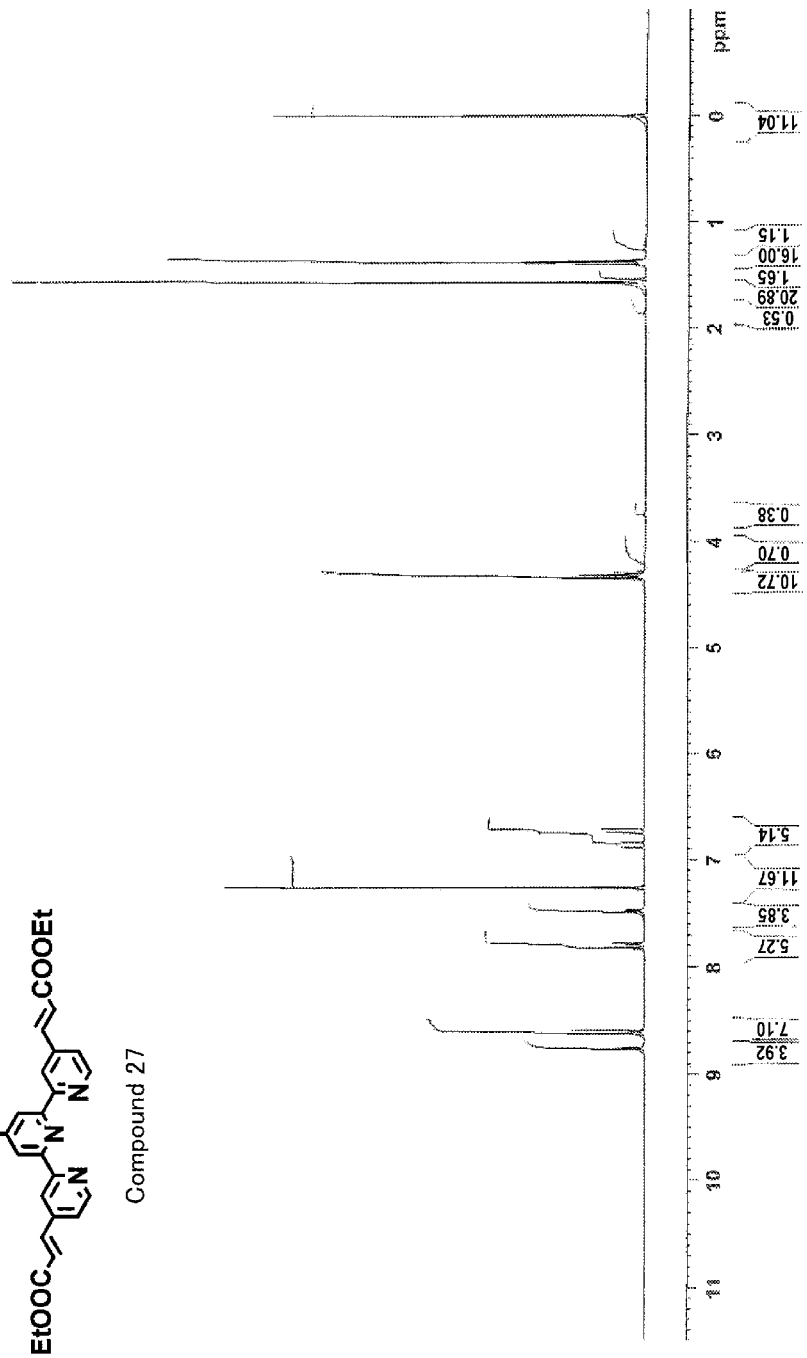

{Fig. 32}
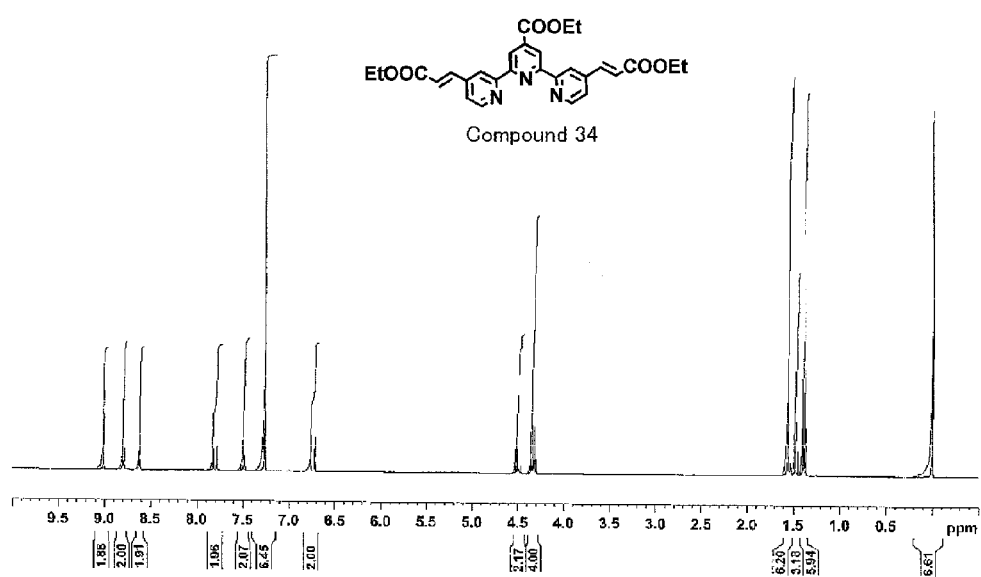

PHOTOELECTRIC CONVERSION ELEMENT, DYE-SENSITIZED SOLAR CELL, METAL COMPLEX DYE, DYE SOLUTION, DYE-ADSORBED ELECTRODE, AND METHOD FOR PRODUCING DYE-SENSITIZED SOLAR CELL

CROSS-REFERENCE TO RELATED APPLICATIONS

This application is a Continuation of PCT International Application No. PCT/JP2013/080883 filed on Nov. 15, 2013, which claims priority under 35 U.S.C. § 119 (a) to Japanese Patent Application No. 2012-252700 filed on Nov. 16, 2012, Japanese Patent Application No. 2012-252701 filed on Nov. 16, 2012, Japanese Patent Application No. 2013-062895 filed on Mar. 25, 2013, Japanese Patent Application No. 2013-129046 filed on Jun. 19, 2013, Japanese Patent Application No. 2013-151149 filed on Jul. 19, 2013, Japanese Patent Application No. 2013-205533 filed on Sep. 30, 2013, and Japanese Patent Application No. 2013-235218 filed on Nov. 13, 2013. Each of the above applications is hereby expressly incorporated by reference, in its entirety, into the present application.

TECHNICAL FIELD

The present invention relates to a photoelectric conversion element, a dye-sensitized solar cell, a metal complex dye, a dye solution, a dye-adsorbed electrode, and a method for producing dye-sensitized solar cell.

BACKGROUND ART

Photoelectric conversion elements are used in various photosensors, copying machines, solar cells or the like. These photoelectric conversion elements have adopted various systems to be put into use, such as elements utilizing metals, elements utilizing semiconductors, elements utilizing organic pigments or dyes, or elements utilizing combinations of these. In particular, solar cells that make use of non-exhaustive solar energy do not necessitate fuels, and full-fledged practicalization of solar cells as an inexhaustible clean energy is being highly expected. Above all, research and development of silicon-based solar cells have long been in progress. Based on a policy-wise consideration in each country, widespread use thereof is still in progress. However, silicon is an inorganic material, and has its own limitations in terms of improving throughput and cost.

Under such circumstances, research is being vigorously carried out on dye-sensitized solar cells. Especially, to have built momentum toward such research is research results by Graetzel et al. of École Polytechnique Fédérale de Lausanne in Switzerland. They employed a structure in which a dye formed from a ruthenium complex was fixed at the surface of a porous titanium oxide thin film, and realized a photoelectric conversion efficiency that was comparable to that of amorphous silicon. Thus, the dye-sensitized solar cells that can be produced even without using an expensive vacuum apparatus instantly attracted the attention of researchers all over the world.

Hitherto, as metal complex dyes to be used in photoelectric conversion elements, dyes generally called as N3, N719, Z907, and J2 have been developed.

On the other hand, investigations on the adsorptive group to the surface of semiconductor fine particles in terms of the kind and introduction method thereof have been conducted in order to utilize the light in the wavelength region of 800 nm or more or the light having a wavelength in the visible or infrared region. There were proposals that an adsorptive group such as acidic group be introduced to a pyridine ring via an ethenylene group (see Patent Literature 1) and that an ethenyl group substituted with an acidic group and a specific electron withdrawing group at the 2-position be bonded to the chromophore via a conjugated system (see Patent Literature 2). However, these proposals were not entirely satisfactory for an improvement in the photoelectric conversion efficiency and durability.

CITATION LIST

Patent Literatures

Patent Literature 1: JP-A-2002-105346 ("JP-A" means unexamined published Japanese patent application)
Patent Literature 2: JP-T-2011-502187 ("JP-T" means published Japanese translation of PCT application)

SUMMARY OF INVENTION

Technical Problem

In view of the above situation, the present invention aims to provide a photoelectric conversion element and a dye-sensitized solar cell which are excellent in adsorption stability onto the surface of semiconductor fine particles or durability as well as improved with the photoelectric conversion efficiency by increasing the optical absorption in a long wavelength region in the absorption properties of the metal complex dye so as to improve the spectral sensitivity characteristics in the long wavelength region. In addition, the present invention also aims to provide a metal complex dye, a dye solution and a dye-adsorbed electrode which are suitable for use in the photoelectric conversion element and the dye-sensitized solar cell, and a method for producing dye-sensitized solar cell.

Solution to Problem

The present inventors have conducted various investigations to improve the spectral sensitivity characteristics, namely the quantum yield (IPCE), in a long wavelength region since conventional dyes do not always have sufficient spectral sensitivity characteristics in a long wavelength region. On the other hand, in metal complex dyes coordinated by a ligand of a nitrogen-containing aromatic heterocyclic ring such as pyridine ring, for example, bipyridine, it has been attempted to enhance the spectral sensitivity characteristics in a long wavelength region by changing the ligand which does not have the function to adsorb onto the surface of semiconductor fine particles. However, there was a great obstacle to the compatibility between improvement in photoelectric conversion efficiency and improvement in durability. Hence, contrary to conventional knowledge, an investigation on enhancing the spectral sensitivity characteristics in a long wavelength region, by changing the chemical structure of the ligand having the function to adsorb onto the surface of semiconductor fine particles, has been conducted, and also various investigations on the ligand which does not have the function to adsorb onto the surface of semiconductor fine particles, have been conducted, thereby investigating further extension to a longer wavelength and enhancement in adsorption stability or durability. As a result, it has been found out that the structures near various kinds of adsorptive groups and the linking or substitution method of the adsorptive group to the nitrogen-containing aromatic heterocyclic ring are important, and that the combination with a bidentate ligand or tridentate ligand is important, from the viewpoint of extension to a longer wavelength by the expansion of the conjugated system of the ligand, and adsorption performance or durability, thereby completing the present invention.

In other words, the problems of the present invention have been overcome by the following means.

(1) A photoelectric conversion element, having an electrically conductive support, a photoconductor layer containing an electrolyte, a charge transfer layer containing an electrolyte, and a counter electrode, wherein the photoconductor layer contains semiconductor fine particles carrying a metal complex dye represented by the following Formula (I):

$$M(LA)(LD)(LX)_{mX'}(CI)_{mY} \qquad \text{Formula (I)}$$

wherein, in the formula, M represents a metal ion,

LA represents a tridentate ligand represented by the following Formula (AL),

LD represents a bidentate ligand or a tridentate ligand different from LA, in which, at least one of coordinating atoms which bond to the metal ion M in the bidentate ligand or the tridentate ligand is an anion, LX represents a monodentate ligand; mX is 1 when LD is the bidentate ligand and mX is 0 when LD is the tridentate ligand;

CI represents a counter ion necessary for neutralizing an electric charge;

mY represents an integer of 0 to 3;

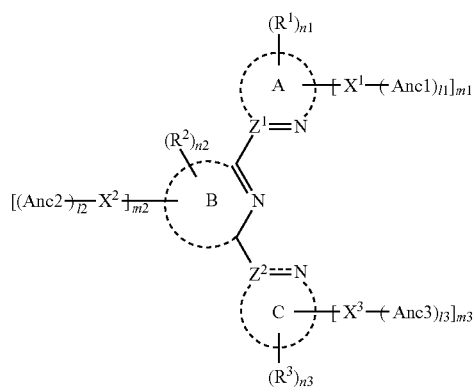

Formula (AL)

wherein, in the formula, the ring A, the ring B, and the ring C each independently represent a nitrogen-containing aromatic heterocyclic ring, herein, the bond between $Z^1$ and the N atom and the bond between $Z^2$ and the N atom may be a single bond or a double bond; $Z^1$ and $Z^2$ each independently represent a carbon atom or a nitrogen atom;

Anc1 to Anc3 each independently represent an acidic group; l1 and l3 each independently are an integer of 1 to 4, and l2 is an integer of 1 to 5, respectively;

$X^1$ and $X^3$ each independently represent a single bond or a linking group, $X^2$ is a single bond or a linking group to link an atom of $X^2$ bonded to at least one Anc2 with the nitrogen-containing aromatic heterocyclic ring of the ring B through π-conjugation, and when $X^2$ is the linking group, $X^2$ contains an ethenylene group, an ethynylene group, an arylene group or a heteroarylene group, in the linking chain thereof; each combinations of $X^1$ and the ring A, $X^2$ and the ring B, and $X^3$ and the ring C may bond to each other to form a fused ring; m1 and m3 each independently represent an integer of 0 to 4, and m2 represents an integer of 1 to 3; when $X^2$ is the single bond, m1 or m3 represents an integer of 1 to 4, and $X^1$ or $X^3$ represents the linking group;

$R^1$ to $R^3$ each independently represent a substituent that does not have any of Anc1 to Anc3; n1 and n2 each independently represent an integer of 0 to 3, and n3 represents an integer of 0 to 4; when a plurality of $R^1$s, a plurality of $R^2$s, or a plurality of $R^3$ exist, each of these may bond with each other to form a ring.

(2) The photoelectric conversion element according to (1), wherein M is $Os^{2+}$ or $Ru^{2+}$.

(3) The photoelectric conversion element according to (1) or (2), wherein $X^2$ each independently represents a single bond or any one of the following Formulas (X-1) to (X-6) or a group of any combination of these:

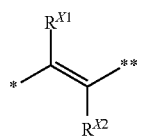

Formula (X-1)

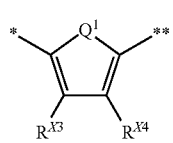

Formula (X-2)

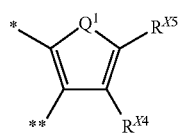

Formula (X-3)

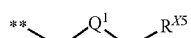

Formula (X-4)

Formula (X-5)

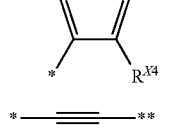

Formula (X-6)

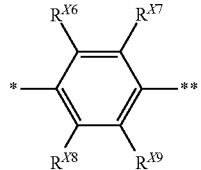

wherein, in the formulas, $Q^1$ represents a group selected from —S—, —O—, —N($R^{XA}$)—, —C($R^{XB}$)($R^{XC}$)—, and —Si($R^{XB}$)($R^{XC}$)—, in which $R^{XA}$ to $R^{XC}$ each independently represent a hydrogen atom or a substituent, and $R^{XB}$ and $R^{XC}$ may bond with each other to form a ring; $R^{X1}$ to $R^{X9}$ each independently represent a hydrogen atom or a substituent; herein, each combination of $R^{X1}$ and $R^{X2}$, $R^{X3}$ and $R^{X4}$, $R^{X4}$ and $R^{X5}$, $R^{X5}$ and $R^{XA}$, $R^{X5}$ and $R^{XB}$, $R^{X6}$ and $R^{X7}$, and $R^{X8}$ and $R^{X9}$ may bond with each other to form a ring; $R^{X1}$ to $R^{X4}$ and $R^{X6}$ to $R^{X9}$ each may bond to the ring B to form a fused ring; * represents a bonding position with the ring B, and ** represents a bonding position with Anc2.

(4) The photoelectric conversion element according to any one of (1) to (3), wherein at least one of $X^1$ and $X^3$ is each independently any one of the following Formulas (X-1) to (X-6) or a group of any combination of these:

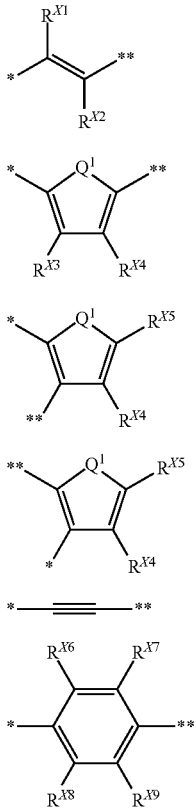

Formula (X-1)

Formula (X-2)

Formula (X-3)

Formula (X-4)

Formula (X-5)

Formula (X-6)

wherein, in the formulas, $Q^1$ represents a group selected from —S—, —O—, —N($R^{XA}$)—, —C($R^{XN}$)($R^{XC}$)—, and —Si($R^{XB}$)($R^{XC}$)—, in which $R^{XA}$ to $R^{XC}$ each independently represent a hydrogen atom or a substituent, and $R^{XB}$ and $R^{XC}$ may bond with each other to form a ring; $R^{X1}$ to $R^{X9}$ each independently represent a hydrogen atom or a substituent; herein, each combination of $R^{X1}$ and $R^{X2}$, $R^{X3}$ and $R^{X4}$, $R^{X4}$ and $R^{X5}$, $R^{X5}$ and $R^{X4}$, $R^{X5}$ and $R^{XB}$, $R^{X6}$ and $R^{X7}$, and $R^{X8}$ and $R^{X9}$ may bond with each other to form a ring; $R^{X1}$ to $R^{X4}$ and $R^{X6}$ to $R^{X9}$ may bond to the ring A or the ring C to form a fused ring. * represents a bonding position with the ring A or the ring C, and ** represents a bonding position with Anc1 or Anc3.

(5) The photoelectric conversion element according to (3) or (4), wherein $R^{X1}$ and $R^{X2}$ in Formula (X-1) are both a hydrogen atom.

(6) The photoelectric conversion element according to (3) or (4), wherein $X^2$ is a group represented by Formula (X-1), and $R^{X1}$ or $R^{X2}$ is an alkyl group or an aryl group.

(7) The photoelectric conversion element according to any one of (1) to (4) and (6), wherein $X^2$ has a structure represented by =C(Rz)- in a partial structure of the π-conjugation, herein the "=" bonding arm is located on the side of the ring B, the "—" bonding arm is located on the side of Anc2, and Rz represents a substituent having a σp value in the Hammett equation of 0.05 or more.

(8) The photoelectric conversion element according to any one of (1) to (4) and (7), wherein $X^2$ is represented by the following Formula (X-1A) or (X-2A):

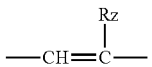

Formula (X-1A)

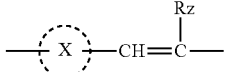

Formula (X-2A)

wherein, in the formulas, Rz represents a substituent having a σp value in the Hammett equation of 0.05 or more; the ring X represents an aromatic carbocyclic group or an aromatic heterocyclic group; herein, the bonding arm on the left side as seen bonds to the ring B, and the bonding arm on the right side as seen bonds to Anc2.

(9) The photoelectric conversion element according to any one of (1) to (8), wherein $X^1$ and $X^3$ each independently are a linking group represented by $X^2$.

(10) The photoelectric conversion element according to any one of (1) to (9), wherein the ring B is a pyridine ring.

(11) The photoelectric conversion element according to any one of (1) to (10), wherein the ring A and the ring C each independently are a ring selected from a pyridine ring, a quinoline ring, a pyrimidine ring, a triazine ring, an imidazole ring, a benzimidazole ring, an oxazole ring, a thiazole ring, a benzothiazole ring, an oxadiazole ring, a thiadiazole ring, an isoxazole ring, an isothiazole ring, a triazole ring, and a pyrazole ring.

(12) The photoelectric conversion element according to any one of (1) to (11), wherein the ring A to the ring C are a pyridine ring.

(13) The photoelectric conversion element according to any one of (1) to (12), wherein at least one of m1 and m3 is 1 and m2 is 1.

(14) The photoelectric conversion element according to any one of (1) to (13), wherein m1 to m3 are all 1.

(15) The photoelectric conversion element according to any one of (1) to (8) and (10) to (14), wherein m1 to m3 are all 1 and $X^2$ is a single bond.

(16) The photoelectric conversion element according to any one of (1) to (15), wherein LD is a bidentate ligand represented by any one of the following Formulas (2L-1) to (2L-5):

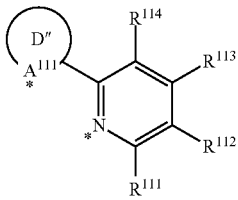

Formula (2L-1)

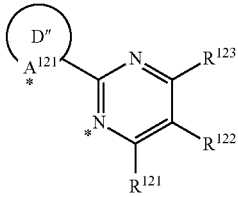

Formula (2L-2)

Formula (2L-3)

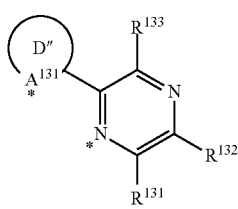

Formula (2L-4)

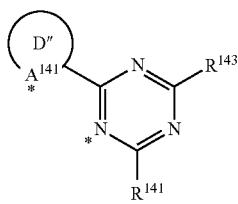

Formula (2L-5)

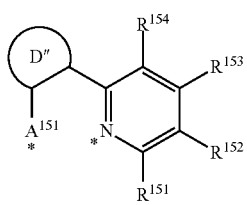

wherein, in the formulas, the ring D″ represents an aromatic ring; $A^{111}$ to $A^{141}$ each independently represent a nitrogen atom anion or a carbon atom anion, $A^{151}$ represents a nitrogen atom anion, an oxygen atom anion, or a sulfur atom anion; $R^{111}$ to $R^{154}$ each independently represent a hydrogen atom or a substituent that does not have any of Anc1, Anc2, and Anc3; and * represents a bonding position to the metal ion M.

(17) The photoelectric conversion element according to any one of (1) to (15), wherein LD is a tridentate ligand represented by any one of the following Formulas (3L-1) to (3L-4):

Formula (3L-1)

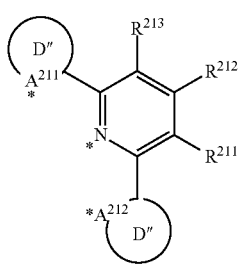

Formula (3L-2)

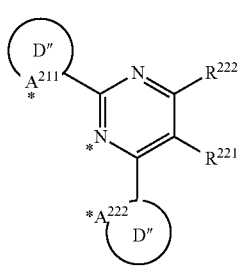

Formula (3L-3)

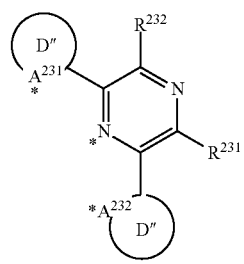

Formula (3L-4)

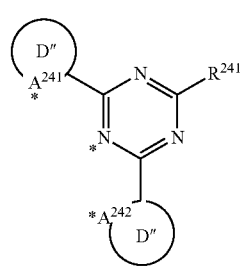

wherein, in the formulas, the ring $D^1$ represents an aromatic ring; $A^{211}$ to $A^{242}$ each independently represent a nitrogen atom or a carbon atom; at least one of $A^{211}$ and $A^{212}$, of $A^{221}$ and $A^{222}$, of $A^{231}$ and $A^{232}$, and of $A^{241}$ and $A^{242}$ is an anion, respectively; $R^{211}$ to $R^{241}$ each independently represent a hydrogen atom or a substituent that does not have any of Anc1, Anc2 and Anc3; and * represents a bonding position to the metal ion M.

(18) The photoelectric conversion element according to any one of (1) to (17), wherein the bidentate or tridentate ligand in LD has a nitrogen anion or a carbon anion as an atom coordinating to the metal ion M and the following Formula (SA) as a partial structure:

Formula (SA)

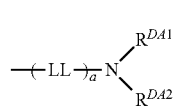

wherein, in the formula, $R^{DA1}$ represents an aryl group, and $R^{DA2}$ represents an alkyl group or an aryl group; $R^{DA1}$ and $R^{DA2}$ may bond with each other to form a ring; LL represents an ethenyl group, an ethynyl group, an arylene group, or a heteroarylene group; a represents an integer of 0 to 5.

(19) The photoelectric conversion element according to any one of (1) to (18), wherein Formula (I) is represented by the following Formula (I-1) or (I-2):

Formula (I-1)

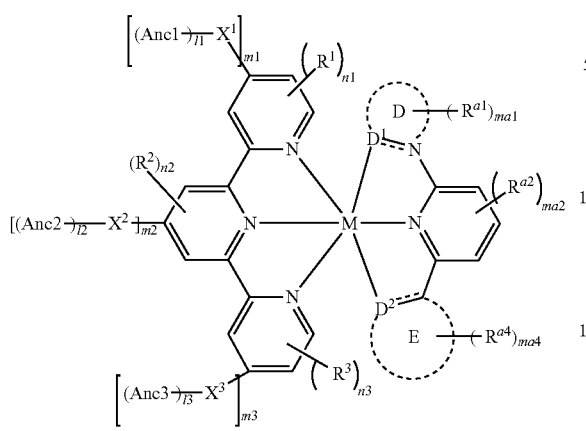

Formula (I-2)

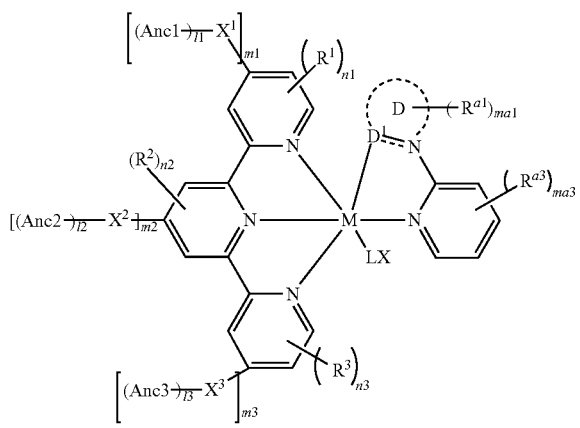

wherein, in the formulas, M and LX have the same meaning as M and LX in Formula (I); and Anc1 to Anc3, $X^1$ to $X^3$, l1 to l3, m1 to m3, $R^1$ to $R^3$, and n1 to n3 have the same meaning as Anc1 to Anc3, $X^1$ to $X^3$, l1 to l3, m1 to m3, $R^1$ to $R^3$, and n1 to n3 in Formula (AL);

the ring D and the ring E each independently represent a 5- or 6-membered aromatic ring; $D^1$ and $D^2$ each independently represent a carbon atom that bonds to M by dissociation of a hydrogen atom or a nitrogen atom that bonds to M by dissociation of a hydrogen atom; herein the bond linking $D^1$ in the ring D with the carbon atom bonding to the pyridine ring and the bond linking $D^2$ in the ring E with the carbon atom bonding to the pyridine ring each may be a single bond or a double bond;

$R^{a1}$ to $R^{a4}$ each independently represent a substituent; ma1, ma2, and ma4 each independently represent an integer of 0 to 3; ma3 represents an integer of 0 to 4;

when each of ma1 to ma4 is an integer of 2 or more, each of a plurality of $R^{a1}$s to a plurality of $R^{a4}$s may bond with each other to form a ring.

(20) The photoelectric conversion element according to (19), wherein the ring D and the ring E in Formula (I-1) or (I-2) each independently are a pyrazole ring, a triazole ring or a benzene ring.

(21) The photoelectric conversion element according to any one of (1) to (20), wherein the semiconductor fine particles further carry a co-adsorbent having one or more acidic groups.

(22) The photoelectric conversion element according to (21), wherein the co-adsorbent is represented by the following Formula (CA):

Formula (CA)

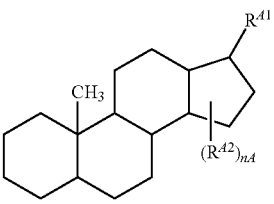

wherein, in the formula, $R^{A1}$ represents a substituent having an acidic group; $R^{A2}$ represents a substituent; nA represents an integer of 0 or more.

(23) A dye-sensitized solar cell including the photoelectric conversion element according to any one of (1) to (22).

(24) A metal complex dye represented by the following Formula (I):

$$M(LA)(LD)(LX)_{mX}(CI)_{mY}$$  Formula (I)

wherein, in the formula, M represents a metal ion,

LA represents a tridentate ligand represented by the following Formula (AL),

LD represents a bidentate ligand or a tridentate ligand different from LA, herein, at least one of coordinating atoms which bond to the metal ion M in the bidentate ligand or the tridentate ligand is an anion, LX represents a monodentate ligand; mX is 1 when LD is the bidentate ligand and mX is 0 when LD is the tridentate ligand;

CI represents a counter ion necessary for neutralizing an electric charge;

mY represents an integer of 0 to 3;

Formula (AL)

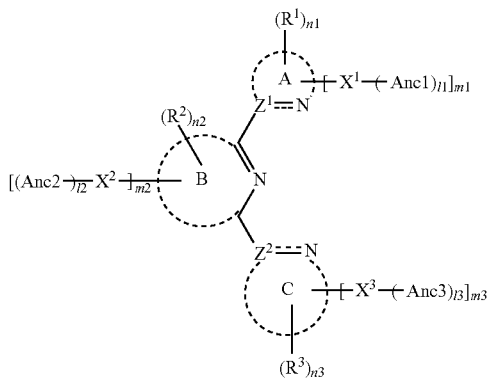

wherein, in the formula, the ring A, the ring B, and the ring C each independently represent a nitrogen-containing aromatic heterocyclic ring, herein, the bond between $Z^1$ and the N atom and the bond between $Z^2$ and the N atom may be a single bond or a double bond; $Z^1$ and $Z^2$ each independently represent a carbon atom or a nitrogen atom;

Anc1 to Anc3 each independently represent an acidic group; l1 and l3 each independently are an integer of 1 to 4, and l2 is an integer of 1 to 5, respectively;

$X^1$ and $X^3$ each independently represent a single bond or a linking group, $X^2$ is a single bond or a linking group to link an atom of $X^2$ bonded to at least one Anc2 with the nitrogen-containing aromatic heterocyclic ring of the ring B through π-conjugation, and when $X^2$ is the linking group, $X^2$ contains an ethenylene group, an ethynylene group, an arylene group, or a heteroarylene group, in the linking chain thereof; each combination of $X^1$ and the ring A, $X^2$ and the ring B, and $X^3$ and the ring C may bond to each other to form a fused ring; m1 and m3 each independently represent an integer of 0 to 4, and m2 represents an integer of 1 to 3; when $X^2$ is the single bond, m1 or m3 represents an integer of 1 to 4, and $X^1$ or $X^3$ represents the linking group;

$R^1$ to $R^3$ each independently represent a substituent that does not have any of Anc1 to Anc3; n1 and n2 each independently represent an integer of 0 to 3, and n3 represents an integer of 0 to 4; when a plurality of $R^1$s, a plurality of $R^2$s, or a plurality of $R^3$ exist, each of these may bond with each other to form a ring.

(25) The metal complex dye according to (24), wherein $X^2$ each independently represents a single bond or any one of the following Formulas (X-1) to (X-6) or a group of any combination of these:

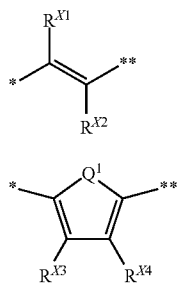

Formula (X-1)

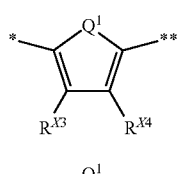

Formula (X-2)

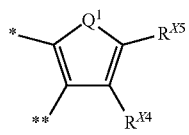

Formula (X-3)

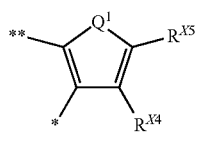

Formula (X-4)

Formula (X-5)

Formula (X-6)

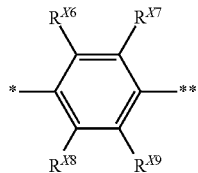

wherein, in the formulas, $Q^1$ represents a group selected from —S—, —O—, —N($R^{XA}$)—, —C($R^{XB}$)($R^{XC}$)—, and —Si($R^{XB}$)($R^{XC}$)—, in which $R^{XA}$ to $R^{XC}$ each independently represent a hydrogen atom or a substituent, and $R^{XB}$ and $R^{XC}$ may bond with each other to form a ring; $R^{X1}$ to $R^{X9}$ each independently represent a hydrogen atom or a substituent; herein, each combination of $R^{X1}$ and $R^{X2}$, $R^{X3}$ and $R^{X4}$, $R^{X4}$ and $R^{X5}$, $R^{X5}$ and $R^{X4}$, $R^{X5}$ and $R^{XB}$, $R^{X6}$ and $R^{X7}$, and $R^{X8}$ and $R^{X9}$ may bond with each other to form a ring; $R^{X1}$ to $R^{X4}$ and $R^{X6}$ to $R^{X9}$ each may bond to the ring B to form a fused ring; * represents a bonding position with the ring B, and ** represents a bonding position with Anc2.

(26) The metal complex dye according to (24) or (25), wherein LD is a bidentate ligand represented by any one of the following Formulas (2L-1) to (2L-5):

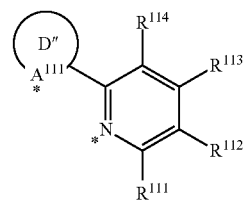

Formula (2L-1)

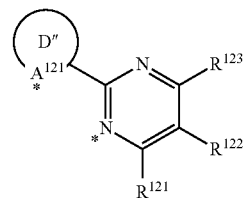

Formula (2L-2)

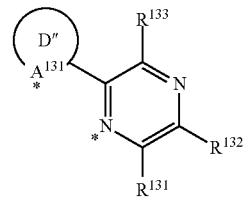

Formula (2L-3)

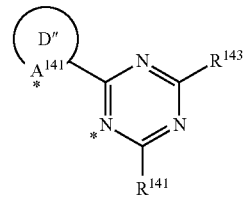

Formula (2L-4)

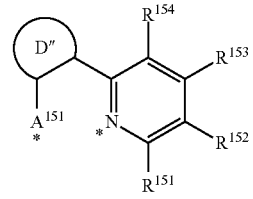

Formula (2L-5)

wherein, in the formulas, the ring $D^1$ represents an aromatic ring; $A^{111}$ to $A^{141}$ each independently represent a nitrogen atom anion or a carbon atom anion, $A^{151}$ represents a nitrogen atom anion, an oxygen atom anion, or a sulfur atom anion; $R^{111}$ to $R^{154}$ each independently represent a hydrogen atom or a substituent that does not have any of Anc1, Anc2, and Anc3; and * represents a bonding position to the metal ion M.

(27) The metal complex dye according to (24) or (25), wherein LD is a tridentate ligand represented by any one of the following Formulas (3L-1) to (3L-4):

Formula (3L-1)

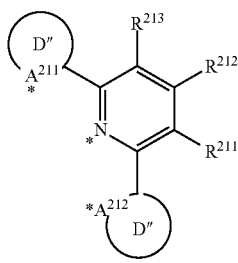

Formula (3L-2)

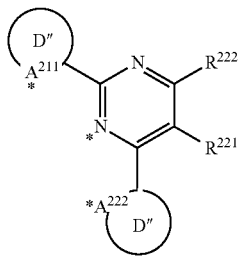

Formula (3L-3)

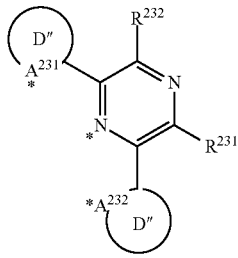

Formula (3L-4)

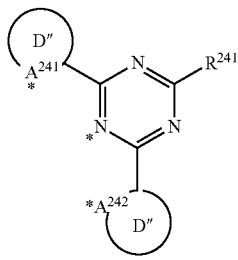

wherein, in the formulas, the ring D″ represents an aromatic ring; $A^{211}$ to $A^{242}$ each independently represent a nitrogen atom or a carbon atom; at least one of $A^{211}$ and $A^{212}$, of $A^{221}$ and $A^{222}$, of $A^{231}$ and $A^{232}$, and of $A^{241}$ and $A^{242}$ is an anion, respectively;

$R^{211}$ to $R^{241}$ each independently represent a hydrogen atom or a substituent that does not have any of Anc1, Anc2 and Anc3; and * represents a bonding position to the metal ion M.

(28) The metal complex dye according to any one of (24) to (27), wherein the bidentate or tridentate ligand in LD has a nitrogen anion or a carbon anion as an atom coordinating to the metal ion M and the following Formula (SA) as a partial structure:

Formula (SA)

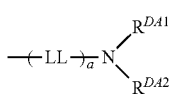

wherein, in the formula, $R^{DA1}$ represents an aryl group, and $R^{DA2}$ represents an alkyl group or an aryl group; $R^{DA1}$ and $R^{DA2}$ may bond with each other to form a ring;

LL represents an ethenyl group, an ethynyl group, an arylene group, or a heteroarylene group; a represents an integer of 0 to 5.

(29) The metal complex dye according to any one of (24) to (28), wherein $X^2$ is represented by the following Formula (X-1A) or (X-2A):

Formula (X-1A)

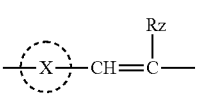

Formula (X-2A)

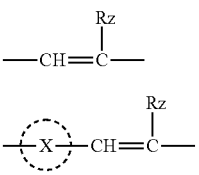

wherein, in the formulas, Rz represents a substituent having a σp value in the Hammett equation of 0.05 or more; the ring X represents an aromatic carbocyclic group or an aromatic heterocyclic group; herein, the bonding arm on the left side as seen bonds to the ring B, and the bonding arm on the right side as seen bonds to Anc2.

(30) A dye solution formed by dissolving the metal complex dye according to any one of (24) to (29).

(31) The dye solution according to (30), containing, in an organic solvent, the metal complex dye in an amount of 0.001 to 0.1% by mass and water in an amount controlled to 0.1% by mass or less.

(32) A dye-adsorbed electrode for dye-sensitized solar cell, wherein an electrically conductive support provided with semiconductor fine particles is coated with the dye solution according to (30) or (31) and cured by reaction to form a photoconductor layer.

(33) A method for producing dye-sensitized solar cell, including assembling a dye-sensitized solar cell using the dye-adsorbed electrode for dye-sensitized solar cell according to claim 32, and respective materials to be an electrolyte and a counter electrode.

(34) A compound represented by the following Formula (AL):

Formula (AL)

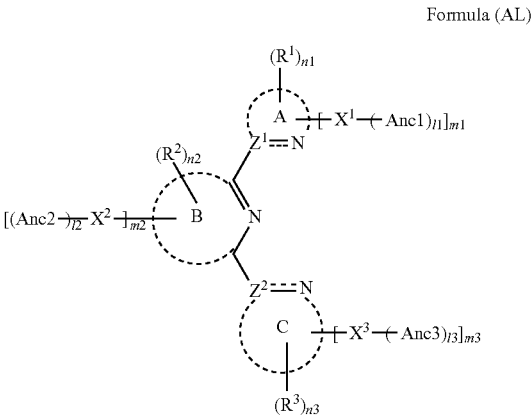

wherein, in the formula, the ring A, the ring B, and the ring C each independently represent a nitrogen-containing aromatic heterocyclic ring, herein, the bond between $Z^1$ and the N atom and the bond between $Z^2$ and the N atom may be a single bond or a double bond; $Z^1$ and $Z^2$ each independently represent a carbon atom or a nitrogen atom;

Anc1 to Anc3 each independently represent an acidic group; l1 and l3 each independently are an integer of 1 to 4, and l2 is an integer of 1 to 5, respectively;

$X^1$ and $X^3$ each independently represent a single bond or a linking group, $X^2$ is a single bond or a linking group to link an atom of $X^2$ bonded to at least one Anc2 with the nitrogen-containing aromatic heterocyclic ring of the ring B through π-conjugation, and when $X^2$ is the linking group, $X^2$ contains an ethenylene group, an ethynylene group, an arylene group, or a heteroarylene group, in the linking chain thereof; each combination of $X^1$ and the ring A, $X^2$ and the ring B, and $X^3$ and the ring C may bond to each other to form a fused ring; m1 and m3 each independently represent an integer of 0 to 4, and m2 represents an integer of 1 to 3; when $X^2$ is the single bond, m1 or m3 represents an integer of 1 to 4, and $X^1$ or $X^3$ represents the linking group;

$R^1$ to $R^3$ each independently represent a substituent that does not have any of Anc1 to Anc3; n1 and n2 each independently represent an integer of 0 to 3, and n3 represents an integer of 0 to 4; when a plurality of $R^1$s, a plurality of $R^2$s, or a plurality of $R^3$ exist, each of these may bond with each other to form a ring.

(35) The compound according to (34), wherein $X^2$ is a single bond, m1 or m3 is an integer of 1 to 4, and $X^1$ or $X^3$ is a linking group.

In the present specification, unless otherwise specified, with respect to the carbon-carbon double bond, in the case where the E configuration or the Z configuration exists in the molecule, it may be either one of the two configurations or a mixture thereof. When there are two or more substituents, linking groups, ligands or the like (hereinafter referred to as substituents or the like) represented by a specific symbol, or when two or more substituents or the like are defined at the same time or alternatively, each of the substituents or the like may be the same or different from one another, unless otherwise specified. This also applies to definition of the number of substituents or the like. Further, when a plurality of substituents or the like are close to one another (particularly adjacent to each other), they may be linked to one another to form a ring, unless otherwise specified. Further, a ring, for example, an aliphatic ring, an aromatic ring, or a heterocycle, may be fused to form a fused ring.

In the present specification, each substituent may further be substituted with another substituent, unless otherwise specified.

Advantageous Effects of Invention

According to the present invention, it is possible to provide a photoelectric conversion element and a dye-sensitized solar cell which have excellent adsorption stability onto the surface of semiconductor fine particles or durability as well as improved photoelectric conversion efficiency by increasing the optical absorption in a long wavelength region so as to improve the spectral sensitivity characteristics in the long wavelength region. In addition, it is possible to provide a metal complex dye, a dye solution and a dye-adsorbed electrode which are suitably used for these, and a method for producing dye-sensitized solar cell.

Other and further features and advantages of the invention will appear more fully from the following description, appropriately referring to the accompanying drawings.

BRIEF DESCRIPTION OF DRAWINGS

FIG. 1 is a cross-sectional view schematically showing one embodiment of the photoelectric conversion element of the present invention, including an enlarged view of the circled portion in the layer thereof FIG. 2 is a cross-sectional view schematically showing a dye-sensitized solar cell of a second embodiment of the photoelectric conversion element of the present invention.

FIG. 3 is a visible absorption spectrum diagram of Exemplified metal complex dye D-25 synthesized in Examples of the present invention, in a DMF solution.

FIG. 4 is a visible absorption spectrum diagram of Exemplified metal complex dye D-25 synthesized in Examples of the present invention, in a 340 mmol/L methanol solution of tetrabutylammonium hydroxide.

FIG. 5 is a visible absorption spectrum diagram of Exemplified metal complex dye D-26 synthesized in Examples of the present invention, in a 340 mmol/L methanol solution of tetrabutylammonium hydroxide.

FIG. 6 is a visible absorption spectrum diagram of Exemplified metal complex dye D-26 synthesized in Examples of the present invention, in a titanium oxide film formed by adsorbing it on titanium oxide.

FIG. 7 is a visible absorption spectrum diagram of Exemplified metal complex dye D-28 synthesized in Examples of the present invention, in a DMF solution.

FIG. 8 is a visible absorption spectrum diagram of Exemplified metal complex dye D-28 synthesized in Examples of the present invention, in a titanium oxide film formed by adsorbing it on titanium oxide.

FIG. 9 is a visible absorption spectrum diagram of Exemplified metal complex dye D-45 synthesized in Examples of the present invention, in a 340 mmol/L methanol solution of tetrabutylammonium hydroxide.

FIG. 10 is a visible absorption spectrum diagram of Exemplified metal complex dye D-59 synthesized in Examples of the present invention, in a 340 mmol/L methanol solution of tetrabutylammonium hydroxide.

FIG. 11 is a visible absorption spectrum diagram of Exemplified metal complex dye D-62 synthesized in Examples of the present invention, in a DMF solution.

FIG. 12 is a visible absorption spectrum diagram of Exemplified metal complex dye D-62 synthesized in Examples of the present invention, in a titanium oxide film formed by adsorbing it on titanium oxide.

FIG. 13 is a visible absorption spectrum diagram of Exemplified metal complex dye D-97 synthesized in Examples of the present invention, in a DMF solution.

FIG. 14 is a visible absorption spectrum diagram of Exemplified metal complex dye D-97 synthesized in Examples of the present invention, in a titanium oxide film formed by adsorbing it on titanium oxide.

FIG. 15 is a visible absorption spectrum diagram of Exemplified metal complex dye D-101 synthesized in Examples of the present invention, in a DMF solution.

FIG. 16 is a visible absorption spectrum diagram of Exemplified metal complex dye D-101 synthesized in Examples of the present invention, in a titanium oxide film formed by adsorbing it on titanium oxide.

FIG. 17 is a visible absorption spectrum diagram of Exemplified metal complex dye D-136 synthesized in Examples of the present invention, in a DMF solution.

FIG. 18 is a visible absorption spectrum diagram of Exemplified metal complex dye D-136 synthesized in Examples of the present invention, in a titanium oxide film formed by adsorbing it on titanium oxide.

FIG. 19 is a visible absorption spectrum diagram of Exemplified metal complex dye D-140 synthesized in Examples of the present invention, in a DMF solution.

FIG. 20 is a visible absorption spectrum diagram of Exemplified metal complex dye D-140 synthesized in Examples of the present invention, in a titanium oxide film formed by adsorbing it on titanium oxide.

FIG. 21 is a visible absorption spectrum diagram of Exemplified metal complex dye D-141 synthesized in Examples of the present invention, in a DMF solution.

FIG. 22 is a visible absorption spectrum diagram of Exemplified metal complex dye D-141 synthesized in Examples of the present invention, in a titanium oxide film formed by adsorbing it on titanium oxide.

FIG. 23 is a visible absorption spectrum diagram of Exemplified metal complex dye D-187 synthesized in Examples of the present invention, in a DMF solution.

FIG. 24 is a visible absorption spectrum diagram of Exemplified metal complex dye D-187 synthesized in Examples of the present invention, in a titanium oxide film formed by adsorbing it on titanium oxide.

FIG. 25 is a visible absorption spectrum diagram of Exemplified metal complex dye D-188 synthesized in Examples of the present invention, in a DMF solution.

FIG. 26 is a visible absorption spectrum diagram of Exemplified metal complex dye D-188 synthesized in Examples of the present invention, in a titanium oxide film formed by adsorbing it on titanium oxide.

FIG. 27 is a visible absorption spectrum diagram of Exemplified metal complex dye D-57 synthesized in Examples of the present invention, in a titanium oxide film formed by adsorbing it on titanium oxide.

FIG. 28 is a visible absorption spectrum diagram of Exemplified metal complex dye D-280 synthesized in Examples of the present invention, in a titanium oxide film formed by adsorbing it on titanium oxide.

FIG. 29 is a $^1$H-NMR spectrum diagram of Compound 13 synthesized in Examples of the present invention.

FIG. 30 is a $^1$H-NMR spectrum diagram of Compound 26 synthesized in Examples of the present invention.

FIG. 31 is a $^1$H-NMR spectrum diagram of Compound 27 synthesized in Examples of the present invention.

FIG. 32 is a $^1$H-NMR spectrum diagram of Compound 34 synthesized in Examples of the present invention.

DESCRIPTION OF EMBODIMENTS

<<Photoelectric Conversion Element and Dye-Sensitized Solar Cell>>

In the photoelectric conversion element of the present invention, for example, as shown in FIG. 1, the photoelectric conversion element 10 is composed of: an electrically-conductive support 1; a photoconductor layer 2 containing semiconductor fine-particles which has been sensitized by a dye (metal complex dye) 21; a charge-transfer layer 3 which is a hole-transport layer, and a counter electrode 4. In the present invention, it is preferred that a co-adsorbent has been adsorbed, together with the dye (metal complex dye) 21, onto semiconductor fine-particles 22. The electrically conductive support 1 in which the photoconductor layer 2 has been provided functions as a working electrode in the photoelectric conversion element 10. In this embodiment, the photoelectric conversion element 10 is shown as a system 100 utilizing a dye-sensitized solar cell, in which the photoelectric conversion element 10 is made to usable for a cell purpose which makes an operation means M to work via an external circuit 6.

In this embodiment, the light-receiving electrode 5 is an electrode having an electrically-conductive support 1, and a photoconductor layer 2 containing semiconductor fine-particles 22 to which a dye (metal complex dye) 21 has been adsorbed. The photoconductor layer 2 is designed according to the intended purpose, and it may have a single-layer structure or a multilayer structure. The dye (metal complex dye) 21 in one photoconductor layer may be a single species or a mixture, but as at least one of them, the metal complex dye of the present invention is used. Light incident to the photoconductor layer 2 excites the dye (metal complex dye) 21. The excited dye has electrons having high energy, and these electrons are transferred from the dye (metal complex dye) 21 to a conduction band of the semiconductor fine particles 22, and further reach the electrically conductive support 1 by diffusion. At this time, the dye (metal complex dye) 21 is in an oxidized form. The electrons on the electrode, while working in an external circuit 6, return through the counter electrode 4 to the photoconductor layer 2 in which the oxidized form of the dye (metal complex dye) 21 and the electrolyte exist, to function as the solar cell.

In the present invention, regarding materials for use in the photoelectric conversion element and the dye-sensitized solar cell, and a method of producing each member, ordinary ones in this kind may be adopted, unless otherwise specified, and reference can be made to, for example, U.S. Pat. Nos. 4,927,721, 4,684,537, 5,084,365, 5,350,644, 5,463,057, 5,525,440, JP-A-7-249790, JP-A-2004-220974 or JP-A-2008-135197.

Hereinafter, an outline of main members will be described.

<Photoconductor Layer>

The photoconductor layer is a layer that contains an electrolyte described later and semiconductor fine-particles carrying a sensitizing dye including the metal complex dye of the present invention described later.

<<Metal Complex Dye>>

A metal complex dye of the present invention is represented by Formula (I).

Formula (I)

In Formula (I), M represents a metal ion.

LA represents a tridentate ligand represented by the following Formula (AL).

LD represents a bidentate ligand or a tridentate ligand different from LA.

Herein, at least one of the coordinating atoms which bond to the metal ion M in the bidentate ligand or the tridentate ligand is an anion. To be an anion means that the atom bonds with M by dissociation of a hydrogen atom.

LX represents a monodentate ligand. mX represents 1 when LD is a bidentate ligand, and 0 when LD is a tridentate ligand.

CI represents a counter ion necessary for neutralizing an electric charge.

mY represents an integer of 0 to 3.

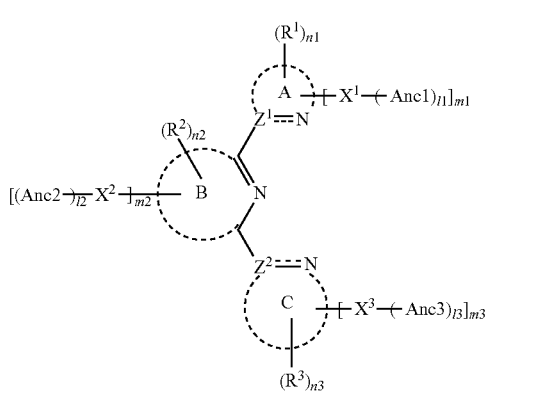

Formula (AL)

Hereinafter, the tridentate ligand or compound represented by Formula (AL) in the present invention will be described in detail.

The aromatic heterocyclic ring in the ring A to the ring C may be any ring as long as it includes a nitrogen atom as a heteroatom constituting the ring and is an aromatic ring.

The aromatic heterocyclic ring in the ring A to the ring C is preferably a 5- or 6-membered ring, and these aromatic heterocyclic rings may be fused with an aromatic carbon ring, an aromatic heterocyclic ring, a non-aromatic heterocyclic ring, and an alicyclic ring. In addition, the heteroatom constituting the ring of the aromatic heterocyclic ring may be 2 to 6 nitrogen atoms or may include another heteroatom, for example, an oxygen atom and a sulfur atom, in addition to the nitrogen atom.

In the present invention, the aromatic heterocyclic ring is preferably an unfused 6-membered ring, a 6-membered ring fused with a 5-membered ring, a 5-membered ring fused with a benzene ring, or a 6-membered ring fused with a benzene ring; more preferably an unfused 6-membered ring or a 6-membered ring fused with a 5-membered ring; and still more preferably an unfused 6-membered ring.

As the aromatic heterocyclic ring, the 6-membered ring may include, for example, a pyridine ring, a pyrimidine ring, a pyrazine ring, a triazine ring, a quinoline ring, and a quinazoline ring, and the 5-membered ring may include, for example, a pyrrole ring, an imidazole ring, a pyrazole ring, an oxazole ring, a thiazole ring, a benzimidazole ring, a benzoxazole ring, a benzothiazole ring, an indoline ring, and an indazole ring.

The ring B is preferably an unfused 6-membered ring, more preferably a pyridine ring, a pyrazine ring, a pyrimidine ring, a triazole ring, still more preferably a pyridine ring and a pyrimidine ring, and particularly preferably a pyridine ring.

The ring A and the ring C are preferably an unfused 6-membered ring, a 6-membered ring fused with a 5-membered ring, and a 6-membered ring fused with a benzene ring. As the 6-membered ring, each ring independently selected from a pyridine ring, a pyrimidine ring, a triazine ring, an imidazole ring, a benzimidazole ring, an oxazole ring, a thiazole ring, a benzothiazole ring, an oxadiazole ring, a thiadiazole ring, an isoxazole ring, an isothiazole ring, a triazole ring, and a pyrazole ring is more preferred; a pyridine ring and a pyrimidine ring are still more preferred among them; and a pyridine ring is particularly preferred. As the 6-membered ring fused with a 5-membered ring, a pyridine ring fused with a furan ring, a pyridine ring fused with a thiophene ring, a pyridine ring fused with a pyrrole ring, a pyridine ring fused with a silole ring, a pyridine ring fused with a cyclopentadienyl ring, are preferred; a pyridine ring fused with a furan ring, and a pyridine ring fused with a thiophene ring are more preferred; and a pyridine ring fused with a thiophene ring is still more preferred.

It is preferred that at least one of $Z^1$ and $Z^2$ is a carbon atom, and a case is more preferred where both of them are a carbon atom, from the viewpoint of extension to a longer wavelength.

Anc1 to Anc3 are an adsorptive group that adsorbs onto the surface of semiconductor fine particles, and at least one adsorptive group of these adsorbs onto the surface of semiconductor fine particles.

Anc1 to Anc3 represent an acidic group which is an adsorptive group.

In the present invention, in the ligand represented by Formula (AL), it is preferable to have at least two acidic groups, and it is more preferred to have three acidic groups.

In Formula (AL), the ring A, the ring B, and the ring C each independently represent a nitrogen-containing aromatic heterocyclic ring. Herein, the bond between $Z^1$ and the N atom and the bond between $Z^2$ and the N atom may be a single bond or a double bond. $Z^1$ and $Z^2$ each independently represent a carbon atom or a nitrogen atom.

Anc1 to Anc3 each independently represent an acidic group. l1 and l3 each independently are an integer of 1 to 4, and l2 is an integer of 1 to 5, respectively.

$X^1$ and $X^3$ each independently represent a single bond or a linking group, $X^2$ is a single bond or a linking group to link an atom of $X^2$ bonded to at least one Anc2 with the nitrogen-containing aromatic heterocyclic ring of the ring B through π-conjugation. When $X^2$ is the linking group, it contains an ethenylene group, an ethynylene group, an arylene group or a heteroarylene group, in the linking chain thereof. $X^1$ and the ring A, $X^2$ and the ring B, and $X^3$ and the ring C may bond to each other to form a fused ring. m1 and m3 each independently represent an integer of 0 to 4, and m2 represents an integer of 1 to 3. When $X^2$ is a single bond, m1 or m3 represents an integer of 1 to 4, and $X^1$ or $X^3$ represents a linking group.

$R^1$ to $R^3$ each independently represent a substituent that does not have any of Anc1 to Anc3. n1 and n2 each independently represent an integer of 0 to 3, and n3 represents an integer of 0 to 4. When a plurality of $R^1$s, a plurality of $R^2$s, or a plurality of $R^3$ exist, each of these may bond with each other to form a ring. The ring A and the ring B, and the ring B and the ring C may bond with each other via a linking group.

—Metal ion M—

M is a central metal of the metal complex dye, and examples thereof may include elements of Group 6 to Group 12 in the long-form periodic table.

As such elements, Ru, Fe, Os, Cu, W, Cr, Mo, Ni, Pd, Pt, Co, Ir, Rh, Re, Mn and Zn may be mentioned.

In the present invention, the metal ion M is preferably $Os^{2+}$, $Ru^{2+}$, or $Fe^{2+}$, more preferably $Os^{2+}$ or $Ru^{2+}$, and particularly preferably $Ru^{2+}$ among them.

In addition, in a state of being incorporated in the photoelectric conversion element, the valence of M may be changed by the redox reaction with the surrounding material.

—Ligand LA—

The ligand LA is a tridentate ligand or compound represented by Formula (AL) above, in the present invention.

The ligand LA is a ligand having an adsorptive group that adsorbs onto the surface of semiconductor fine particles.

(Acidic Group)

The acidic group means a substituent having a dissociative proton and having a pKa of 11 or lower. Examples thereof include: an acid group which shows an acid property, such as a carboxyl group, a phosphonyl group, a phosphoryl group, a sulfo group, and a boric acid group; or a group having any of these groups, and from the viewpoint of electron injection, a carboxyl group or a group having the same is preferred. Further, the acidic group may be in a dissociation form due to release of a proton, or may be a salt thereof.

Further, in the case where the acidic group is a salt thereof, a counter ion which forms the salt is not limited in particular. Examples thereof include positive ions mentioned as a counter ion CI in Formula (I) described later.

In the present invention, from the viewpoint of electron transfer, a carboxyl group is preferred in particular.

In addition, as a preferable aspect of the acid group, the following Formula (Anc) can be mentioned.

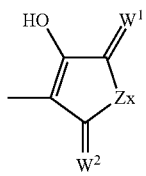

Formula (Anc)

In the formula, Zx represents a single bond or —[C(=W³)]nx-. Herein, nx represents an integer of 1 to 3. =W¹, =W², and =W³ each independently represent =O or =C(Ra1)(Ra2). Ra1 and Ra2 each independently represent a substituent. Further, —OH in the above formula may be in a salt form.

In Formula (Anc), as the substituent of Ra1 and Ra2 in =C(Ra1)(Ra2) of W¹ to W³, the substituent T described later may be mentioned. Ra1 and Ra2 are more preferably an alkyl group, an aryl group, a heterocyclic group, a cyano group, an acyl group, a sulfonyl group, an alkoxycarbonyl group, an aryloxycarbonyl group, a carbamoyl group, and a sulfamoyl group; and still more preferably an alkyl group, an aryl group, and a cyano group.

The group represented by Formula (Anc) is preferably a group represented by any one of the following Formulas (Anc-1) to (Anc-5).

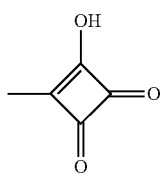
(Anc-1)

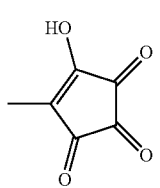
(Anc-2)

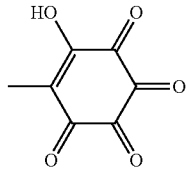
(Anc-3)

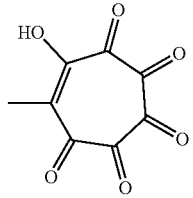
(Anc-4)

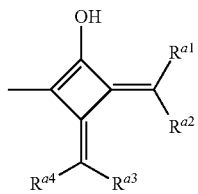
(Anc-5)

In the formulas, Ra1 to Ra4 each independently represent a substituent. —OH in the above formulas may be in a salt form.

The substituent in Ra1 to Ra4 has the same meaning as that of Ra1 and Ra2 described above, and the preferred range thereof is also the same.

Among the groups represented by Formulas (Anc-1) to (Anc-5), the groups represented by Formulas (Anc-1) and (Anc-5) are preferred, and the group represented by Formula (Anc-1) is particularly preferred.

$X^1$ to $X^3$ in Formula (AL) represent a single bond or a linking group. Provided that, $X^2$ is a linking group to link the atom of $X^2$ bonded to at least one Anc2 with a nitrogen-containing aromatic heterocyclic ring of the ring B through π-conjugation or a single bond; and when $X^2$ is a linking group, an ethenylene group or an ethynylene group is contained in the linking chain. In the case of containing an ethenylene group, a substituent on the ethenylene group may bond with an adjacent group to form a ring. In the case of forming a ring, a case to form an aromatic ring is also included. $X^1$ and the ring A, $X^2$ and the ring B, and $X^3$ and the ring C may bond with each other to form a fused ring. When $X^2$ is a single bond, m1 or m3 is an integer of 1 to 4 and $X^1$ or $X^3$ represents a linking group.

$X^2$ is not particularly limited as long as the above conditions are satisfied. Examples of the linking group may include an ethenylene group, an ethynylene group, an arylene group, and a heteroarylene group, which are substituted or unsubstituted, and a group formed by combining any of these groups. The heteroarylene group is a ring formed by the linking of the ethenylene group in $X^2$, and examples of the aromatic heterocyclic ring in such a heteroarylene group formed by the linking in $X^2$ to form a ring may include a furan ring, a thiophene ring, a pyrrole ring, a cyclopentadiene ring, and a silole ring. The arylene group is a ring formed by the linking of the ethenylene group in $X^2$, and examples of the aryl ring in such an arylene group formed by the linking in $X^2$ to form a ring may include a benzene ring and a naphthalene ring, and a benzene ring is preferred.

As the aromatic heterocyclic ring in the heteroarylene, a furan ring and a thiophene ring are preferred, and a thiophene ring is more preferred.

As the group formed by combining any of an ethenylene group, an ethynylene group, an arylene group, and a heteroarylene group, for example, the same group may be consecutively combined, such as two or more alkenylene groups (preferably 2 or 3) and two or more alkynylene groups (preferably 2 or 3) or different groups may be combined. In this case, examples thereof may include -ethenylene-ethynylene-, -ethynylene-ethenylene-, -ethenylene-heteroarylene group-, -ethynylene-heteroarylene group-, -heteroarylene group-ethenylene-, -heteroarylene group-ethynylene-, -arylene group-ethenylene-, -heteroarylene group-ethynylene-, and -heteroarylene group-heteroarylene group-. Examples thereof may include -divalent thiophene ring-ethynylene-, -divalent thiophene ring-ethenylene-, -ethenylene-divalent thiophene ring-, -ethynylene-divalent thiophene ring-, -divalent furan ring-ethynylene-, -divalent benzene ring-ethynylene-, -divalent thiophene ring-divalent thiophene ring-, -divalent furan ring-divalent furan ring-, and -ethynylene-ethynylene-.

Preferably, a plurality of $X^2$s each independently are a single bond or any one of the following Formulas (X-1) to (X-6) or a group of any combination of these.

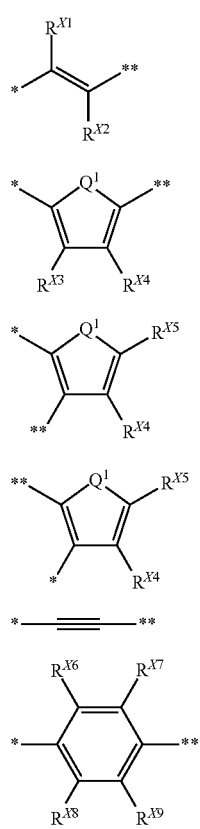

Formula (X-1)

Formula (X-2)

Formula (X-3)

Formula (X-4)

Formula (X-5)

Formula (X-6)

In the formulas, $Q^1$ represents a group selected from —S—, —O—, —N($R^{XA}$)—, —C($R^{XB}$)($R^{XC}$)— and —Si($R^{XB}$)($R^{XC}$)—. Herein, $R^{XA}$ to $R^{XC}$ each independently represent a hydrogen atom or a substituent. In addition, $R^{X1}$ and $R^{XC}$ may bond with each other to form a ring. $R^{X1}$ to $R^{X9}$ each independently represent a hydrogen atom or a substituent. Herein, each combination of $R^{X1}$ and $R^{X2}$, $R^{X3}$ and $R^{X4}$, $R^{X4}$ and $R^{X5}$, $R^{X5}$ and $R^{X4}$, $R^{X5}$ and $R^{XB}$, $R^{X6}$ and $R^{X7}$, and $R^{X8}$ and $R^{X9}$ may bond with each other to form a ring. $R^{X1}$ to $R^{X4}$ and $R^{X6}$ to $R^{X9}$ each may be bonded to the ring B to form a fused ring. * represents a bonding position with the ring B, and ** represents a bonding position with Anc2.

Preferably, a plurality of $X^2$s each independently are either of Formula (X-1) or (X-5) from the viewpoint of extension to a longer wavelength. $X^2$ is preferably a single bond or Formula (X-6) from the viewpoint of improving the molar extinction coefficient. In addition, $X^2$ is preferably a single bond from the viewpoint of improving quantum yield of the photoelectric conversion element.

There are an aspect A and an aspect B described later as preferred aspects, and the aspect A is more preferred.

Aspect A $X^2$ represents a single bond, any one of the following Formulas (X-1) to (X-6), or a group of any combination of these, and is more preferably a single bond or either of Formula (X-1) or Formula (X-5). Provided that, in Formula (X-1), $R^{X1}$ and $R^{X2}$ are both a hydrogen atom, or $R^{X1}$ is a hydrogen atom and $R^{X2}$ is an alkyl group or an aryl group, or $R^{X1}$ is an alkyl group or an aryl group and $R^{X2}$ is a hydrogen atom. The alkyl group and the aryl group may have a substituent, and examples of the substituent may include the substituent T described later. It is more preferred that $R^{X1}$ and $R^{X2}$ are both a hydrogen atom, or that $R^{X1}$ is a hydrogen atom and $R^{X2}$ is an alkyl group. This makes it possible to enhance the absorption efficiency, photoelectric conversion efficiency, and durability.

Aspect B $X^2$ has a structure represented by =C(Rz)- in the partial structure in the π-conjugation. Herein, the "=" bonding arm is located on the side of the ring B, and the "—" bonding arm is located on the side of Anc2.

Rz above represents a substituent having a σp value in the Hammett equation of 0.05 or more. This makes it possible to improve the absorption efficiency particularly in a long wavelength region of 900 nm or more and to enhance the adsorption stability.

Examples of the substituent having a σp value in the Hammett equation of 0.05 or more may include a cyano group, an acyl group, an arylcarbonyl group, a heteroarylcarbonyl group, a sulfonyl group, an alkoxycarbonyl group, an aryloxycarbonyl group, a carbamoyl group, a sulfamoyl group, a perfluoroalkyl group, a halogen atom, a nitro group, a heteroaryl group, or an aryl group having any of these groups.

Rz is preferably a cyano group, an acyl group (preferably acetyl group), an arylcarbonyl group, a perfluoroalkyl group (preferably a trifluoromethyl group), a halogen atom, a heteroaryl group, or an aryl group having any of these groups; and particularly preferably an acyl group (preferably acetyl group), an arylcarbonyl group, a halogen atom (preferably a fluorine atom), and a heteroaryl group (preferably a pyridyl group and a pyrimidinyl group).

Among them, Rz is preferably —C(=O)$R^{Z1}$, a perfluoroalkyl group, a halogen atom, a heteroaryl group, or a cyano group. Herein, $R^{Z1}$ represents an alkyl group, an aryl group, or a heterocyclic group.

A preferred aspect of such $X^2$ may include a group represented by the following Formula (X-1A) or (X-2A).

Formula (X-1A)

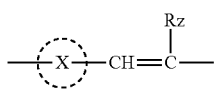

Formula (X-2A)

In the formulas, Rz represents a substituent having a σp value in the Hammett equation of 0.05 or more. The ring X represents an aromatic carbocyclic group or an aromatic heterocyclic group. Herein, the bonding arm on the left side as seen bonds to the ring B, and the bonding arm on the right side as seen bonds to Anc2.

The preferred range of Rz is as described above.

The group represented by Formula (X-1A) or (X-2A) above is still more preferably a group represented by the following Formulas (X-1B) or (X-2B), and particularly preferably Formula (X-1B).

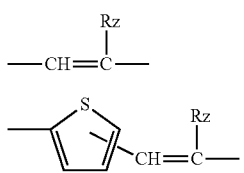

Formula (X-1B)

Formula (X-2B)

In the formulas, the bonding arm on the left side as seen bonds to the ring B. Rz in Formulas (X-1B) and Formula (X-2B) has the same meaning as Rz in Formula (X-1A) and Formula (X-2A), and the preferred range thereof is also the same.

Hereinafter, the matters common in the aspect A and the aspect B will be described.

$X^1$ and $X^3$ in Formula (AL) represent a single bond or a linking group.

The linking group in $X^1$ and $X^3$ may contain —O—, —S—, —NR'— (R' represents a hydrogen atom or a substituent), a divalent or higher-valent saturated aliphatic group, a divalent or higher-valent unsaturated aliphatic group having an unsaturated group which does not conjugate with the rings A or C, a divalent or higher-valent non-aromatic hydrocarbon ring group, and a divalent or higher-valent non-aromatic heterocyclic group, in the linking chain.

The linking group in $X^1$ and $X^3$ may be a conjugated chain of π-conjugation, and examples thereof may include the linking groups mentioned in $X^2$ above in this case.

$X^1$ and $X^3$ are preferably a single bond or the conjugated chain of π-conjugation.

A case where either of $X^1$ or $X^3$ is any one of Formula (X-1) to Formula (X-6) is preferred, and a case where both of them are any one of Formula (X-1) to Formula (X-6) is more preferred. A case where either of $X^1$ or $X^3$ is Formula (X-1) or Formula (X-6) is more preferred, and a case where both of them are Formula (X-1) or Formula (X-6) is still more preferred.

l1 to l3 are preferably 1 or 2 and more preferably 1.

m1 and m3 represent an integer of 0 to 4, and is preferably 0 or 1; and, from the viewpoint of the photoelectric conversion efficiency and adsorption stability, a case where one of m1 and m3 is 0 and the other is 1 or a case where both of them are 1 is preferred, and a case where both of them are 1 is more preferred.

m2 is preferably 1 or 2 and more preferably 1.

$R^1$ to $R^3$ in Formula (AL) represent a substituent, and examples of the substituent may include the substituent T described later. $R^1$ to $R^3$ are preferably an electron withdrawing group having a positive σp value in the Hammett equation, such as an alkyl group, an aryl group, a heterocyclic group, an amino group, an alkoxy group, an aryloxy group, an alkylthio group, an arylthio group, a halogen atom, a cyano group, and a sulfonyl group, and more preferably an alkyl group, an alkylcarbonyl group, an arylcarbonyl group, an aryl group, a heterocyclic group, an amino group, a halogen atom (preferably a fluorine atom), and a cyano group.

n1 and n3 are preferably 0 or 1, n2 is preferably 0.

The ligand represented by Formula (AL) above is preferably a ligand represented by the following Formula (AL-1).

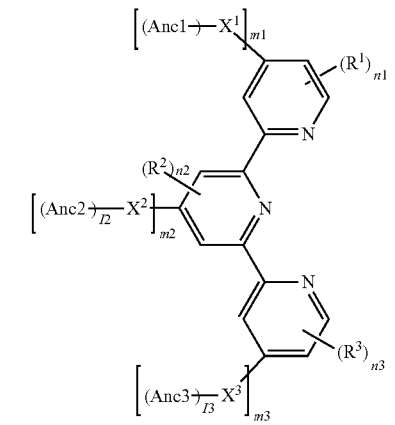

Formula (AL-1)

In the formula, Anc1 to Anc3, $X^1$ to $X^3$, $R^1$ to $R^3$, l1 to l3, m1 to m3, and n1 to n3 have the same meanings as Anc1 to Anc3, $X^1$ to $X^3$, $R^1$ to $R^3$, l1 to l3, m1 to m3, and n1 to n3 in Formula (AL) above, and the preferred ranges thereof are also the same.

Further, the ligand represented by Formula (AL) is preferably a compound in which $X^2$ is a single bond, m1 or m3 is an integer of 1 to 4, and $X^1$ or $X^3$ is a linking group, or a compound in which $X^2$ is Formula (X-1) or Formula (X-5), and in Formula (X-1), $R^{X1}$ is a hydrogen atom and $R^X$ is an alkyl group or an aryl group, m1 or m3 is an integer of 1 to 4, and $X^1$ or $X^3$ is a linking group; more preferably a compound in which $X^2$ is a single bond, m1 or m3 is an integer of 1 to 4, and $X^1$ or $X^3$ is a linking group; and still more preferably a compound in which $X^2$ is a single bond, m1 or m3 is an integer of 1 to 4, and $X^1$ or $X^3$ is Formula (X-1) or Formula (X-5), from the viewpoint of being a compound.

Hereinafter, a preferred structure as the compound can be represented by the following Formula (AC-1) or (AC-2).

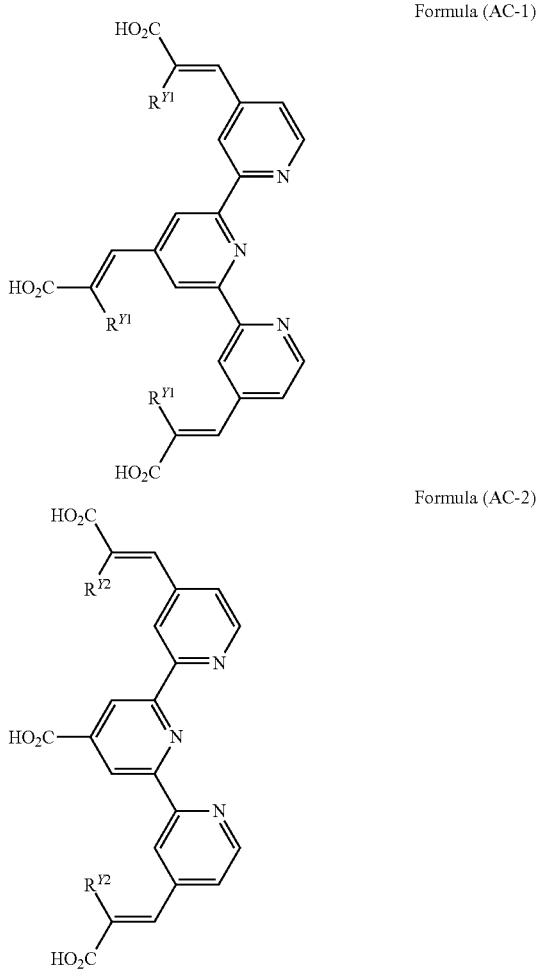

Formula (AC-1)

Formula (AC-2)

In the formulas, $R^{Y1}$ and $R^{Y2}$ represent a hydrogen atom or a substituent.

Examples of the substituent in $R^{Y1}$ and $R^{Y2}$ may include the substituent T described later.

Herein, at least one $R^{Y1}$ represents an alkyl group or an aryl group, it is preferred that at least one $R^{Y1}$ is an alkyl group, and it is more preferred that all of $R^{Y1}$s are an alkyl group.

$R^{Y2}$ is preferably a hydrogen atom or a group that links to the pyridine ring to form a ring J, as in Formula (AC-2') having the following structure. The ring J represents an aromatic ring which may contain a heteroatom, and is preferably a thiophene ring.

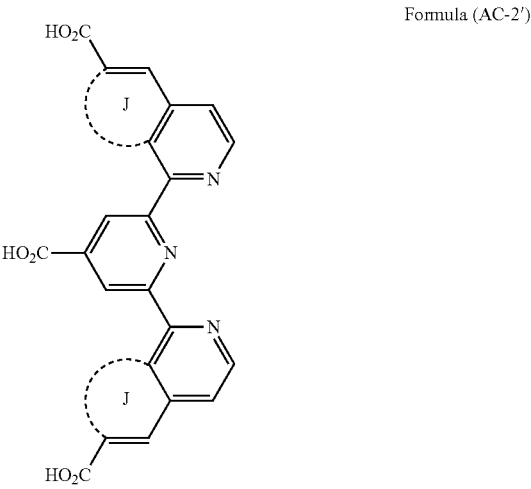 [SMILES: O=C(O)/C=C/c1ccnc(-c2cc(C(=O)O)cc(-c3cc(/C=C/C(=O)O)ccn3)n2)c1]

Formula (AC-2')

Specific examples of the ligand (compound) represented by Formula (AL) according to the present invention are presented below, but the present invention is not limited thereto.

| | RingA—RingB—RingC | | |
|---|---|---|---|
| LA No. | Ring A | Ring B | Ring C |
| LA-1-1 | HO₂C— | CO₂H | CO₂H |
| LA-1-2 | H₂O₃P— | PO₃H₂ | PO₃H₂ |

-continued

| LA No. | Ring A | Ring B | Ring C |
|---|---|---|---|
| LA-1-3 | | | |
| LA-1-4 | | | |
| LA-1-5 | | | |
| LA-1-6 | | | |
| LA-1-7 | | | |

RingA—RingB—RingC

-continued

| LA No. | Ring A | Ring B | Ring C |
|---|---|---|---|
| LA-1-8 | (thiophene-pyridine with HOOC-CH=CH- substituent and methyl on pyridine) | (thiophene-thiophene-pyridine with HOOC-CH=CH- and two methyls on pyridine) | (pyridine-thiophene with -CH=CH-COOH and methyl on pyridine) |
| LA-1-9 | (furan-pyridine with HOOC-CH=CH- substituent and methyl on pyridine) | (furan-furan-pyridine with HOOC-CH=CH- and two methyls on pyridine) | (pyridine-furan with -CH=CH-COOH and methyl on pyridine) |
| LA-1-10 | (bithiophene-pyridine with HOOC- and methyl on pyridine) | (bithiophene-thiophene-pyridine with COOH and two methyls on pyridine) | (pyridine-bithiophene with -COOH and methyl on pyridine) |
| LA-1-11 | (bifuran-pyridine with HOOC- and methyl on pyridine) | (bifuran-furan-pyridine with COOH and two methyls on pyridine) | (pyridine-bifuran with -COOH and methyl on pyridine) |

-continued

| LA No. | Ring A | Ring B | Ring C |
|---|---|---|---|
| LA-1-12 | (pyridine with CH=CH-CO₂H and methyl) | (thiophene-COOH linked to dimethylpyridine) | (pyridine with CH=CH-CO₂H and methyl) |
| LA-1-13 | (thiophene-pyridine with CH=CH-COOH) | (furan-COOH linked to dimethylpyridine) | (pyridine-thiophene with CH=CH-COOH) |
| LA-1-14 | (methylpyridine with CH=CH-CO₂H) | (dimethylpyridine-COOH) | (methylpyridine with CH=CH-CO₂H) |
| LA-1-15 | (methylpyridine with CH=CH-PO₃H₂) | (dimethylpyridine-COOH) | (methylpyridine with CH=CH-PO₃H₂) |
| LA-1-16 | (methylpyrimidine with CH=CH-CO₂H) | (dimethylpyridine-COOH) | (methylpyrimidine with CH=CH-CO₂H) |
| LA-1-17 | (methylpyridine with CH=CH-CO₂H) | (dimethylpyridine-COOH) | (methylpyrimidine with CH=CH-CO₂H) |
| LA-1-18 | (thiophene-COOH linked to methylpyridine) | (dimethylpyridine-COOH) | (methylpyridine-thiophene-COOH) |
| LA-1-19 | (furan-COOH linked to methylpyridine) | (dimethylpyridine-COOH) | (methylpyridine-furan-COOH) |

-continued

| LA No. | Ring A | Ring B | Ring C |
|---|---|---|---|
| LA-1-20 | | | |
| LA-1-21 | | | |
| LA-1-22 | | | |
| LA-1-23 | | | |
| LA-1-24 | | | |
| LA-1-25 | | | |
| LA-1-26 | | | |

-continued

| LA No. | Ring A | Ring B | Ring C |
|---|---|---|---|
| LA-1-27 | | | |
| LA-1-28 | | | |
| LA-1-29 | | | |
| LA-1-30 | | | |
| LA-1-31 | | | |

-continued
| LA No. | Ring A | Ring B | Ring C |
|---|---|---|---|
| LA-1-32 | 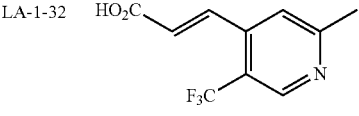 | 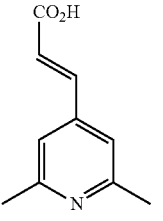 | 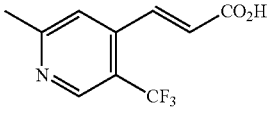 |
| LA-1-33 | 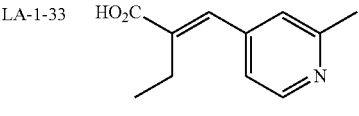 | 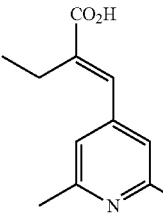 | 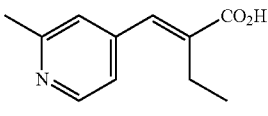 |
| LA-1-34 | 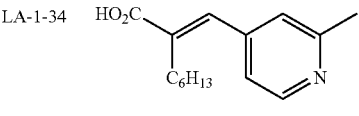 | 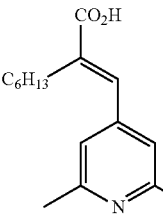 | 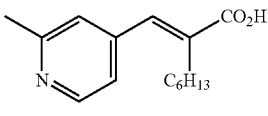 |
| LA-1-35 | 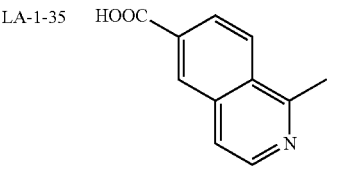 | 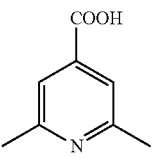 | 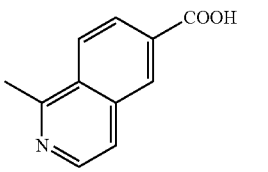 |
| LA-1-36 | 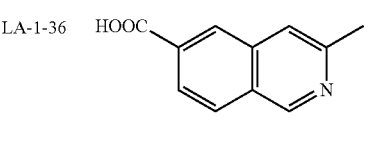 | 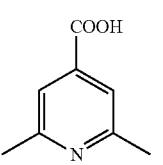 | 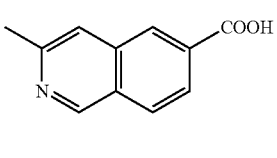 |
| LA-1-37 | 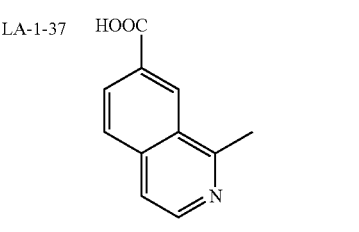 | 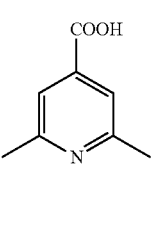 | 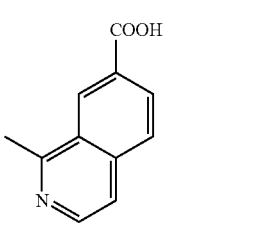 |
| LA-1-38 | 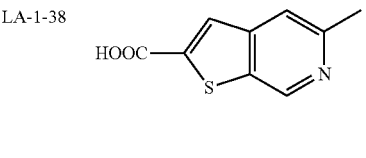 | 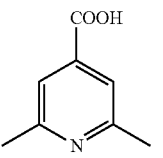 | 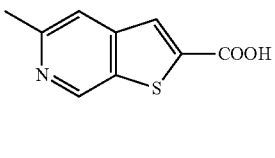 |
| LA-1-39 | 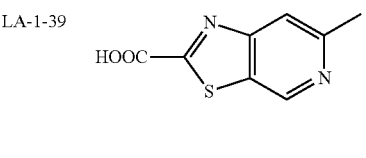 | 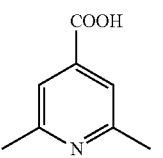 | 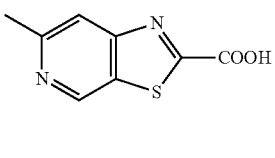 |

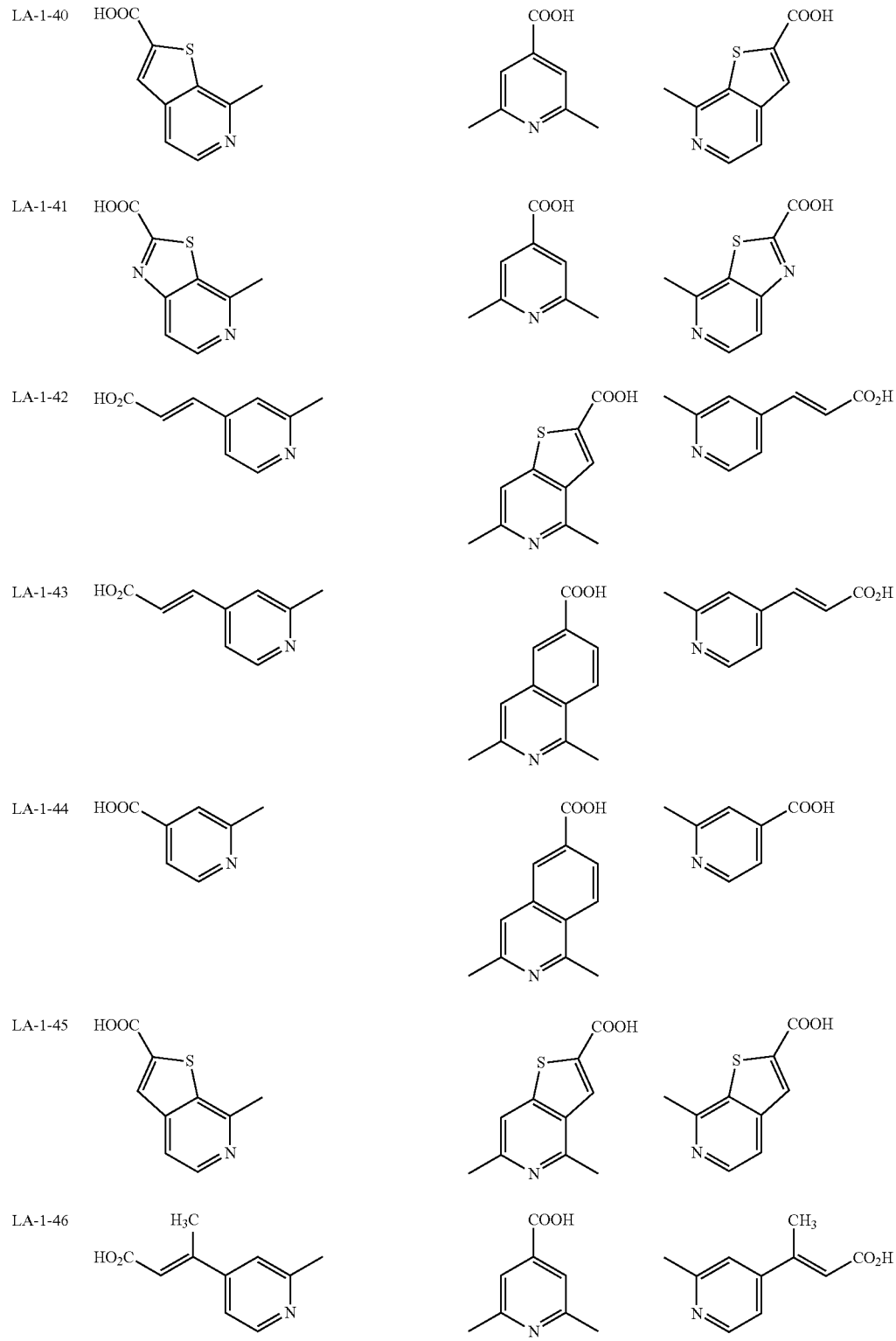

-continued

| LA No. | Ring A | Ring B | Ring C |
|---|---|---|---|
| LA-1-46 | | | |
| LA-1-47 | | | |
| LA-1-48 | | | |
| LA-1-49 | | | |
| LA-1-50 | | | |
| LA-1-51 | | | |
| LA-1-52 | | | |
| LA-1-53 | | | |

-continued

| LA No. | Ring A | Ring B | Ring C |
|---|---|---|---|
| LA-1-54 | (2-methylpyridin-4-yl)-(5-carboxy-thiophene-1,1-dioxide) | 2,6-dimethyl-4-carboxypyridine | (2-methylpyridin-4-yl)-(5-carboxy-thiophene-1,1-dioxide) |
| LA-1-55 | (2-methylpyridin-4-yl)-(5-carboxy-thiophene-1-oxide) | 2,6-dimethyl-4-carboxypyridine | (2-methylpyridin-4-yl)-(5-carboxy-thiophene-1-oxide) |
| LA-1-56 | 4-(4-carboxybuta-1,3-dien-1-yl)-2-methylpyridine | 2,6-dimethyl-4-carboxypyridine | 4-(4-carboxybuta-1,3-dien-1-yl)-2-methylpyridine |
| LA-3-1 | 2-methylpyridine | 2-cyano-3-(2,6-dimethylpyridin-4-yl)acrylic acid | 2-methylpyridine |
| LA-3-2 | 2-methylpyridine | 5-(2,6-dimethylpyridin-4-yl)thiophene-2-carboxylic acid | 2-methylpyridine |
| LA-3-3 | 2-methylpyridine | 2-cyano-3-[5-(2,6-dimethylpyridin-4-yl)thiophen-2-yl]acrylic acid | 2-methylpyridine |

-continued
| LA No. | Ring A | Ring B | Ring C |
|---|---|---|---|
| LA-3-4 | 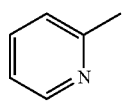 | 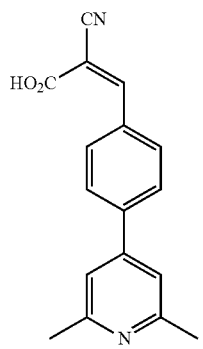 | 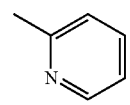 |
| LA-3-5 | 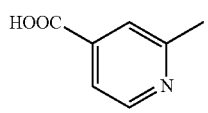 | 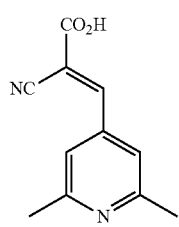 | 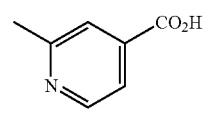 |
| LA-3-6 | 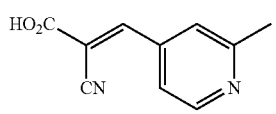 | 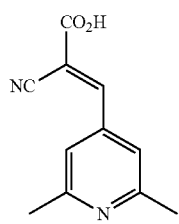 | 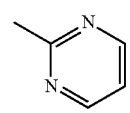 |
| LA-3-7 | 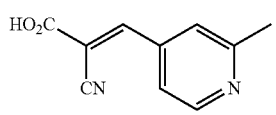 | 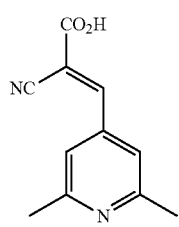 | 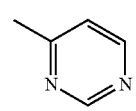 |
| LA-3-8 | 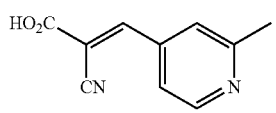 | 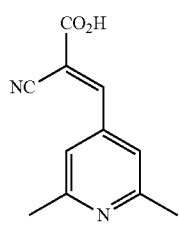 | 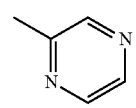 |
| LA-3-9 | 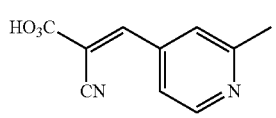 | 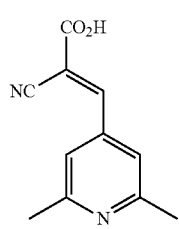 | 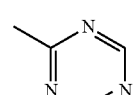 |

-continued
| LA No. | Ring A | Ring B | Ring C |
|---|---|---|---|
| LA-3-10 | 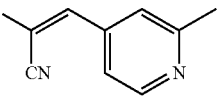 | 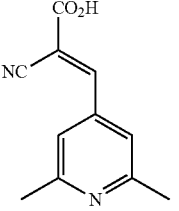 | 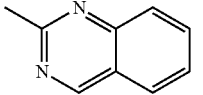 |
| LA-3-11 | 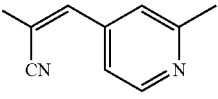 | 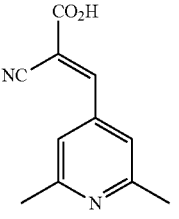 | 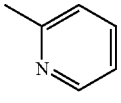 |
| LA-3-12 | 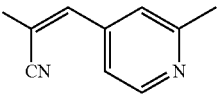 | 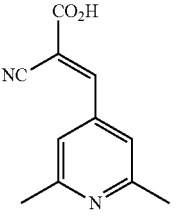 | 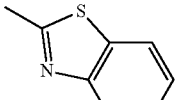 |
| LA-3-13 | 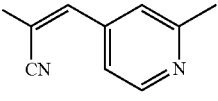 | 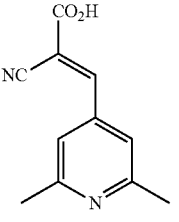 | 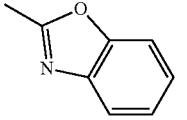 |
| LA-3-14 | 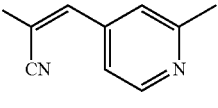 | 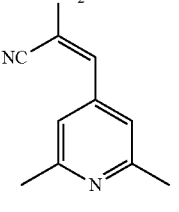 | 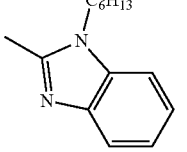 |
| LA-3-15 | 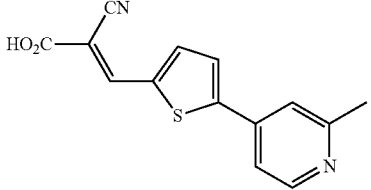 | 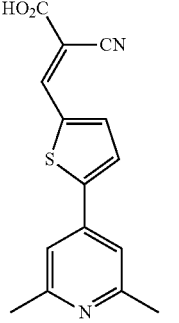 | 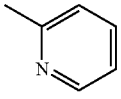 |

-continued

| LA No. | Ring A | Ring B | Ring C |
|---|---|---|---|
| LA-3-16 | | | |
| LA-3-17 | | | |
| LA-3-18 | | | |
| LA-3-19 | | | |
| LA-3-20 | | | |
| LA-3-21 | | | |

| LA No. | Ring A | Ring B | Ring C |
|---|---|---|---|
| LA-3-22 | H₃CO₂S, HOOC, CO₂H, pyridine-methyl | CO₂H, dimethylpyridine | SO₂CH₃, COOH, methylpyridine |
| LA-3-23 | NC, HOOC, methylpyridine | CO₂H, dimethylpyridine | CN, COOH, methylpyridine |
| LA-3-24 | NC, HOOC, thiophene-methylpyridine | CO₂H, dimethylpyridine | CN, COOH, thiophene-methylpyridine |
| LA-3-25 | H₃C-C(=O), HOOC, thiophene-methylpyridine | CO₂H, dimethylpyridine | CH₃-C(=O), COOH, thiophene-methylpyridine |
| LA-3-26 | Ph-C(=O), HOOC, thiophene-methylpyridine | HOOC-thiophene-dimethylpyridine | C(=O)-Ph, COOH, thiophene-methylpyridine |
| LA-3-27 | Ph-C(=O), HOOC, thiophene-methylpyridine | CO₂H, dimethylpyridine | C(=O)-Ph, COOH, thiophene-methylpyridine |

-continued

| LA No. | Ring A | Ring B | Ring C |
|---|---|---|---|
| LA-3-28 | | | |
| LA-3-29 | | | |
| LA-3-30 | | | |
| LA-3-31 | | | |
| LA-3-32 | | | |
| LA-3-33 | | | |

-continued

| LA No. | Ring A | Ring B | Ring C |
|---|---|---|---|
| LA-3-34 | | | |
| LA-3-35 | | | |
| LA-3-36 | | | |
| LA-3-37 | | | |
| LA-3-38 | | | |
| LA-3-39 | | | |

-continued

| LA No. | Ring A | Ring B | Ring C |
|---|---|---|---|
| LA-3-40 | | | |
| LA-3-41 | | | |
| LA-3-42 | | | |
| LA-3-43 | | | |
| LA-3-44 | | | |
| LA-3-45 | | | |

RingA—RingB—RingC

-continued

| LA No. | Ring A | Ring B | Ring C |
|---|---|---|---|
| LA-3-46 | | | |
| LA-3-47 | | | |
| LA-3-48 | | | |
| LA-3-49 | | | |
| LA-3-50 | | | |
| LA-4-1 | | | |

-continued

| LA No. | Ring A | Ring B | Ring C |
|---|---|---|---|
| | | RingA—RingB—RingC | |
| LA-4-2 | (structure) | (structure) | (structure) |
| LA-4-3 | (structure) | (structure) | (structure) |
| LA-4-4 | (structure) | (structure) | (structure) |
| LA-4-5 | (structure) | (structure) | (structure) |
| LA-4-6 | (structure) | (structure) | (structure) |

| LA No. | Cy101 | Cy102 | Cy103 |
|---|---|---|---|
| | | Cy101—Cy102—Cy103 | |
| LA-5-1 | (structure) | (structure) | (structure) |

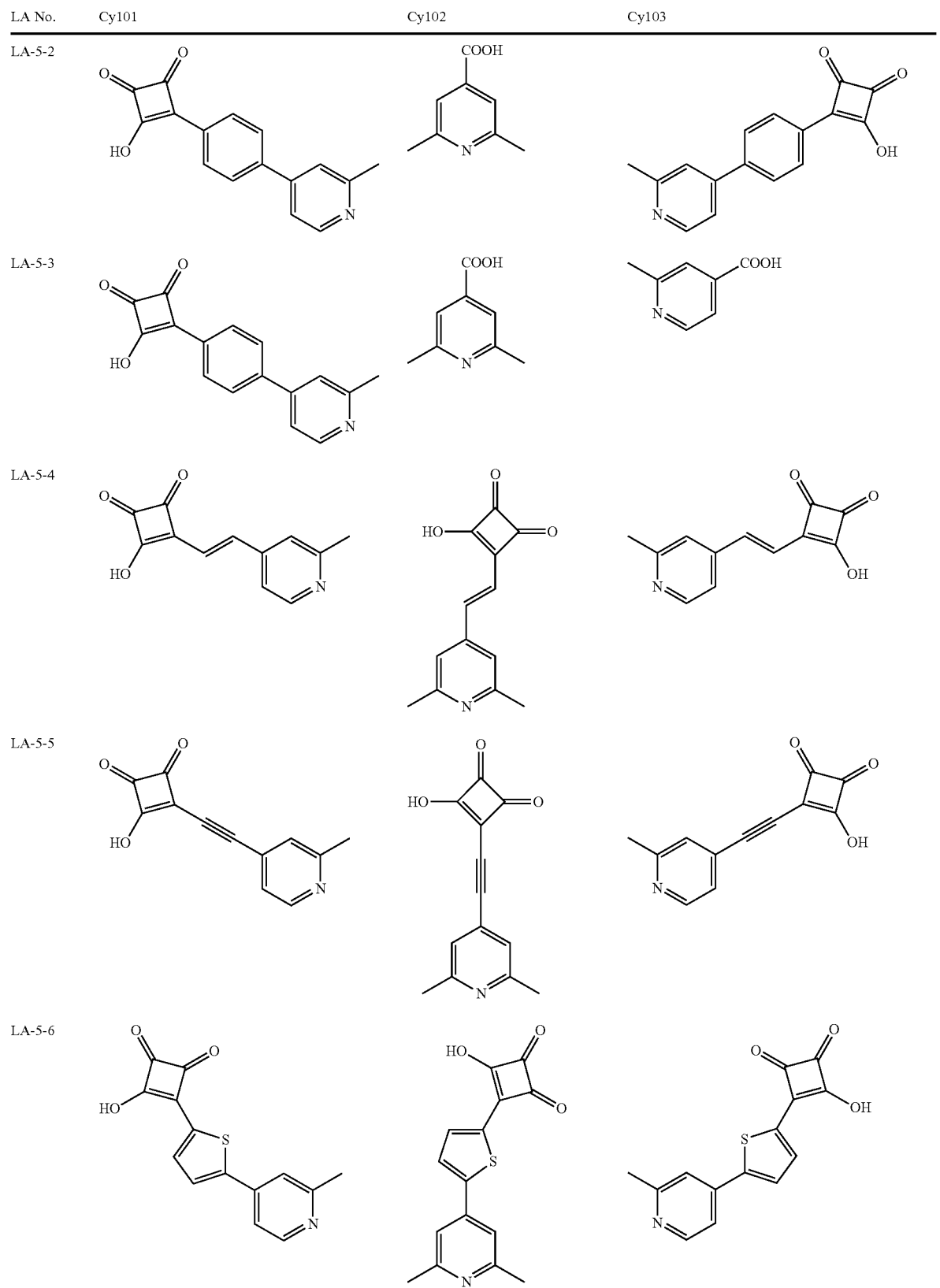

-continued

| LA No. | Cy101 | Cy102 | Cy103 |
|---|---|---|---|
| LA-5-7 | | | |
| LA-5-8 | | | |
| LA-5-9 | | | |
| LA-5-10 | | | |
| LA-5-11 | | | |

-continued

| | Cy101—Cy102—Cy103 | | |
|---|---|---|---|
| LA No. | Cy101 | Cy102 | Cy103 |
| LA-5-12 | | | |
| LA-5-13 | | | |
| LA-5-14 | | | |
| LA-5-15 | | | |
| LA-5-16 | | | |

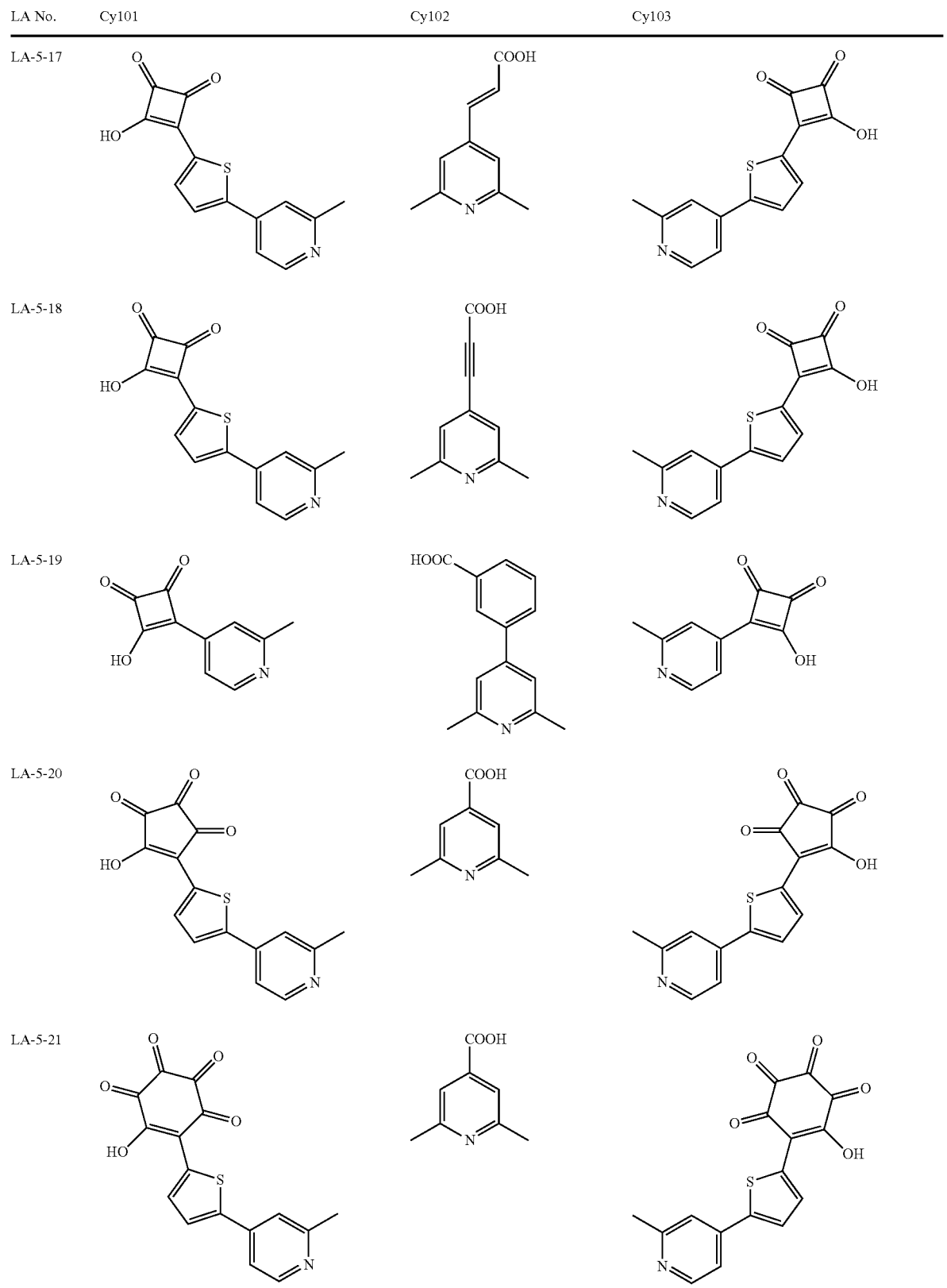

-continued

| LA No. | Cy101 | Cy101—Cy102—Cy103 | | |
|---|---|---|---|---|
| | | Cy102 | Cy103 | |
| LA-5-22 | 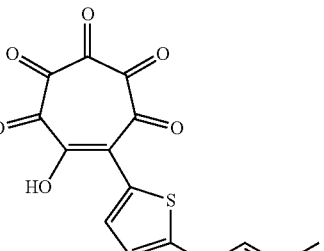 | 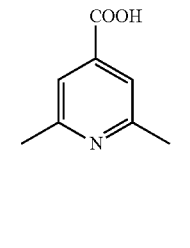 | 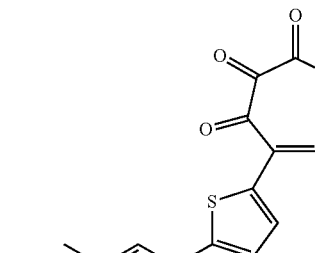 | |
| LA-5-23 | 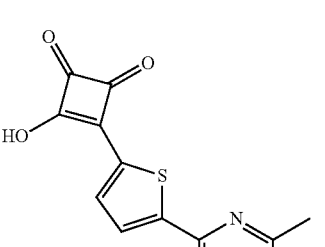 | 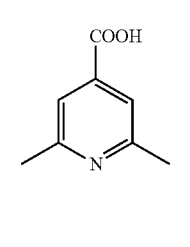 | 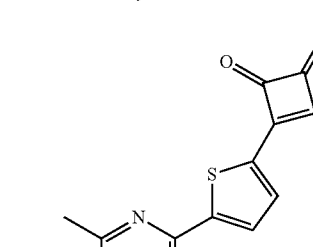 | |

These ligands can be synthesized by the methods described in JP-T-2012-508227, JP-T-2011-502965, JP-T-2011-502187, and Angew. Chem. Int. Ed., 2011, 50, 1-6, the methods described in the references cited in the literatures or the methods according to these methods.

In this connection, the synthetic method of the preferred ligand (compound) according to the present invention is also not particularly limited, but it is preferred to use one of the compounds represented by the following Formulas (AD-1) to (AD-3) from the viewpoint of production suitability or ease of synthesis.

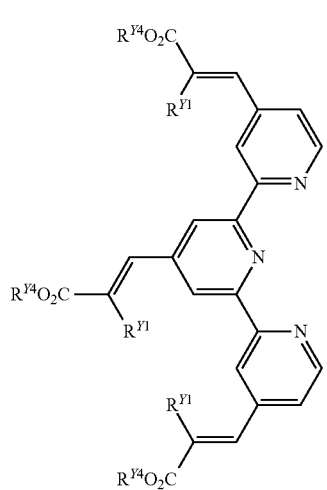

Formula (AD-1)

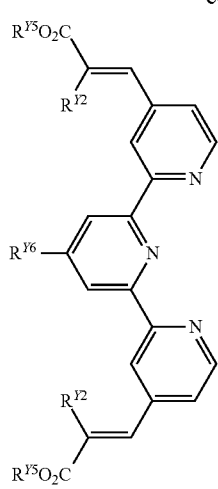

Formula (AD-2)

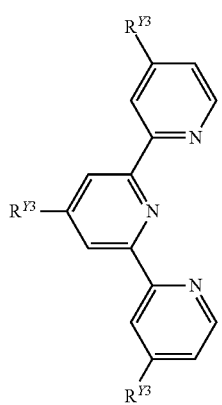

Formula (AD-3)

In the formulas, R¹ and R² have the same meanings as R¹ and R² in Formulas (AC-1) and (AC-2) above, and the preferred ranges thereof are also the same. $R^{Y4}$ and $R^{Y5}$ represent a hydrogen atom or an alkyl group. $R^{Y6}$ represents any one of —COOH, —COOR$^{Y7}$, —CHO (aldehyde). Herein, R⁷ represents an alkyl group.

$R^{Y3}$ represents any one of —COOH, —COOR$^{Y7}$, —CHO (aldehyde), and the following structure (which may be further substituted), provided that, at least one of $R^{Y3}$ represents —CHO (aldehyde) or the following structure.

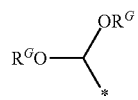

In the formula, two $R^G$s each independently represent an alkyl group, and they may bond with each other to form a ring. Herein, * represents a bonding position.

Specific examples of the compound represented by Formulas (AC-1), (AC-2), or (AD-1) to (AD-3) may include the following compounds.

Herein, Et is an ethyl group (—C₂H₅).

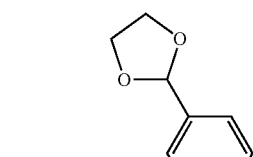 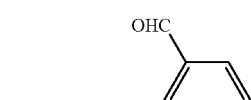 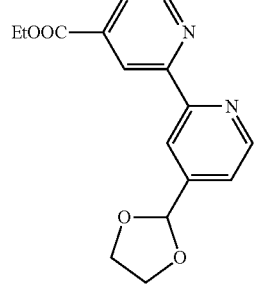 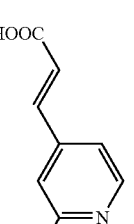

77
-continued

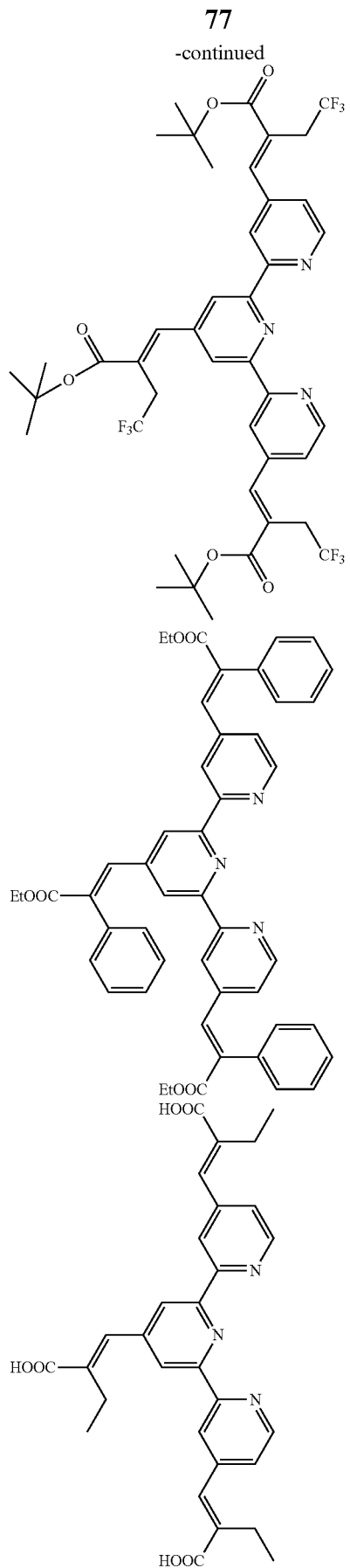

78
-continued

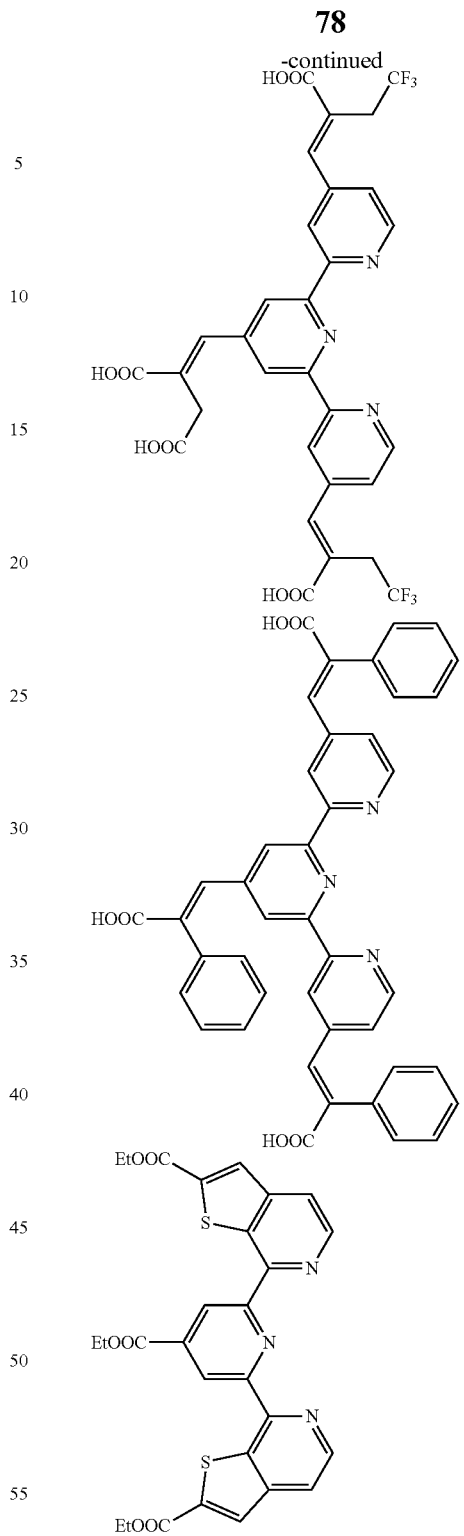

—Ligand LD—

In the present invention, the ligand LD is classified into a donor ligand and is preferably a ligand which does not have an adsorptive group that adsorbs onto the surface of semiconductor fine particles.

In this connection, even if a group corresponding to the adsorptive group is contained in the ligand, it is contained as a group that bonds to the metal ion M and does not adsorb onto the surface of semiconductor fine particles.

Further, the adsorptive group that adsorbs onto the surface of semiconductor fine particles is the substituents Anc1 to Anc3 in the ligand LA.

The ligand LD represents a bidentate ligand or a tridentate ligand different from LA. Herein, at least one of the coordinating atoms which bonds with the metal ion M in the bidentate ligand or tridentate ligand of the ligand LD is an anion. To be an anion means it bonds with M by the dissociation of a hydrogen atom.

The ligand LD is preferably a ligand represented by the following Formula (DL).

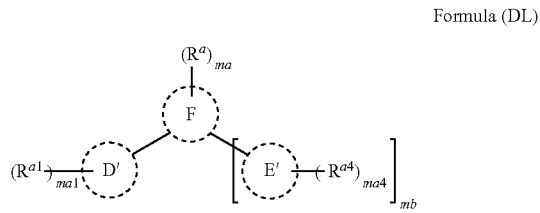

Formula (DL)

In the formula, the ring D', the ring E', and the ring F each independently represent a 5- or 6-membered aromatic ring, $R^a$, $R^{a1}$, and $R^{a4}$ each independently represent a substituent. mb represents 0 or 1. ma1 and ma4 each independently represent an integer of 0 to 3. ma represents an integer of 0 to 4 when mb is 0, and an integer of 0 to 3 when mb is 1.

Herein, a plurality of $R^a$s, a plurality of $R^{a1}$s, and a plurality of $R^{a4}$s may bond with each other to form a ring, when each of ma, ma1, and ma4 is an integer of 2 or more.

The 5- or 6-membered aromatic ring in the ring D', the ring E', and the ring F includes an aromatic carbon ring or an aromatic heterocyclic ring. In addition, the 5- or 6-membered aromatic ring may be fused with an aromatic ring, a heterocyclic ring, or an alicyclic ring.

Examples of the aromatic carbon ring include a benzene ring and a naphthalene ring, and examples of the aromatic heterocyclic ring include the aromatic heterocyclic rings mentioned in the ring A to the ring C in Formula (AL), and these are preferred.

The ring F is preferably a nitrogen-containing aromatic heterocyclic ring, preferably the nitrogen-containing aromatic heterocyclic rings mentioned in the ring B, more preferably a pyridine ring, a pyrimidine ring, and a triazine ring, and still more preferably a pyridine ring and a pyrimidine ring; and a pyridine ring is particularly preferred from the viewpoint of extension to a longer wavelength.

Herein, the ring D', the ring E', and the ring F are preferably those containing a coordinating atom which bonds with the metal ion M, and as the coordinating atom, a carbon atom, a nitrogen atom, a sulfur atom, an oxygen atom, or an anion of these atoms are preferred. It is preferred that at least one of the coordinating atoms bonds with the metal ion M through an ionic bond.

Examples of the group that bonds with the metal ion M through an ionic bond include a —$CO_2^-$ ion, an —$O^-$ ion, a =$C^-$— ion (for example, a carbon ion of an aromatic ring), a —$S^-$ ion, a >$N^-$ ion, a —$N^-SO_2$— ion (if shown as a monovalent group, —$N^-SO_2R^y$ in which $R^y$ represents a substituent).

Among these, a carbon anion and a nitrogen anion such as a =$C^-$— ion and a >$N^-$ ion are preferably mentioned as the atom constituting the ring.

Examples of the substituent in $R^a$, $R^{a1}$, and $R^{a4}$ include the substituent T described later. Examples of $R^a$ include the substituents mentioned in $R^{111}$ to $R^{154}$ described later, and the preferred range thereof is also the same. As $R^{a1}$ and $R^{a4}$, an alkyl group, an alkenyl group (preferably an ethenyl group), an alkynyl group (preferably an ethynyl group), an aryl group, a heterocyclic group (preferably an aromatic heterocyclic group), a halogen atom, an alkoxy group, an aryloxy group, an alkylthio group, arylthio group, an amino group, a cyano group, an alkylsulfonyl group, and an arylsulfonyl group are preferred; a halogenated alkyl group, a halogenated aryl group, a halogen atom, a cyano group, an alkylsulfonyl group, and an arylsulfonyl group are more preferred; a halogenated alkyl group, a halogen atom, and a cyano group are still more preferred; and a halogenated alkyl group is particularly preferred.

ma, ma1, and ma4 are preferably an integer of 0 to 2, and more preferably 1 or 2. mb is preferably 1.

The ligand LD is preferably a ligand represented by the following Formula (DL-1) or (DL-2).

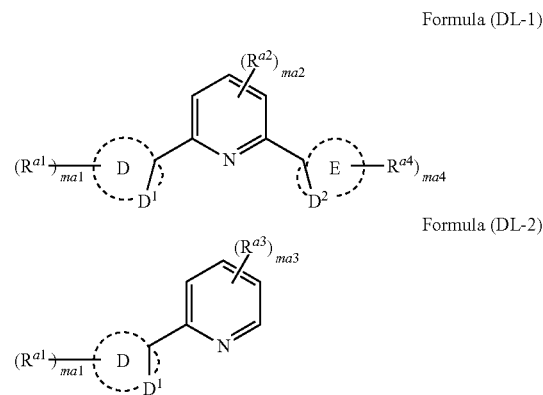

Formula (DL-1)

Formula (DL-2)

$R^{a2}$ and $R^{a3}$ each independently represent a substituent, ma2 represents an integer of 0 to 3, and ma3 represents an integer of 0 to 4. $R^{a1}$, $R^{a4}$, ma1, and ma4 have the same meanings as $R^{a1}$, $R^{a4}$, ma1, and ma4 in Formula (DL) above, and the preferred ranges thereof are also the same.

The substituents represented by $R^{a1}$ and $R^{a3}$ have the same meanings as $R^a$ in Formula (DL) above, and the preferred ranges thereof are also the same.

A plurality of $R^{a1}$s to a plurality of $R^{a4}$s may bond with each other to form a ring, when each of ma1 to ma4 is an integer of 2 or more.

The ring D and the ring E each independently represent a 5- or 6-membered aromatic ring. Examples of the aromatic ring may include the rings mentioned for the ring D' and ring E' in Formula (DL), and the preferred aromatic rings are the same as the rings mentioned for the ring D' and ring E'.

Further, in the ring D and the ring E, the bond between $D^1$ or $D^2$ and the carbon atom bonding to the pyridine ring may be a single bond or a double bond.

$D^1$ and $D^2$ each independently represent a carbon atom anion or a nitrogen atom anion.

The ring D and the ring E are preferably a pyrazole ring, a triazole ring, or a benzene ring.

In addition, in the case where the ligand LD is a bidentate ligand, it is preferably a bidentate ligand represented by any one of the following Formulas (2L-1) to (2L-5).

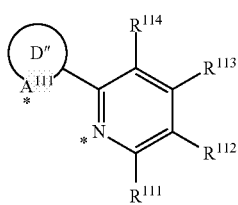

Formula (2L-1)

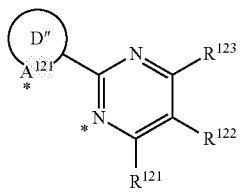

Formula (2L-2)

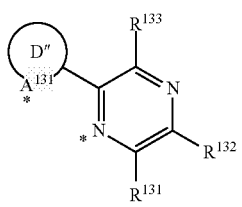

Formula (2L-3)

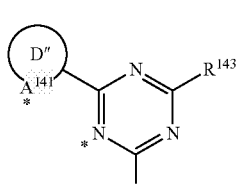

Formula (2L-4)

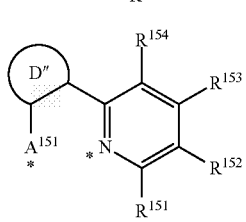

Formula (2L-5)

In the formulas (2L-1) to (2L-5), * represents a bonding position to the metal ion M. The ring D" represents an aromatic ring. $A^{111}$ to $A^{141}$ each independently represent a nitrogen atom anion or a carbon atom anion. $A^{151}$ represents any one of a nitrogen atom anion, an oxygen atoms anion, and a sulfur atom anion. $R^{111}$ to $R^{154}$ each independently represent a hydrogen atom or a substituent that does not have Anc1, Anc2, and Anc3.

Herein, $A^{111}$ to $A^{141}$ are a carbon atom anion or nitrogen atom anion, which is formed by detachment of the hydrogen atom bonded to the carbon atom or nitrogen atom constituting the ring D". $A^{151}$ is particularly preferably a residue formed by removal of active hydrogen from a (substituted) amino group, a hydroxyl group, or a thiol group, among the functional groups in an aromatic carbon ring and a nitrogen-containing aromatic heterocyclic ring. Examples of the ring D" in Formulas (2L-1) to (2L-5) include an aromatic carbon ring, an oxygen-containing aromatic heterocyclic ring, a sulfur-containing aromatic heterocyclic ring, and a nitrogen-containing aromatic heterocyclic ring. Examples of the aromatic carbon ring include a benzene ring and a naphthalene ring, and a benzene ring is preferred; as the oxygen-containing aromatic heterocyclic ring, a furan ring is preferred; and as the sulfur-containing aromatic heterocyclic ring, a thiophene ring is preferred. As the nitrogen-containing aromatic heterocyclic ring, the nitrogen-containing aromatic heterocyclic rings among the aromatic heterocyclic rings mentioned in the ring A to the ring D are preferred, and a pyrrole ring, a pyrazole ring, an imidazole ring, and a triazole ring are more preferred. Preferred examples of the ring D" before $A^{111}$ to $A^{141}$ form an anion in Formulas (2L-1) to (2L-4) and the ring D" to which $A^{151}$ is substituted in Formula (2L-5) include a benzene ring, a thiophene ring, a furan ring, or rings formed by substituting the anionic portion of the groups represented by the following Formulas (a-1) to (a-5), (a-1a), (a-2a), (a-1b), and (a-4a) with a hydrogen atom.

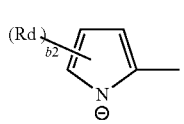

(a-1)

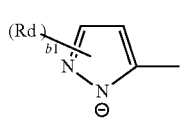

(a-2)

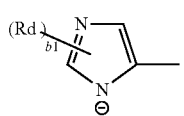

(a-3)

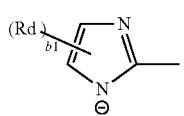

(a-4)

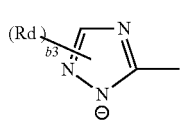

(a-5)

In the formulas, Rd represents a substituent. b1 represents an integer of 0 to 2, b2 represents an integer of from 0 to 3, and b3 represents 0 or 1, respectively. A plurality of Rds may bond with each other to form a ring, when b1 is 2 or when b2 is 2 or more. As Rd, the substituent T described later can be mentioned.

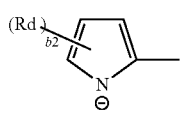

(a-1)

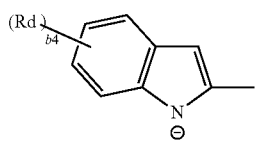

(a-1a)

-continued

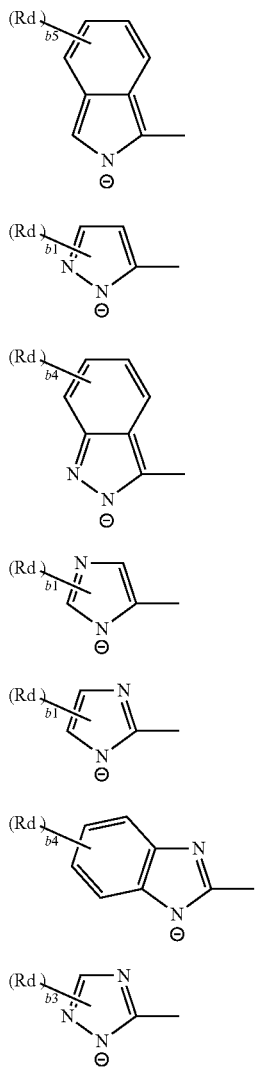

(a-1b)

(a-2)

(a-2a)

(a-3)

(a-4)

(a-4a)

(a-5)

In the formulas, Rd and b1 to b3 have the same meanings as Rd and b1 to b3 in Formulas (a-1) to (a-5) above, and the preferred ranges thereof are also the same. b4 represents an integer of 0 to 4, and b5 represents an integer of 0 to 5, respectively. It is noted that, in Formulas (a-1a) and (a-1b), not only a benzene ring but also a pyrrole ring may have Rd.

Rd is preferably a linear or branched alkyl group, a cycloalkyl group, an alkenyl group, a fluoroalkyl group, an aryl group, a halogen atom, an alkoxycarbonyl group, a cycloalkoxycarbonyl group, or a group formed by combining any of these; still more preferably a linear or branched alkyl group, a cycloalkyl group, an alkenyl group, a fluoroalkyl group, an aryl group, or a group formed by combining any of these; and particularly preferably a linear or branched alkyl group, a cycloalkyl group, an alkenyl group, a fluoroalkyl group, or a group formed by combining any of these.

Examples of the substituent represented by $R^{111}$ to $R^{154}$ may include the substituent T described later; among them, an aromatic heterocyclic group, an aromatic carbocyclic group, an ethenyl group, an ethynyl group, a halogen atom, an alkyl group, an amino group (including an alkylamino group, a dialkylamino group, an arylamino group, a diary- lamino group, an N-alkyl-N-arylamino group, and the like), an alkoxy group, an aryloxy group, an alkylthio group, an arylthio group, and a silyl group are preferred; an aromatic heterocyclic group, an aromatic carbocyclic group, an ethenyl group, an alkyl group, an amino group (including an alkylamino group, a dialkylamino group, an arylamino group, a diarylamino group, and the like) are more preferred; an aromatic heterocyclic group, an aromatic carbocyclic group having an alkyl group or an alkoxy group or an amino group (including an alkylamino group, a dialkylamino group, an arylamino group, a diarylamino group and the like), and an amino group (including an alkylamino group, a dialkylamino group, an arylamino group, a diarylamino group, and the like) are still more preferred; and an aromatic carbocyclic group having an amino group (including an alkylamino group, a dialkylamino group, an arylamino group, a diarylamino group, and the like), and an amino group (including an alkylamino group, a dialkylamino group, an arylamino group, a diarylamino group, and the like) are particularly preferred.

In the case where the ligand LD is a tridentate ligand, it is preferably a tridentate ligand represented by any one of the following Formulas (3L-1) to (3L-4).

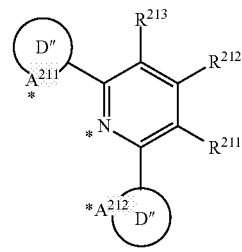

Formula (3L-1)

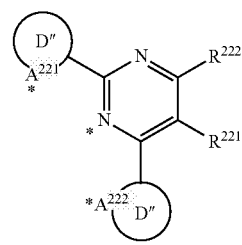

Formula (3L-2)

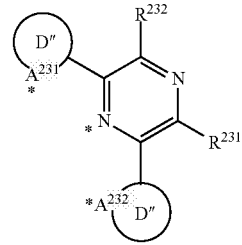

Formula (3L-3)

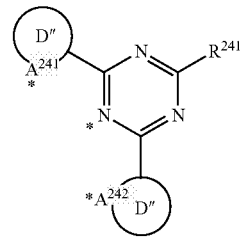

Formula (3L-4)

In formulas (3L-1) to (3L-4), * represents a bonding position to the metal ion M. The ring D" represents an aromatic ring. $A^{211}$ to $A^{242}$ each independently represent a nitrogen atom or a carbon atom. Provided that, at least one of $A^{211}$ and $A^{212}$, of $A^{221}$ and $A^{222}$, of $A^{231}$ and $A^{232}$, and of $A^{241}$ and $A^{242}$ is an anion, respectively. $R^{211}$ to $R^{241}$ each independently represent a hydrogen atom or a substituent that does not have Anc1, Anc2, and Anc3.

Among $A^{211}$ to $A^{242}$, those which are an anion have the same meanings as A" to $A^{141}$ in Formulas (2L-1) to (2L-5) above. Among $A^{211}$ to $A^{242}$, those which do not have an anion are a carbon atom or nitrogen atom which does not have a hydrogen atom. The ring D" in Formulas (3L-1) to (3L-4) have the same meanings as the ring D" in Formulas (2L-1) to (2L-5) above, and specific examples of the ring D" may include an aromatic carbocyclic group and a nitrogen-containing aromatic heterocyclic ring. Examples of the aromatic carbon ring may include a benzene ring and a naphthalene ring; and as the nitrogen-containing aromatic heterocyclic ring, preferred are the nitrogen-containing aromatic heterocyclic rings among the aromatic heterocyclic rings mentioned in the ring A to the ring D. The ring D is more preferably an aromatic ring containing any one of $A^{111}$ to $A^{141}$ and a carbon atom or two carbon atoms. At this time, two ring D"s in each of the formula may be the same as or different from each other. The substituents $R^{211}$ to $R^{241}$ have the same meanings as the substituents $R^{111}$ to $R^{154}$ in Formulas (2L-1) to (2L-5), and the preferred examples thereof are also the same.

Further, in the present invention, among the bidentate or tridentate ligands of LD above, those having a nitrogen anion or a carbon anion as an atom coordinating to the metal ion M, and an arylamino group or a diarylamino group as a substituent are preferred especially, since the absorption extends to a longer wavelength.

Specifically, the above preferred ligand is a ligand having a nitrogen anion or a carbon anion as the atom coordinating to the metal ion M, and the following Formula (SA) in its partial structure.

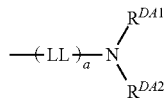

Formula (SA)

In the formula, $R^{DA1}$ represents an aryl group, and $R^{DA2}$ represents an alkyl group or an aryl group. $R^{DA1}$ and $R^{DA2}$ may bond with each other to form a ring. LL represents an ethenyl group, an ethynyl group, an arylene group, or a heteroarylene group. a represents an integer of 0 to 5.

The group represented by Formula (SA) above is preferably those which attached to an aromatic hydrocarbon ring or nitrogen-containing aromatic heterocyclic ring which coordinates to the metal ion M, and more preferably those which attached to a nitrogen-containing aromatic heterocyclic ring.

Among the groups represented by Formula (SA) above, those of which $R^{DA1}$ and $R^{DA2}$ are both an aryl group are preferred. The aryl group may have a substituent, and examples of the substituent may include the substituent T described later.

Examples of the aryl group may include a phenyl group, a naphthyl group, and the like, and a phenyl group is preferred.

LL is preferably those in which an aromatic hydrocarbon ring or nitrogen-containing aromatic heterocyclic ring which contains a coordinating atom of the ligand bonds with the nitrogen atom of —N($R^{DA1}$)($R^{DA2}$) through a single bond or a π-conjugation.

As the arylene group in LL, a phenylene group and a naphthylene group can be mentioned; and the heteroarylene group is preferably a divalent 5- or 6-membered ring which contains an oxygen atom, a sulfur atom, or a nitrogen atom, as an atom constituting the ring, and may be fused with a benzene ring or a heterocyclic ring.

Examples of the hetero ring of the heteroarylene group include a furan ring, a thiophene ring, a pyrrole ring, and a pyridine ring, and a furan ring and a thiophene ring are preferred.

The ethenyl group, the arylene group, and the heteroarylene group in LL may have a substituent, and examples of the substituent may include the substituent T described later.

In Formula (SA) above, it is preferred that a is 0, or a is 1 and LL is an ethenyl group, an ethynyl group, a phenylene group, or a heteroarylene group; it is more preferred that a is 0, or a is 1 and LL is a phenylene group or a heteroarylene group; it is still more preferred that a is 0, or a is 1 and LL is a phenylene group, a divalent furan ring group, or a divalent thiophene ring group; and it is particularly preferred that a is 0, or a is 1 and LL is a phenylene group.

In the present invention, it is also preferred that $R^{DA1}$ and $R^{DA2}$ bond to each other to form a ring.

As the ring to be formed, preferred is a 5- or 6-membered ring, and more preferred is a ring formed through bonding of $R^{DA1}$ and $R^{DA2}$ when $R^{DA1}$ and $R^{DA2}$ are both an aryl group.

As the ring formed through mutual bonding between $R^{DA1}$ and $R^{DA2}$, the following rings are preferred.

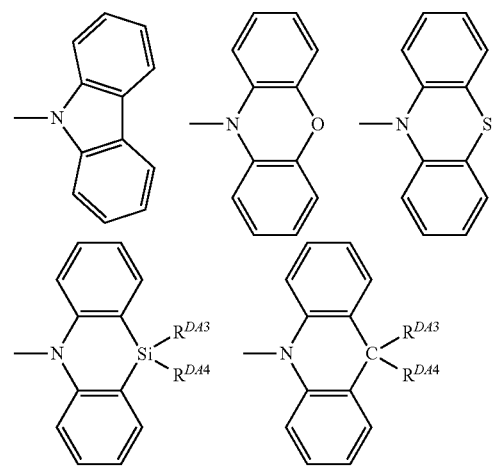

Herein, $R^{DA3}$ and $R^{DA4}$ each independently represent an alkyl group.

Further, the ring may have a substituent, and examples of the substituent may include the substituent T.

Specific examples of the ligand represented by Formula (DL) according to the present invention are presented below, but the present invention is not limited thereto.

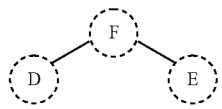

| LD No. | Ring D | Ring F | Ring E |
|---|---|---|---|
| LD-3-1 | pyridine | 2,5-dimethylpyrrole anion | pyridine |
| LD-3-2 | pyridine | 3,5-dimethyl-1,2,4-triazole anion | pyridine |
| LD-3-3 | pyridine | 2,5-dimethylimidazole anion | pyridine |
| LD-3-4 | pyridine | 3,5-dimethylphenyl anion | pyridine |
| LD-3-5 | pyridine | 3-fluoro-5-methylphenyl anion (with additional methyl) | pyridine |
| LD-3-6 | pyridine | 2,5-dimethylpyrrole anion | 3-(trifluoromethyl)-5-methylpyrazole anion |
| LD-3-7 | pyridine | 2,5-dimethylimidazole anion | 3-(trifluoromethyl)-5-methylpyrazole anion |
| LD-3-8 | pyridine | 3,5-dimethyl-1,2,4-triazole anion | 3-(trifluoromethyl)-5-methylpyrazole anion |
| LD-3-9 | pyridine | 2,5-dimethylimidazole anion | 3-(trifluoromethyl)-5-methyl-1,2,4-triazole anion |
| LD-3-10 | pyridine | 3-fluoro-5-methylphenyl anion | 3-(trifluoromethyl)-5-methylpyrazole anion |
| LD-3-11 | 3-(trifluoromethyl)-5-methylpyrazole anion | 2,5-dimethylpyrrole anion | 3-(trifluoromethyl)-5-methylpyrazole anion |

-continued
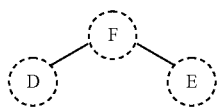
| LD No. | Ring D | Ring F | Ring E |
|---|---|---|---|
| LD-3-12 | | | |
| LD-3-13 | | | |
| LD-3-14 | | | |
| LD-3-15 | | | |
| LD-3-16 | | | |
| LD-3-17 | | | |
| LD-3-18 | | | |
| LD-3-19 | | | |
| LD-3-20 | | | |

-continued
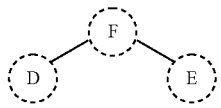
| LD No. | Ring D | Ring F | Ring E |
|---|---|---|---|
| LD-3-21 | 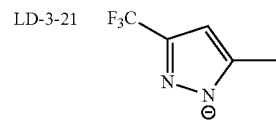 | 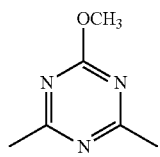 | 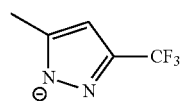 |
| LD-3-22 | 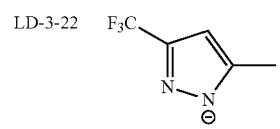 | 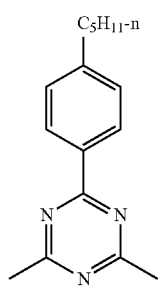 | 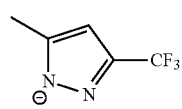 |
| LD-3-23 | 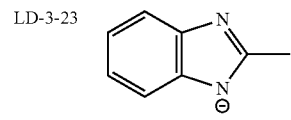 | 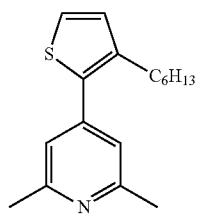 | 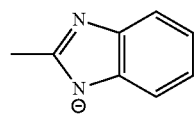 |
| LD-3-24 | 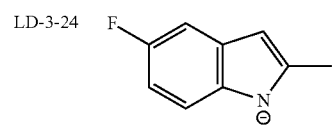 | 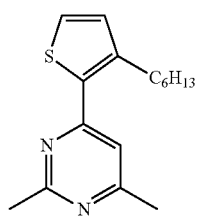 | 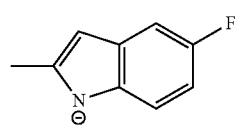 |
| LD-3-25 | 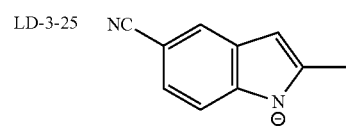 | 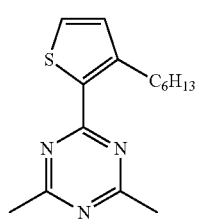 | 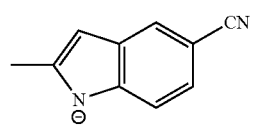 |

| LD No. | R203 | R201 | R202 |
|---|---|---|---|
| LD-2-1 | 3-methyl-5-(trifluoromethyl)pyrazol-1-ide | H | 3-methyl-5-(trifluoromethyl)pyrazol-1-ide |
| LD-2-2 | 3-methyl-5-(trifluoromethyl)pyrazol-1-ide | 5-(2-ethylhexyl)-2-(prop-1-en-1-yl)thiophene (thiophene with propenyl and CH$_2$CH(C$_2$H$_5$)C$_4$H$_9$) | 3-methyl-5-(trifluoromethyl)pyrazol-1-ide |
| LD-2-3 | 3-methyl-5-(trifluoromethyl)pyrazol-1-ide | 2-methyl-5-hexylthiophene (thiophene-C$_6$H$_{13}$) | 3-methyl-5-(trifluoromethyl)pyrazol-1-ide |
| LD-2-4 | 3-methyl-5-(trifluoromethyl)pyrazol-1-ide | 5-(hept-1-yn-1-yl)-2-(prop-1-en-1-yl)thiophene (thiophene with propenyl and C≡C-C$_5$H$_{11}$) | 3-methyl-5-(trifluoromethyl)pyrazol-1-ide |
| LD-2-5 | 3-methyl-5-(trifluoromethyl)pyrazol-1-ide | 4-(octyloxy)phenyl (–C$_6$H$_4$–OC$_8$H$_{17}$) | 3-methyl-5-(trifluoromethyl)pyrazol-1-ide |
| LD-2-6 | 3-methyl-5-(trifluoromethyl)pyrazol-1-ide | 3-hexyl-2-methylthiophene (thiophene with C$_6$H$_{13}$) | 3-methyl-5-(trifluoromethyl)pyrazol-1-ide |
| LD-2-7 | 3-methyl-5-(trifluoromethyl)pyrazol-1-ide | 2,6-bis(octyloxy)phenyl (C$_8$H$_{17}$O / C$_8$H$_{17}$O substituted phenyl) | 3-methyl-5-(trifluoromethyl)pyrazol-1-ide |
| LD-2-8 | 3-methyl-5-(trifluoromethyl)-1,2,4-triazol-1-ide | 3-hexyl-2-methylthiophene | 3-methyl-5-(trifluoromethyl)-1,2,4-triazol-1-ide |
| LD-2-9 | 3-methyl-5-(trifluoromethyl)pyrazol-1-ide | 3-hexyl-2-methylthiophene | 2,4-difluoro-5-methylphenyl anion |
| LD-2-10 | 2-methylpyrrol-1-ide | 3-hexyl-2-methylthiophene | 2-methylpyrrol-1-ide |

Parent structure: pyridine substituted with R$^{201}$ at the 4-position, R$^{202}$ at the 2-position, and R$^{203}$ at the 6-position.

-continued
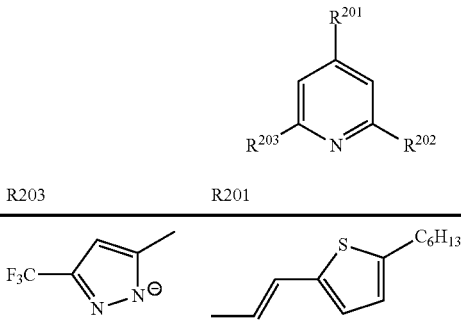
| LD No. | R203 | R201 | R202 |
|---|---|---|---|
| LD-2-11 | 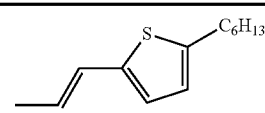 | 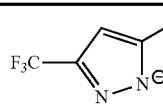 | 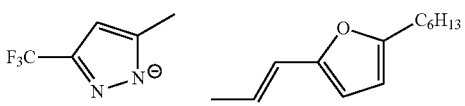 |
| LD-2-12 | 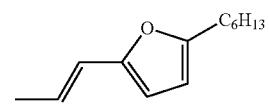 | 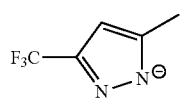 | 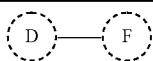 |
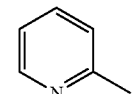
| LD No. | Ring D | Ring F |
|---|---|---|
| LD-6-1 | 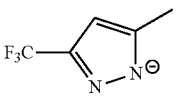 | 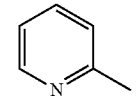 |
| LD-6-2 | 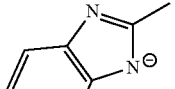 |  |
| LD-6-3 | 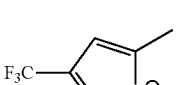 |  |
| LD-6-4 | 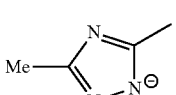 | 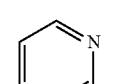 |
| LD-6-5 | 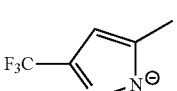 | 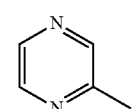 |
| LD-6-6 | 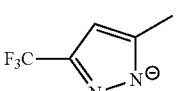 | 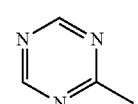 |
| LD-6-7 | 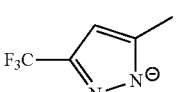 | 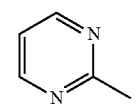 |
| LD-6-8 | 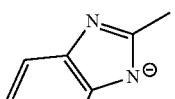 | |

-continued

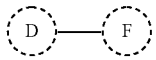

| LD No. | Ring D | Ring F |
|---|---|---|
| LD-6-9 | 2-methylpyrimidine | 2-methyl-4-(trifluoromethyl)pyrrol-1-ide |
| LD-6-10 | 5-hexyl-2-(2-methylpyridin-4-yl)thiophene | 5-methyl-3-(trifluoromethyl)pyrazol-1-ide |
| LD-6-11 | 5-(2-ethylhexyl)-2-[(E)-2-(2-methylpyridin-4-yl)vinyl]thiophene | 5-methyl-3-(trifluoromethyl)pyrazol-1-ide |
| LD-6-12 | 5-(hept-1-yn-1-yl)-2-[(E)-2-(2-methylpyridin-4-yl)vinyl]thiophene | 5-methyl-3-(trifluoromethyl)pyrazol-1-ide |
| LD-6-13 | 4-(octyloxy)-2'-methyl-4'-phenylpyridine | 5-methyl-3-(trifluoromethyl)pyrazol-1-ide |
| LD-6-14 | 5-butyl-2-[(E)-2-(2-methylpyridin-4-yl)vinyl]thiophene | 5-methyl-3-(trifluoromethyl)pyrazol-1-ide |

-continued
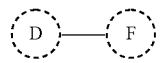
| LD No. | Ring D | Ring F |
|---|---|---|
| LD-6-15 | 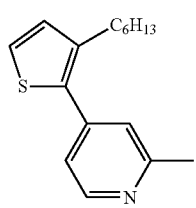 | 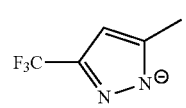 |
| LD-6-16 | 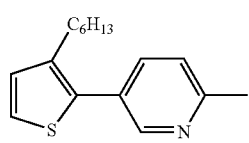 | 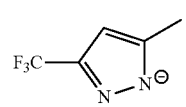 |
| LD-6-17 | 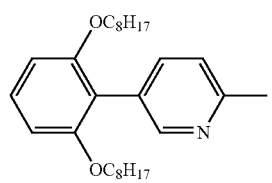 | 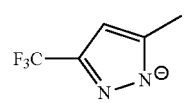 |
| LD-6-18 | 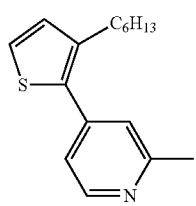 | 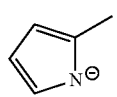 |
| LD-6-19 | 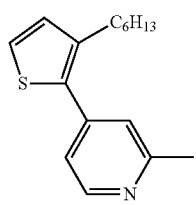 | 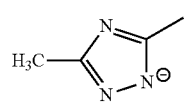 |
| LD-6-20 | 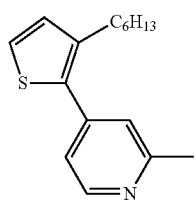 | 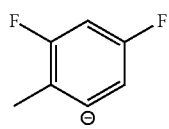 |
| LD-6-21 | 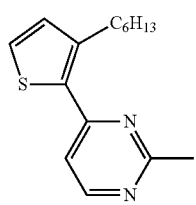 | 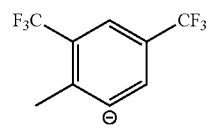 |

-continued
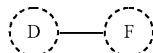
| LD No. | Ring D | Ring F |
|---|---|---|
| LD-6-22 | | |
| LD-6-23 | | |
| LD-6-24 | | |
| LD-6-25 | | |
| LD-6-26 | | |
| LD-6-27 | | |

-continued
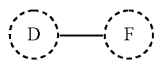
| LD No. | Ring D | Ring F |
|---|---|---|
| LD-6-28 | 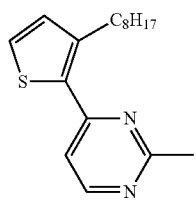 | 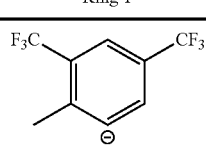 |
| LD-6-29 | 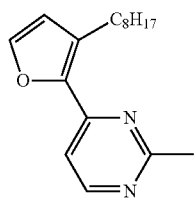 | 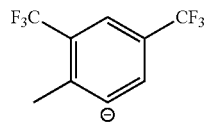 |
| LD-6-30 | 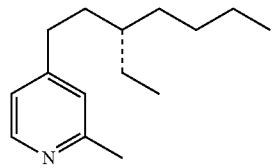 | 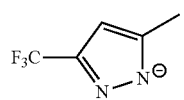 |
| LD-6-31 | 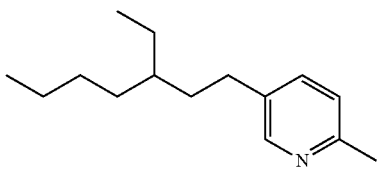 | 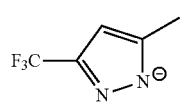 |
| LD-6-32 | 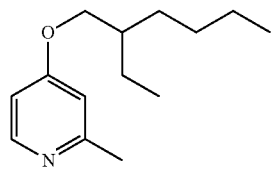 | 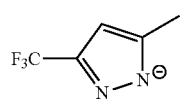 |
| LD-6-33 | 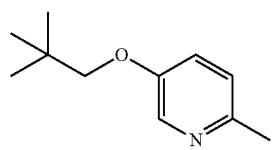 | 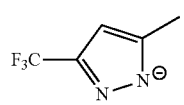 |
| LD-6-34 | 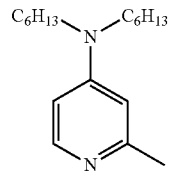 | 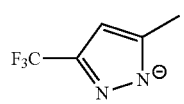 |
| LD-6-35 | 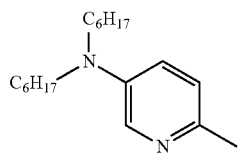 | 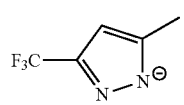 |

-continued

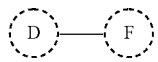

| LD No. | Ring D | Ring F |
|---|---|---|
| LD-6-36 | 4-C₄H₉-C₆H₄, 4-C₄H₉-C₆H₄, 2-methylpyridin-4-yl diarylamine | 3-CF₃-5-methylpyrazol-1-ide |
| LD-6-37 | 4-C₅H₁₁-C₆H₄, 4-C₅H₁₁-C₆H₄, 2-methylpyridin-4-yl diarylamine | 3-CF₃-5-methylpyrazol-1-ide |
| LD-6-38 | 4-tBu-C₆H₄, 4-tBu-C₆H₄, 2-methylpyridin-4-yl diarylamine | 3-CF₃-5-methylpyrazol-1-ide |
| LD-6-39 | 3,5-(CH₃)₂-C₆H₃, 3,5-(CH₃)₂-C₆H₃, 2-methylpyridin-4-yl diarylamine | 3-CF₃-5-methylpyrazol-1-ide |
| LD-6-40 | 4-OC₆H₁₃-C₆H₄, 4-OC₆H₁₃-C₆H₄, 2-methylpyridin-4-yl diarylamine | 3-CF₃-5-methylpyrazol-1-ide |

-continued

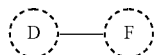

| LD No. | Ring D | Ring F |
|---|---|---|
| LD-6-41 | 4-C4H9-C6H4, 4-C4H9-C6H4, 6-methylpyridin-3-yl substituted amine | 3-(trifluoromethyl)-5-methylpyrazol-1-ide |
| LD-6-42 | 4-C5H11-C6H4, 4-C5H11-C6H4, 6-methylpyridin-3-yl substituted amine | 3-(trifluoromethyl)-5-methylpyrazol-1-ide |
| LD-6-43 | 4-tBu-C6H4, 4-tBu-C6H4, 6-methylpyridin-3-yl substituted amine | 3-(trifluoromethyl)-5-methylpyrazol-1-ide |
| LD-6-44 | 4-OC6H13-C6H4, 4-OC6H13-C6H4, 6-methylpyridin-3-yl substituted amine | 3-(trifluoromethyl)-5-methylpyrazol-1-ide |

-continued
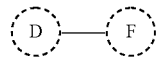
| LD No. | Ring D | Ring F |
|---|---|---|
| LD-6-45 | 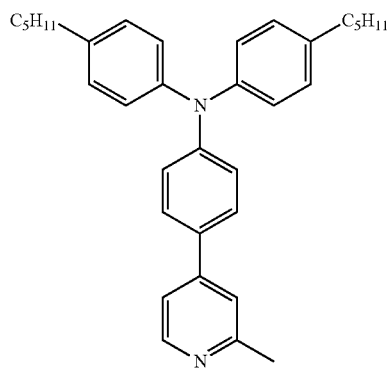 | 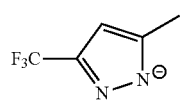 |
| LD-6-46 | 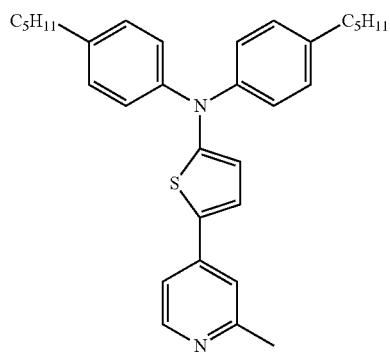 | 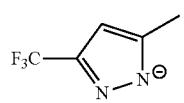 |
| LD-6-47 | 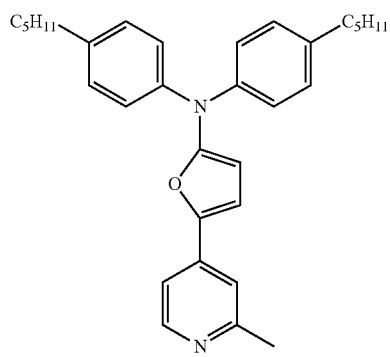 | 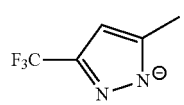 |
| LD-6-48 | 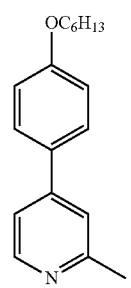 | 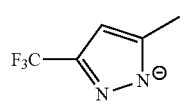 |

-continued
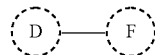
| LD No. | Ring D | Ring F |
|---|---|---|
| LD-6-49 | | |
| LD-6-50 | | |
| LD-6-51 | | |
| LD-6-52 | | |

-continued
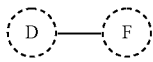
| LD No. | Ring D | Ring F |
|---|---|---|
| LD-6-53 | 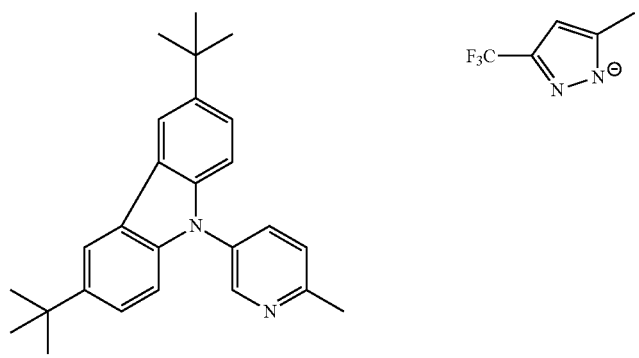 | |
| LD-6-54 | 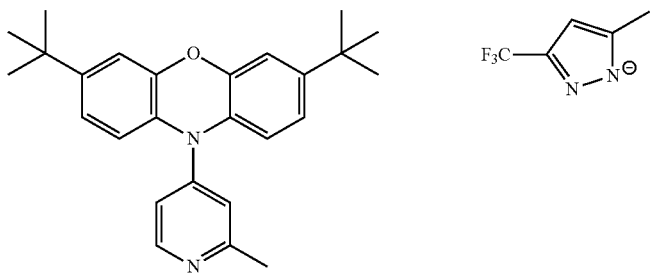 | |
| LD-6-55 | 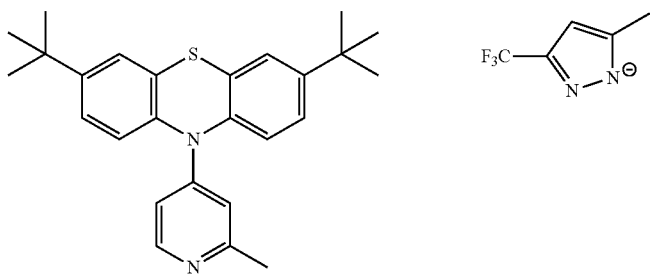 | |
| LD-6-56 | 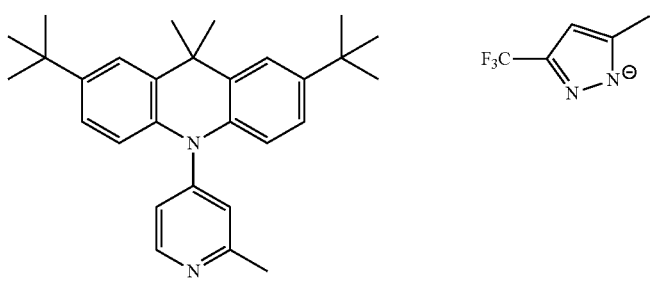 | |
| LD-6-57 | 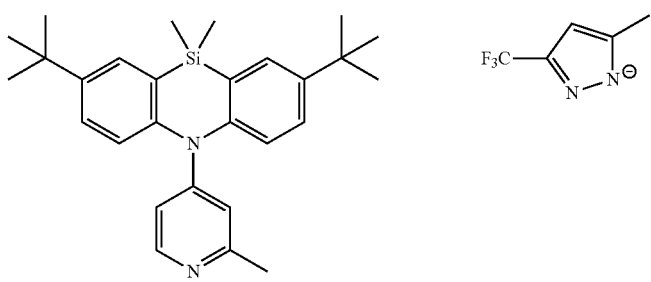 | |

-continued
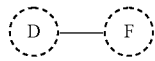
| LD No. | Ring D | Ring F |
|---|---|---|
| LD-6-58 | | |
| LD-6-59 | | |
| LD-6-60 | | |
| LD-6-61 | | |

-continued

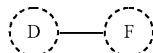

| LD No. | Ring D | Ring F |
|---|---|---|
| LD-6-62 | C5H11-phenyl, C5H11-phenyl, N linked to 2-methylpyridin-4-yl | 3,5-dimethyl-1,2,4-triazol-1-ide |
| LD-6-63 | C5H11-phenyl, C5H11-phenyl, N linked to 2-methylpyridin-4-yl | 2-methylbenzimidazol-1-ide |
| LD-6-64 | C5H11-phenyl, C5H11-phenyl, N linked to 2-methylpyridin-4-yl | 2,4-difluoro-6-methylphenyl anion |
| LD-6-65 | C5H11-phenyl, C5H11-phenyl, N linked to 2-methylpyridin-4-yl | 2,4-bis(trifluoromethyl)-6-methylphenyl anion |
| LD-6-66 | 3,5-dimethylphenyl, 3,5-dimethylphenyl, N linked to 2-methylpyridin-4-yl | 2,4-bis(trifluoromethyl)-6-methylphenyl anion |
| LD-6-67 | 4-hexyloxyphenyl, 4-hexyloxyphenyl, N linked to 2-methylpyridin-4-yl | 2,4-bis(trifluoromethyl)-6-methylphenyl anion |

-continued
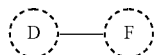
| LD No. | Ring D | Ring F |
|---|---|---|
| LD-6-68 | | |
| LD-6-69 | | |
| LD-6-70 | | |
| LD-6-71 | | |

-continued
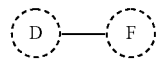
| LD No. | Ring D | Ring F |
|---|---|---|
| LD-6-72 | 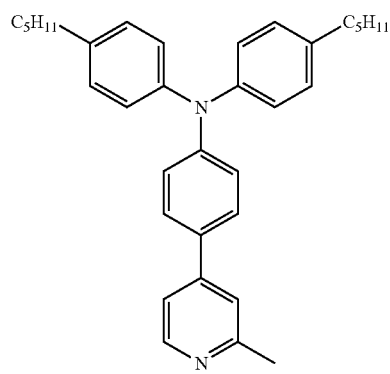 | 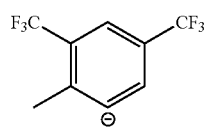 |
| LD-6-73 | 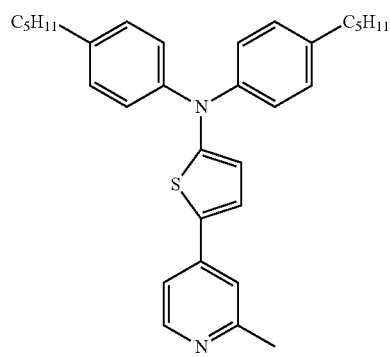 | 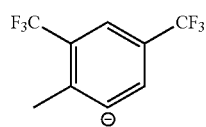 |
| LD-6-74 | 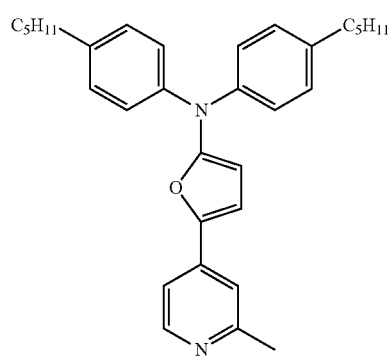 | 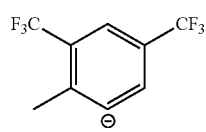 |
| LD-6-75 | 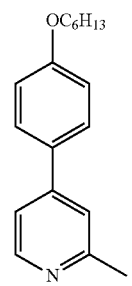 | 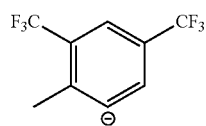 |

-continued
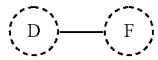
| LD No. | Ring D | Ring F |
|---|---|---|
| LD-6-76 | | |
| LD-6-77 | | |
| LD-6-78 | | |
| LD-6-79 | | |

-continued
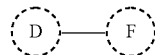
| LD No. | Ring D | Ring F |
|---|---|---|
| LD-6-80 | | |
| LD-6-81 | | |
| LD-6-82 | | |
| LD-6-83 | | |
| LD-6-84 | | |

-continued
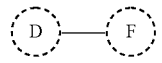
| LD No. | Ring D | Ring F |
|---|---|---|
| LD-6-85 | | |
| LD-6-86 | | |
| LD-6-87 | | |
| LD-6-88 | | |

-continued
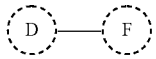
| LD No. | Ring D | Ring F |
|---|---|---|
| LD-6-89 | 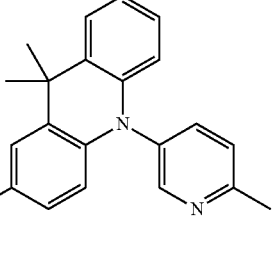 |  |
| LD-6-90 | 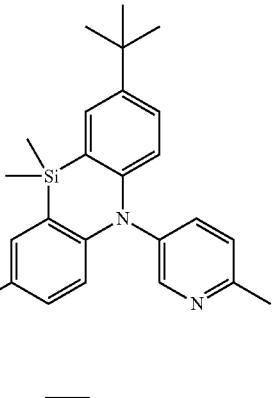 | 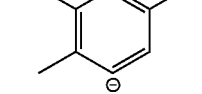 |
| LD-6-91 | 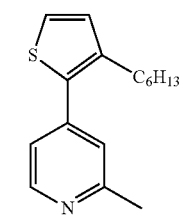 | 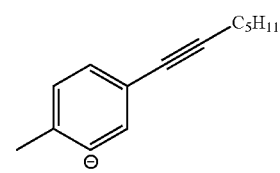 |
| LD-6-92 | 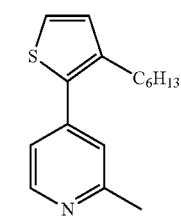 | 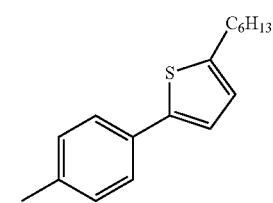 |
| LD-6-93 | 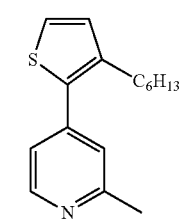 | 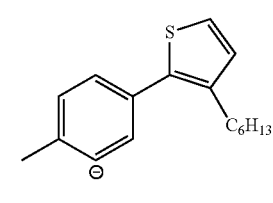 |

-continued
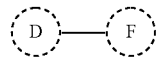
| LD No. | Ring D | Ring F |
|---|---|---|
| LD-6-94 | | |
| LD-6-95 | | |
| LD-6-96 | | |
| LD-6-97 | | |
| LD-6-98 | | |
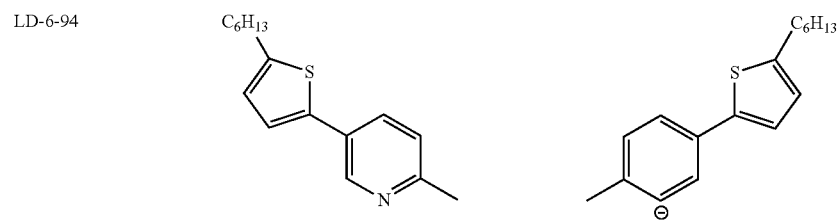
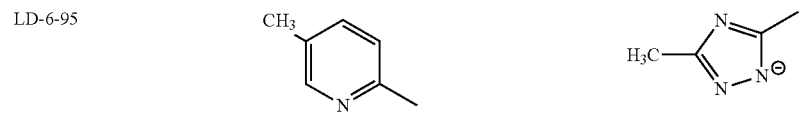
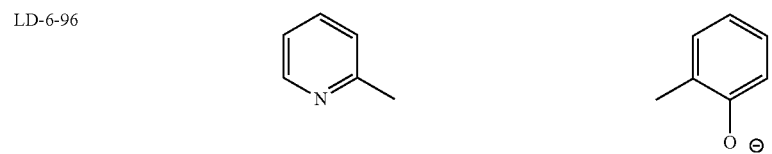
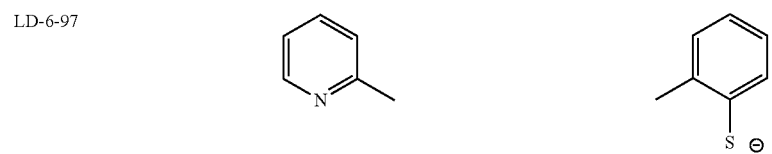
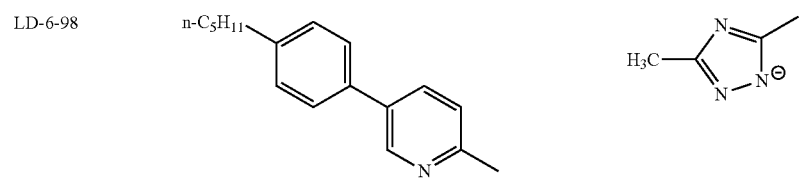

These ligands can be readily synthesized by methods described in US 2010/0258175 A1, Japanese Patent No. 4298799, and Angew. Chem. Int. Ed., 2011, 50, 2054-2058, methods described in references cited in the literatures, or methods according to these methods.

—Ligand LX—

The Ligand LX represents a monodentate ligand, and examples thereof includes: a monodentate ligand which coordinates by an anion selected from the group consisting of acyloxy anion, acylthio anion, thioacyloxy anion, thioacylthio anion, acylaminooxy anion, thiocarbamate anion, dithiocarbamate anion, thiocarbonate anion, dithiocarbonate anion, trithiocarbonate anion, acyl anion, thiocyanate anion, isothiocyanate anion, cyanate anion, isocyanate anion, cyano anion, alkylthio anion, arylthio anion, alkoxy anion, and aryloxy anion; or a monodentate ligand which coordinates by a group derived from these anions; or a monodentate ligand selected from the group of anions, atoms or compounds (including compounds in which a hydrogen atom is substituted to the anion) consisting of a halogen atom, cyano, carbonyl, dialkylketone, carbonamide, thiocarbonamide, and thiourea. In the case where the ligand X contains an alkyl group, an alkenyl group, an alkynyl group, an alkylene group or the like, these may be a straight chain or a branched chain, and these may be substituted or unsubstituted. Further, in the case where the ligand LX contains an aryl group, a heterocyclic group, a cycloalkyl group or the like, these may be substituted or unsubstituted, and may be a single ring or a fused ring.

In the present invention, LX is preferably cyanate anion, isocyanate anion, thiocyanate anion, isothiocyanate anion, selenocyanate anion, and isoselenocyanate anion, more preferably isocyanate anion, isothiocyanate anion, and isoselenocyanate anion, and particularly preferably isothiocyanate anion.

—Counter Ion CI for Neutralizing Charge—

CI represents a counter ion in the case where the counter ion is necessary to neutralize a charge. Generally, whether the dye is cationic or anionic, or has a net ionic charge, depends on the metal, the ligand and the substituent, in the metal complex dye.

In the case where the substituent has a dissociative group or the like, the metal complex dye may have a negative charge arising from dissociation. In this case, an electric charge of the metal complex dye as a whole is electrically neutralized by CI.

When the counter ion CI is a positive counter ion, examples of the counter ion CI include an inorganic or organic ammonium ion (for example, tetraalkyl ammonium ion, pyridinium ion, and the like), a phosphonium ion (for example, a tetralkylphosphonium ion, an alkyltriphenylphosphonium ion, and the like), an alkali metal ion, a metal complex ion, and a proton. As the positive counter ion, an inorganic or organic ammonium ion (triethylammonium, tetrabutylammonium ion, and the like) and proton are preferred.

When the counter ion CI is a negative counter ion, the counter ion CI may be an inorganic negative ion or an organic negative ion. Examples thereof include a hydroxide ion, a halogen negative ion (for example, fluoride ion, chloride ion, bromide ion, iodide ion), a substituted or unsubstituted alkylcarboxylate ion (for example, acetate ion, trifluoroacetate ion), a substituted or unsubstituted arylcarboxylate ion (for example, benzoate ion), a substituted or unsubstituted alkylsulfonate ion (for example, methanesulfonate ion, trifluoromethanesulfonate ion), a substituted or unsubstituted arylsulfonate ion (for example, p-toluene sulfonate ion, p-chlorobenzene sulfonate ion), an aryldisulfonate ion (for example, 1,3-benzene disulfonate ion, 1,5-naphthalene disulfonate ion, 2,6-naphthalene disulfonate ion), an alkylsulfate ion (for example, methylsulfate ion), a sulfate ion, a thiocyanate ion, a perchlorate ion, a tetrafluoroborate ion, a hexafluorophosphae ion, and a picrate ion. Alternatively, as a charge balance counter ion, an ionic polymer or another dye with an opposite charge from the dye in interest may be used. Alternatively, a metal complex ion (for example, bisbenzene-1,2-dithiolatonickel (III) and the like) may be used. As the negative counter ion, a halogen anion, a substituted or unsubstituted alkylcarboxylate ion, a substituted or unsubstituted alkylsulfonate ion, a substituted or unsubstituted arylsulfonate ion, an aryldisulfonate ion, a perchlorate ion, and a hexafluorophosphate ion are preferred; and a halogen anion and a hexafluorophosphate ion are more preferred.

—mX and mY— mX in Formula (I) represents 1 when the ligand LD is a bidentate ligand, and mX represents 0 when the ligand LD is a tridentate ligand.

mY represents an integer of 0 to 3, and is preferably 0 or 1, and more preferably 0.

—Metal Complex Dye of the Present Invention—

The metal complex dye represented by Formula (I) above of the present invention is preferably a metal complex dye represented by the following Formula (I-1) or (I-2).

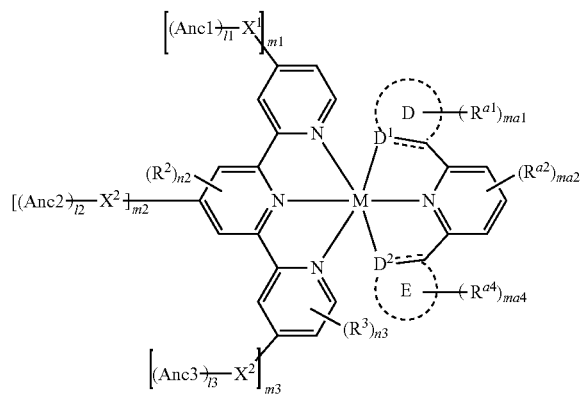

Formula (I-1)

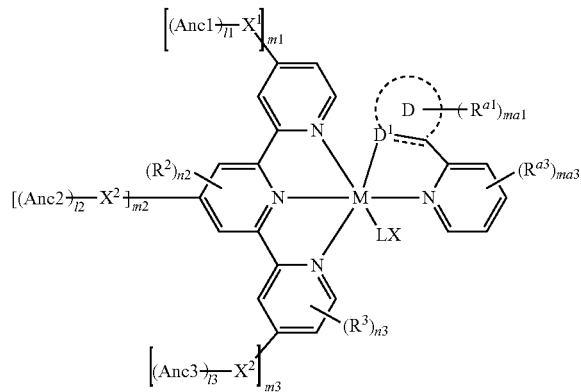

Formula (I-2)

In the formulas, M and LX have the same meanings as M and LX in Formula (I) above, and Anc1 to Anc3, $X^1$ to $X^3$, l1 to l3, m1 to m3, $R^1$ to $R^3$, and n1 to n3 have the same meanings as Anc1 to Anc3, $X^1$ to $X^3$, l1 to l3, m1 to m3, $R^1$ to $R^3$, and n1 to n3 in Formula (AL) above.

The ring D, the ring E, $D^1$, $D^2$, $R^{a1}$ to $R^{a4}$, and ma1 to ma4 have the same meanings as the ring D, the ring E, $D^1$, $D^2$, $R^{a1}$ to $R^{a4}$, and ma1 to ma4 in Formulas (DL-1) and (DL-2) above, and the preferred ranges thereof are also the same.

The ring formed by the ring D or the ring E is preferably a pyrazole ring, a triazole ring, or a benzene ring.

In the present invention, the ligands represented by Formula (I-1) are preferred among the ligands represented by Formulas (I-1) and (I-2).

Specific examples of the metal complex dye represented by Formula (I) of the present invention are presented below, but the present invention is not limited thereto. In the case where these metal complex dyes have optical isomers and geometric isomers, the metal complex dye may be any of these isomers or a mixture of these isomers.

Herein, in the following specific examples, Me represents methyl, and TMS represents trimethylsilyl.

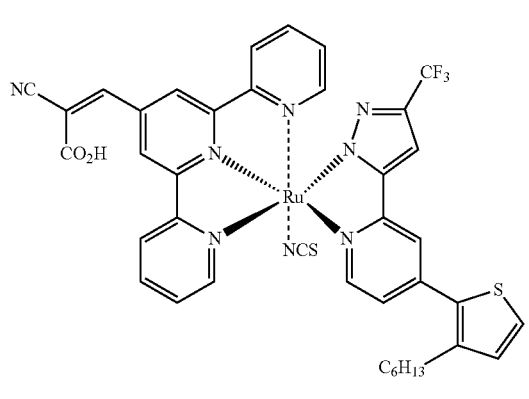

D-1

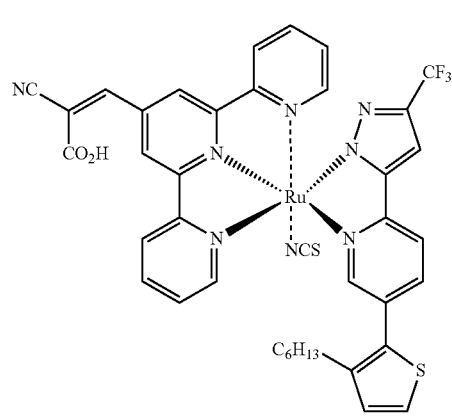

D-2

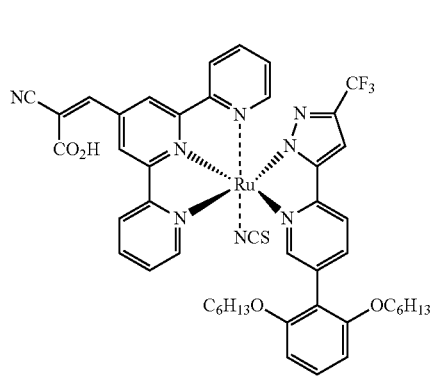

D-3

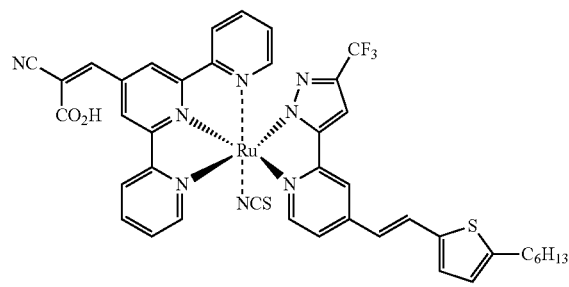

D-4

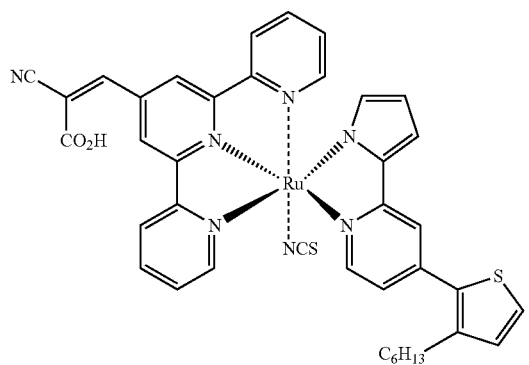

D-5

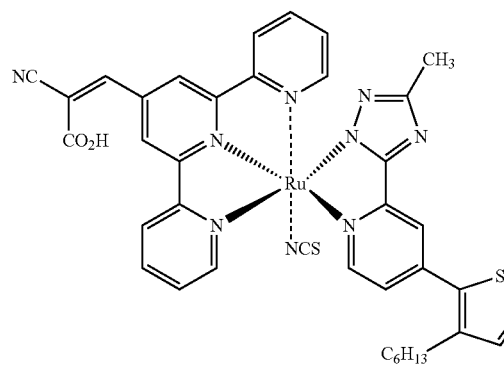

D-6

-continued
D-7
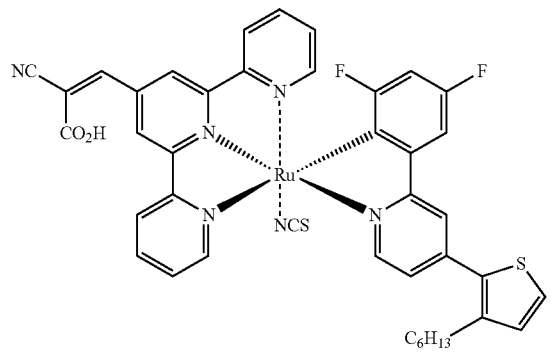
D-8
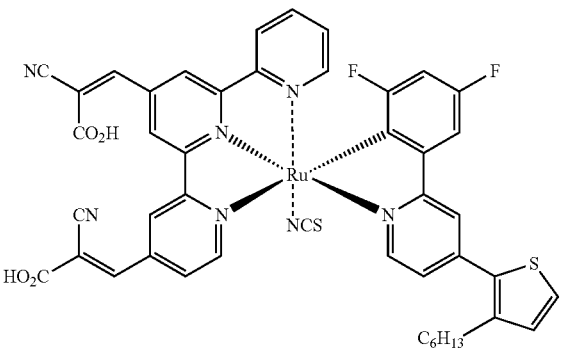
D-9
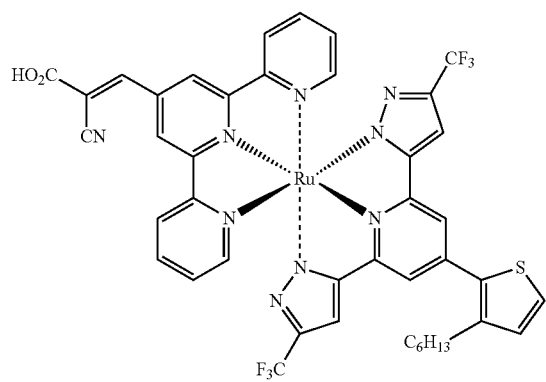
D-10
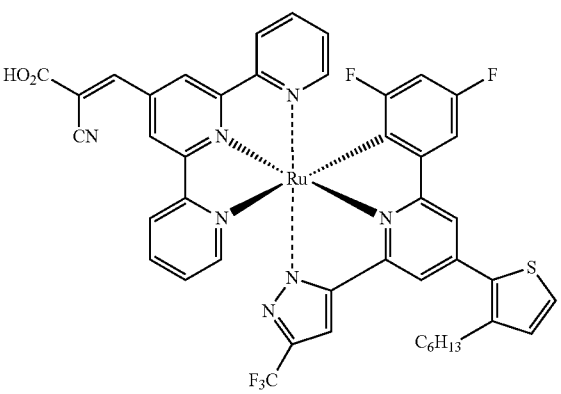
D-11
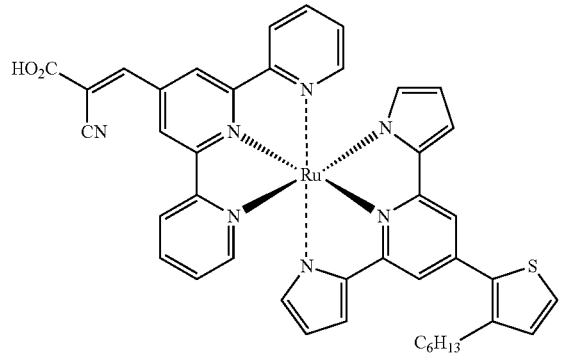
D-12
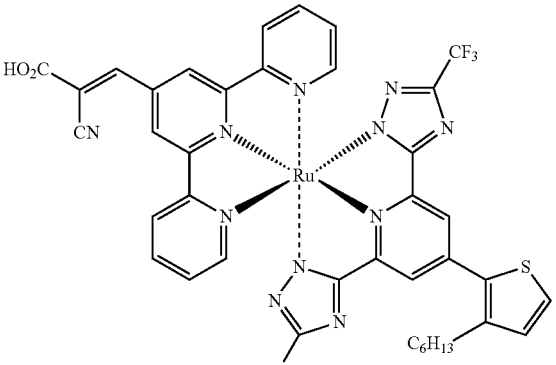
D-13
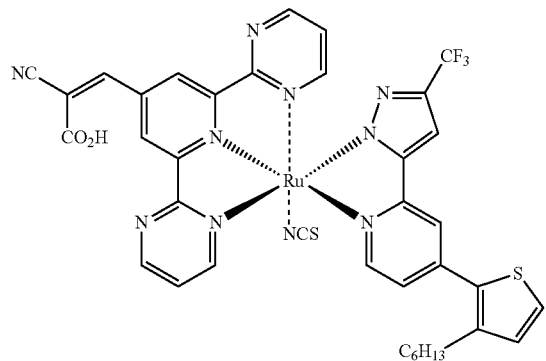
D-14
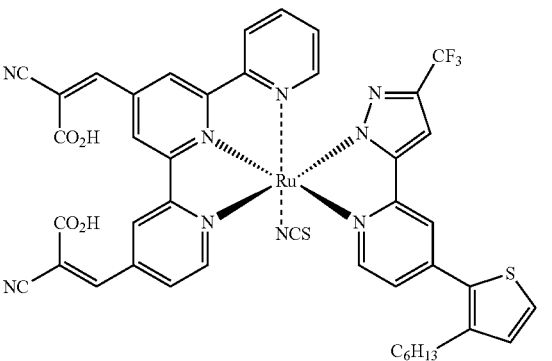

-continued
D-15
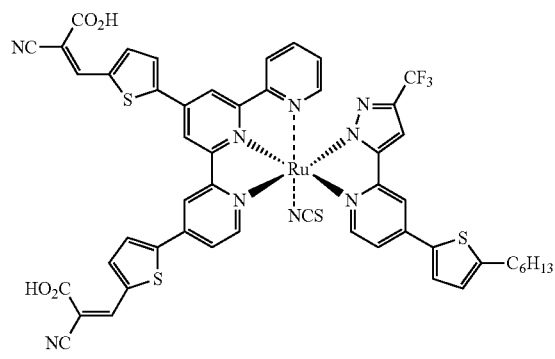
D-16
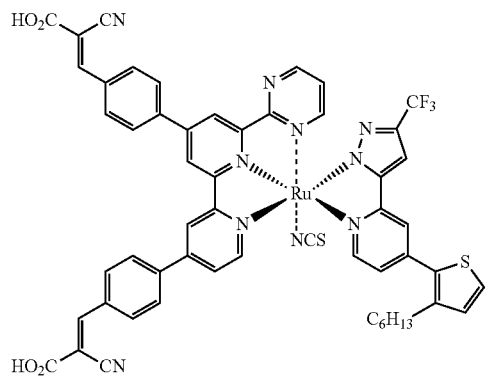
D-17
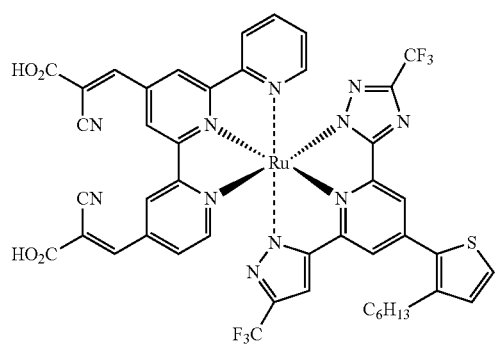
D-18
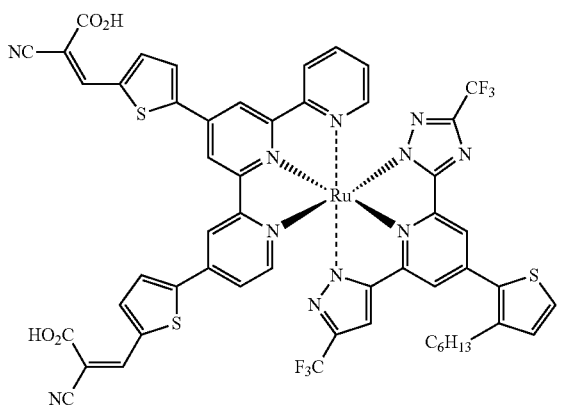
D-19
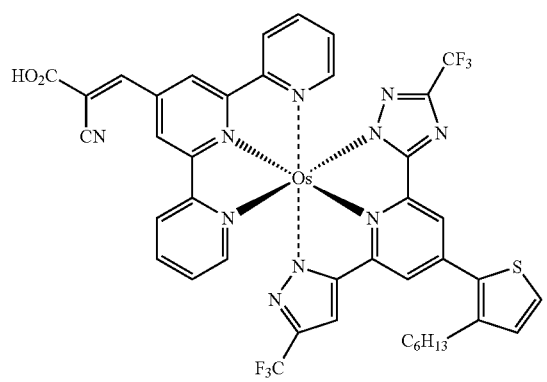
D-20
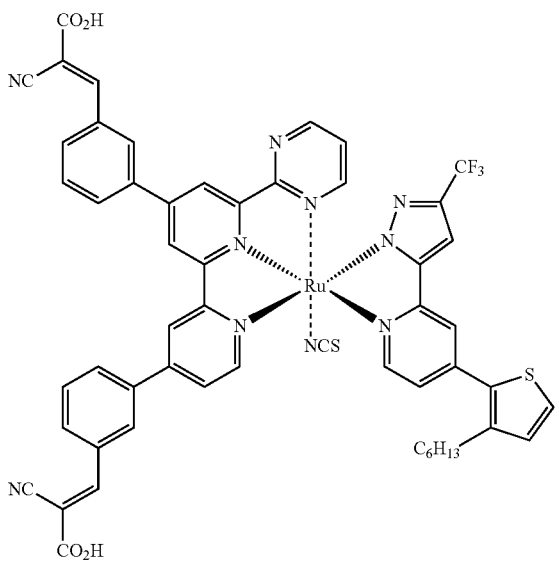

-continued
D-21
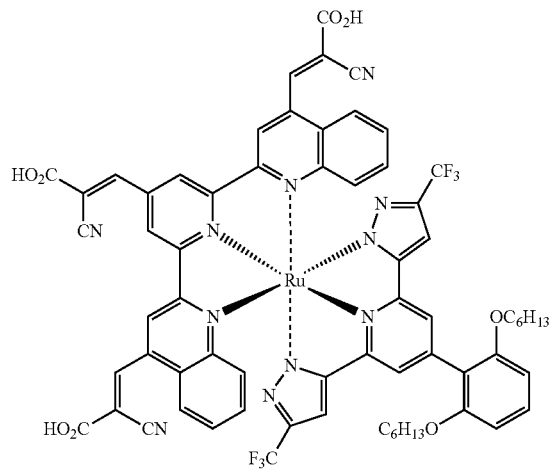
D-22
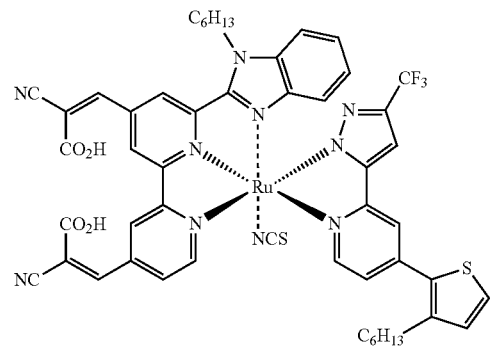
D-23
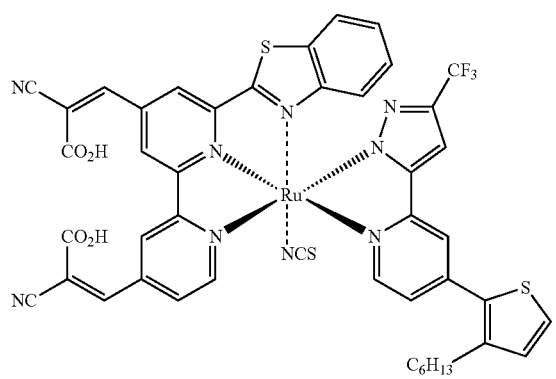
D-24
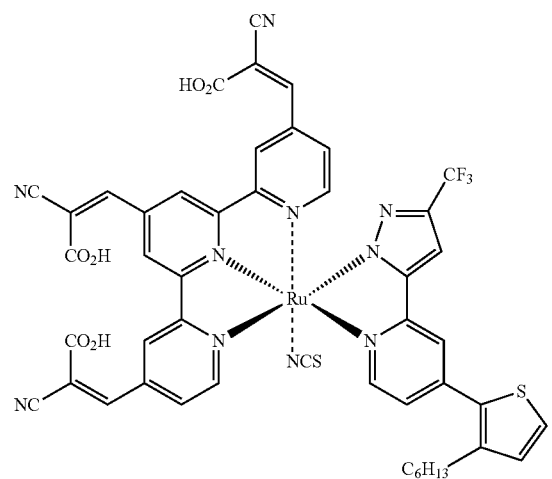
D-25
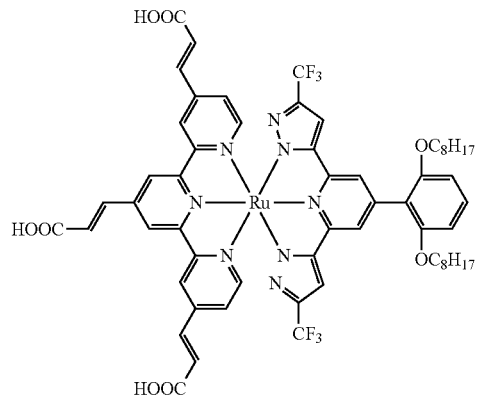
D-26
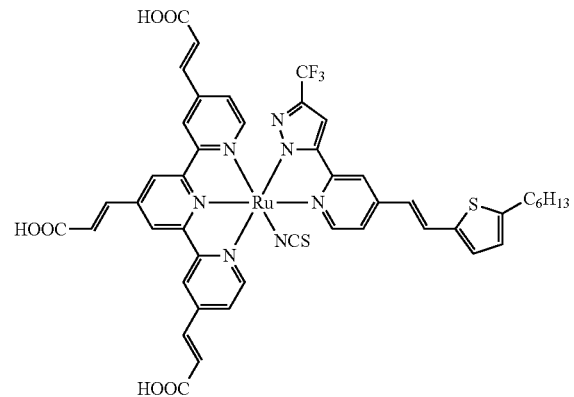

-continued
D-27
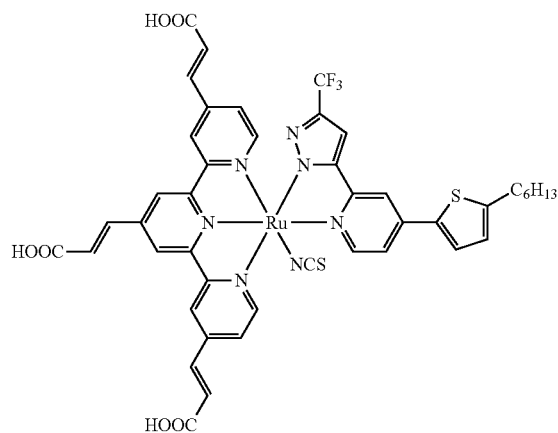
D-28
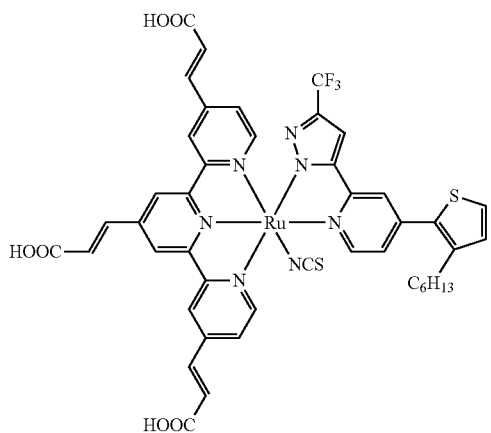
D-29
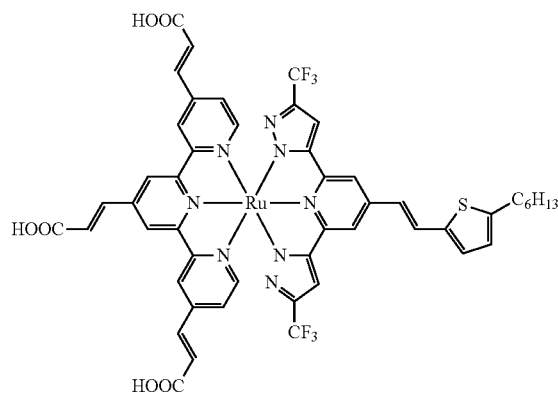
D-30
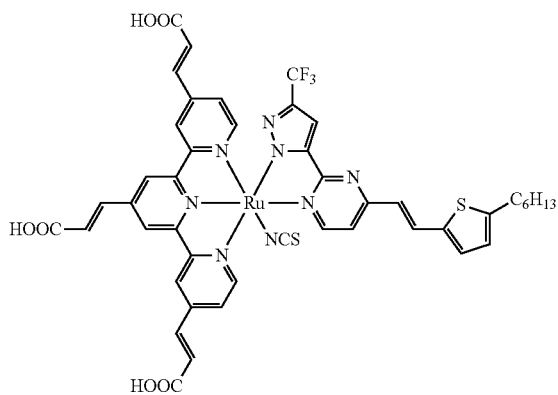
D-31
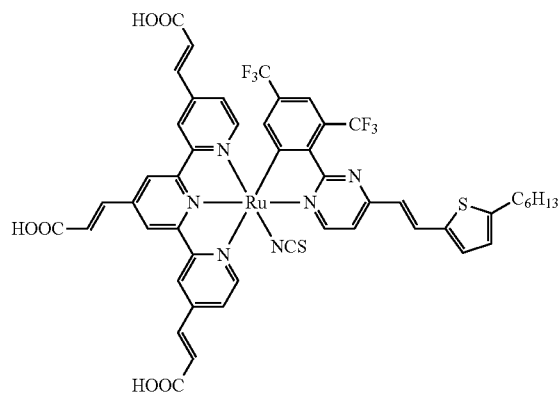
D-32
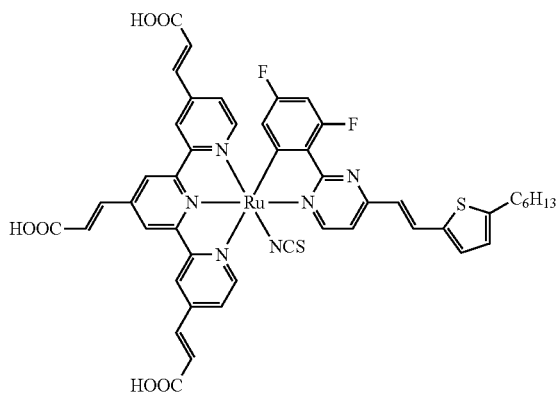

-continued
D-33
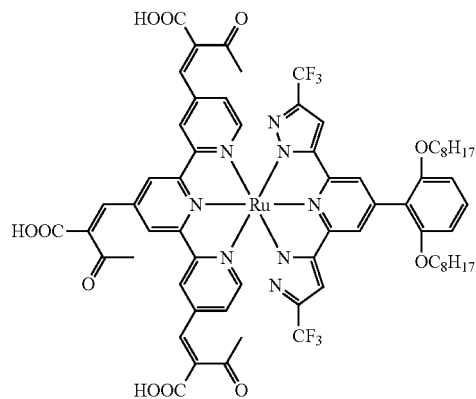
D-34
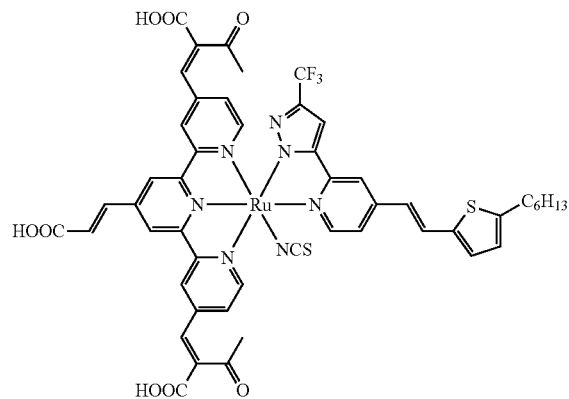
D-35
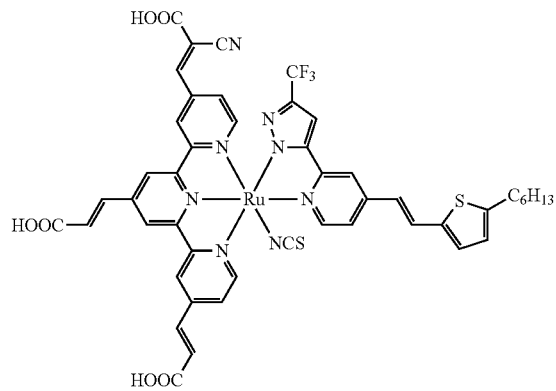
D-36
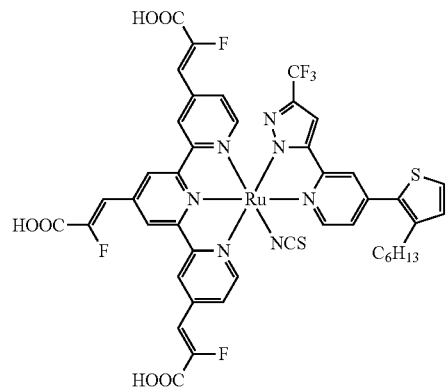
D-37
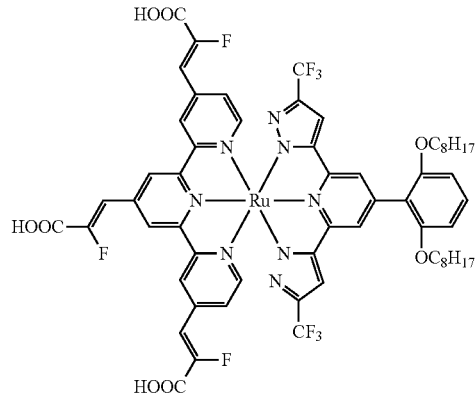
D-38
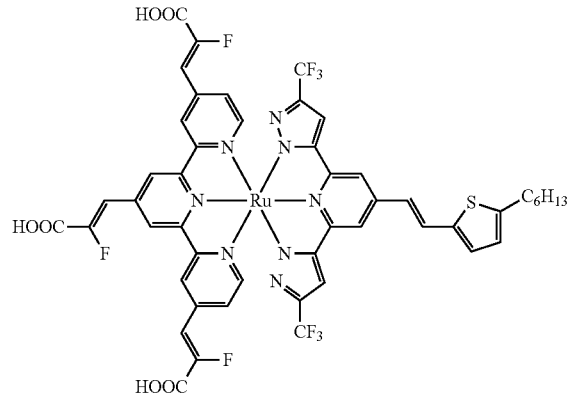

-continued
D-39
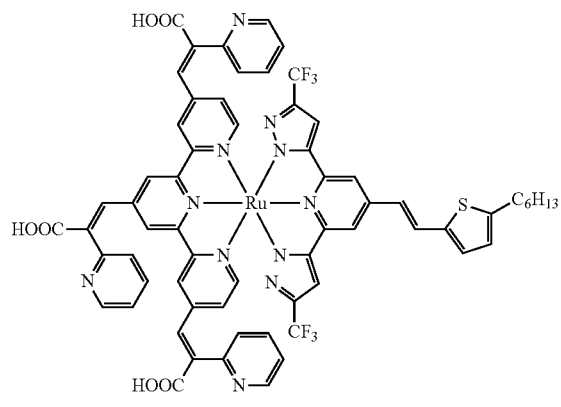
D-40
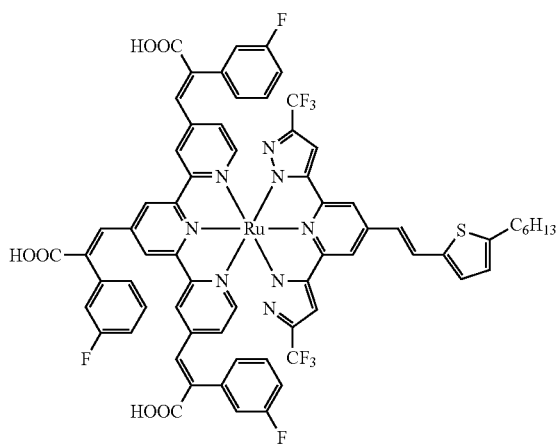
D-41
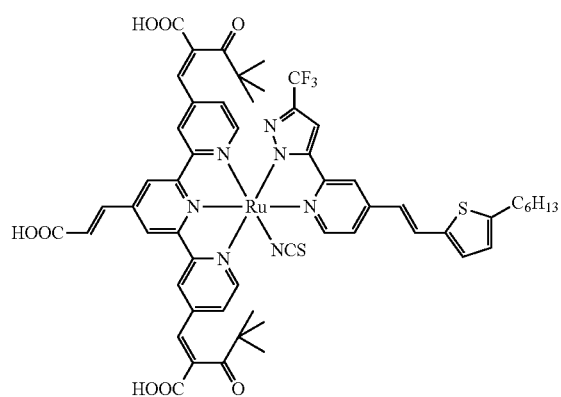
D-42
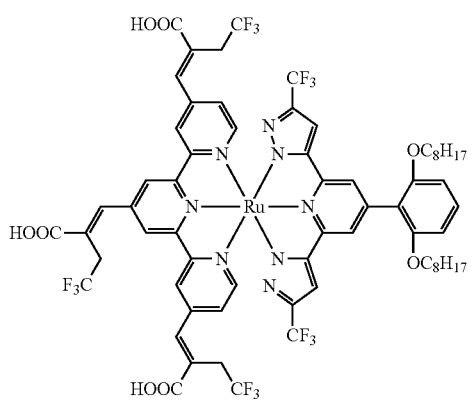
D-43
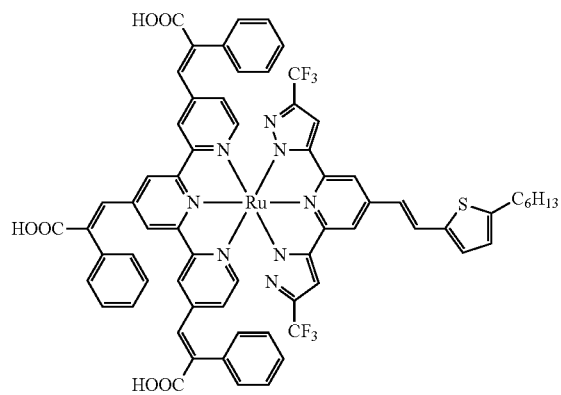
D-44
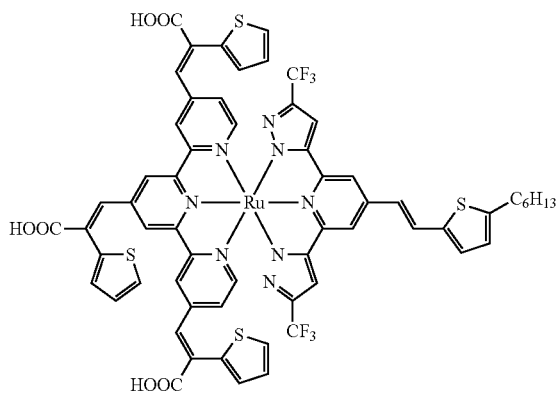

D-45
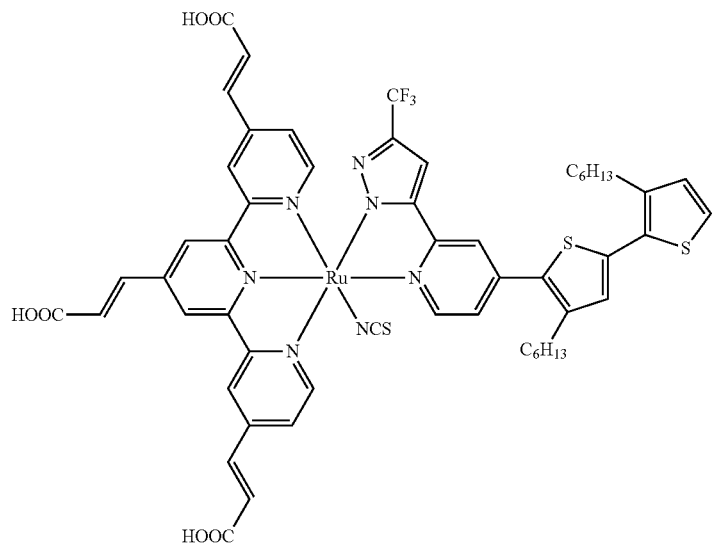
D-46
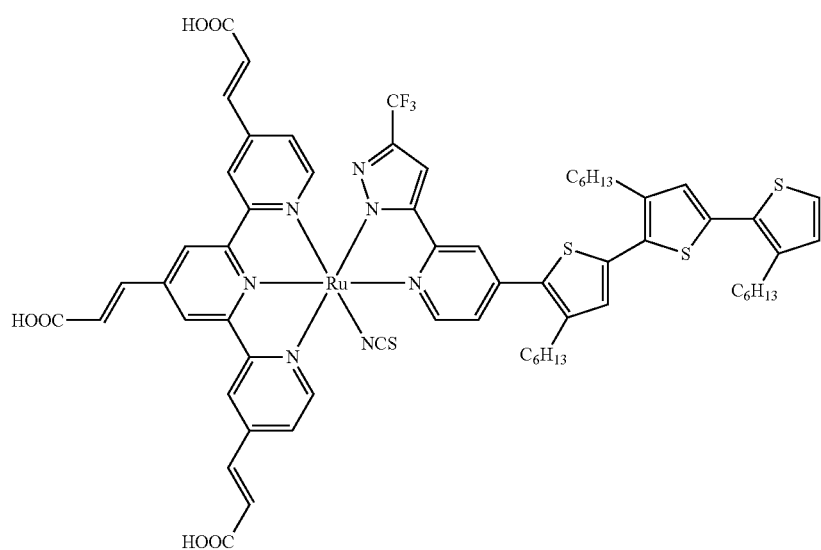
D-47
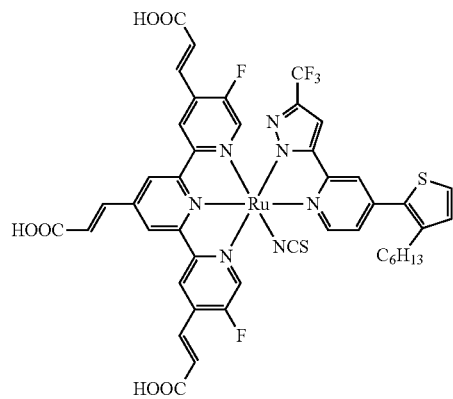
D-48
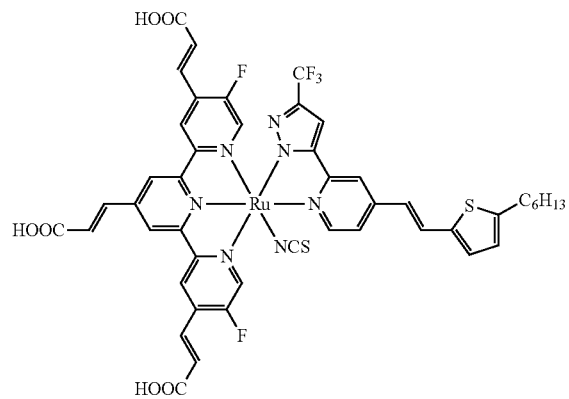

-continued
D-49
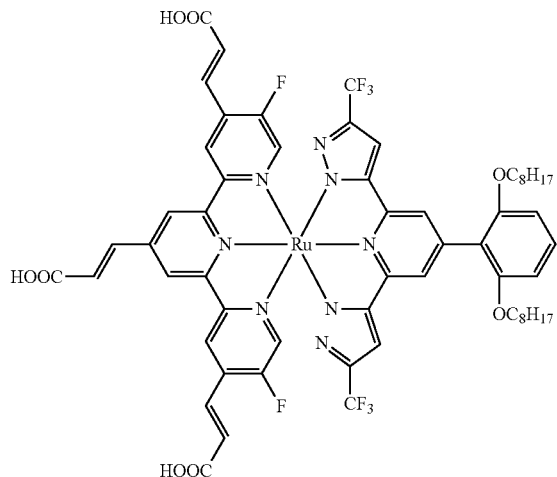
D-50
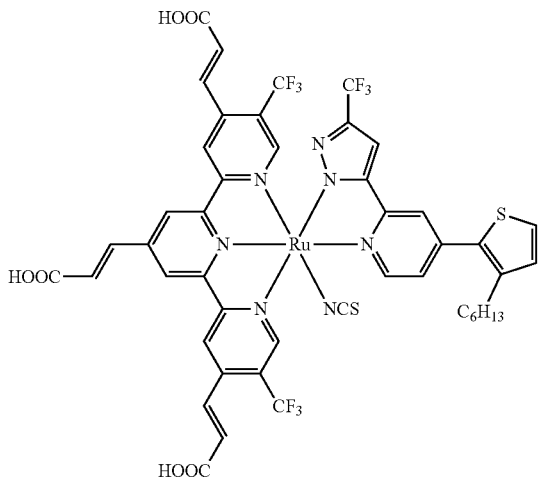
D-51
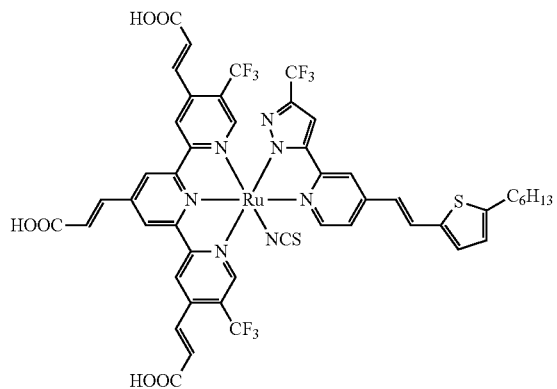
D-52
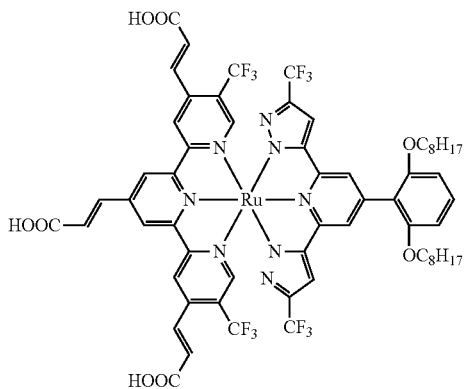
D-53
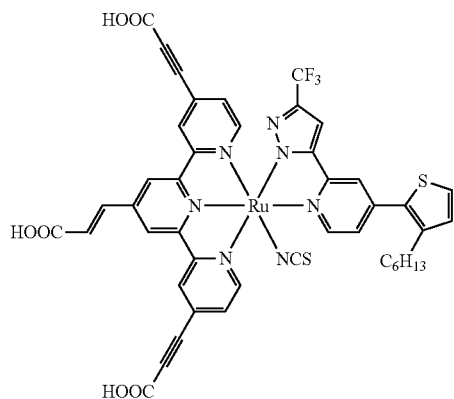
D-54
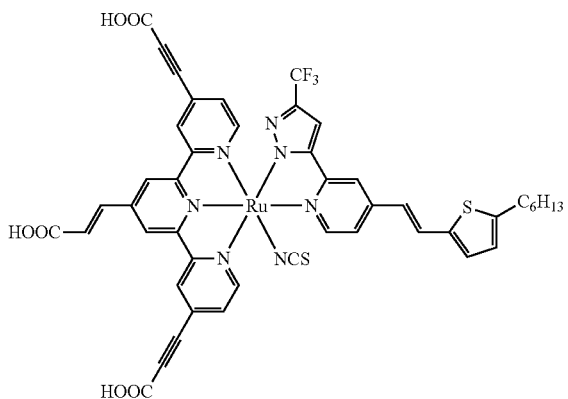

-continued
D-55
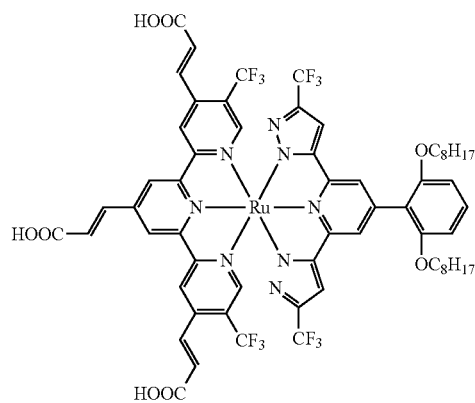
D-56
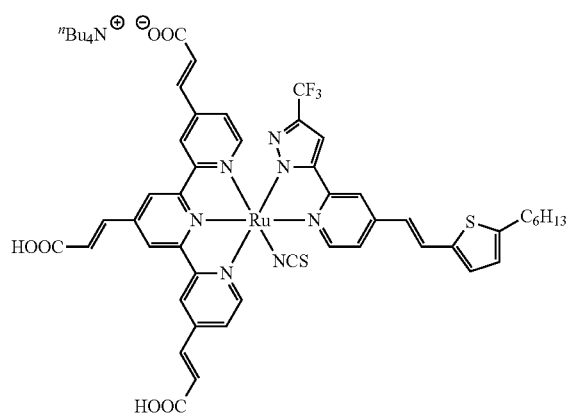
D-57
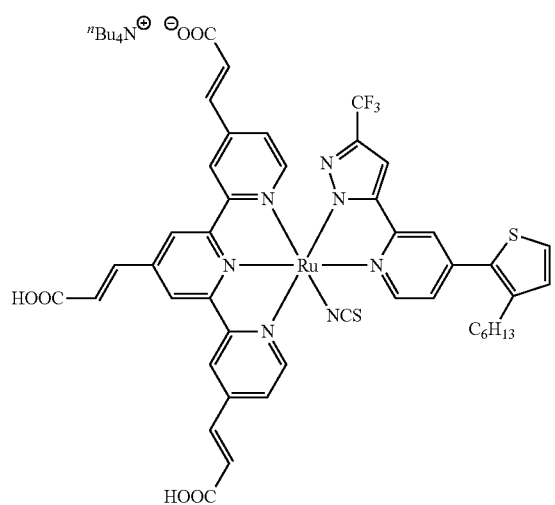
D-58
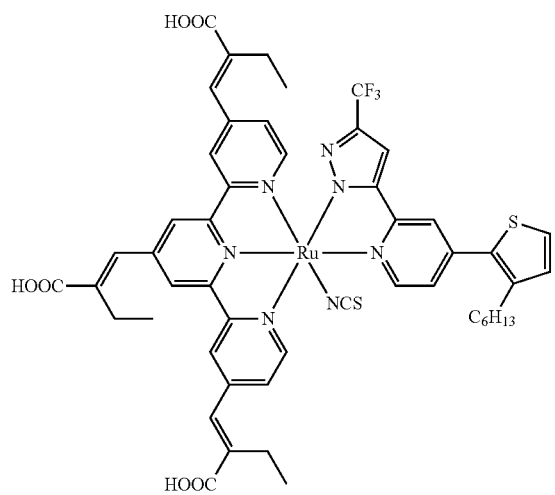
D-59
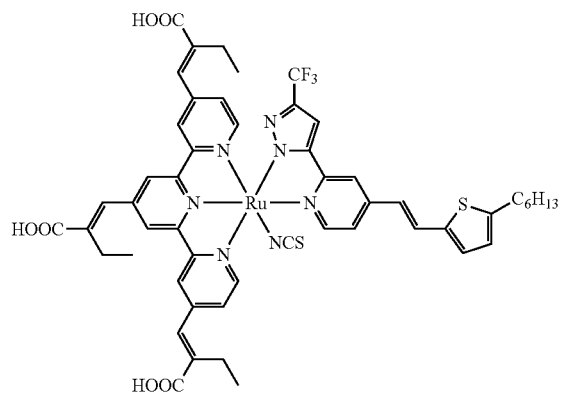
D-60
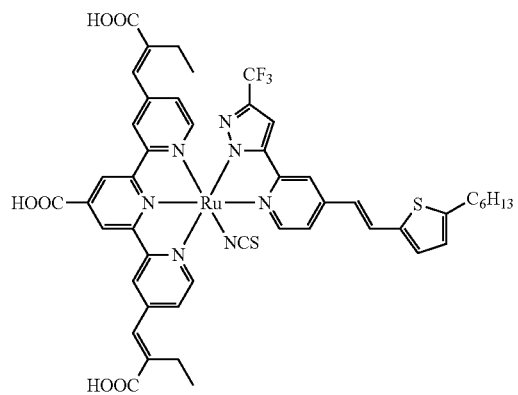

D-61
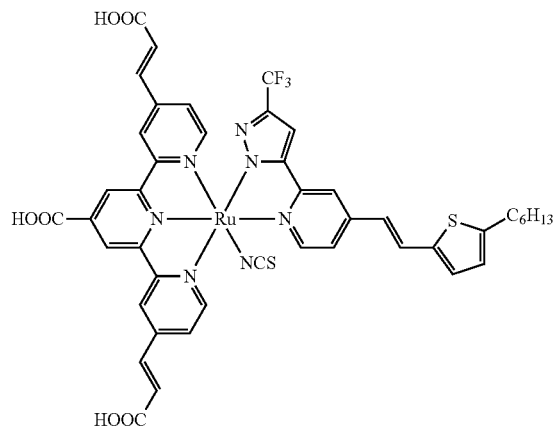
D-62
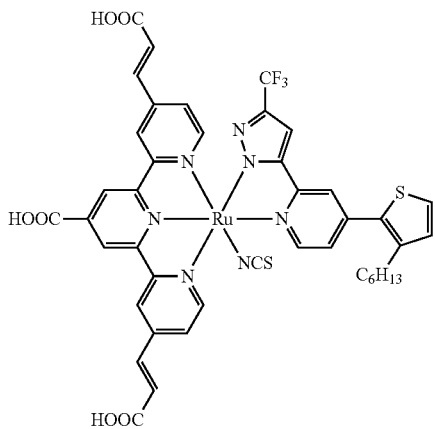
D-63
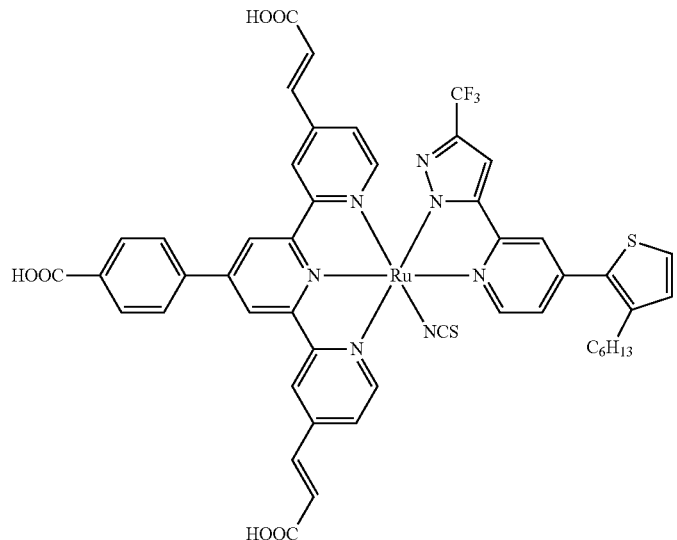
D-64
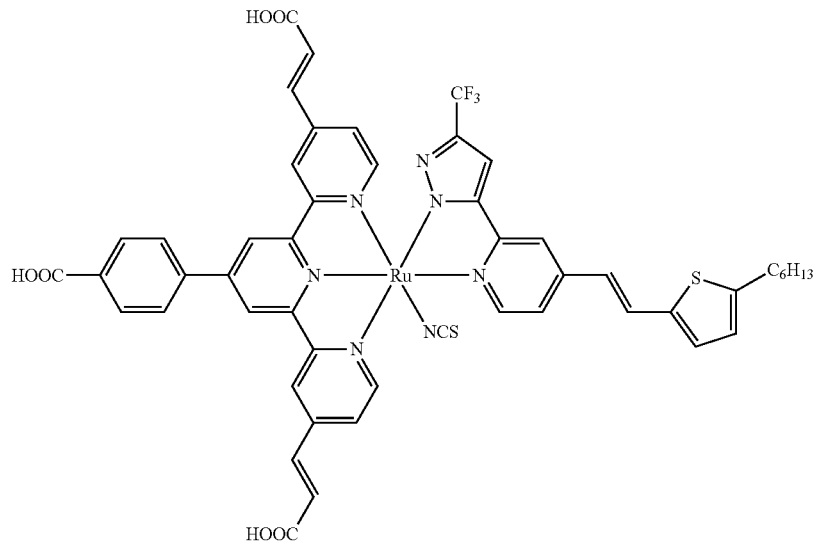

-continued
D-65
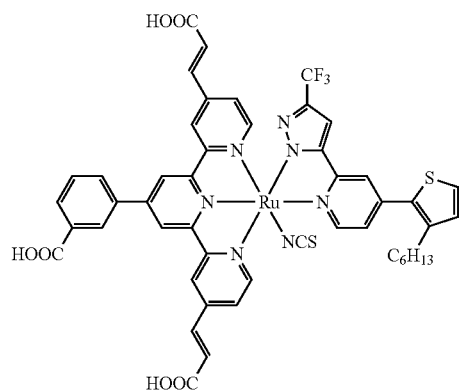
D-66
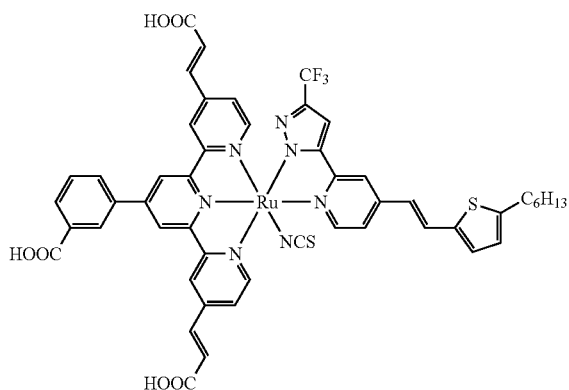
D-67
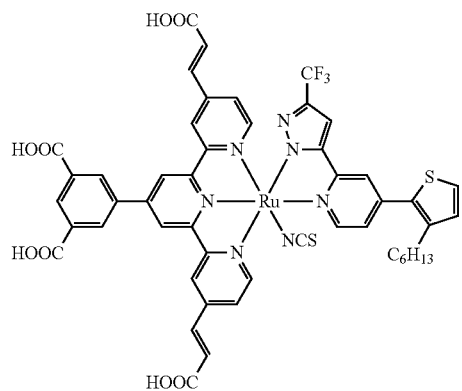
D-68
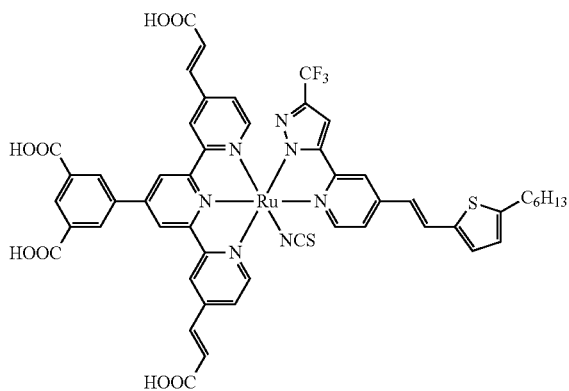
D-69
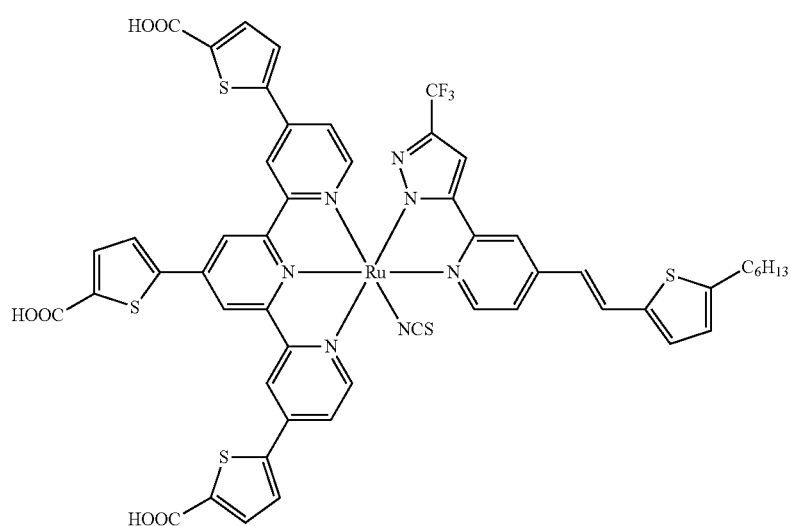

-continued
D-70
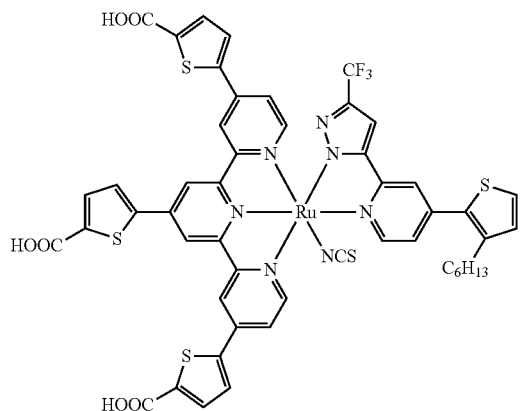
D-71
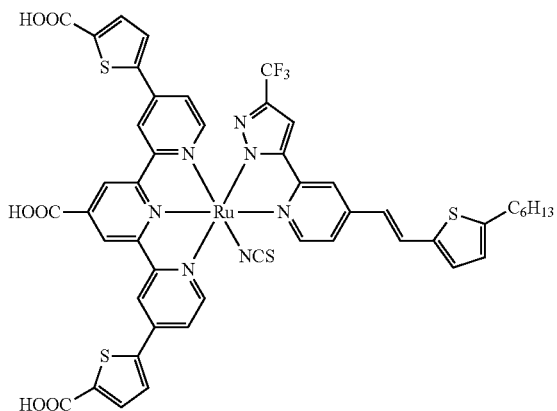
D-72
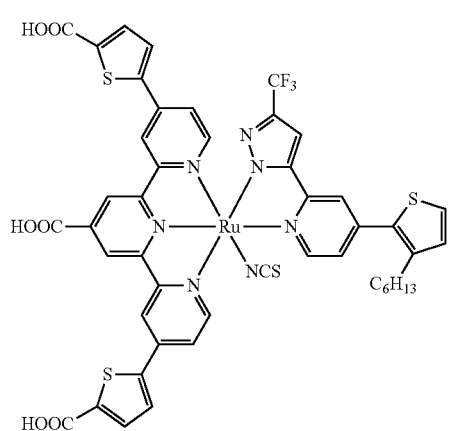
D-73
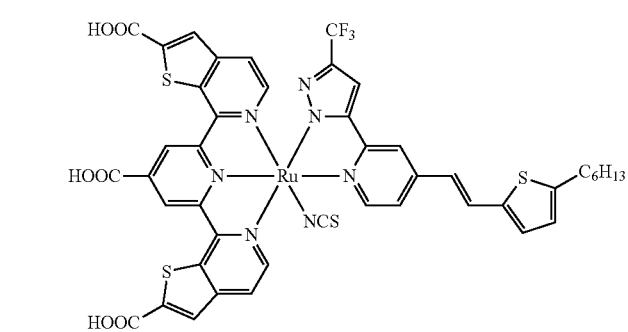
D-74
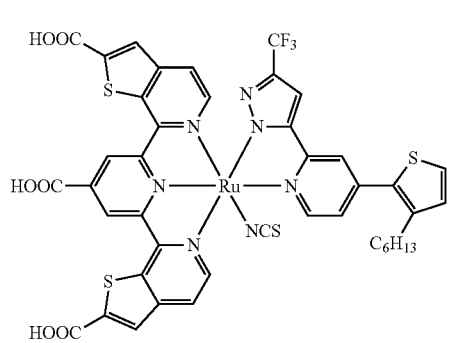
D-75
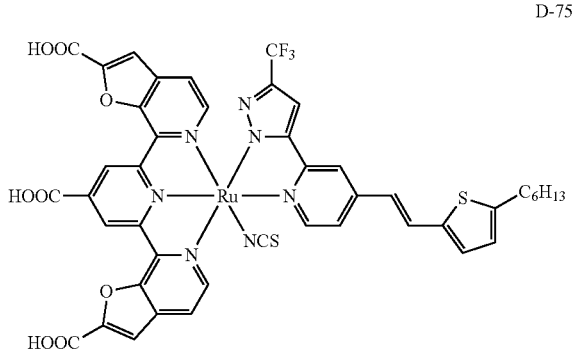
D-76
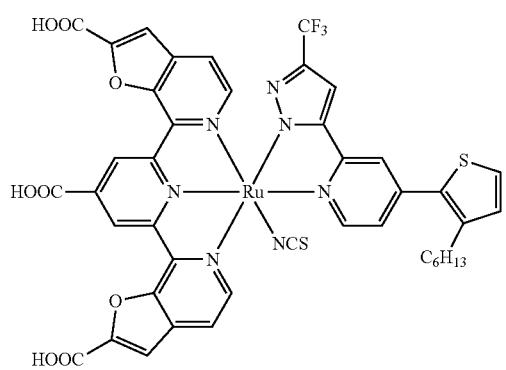
D-77
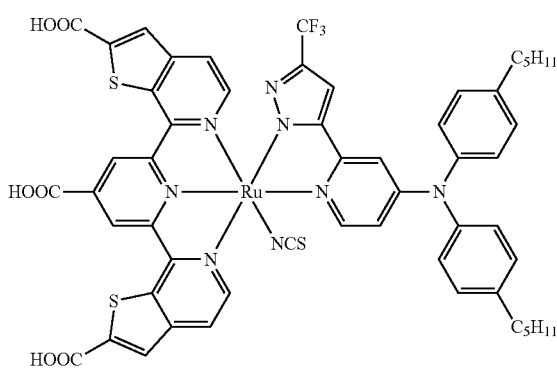

-continued
D-78
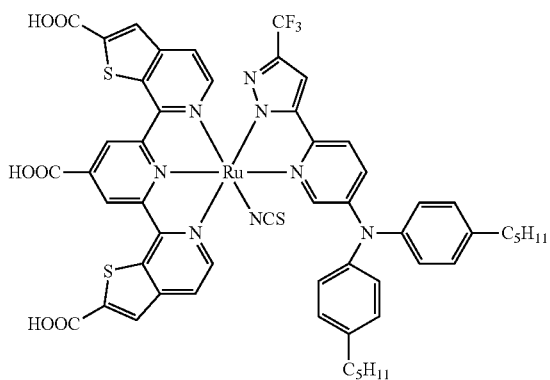
D-79
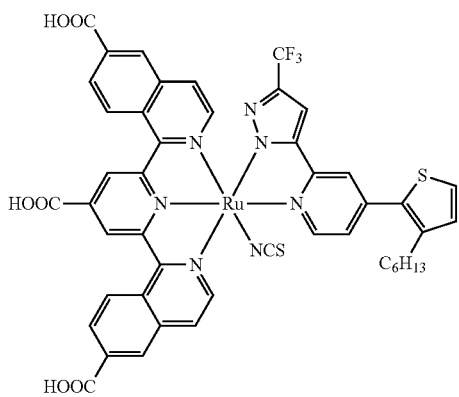
D-80
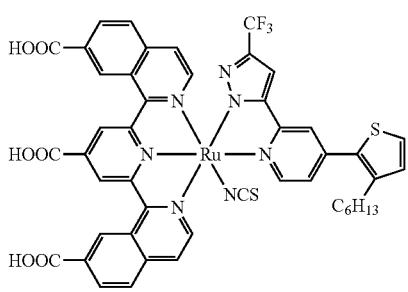
D-81
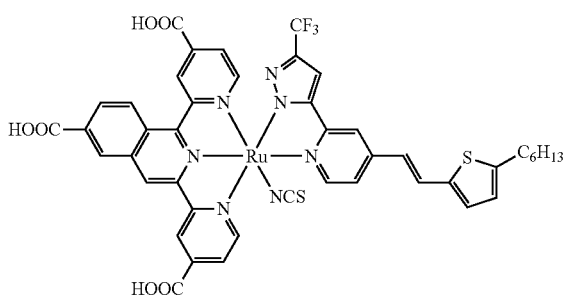
D-82
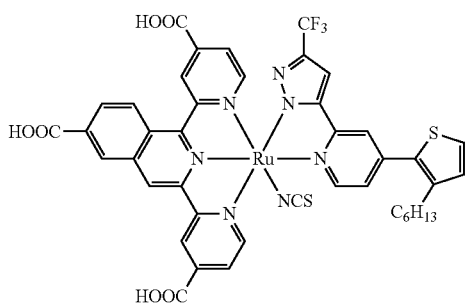
D-83
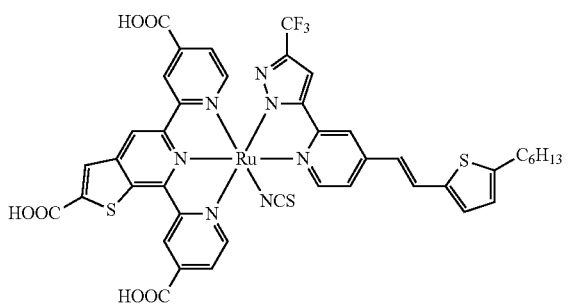
D-84
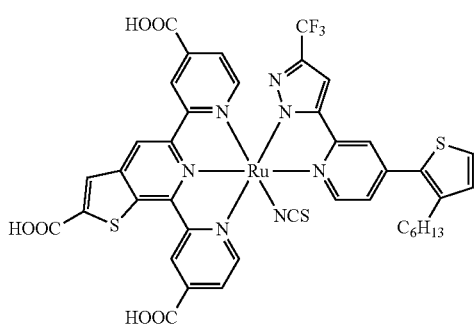
D-85
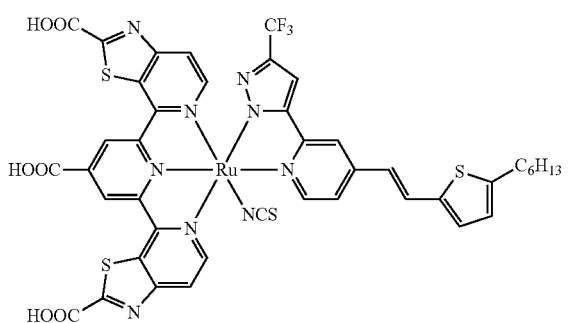

-continued
D-86
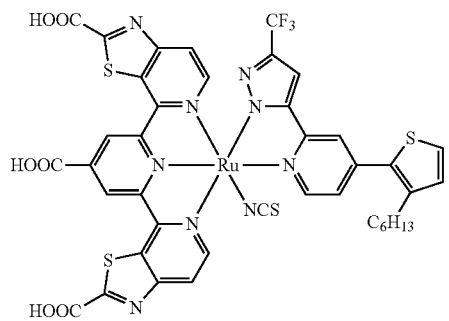
D-87
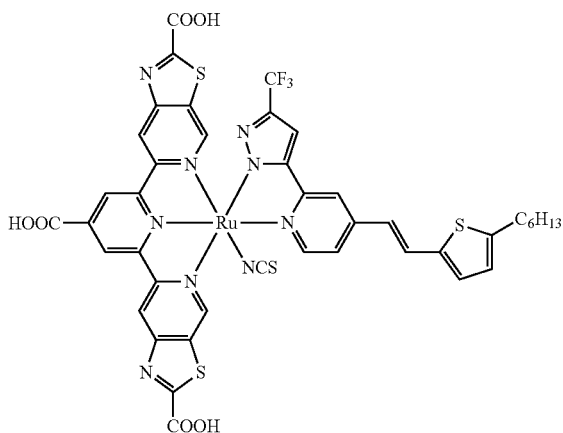
D-88
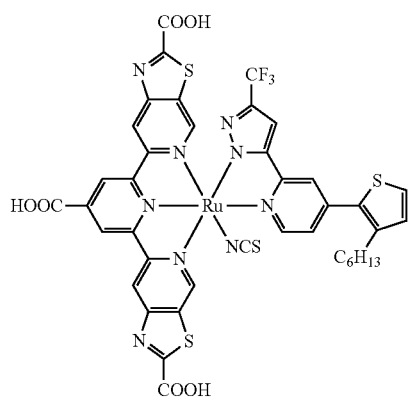
D-89
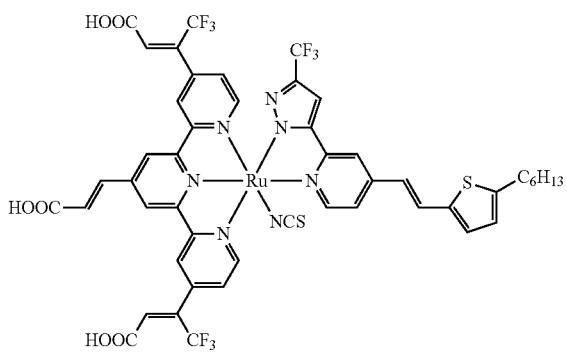
D-90
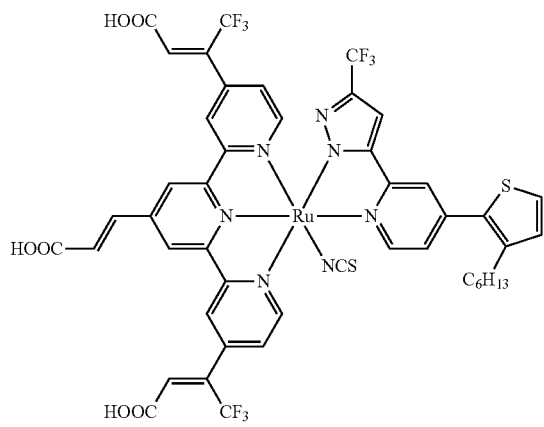
D-91
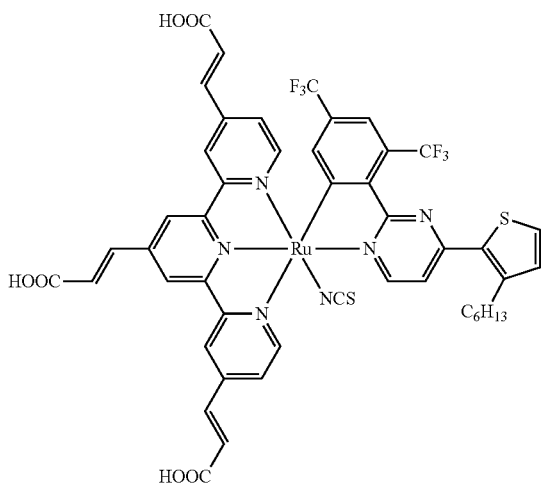

-continued
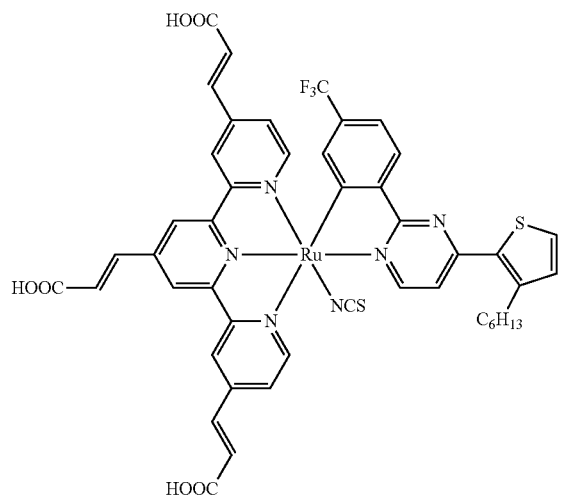
D-92
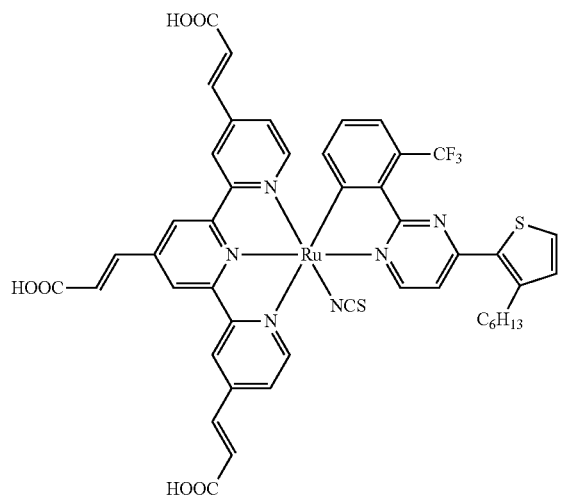
D-93
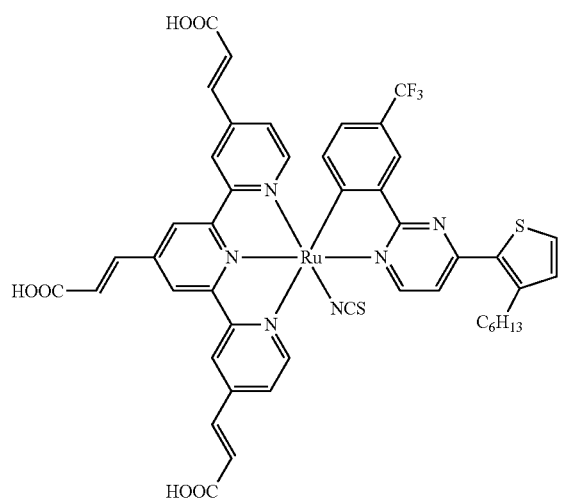
D-94
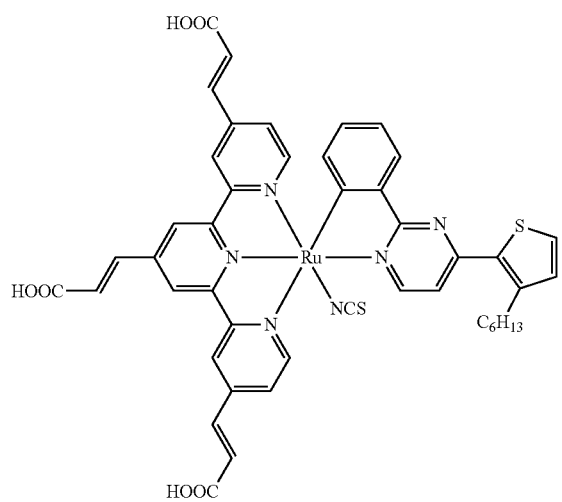
D-95
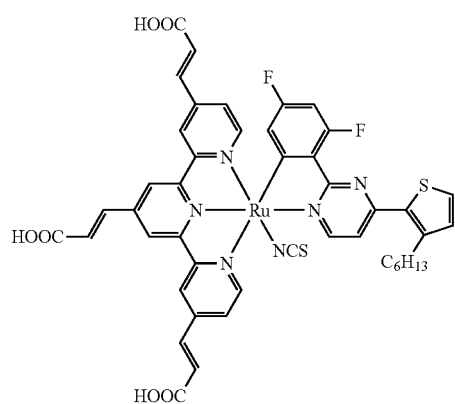
D-96
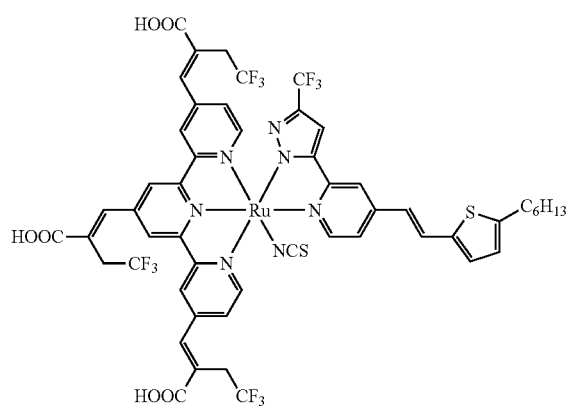
D-97

-continued
D-98
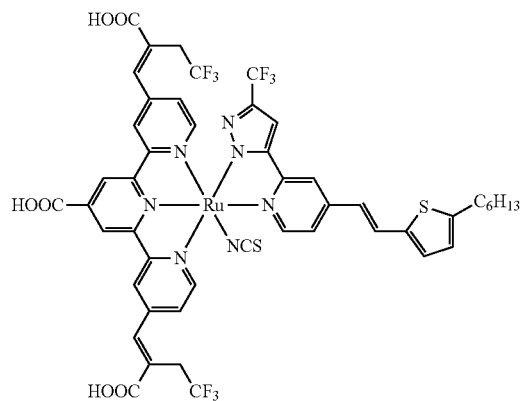
D-99
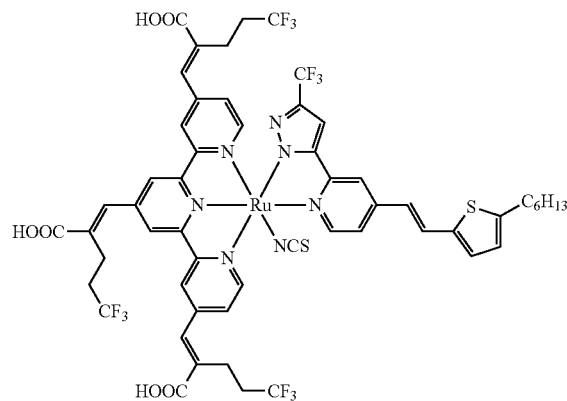
D-100
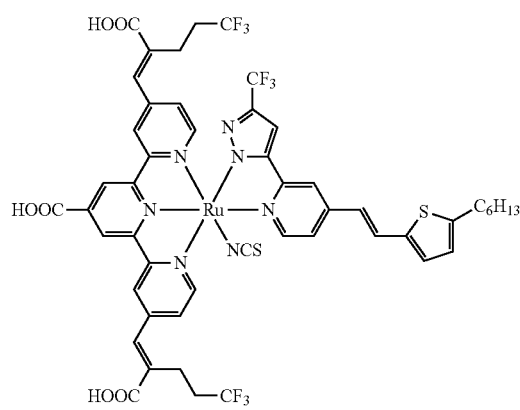
D-101
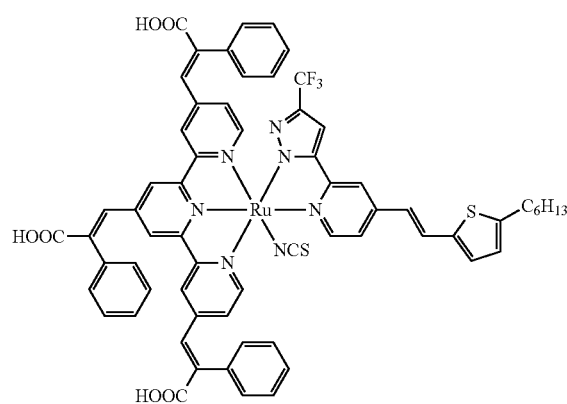
D-102
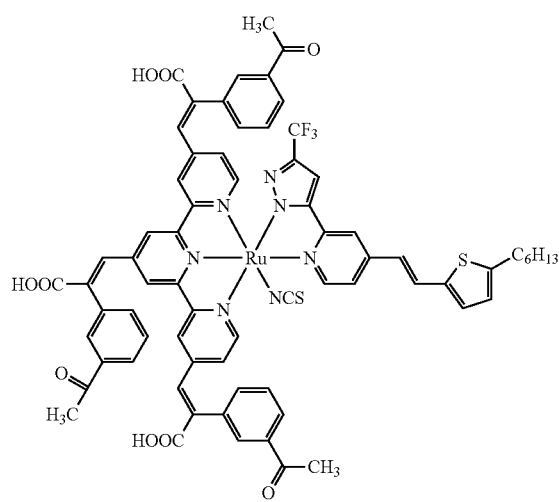
D-103
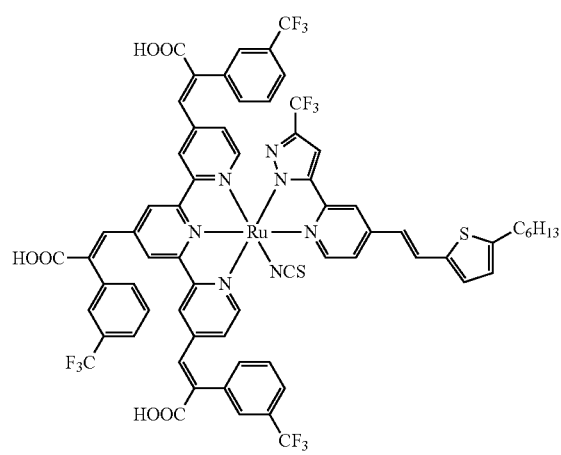

-continued
D-104
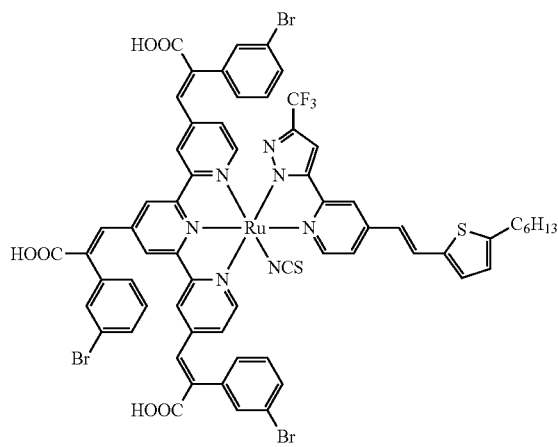
D-105
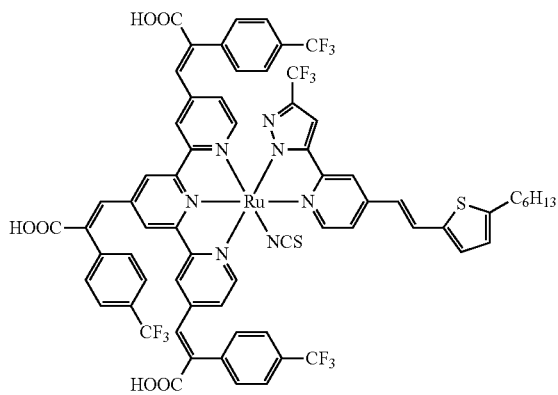
D-106
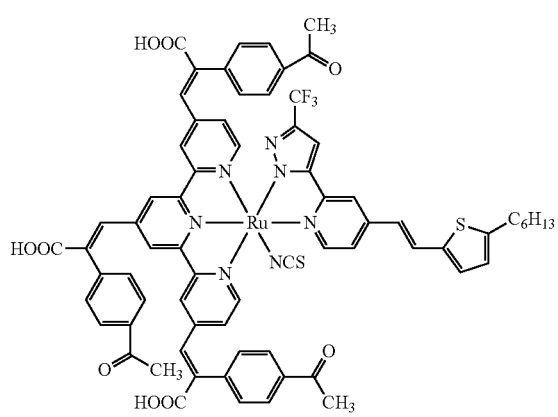
D-107
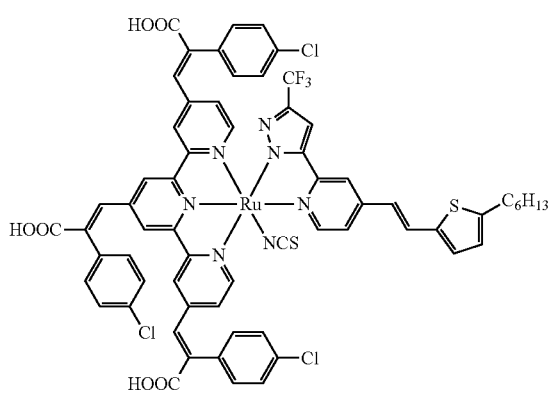
D-108
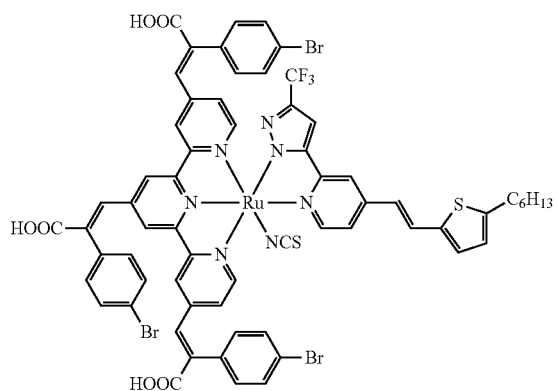
D-109
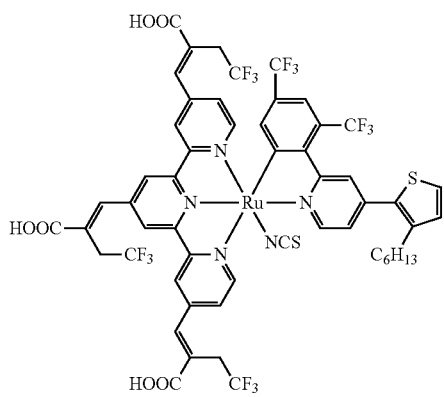

-continued
D-111
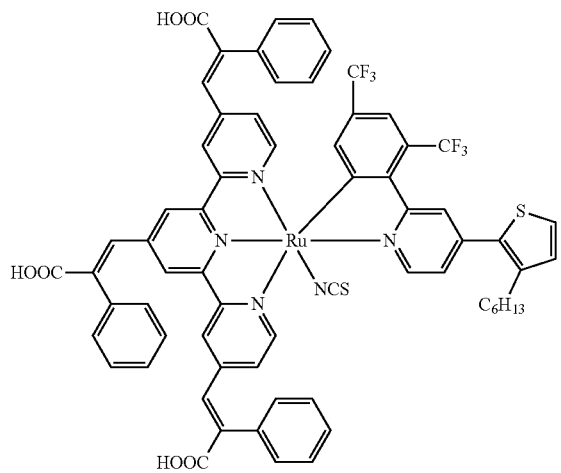
D-112
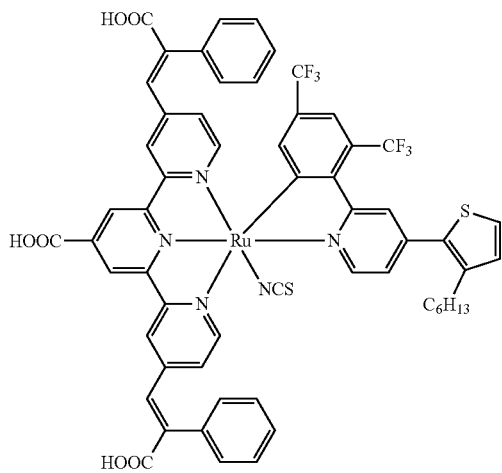
D-113
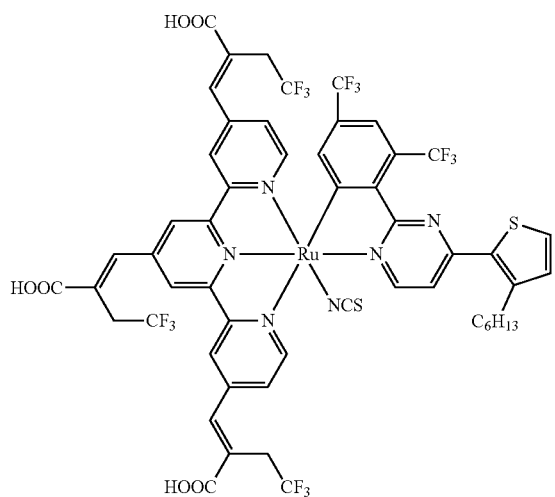
D-114
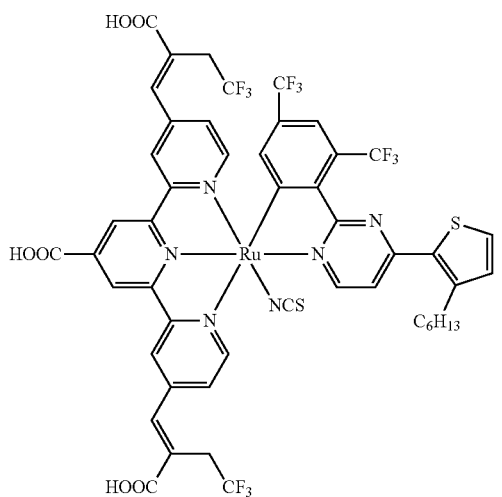
D-115
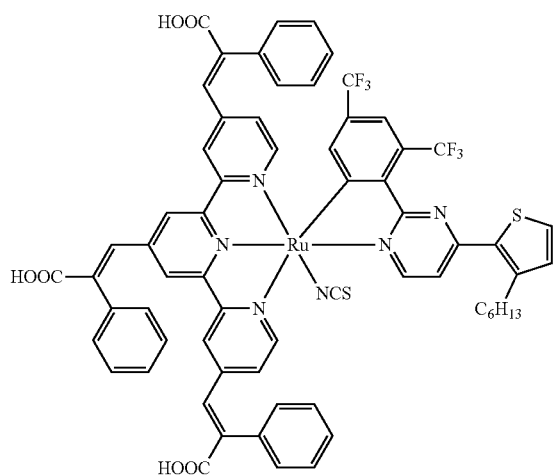
D-116
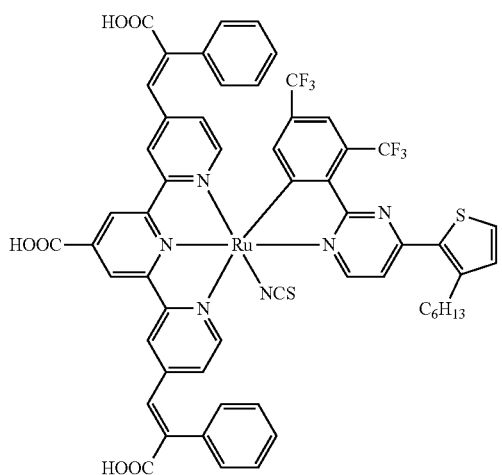

-continued
D-117
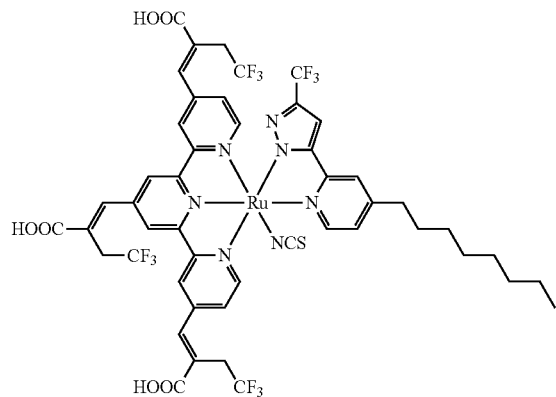
D-118
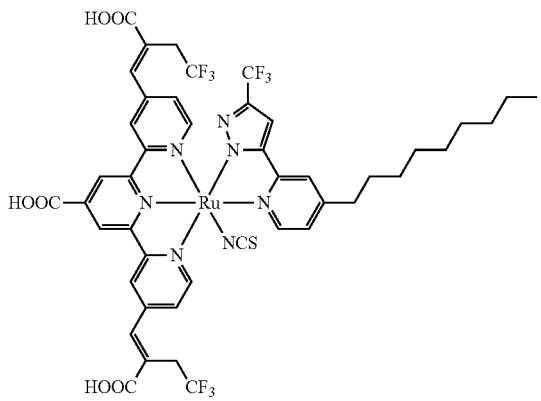
D-119
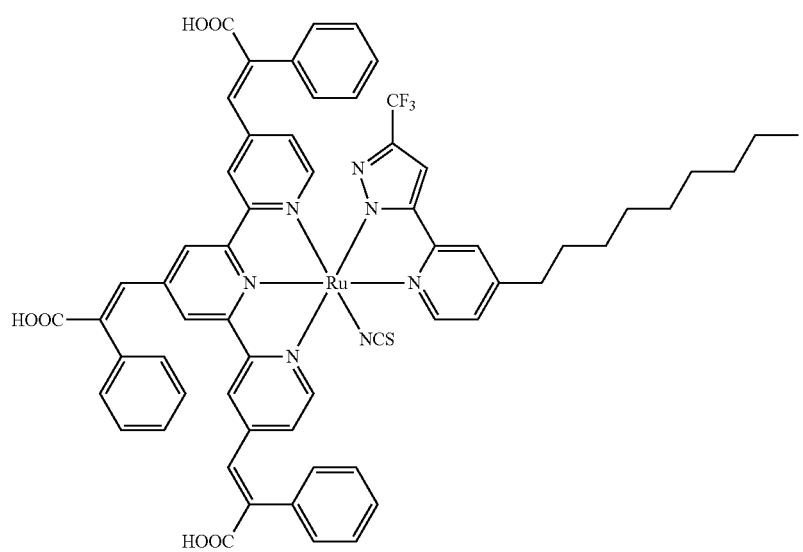
D-120
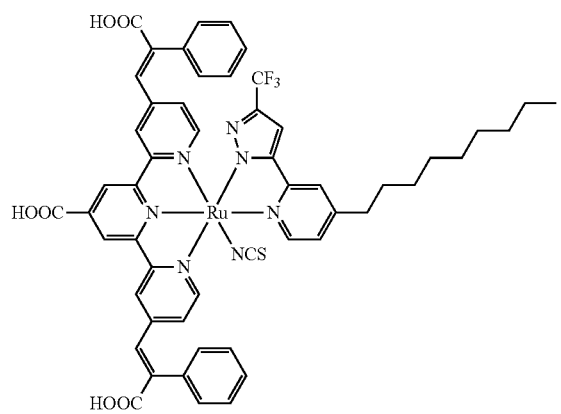
D-121
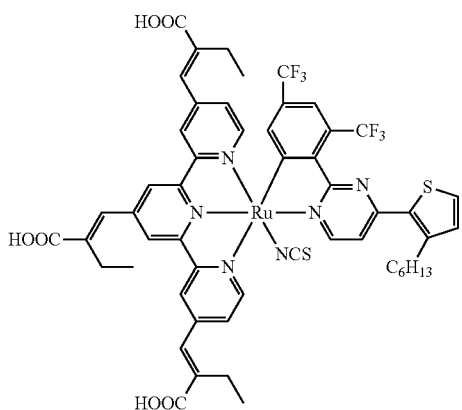

-continued
D-122
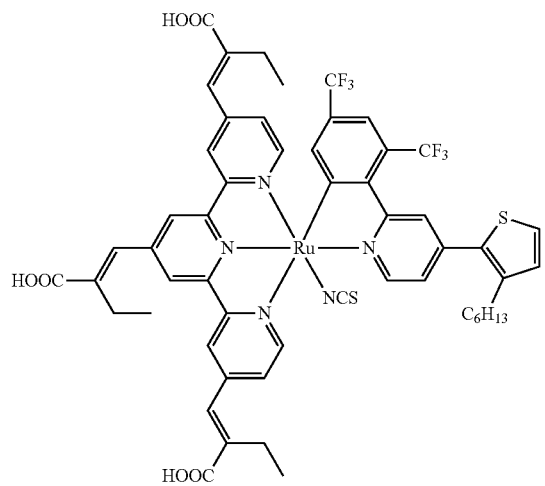
D-123
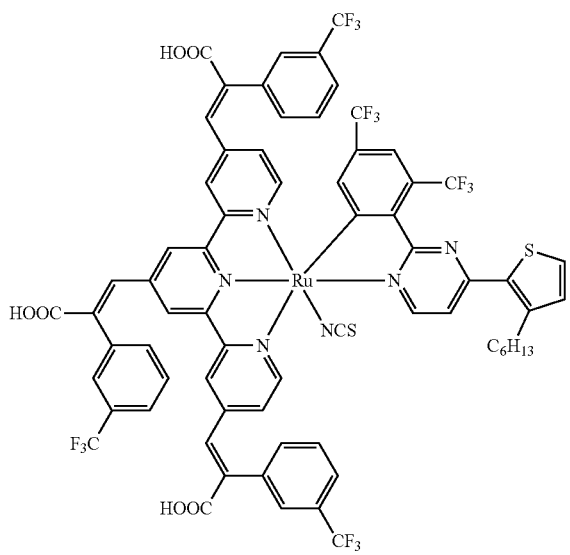
D-124
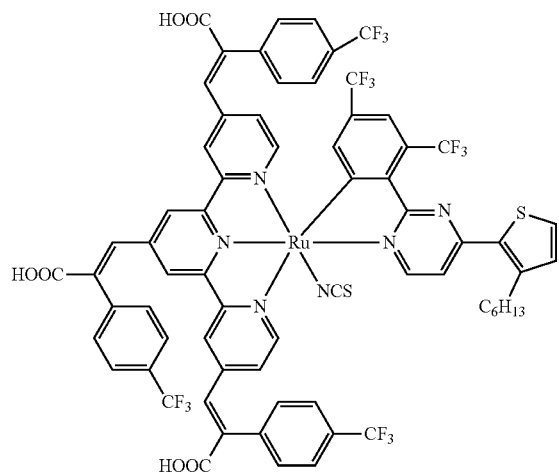
D-125
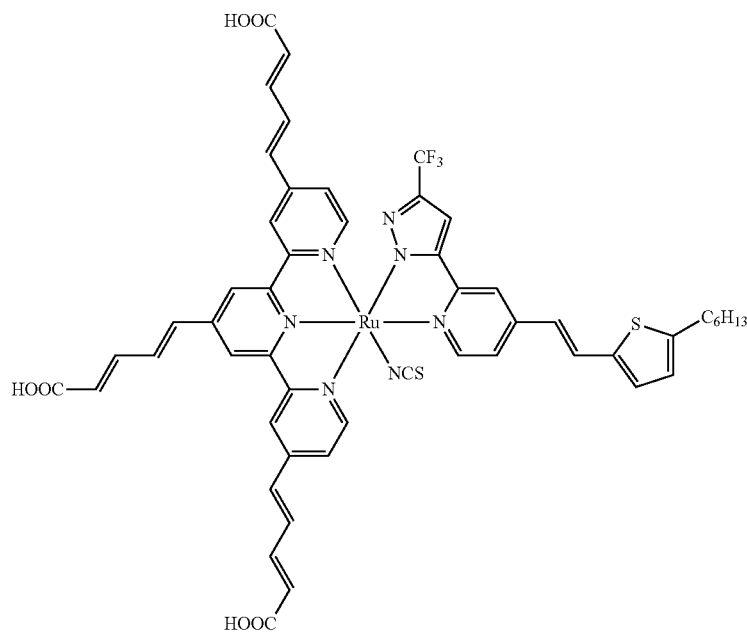

-continued
D-126
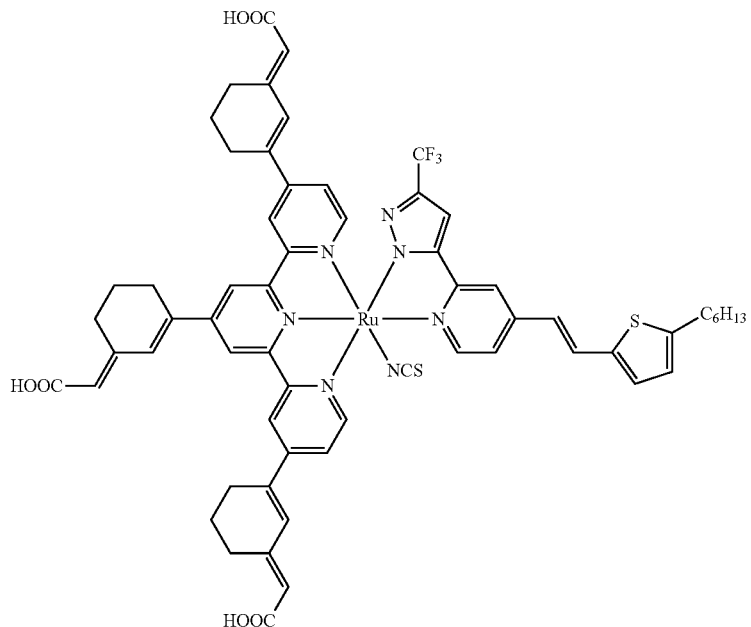
D-127
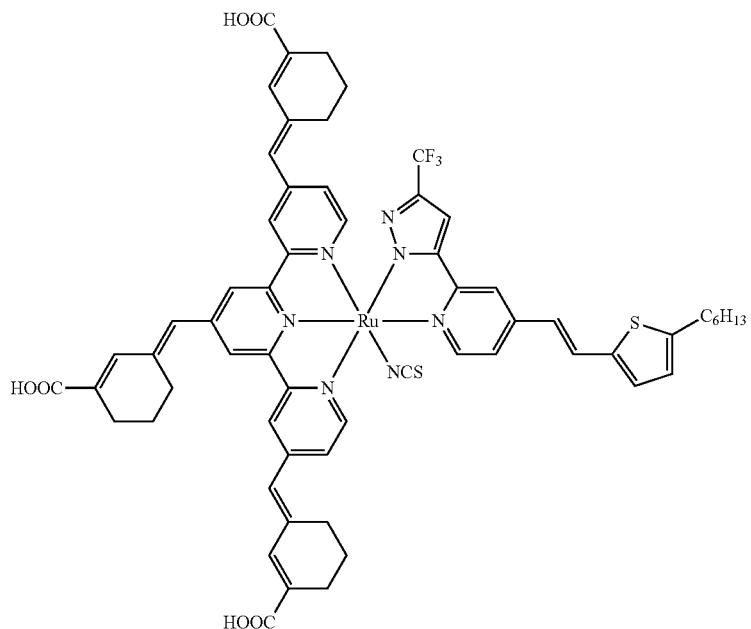
D-128
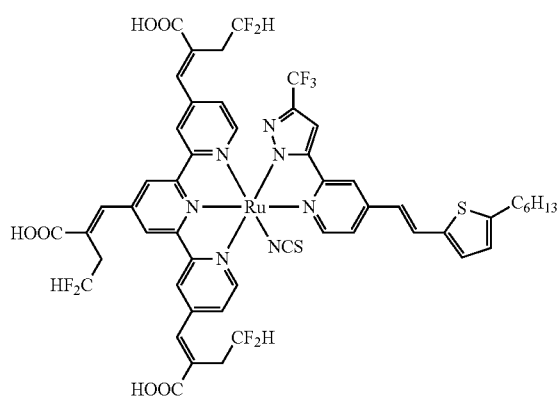
D-129
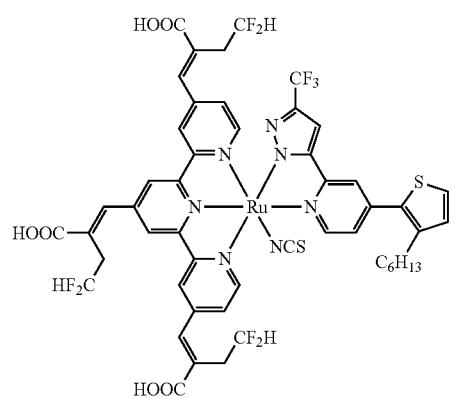

-continued
D-130
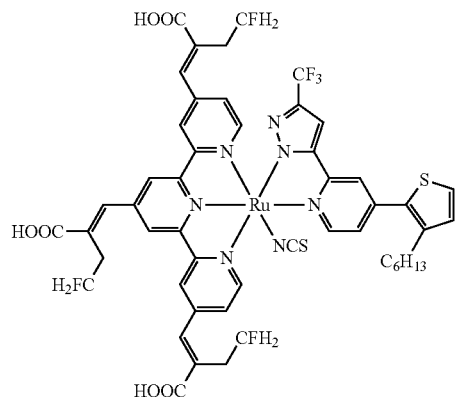
D-131
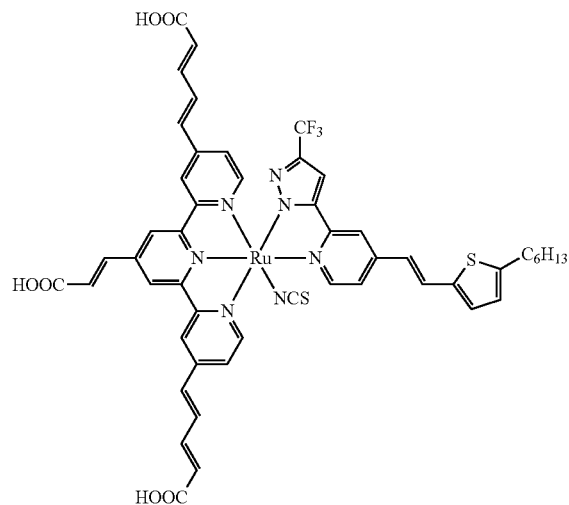
D-132
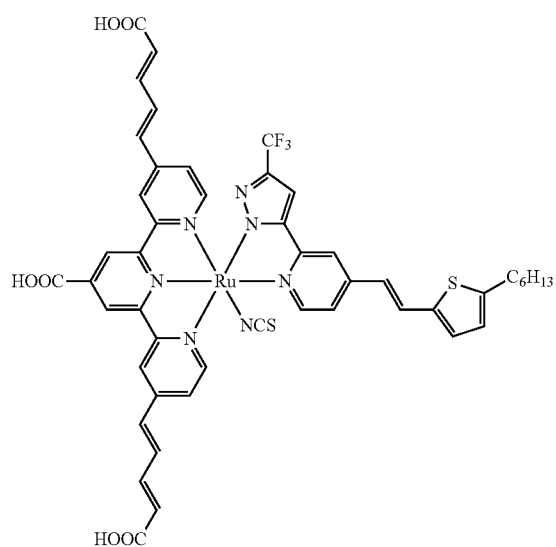
D-133
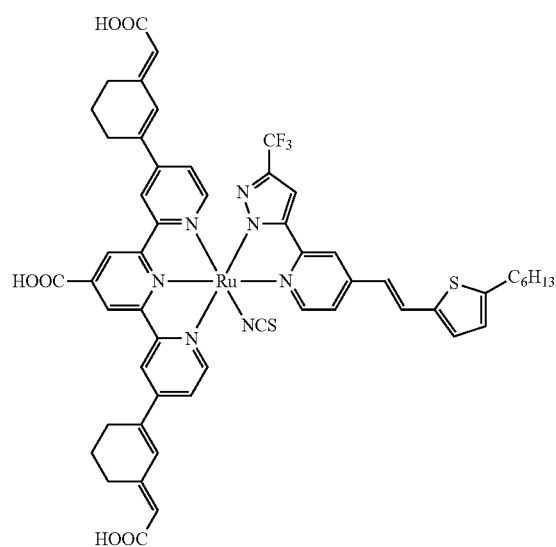
D-134
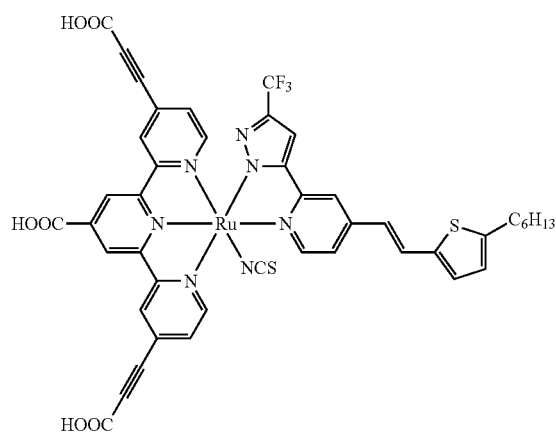
D-135
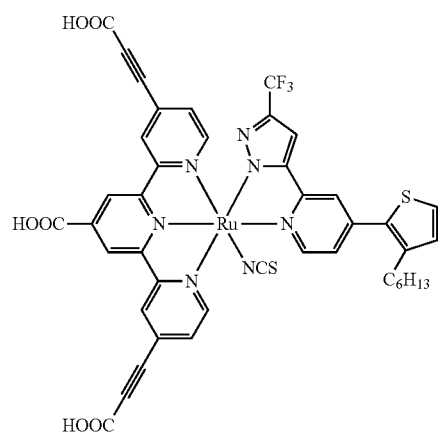

-continued
D-136
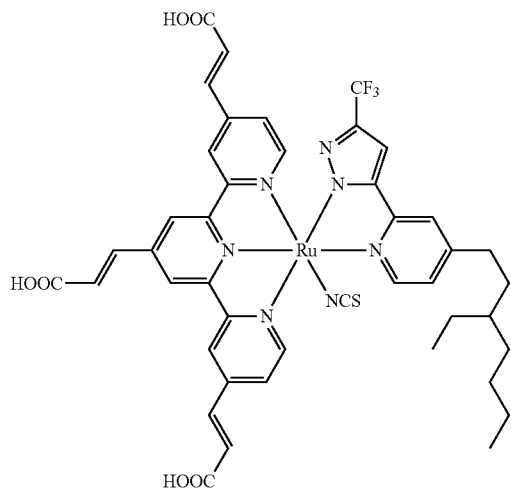
D-137
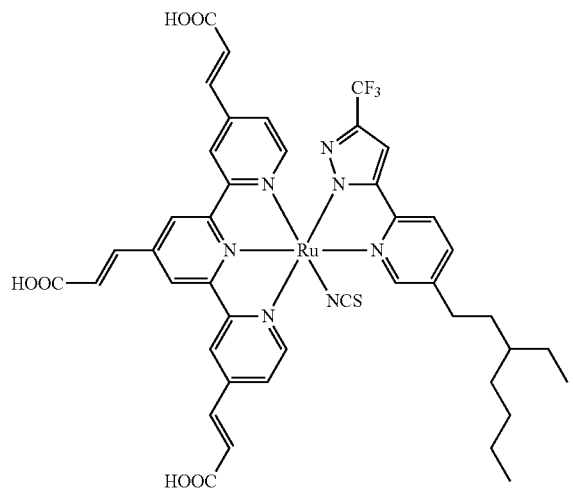
D-138
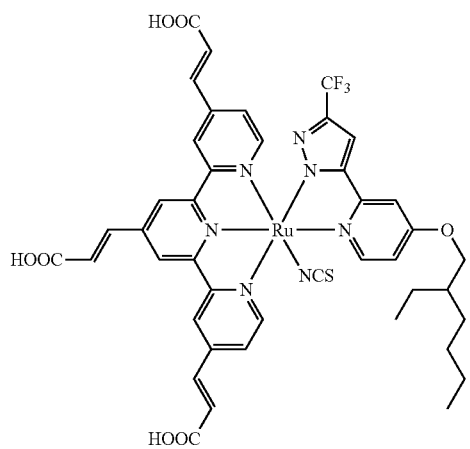
D-139
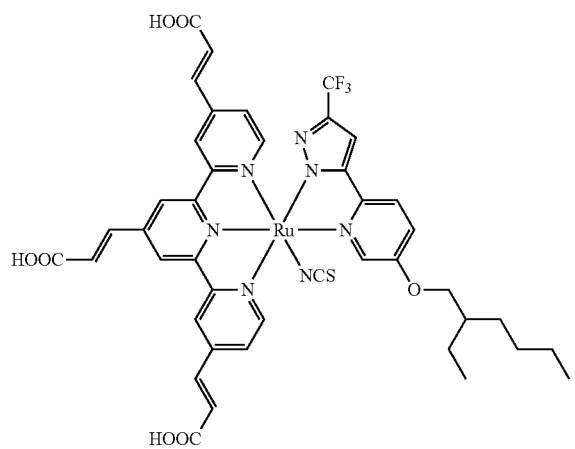
D-140
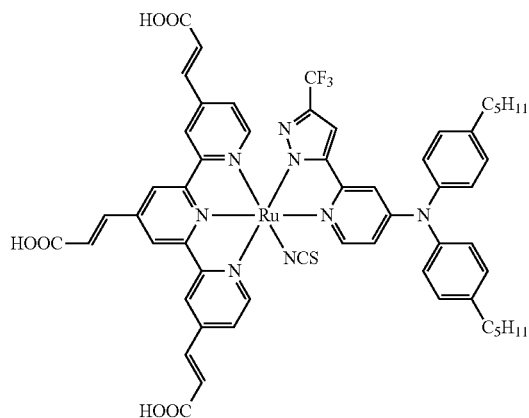
D-141
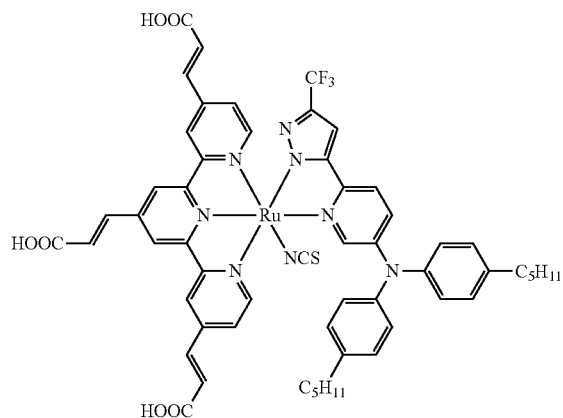

-continued
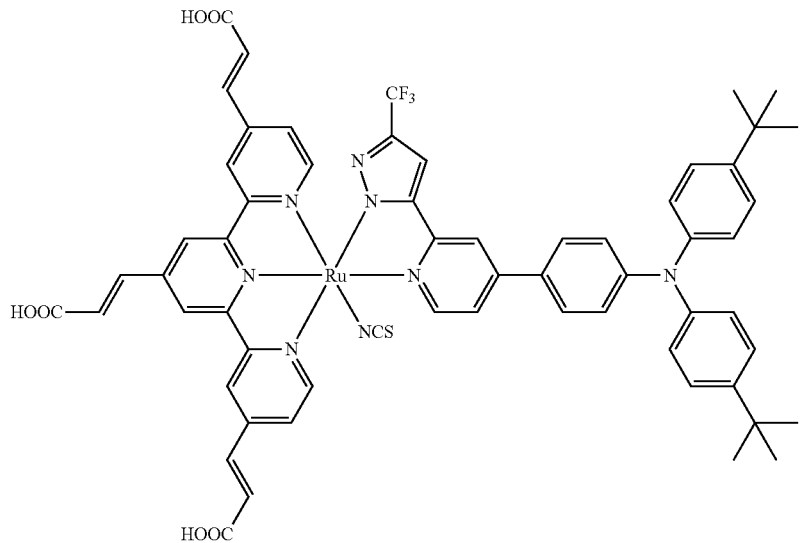
D-142
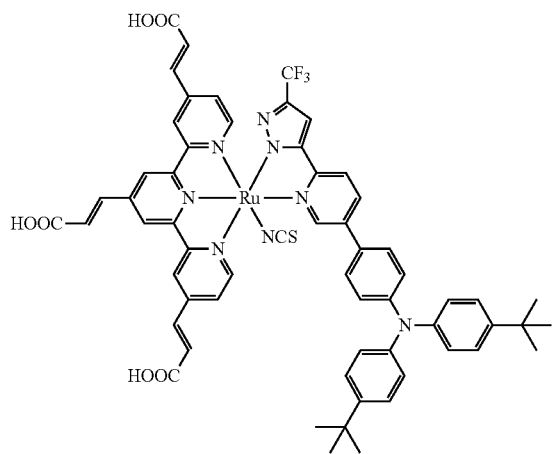
D-143
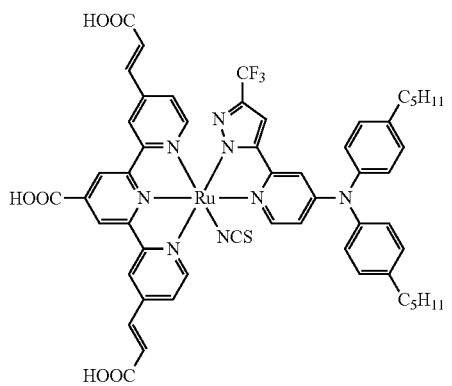
D-144
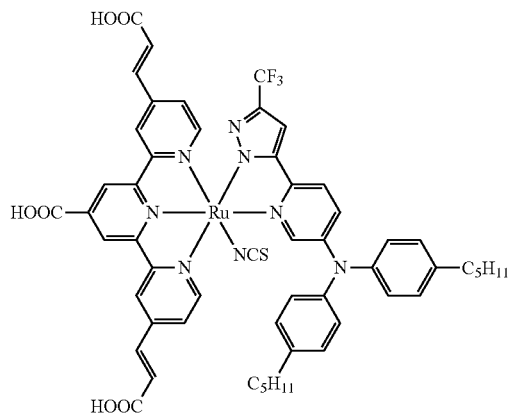
D-145
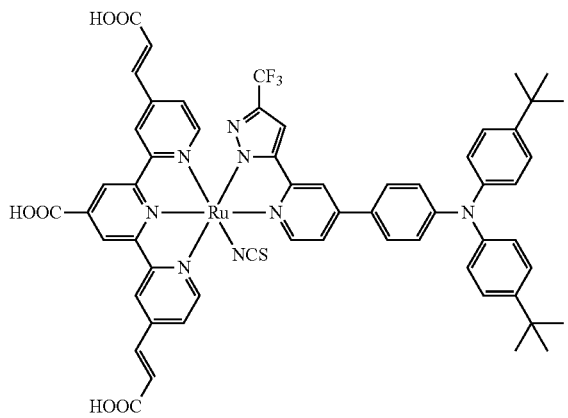
D-146

-continued
D-147
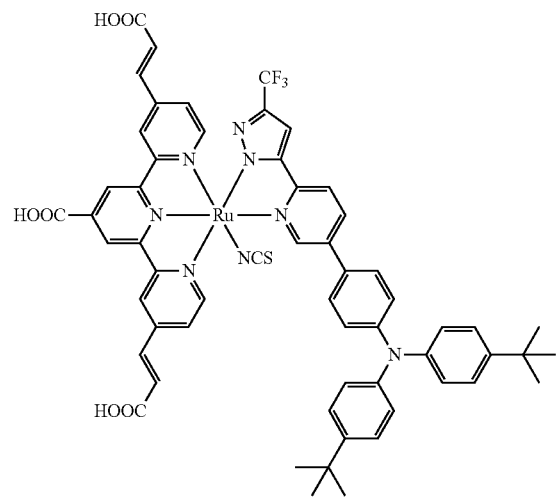
D-148
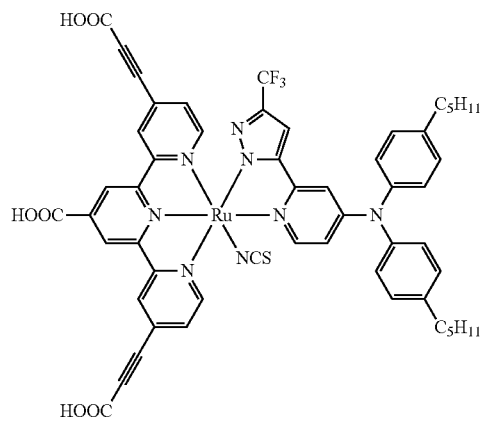
D-149
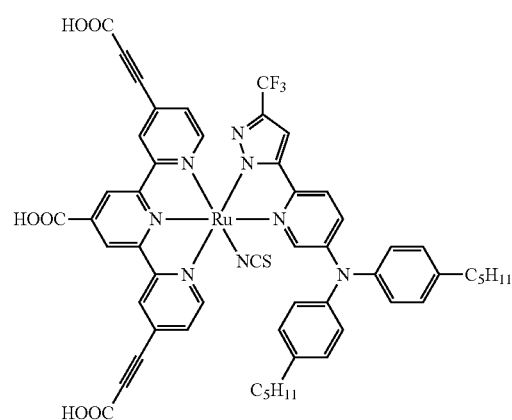
D-150
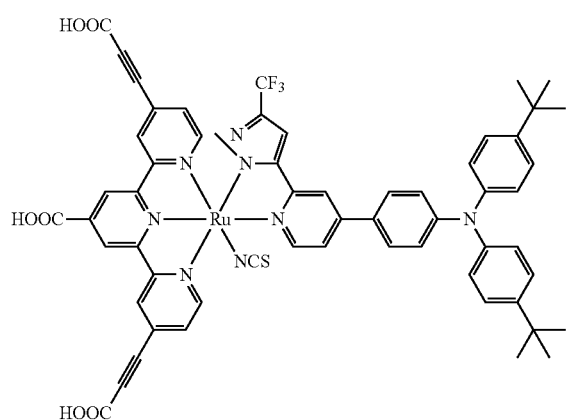
D-151
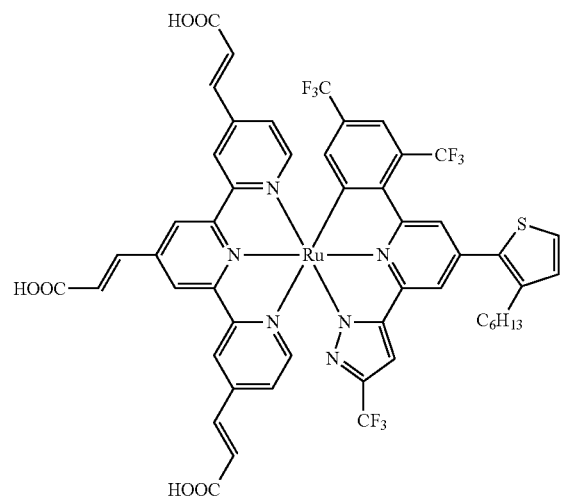
D-152
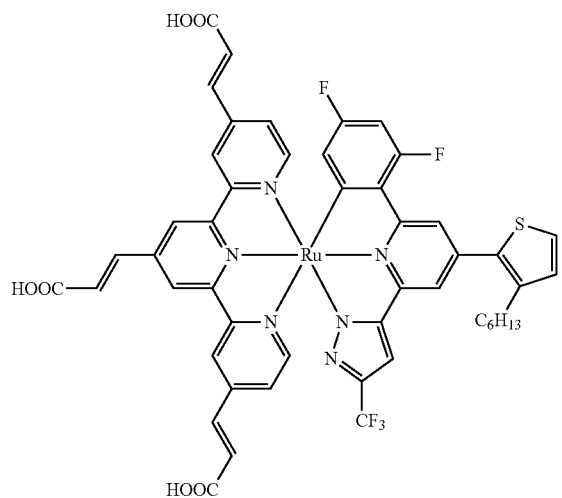

-continued
D-153
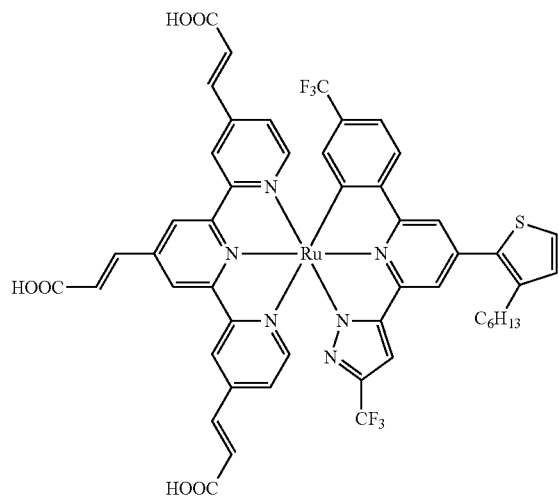
D-154
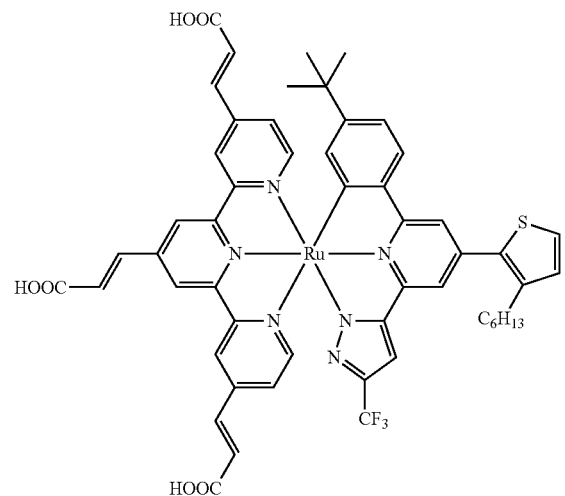
D-155
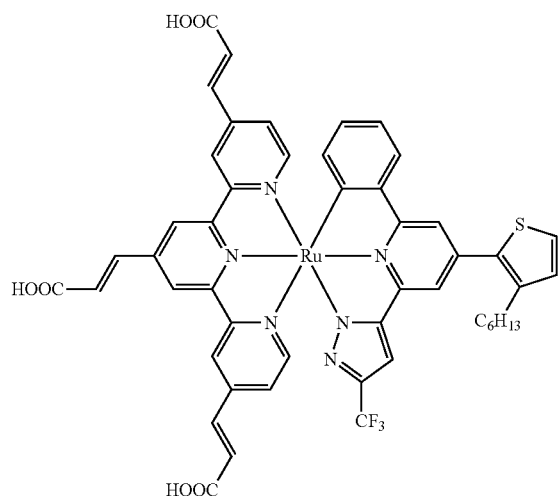
D-156
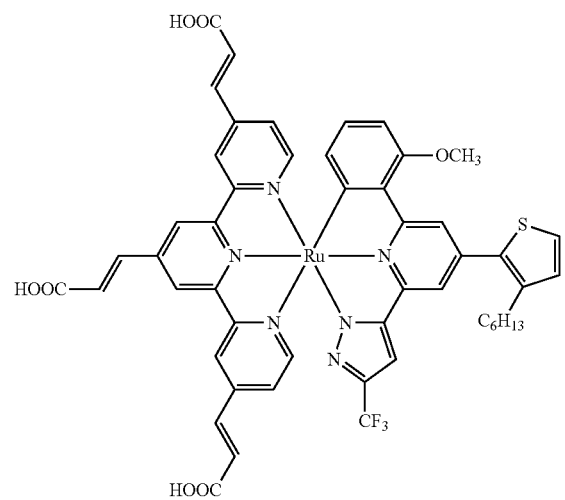
D-157
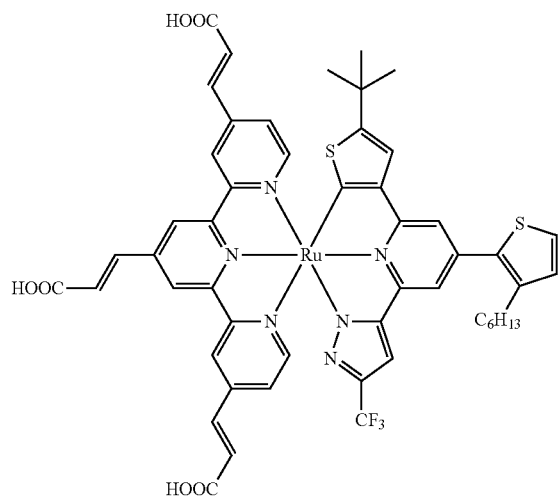
D-158
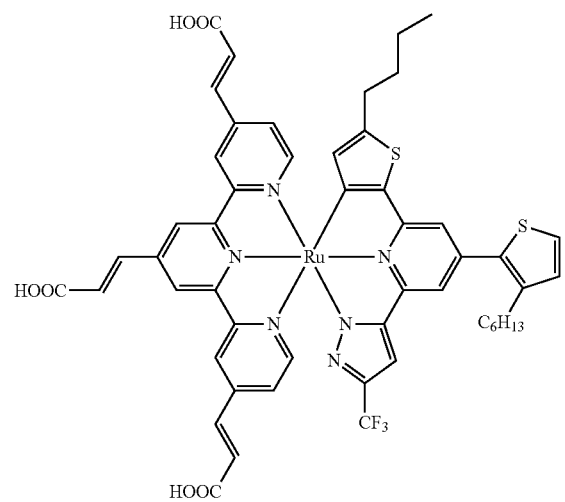

-continued
D-159
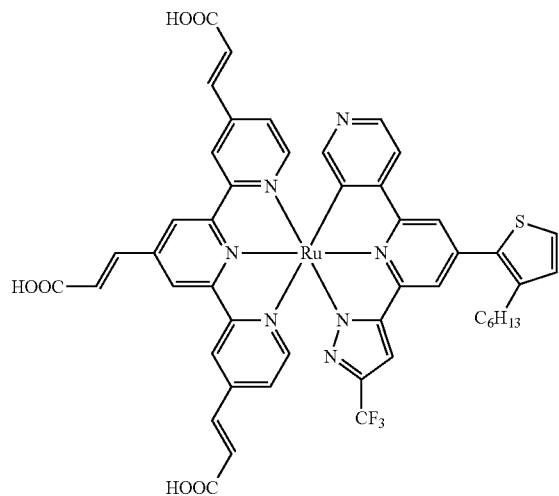
D-160
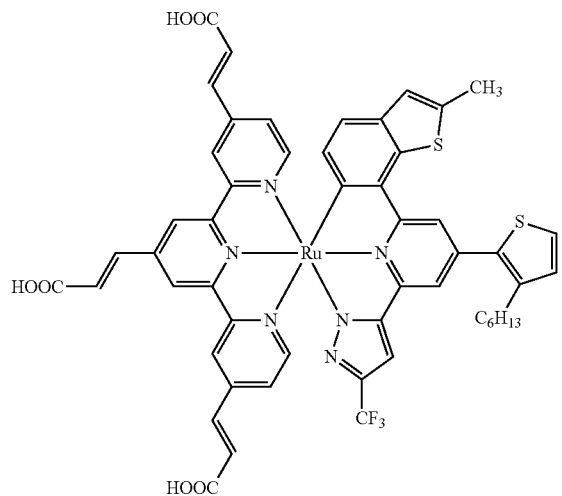
D-161
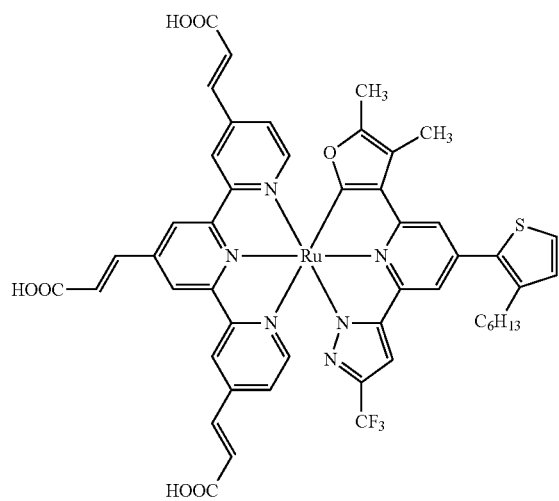
D-162
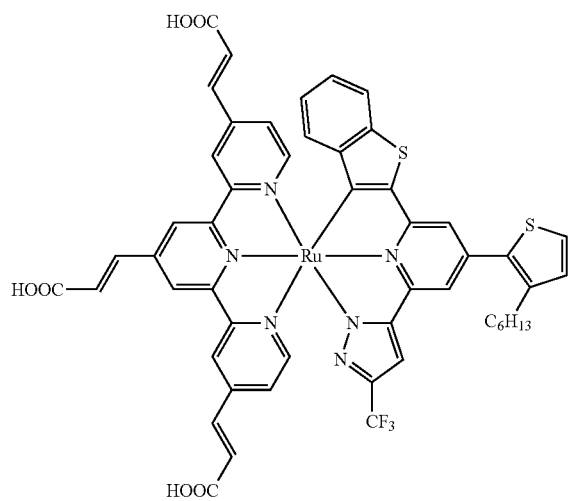
D-163
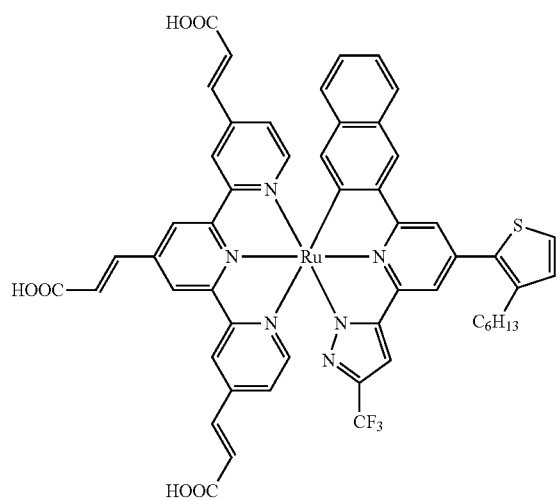
D-164
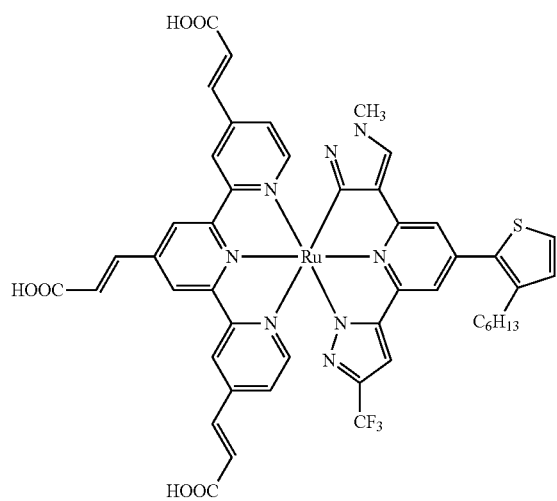

-continued
D-165
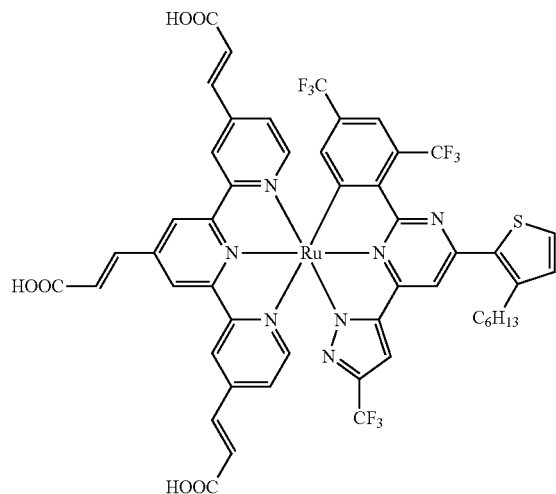
D-166
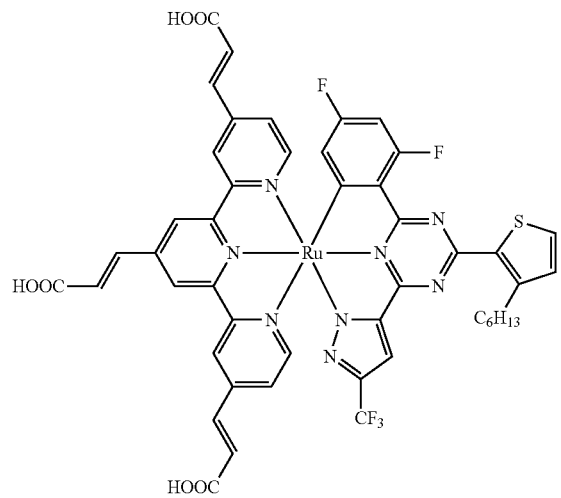
D-167
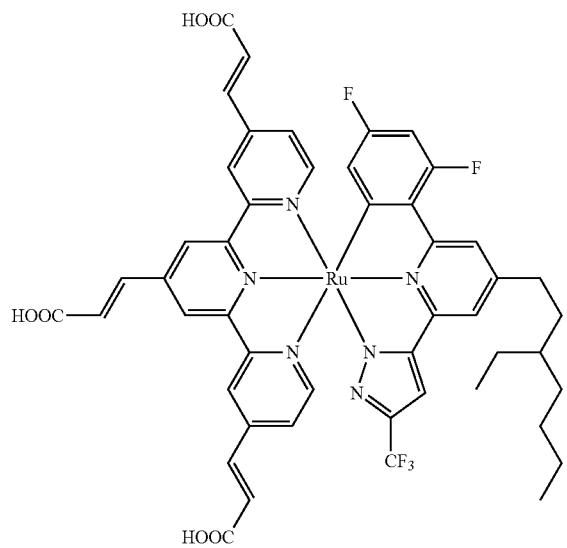
D-168
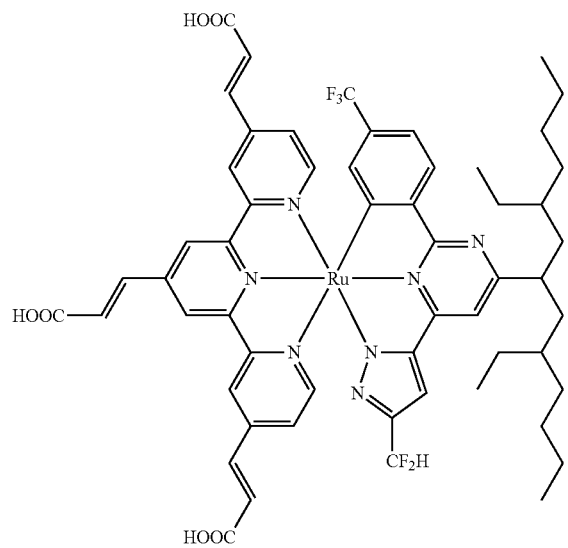
D-169
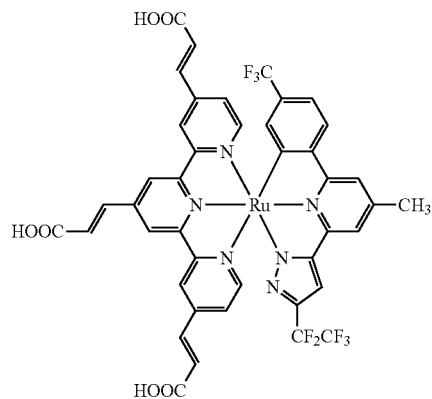
D-170
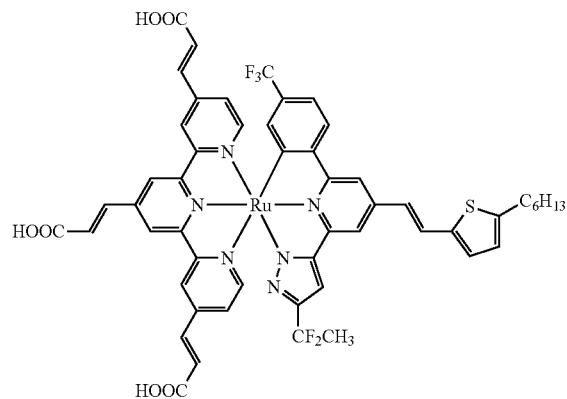

-continued
D-171
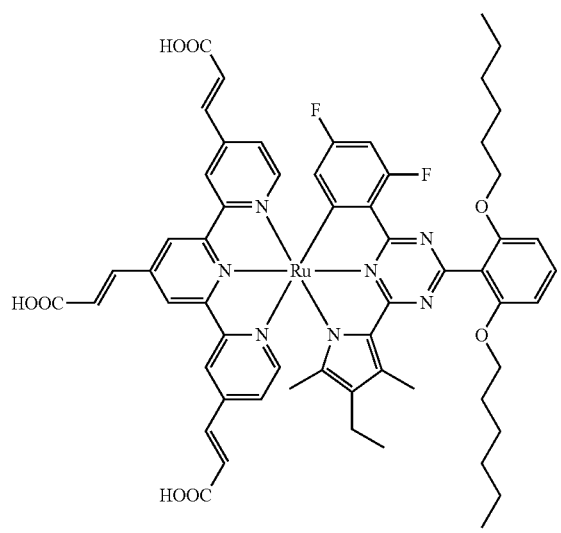
D-172
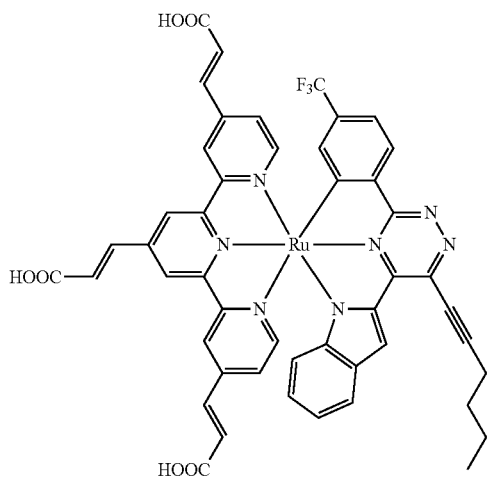
D-173
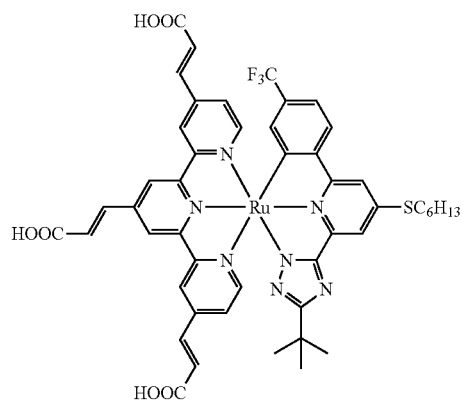
D-174
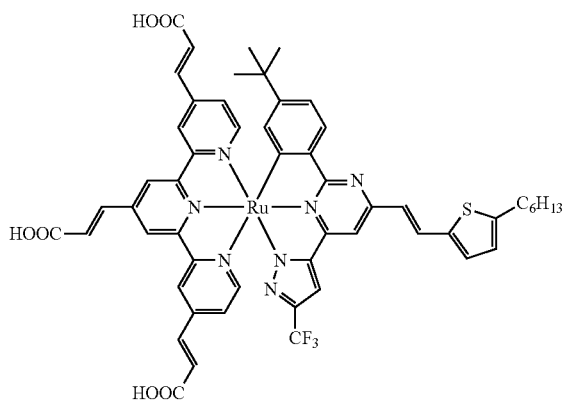
D-175
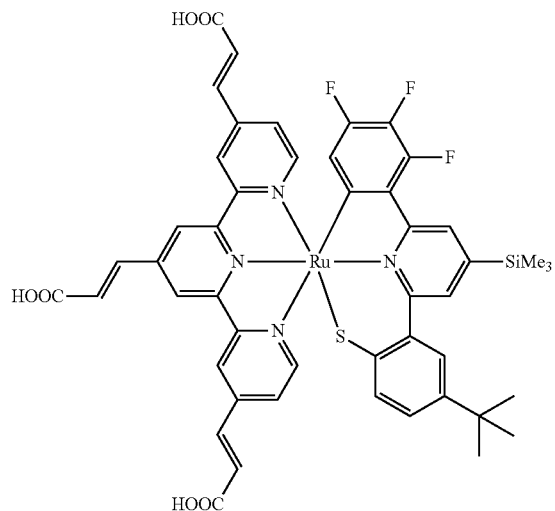
D-176
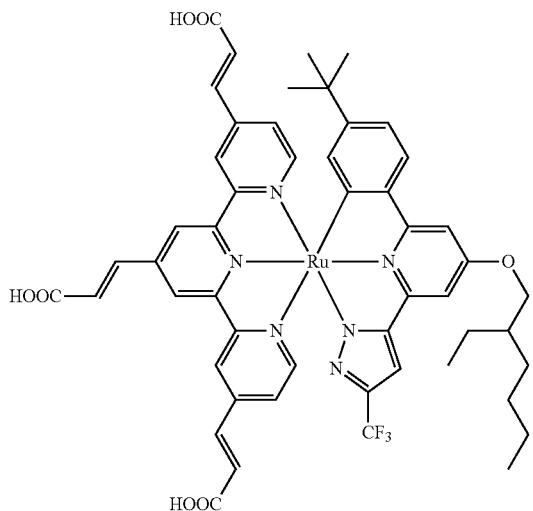

-continued
D-177
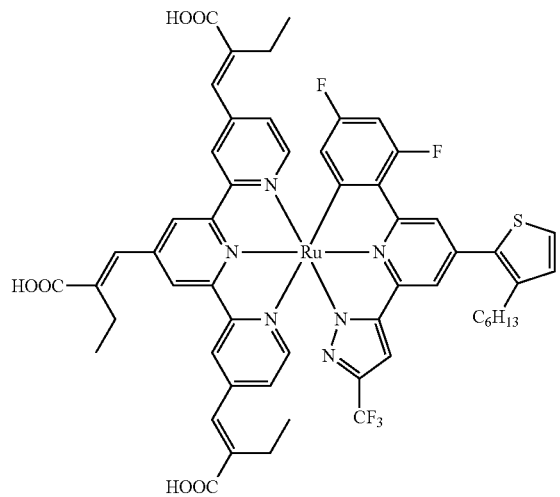
D-178
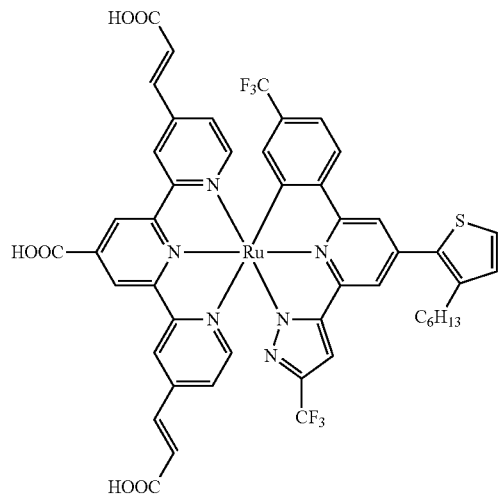
D-179
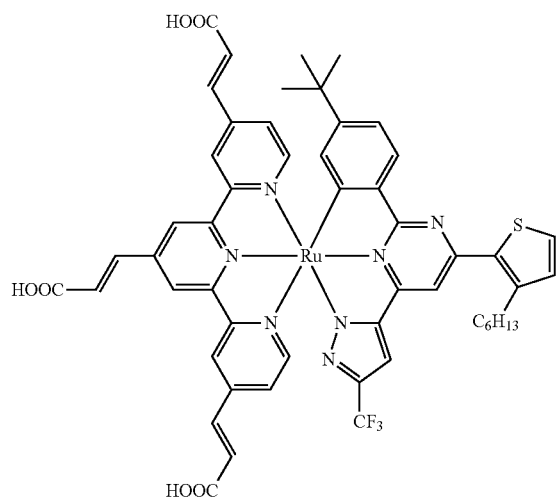
D-180
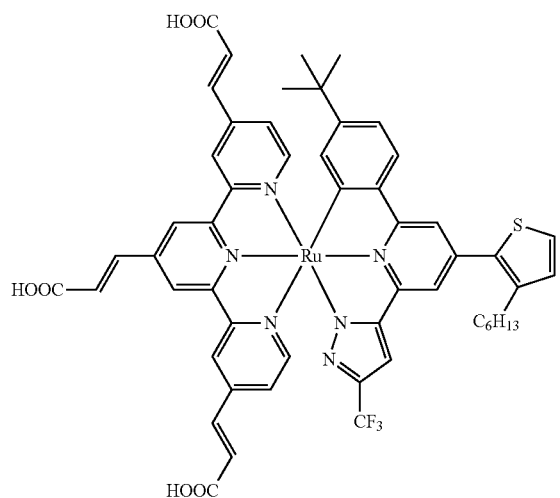
D-181
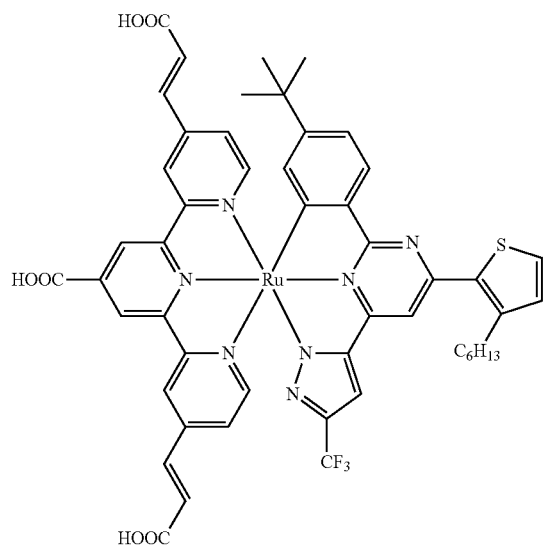
D-182
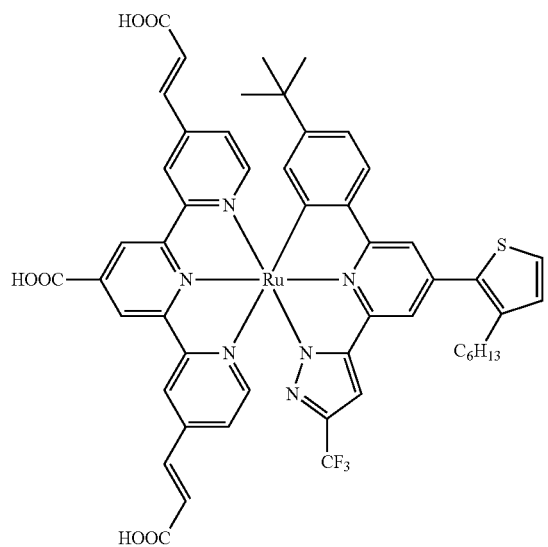

-continued
D-183
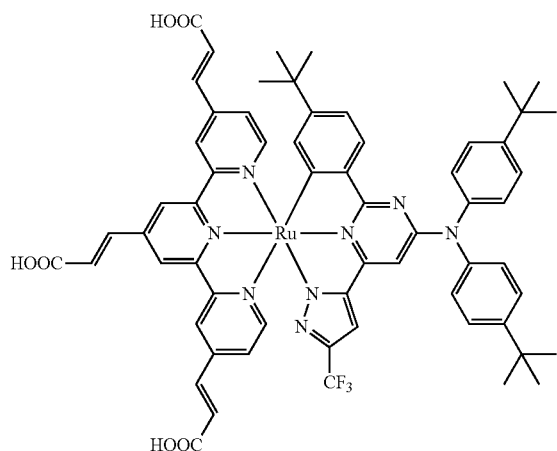
D-184
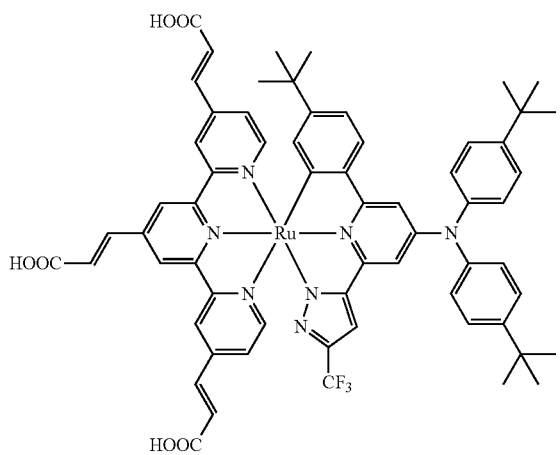
D-185
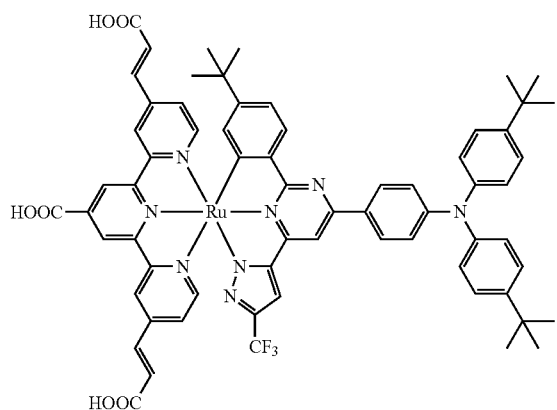
D-186
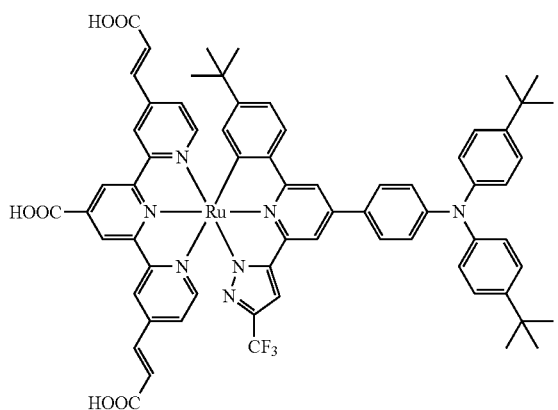
D-187
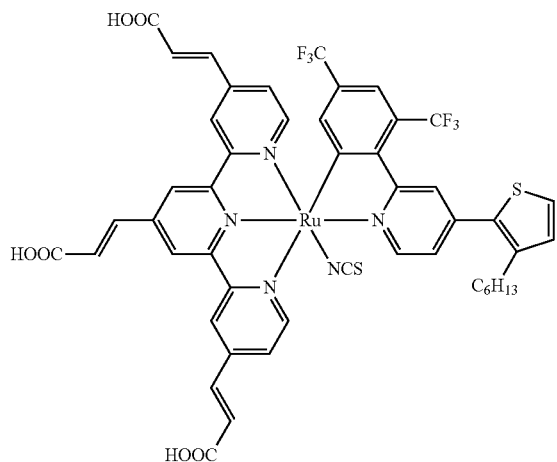
D-188
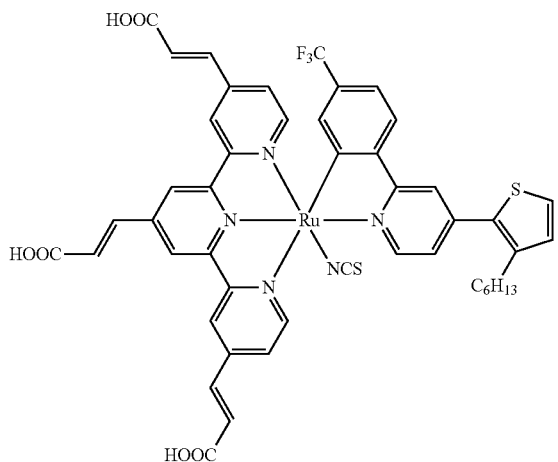

-continued
D-189
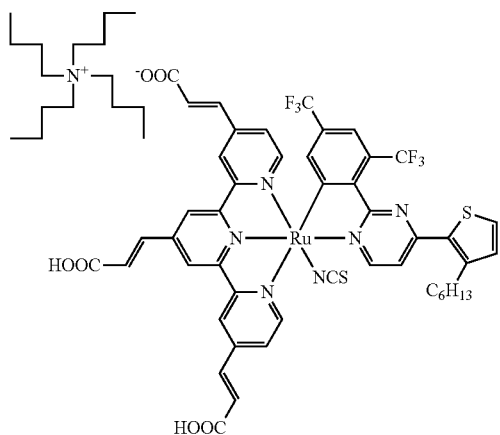
D-190
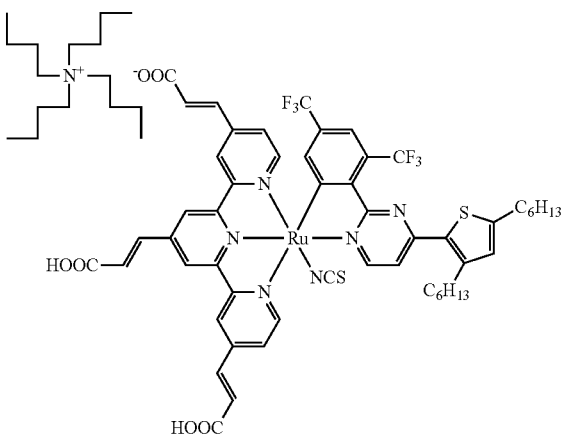
D-191
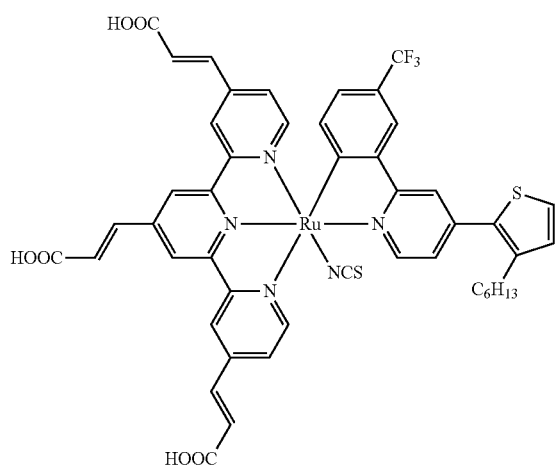
D-192
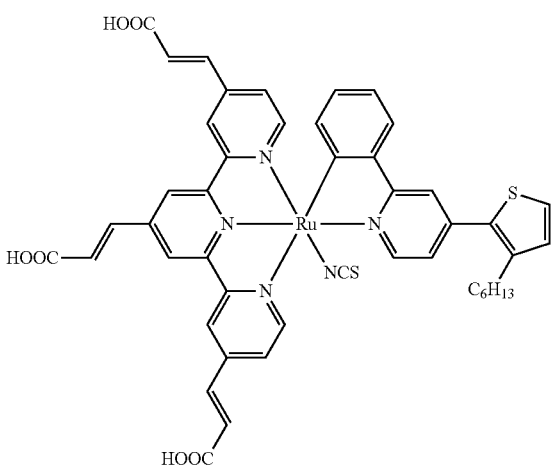
D-193
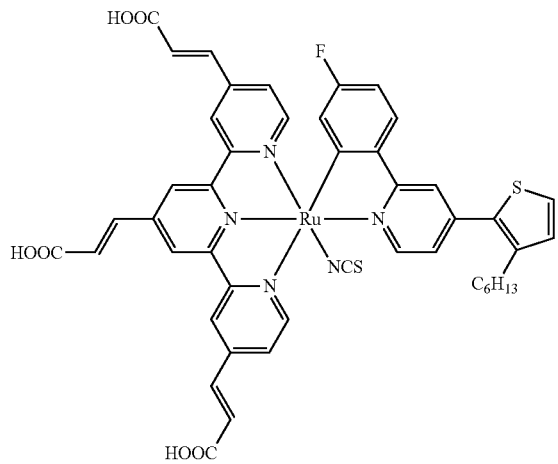
D-194
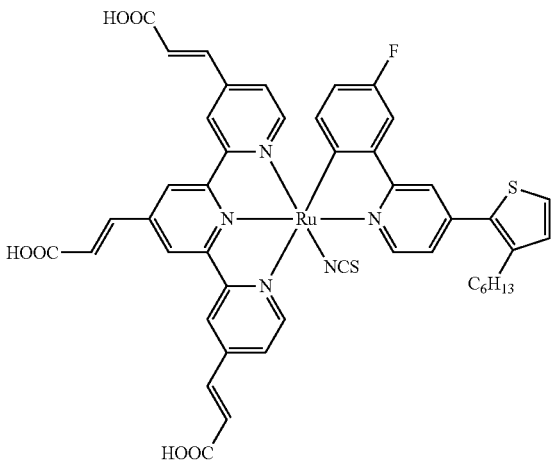

-continued
D-195
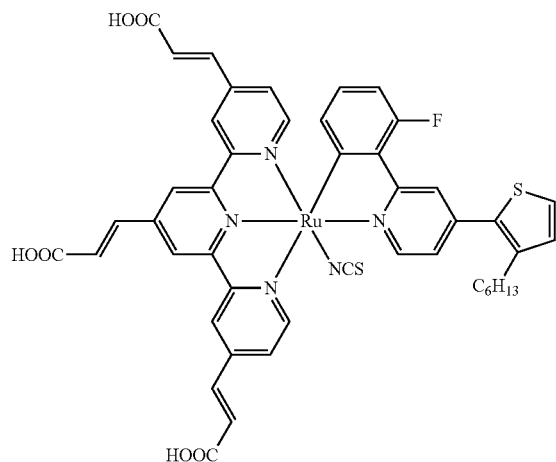
D-196
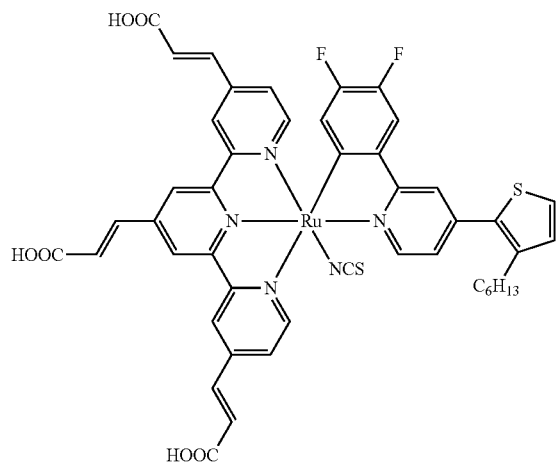
D-197
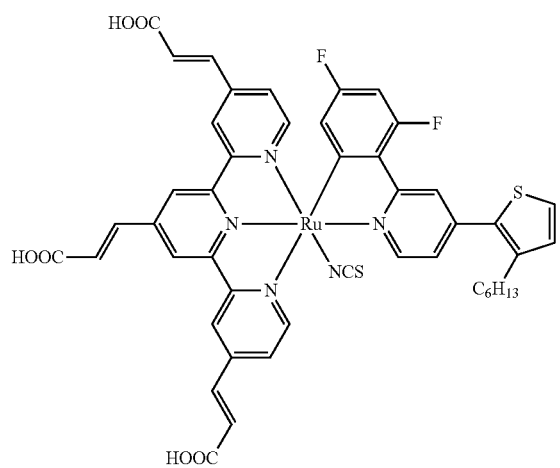
D-198
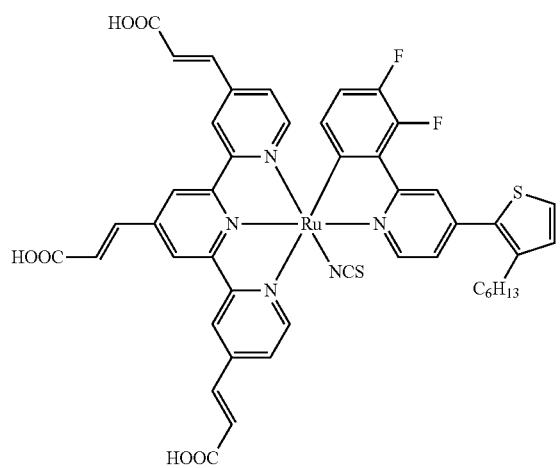
D-199
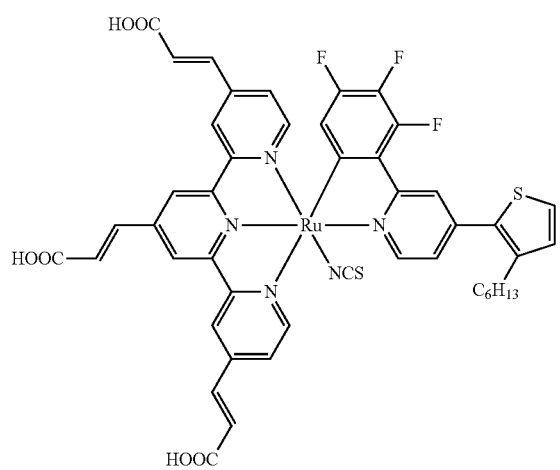
D-200
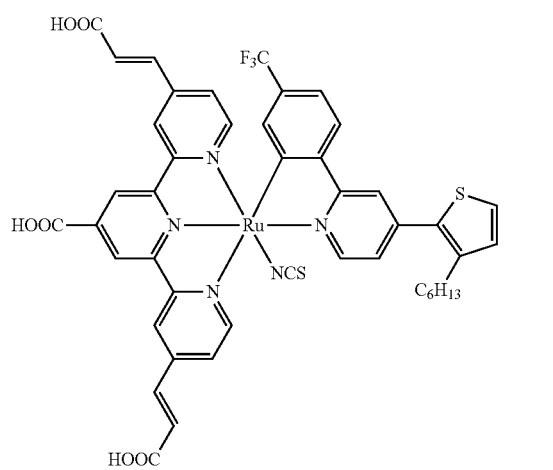

-continued
D-201
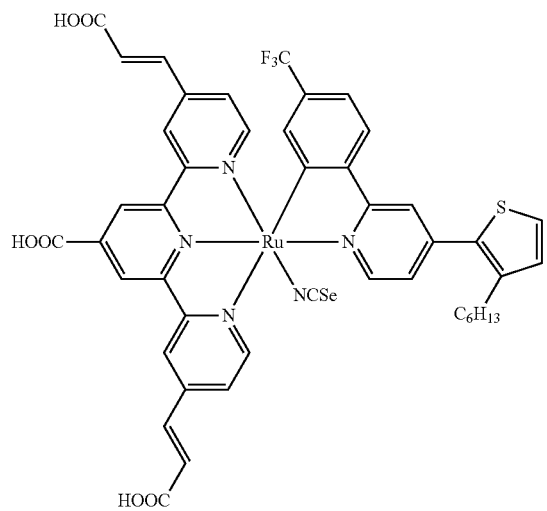
D-202
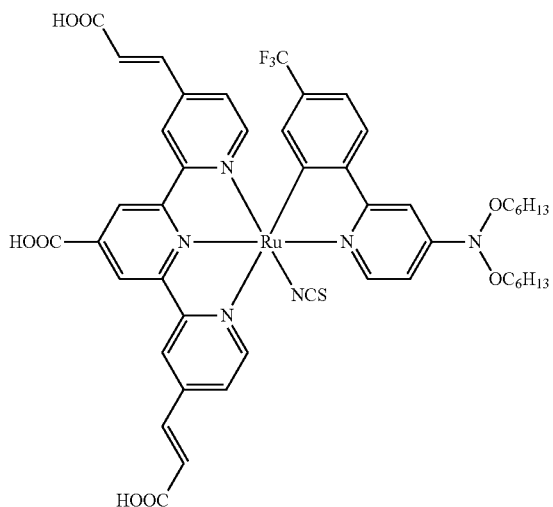
D-203
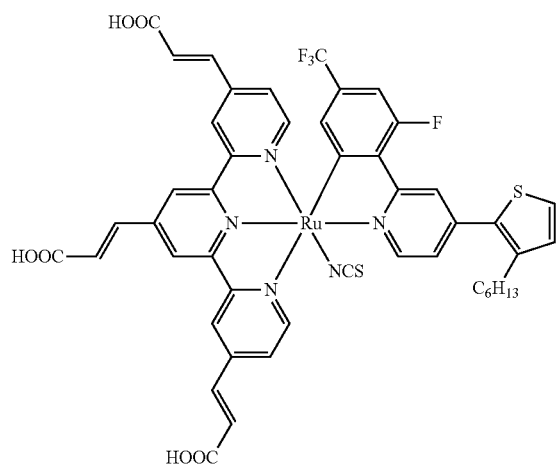
D-204
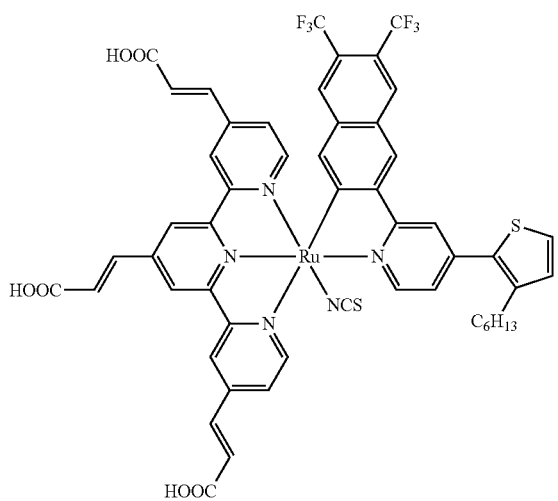
D-205
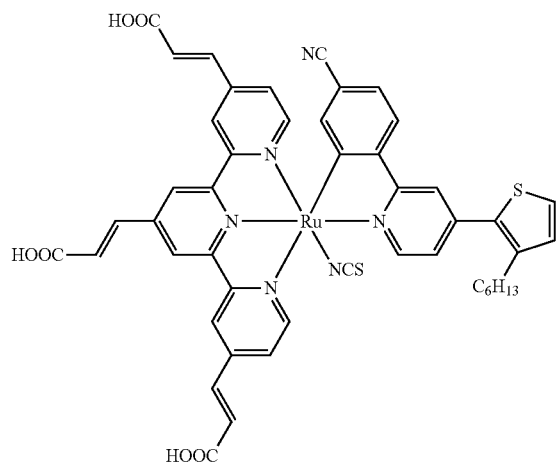
D-206
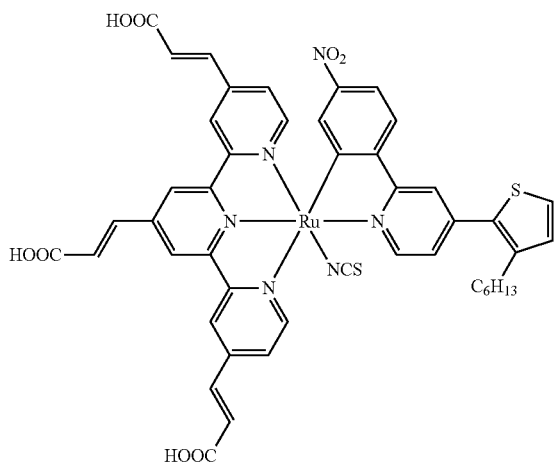

-continued
D-207
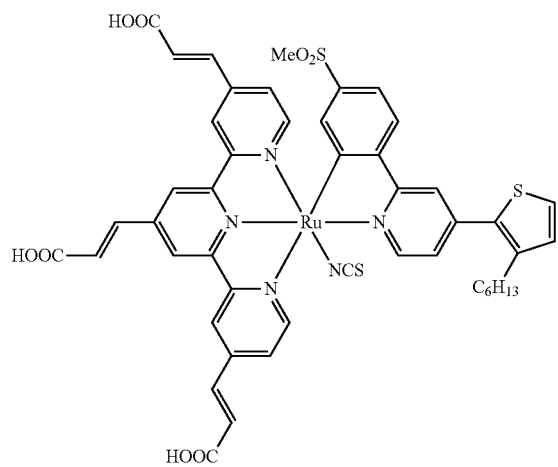
D-208
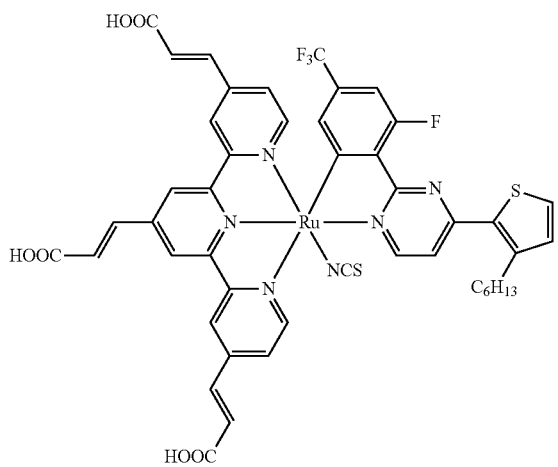
D-209
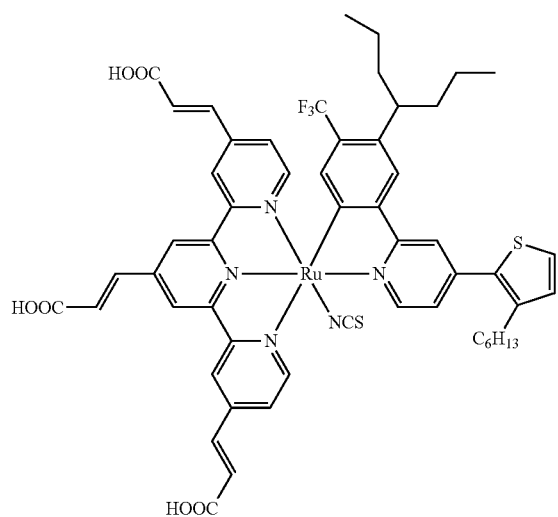
D-210
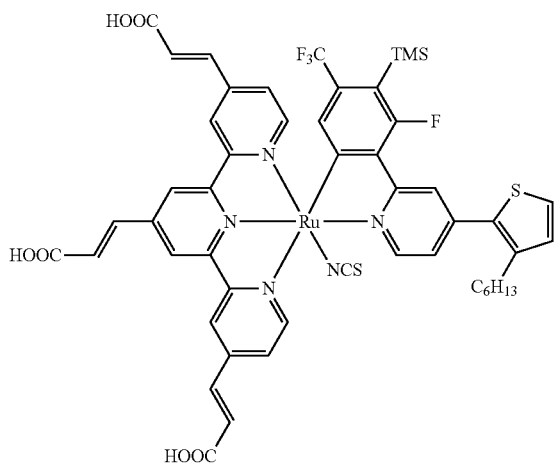
D-211
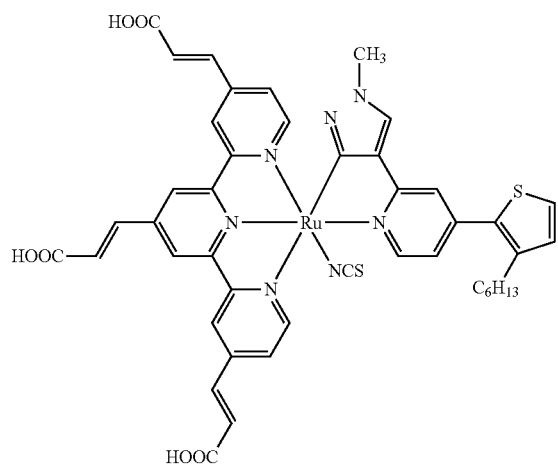
D-212
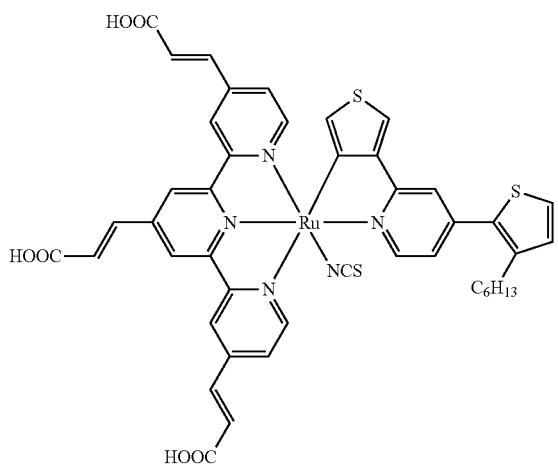

-continued
D-213
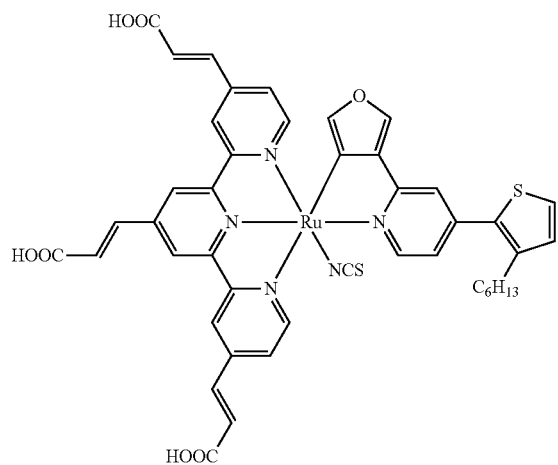
D-214
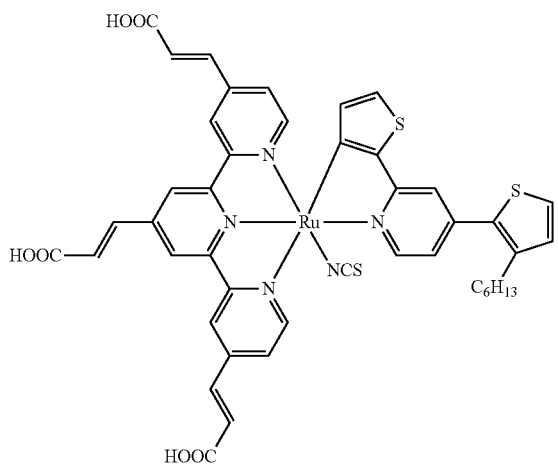
D-215
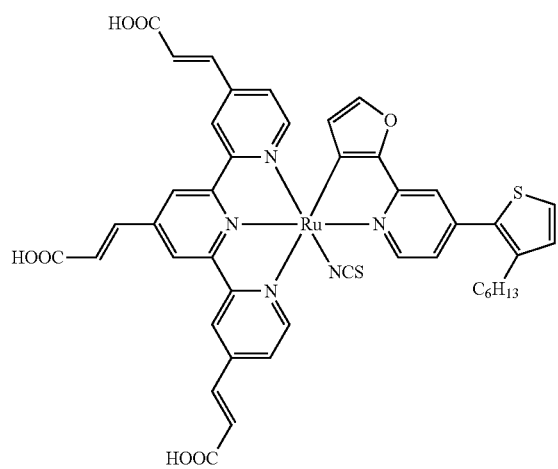
D-216
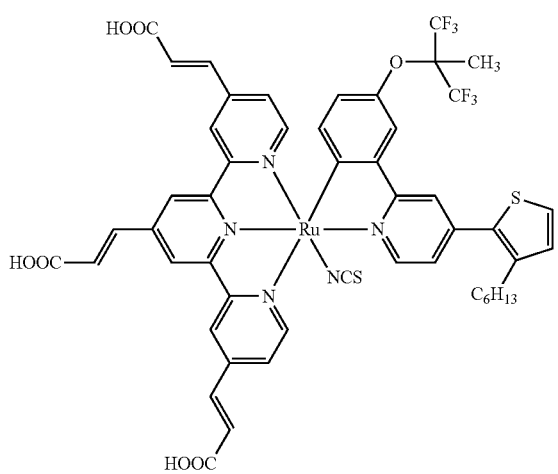
D-217
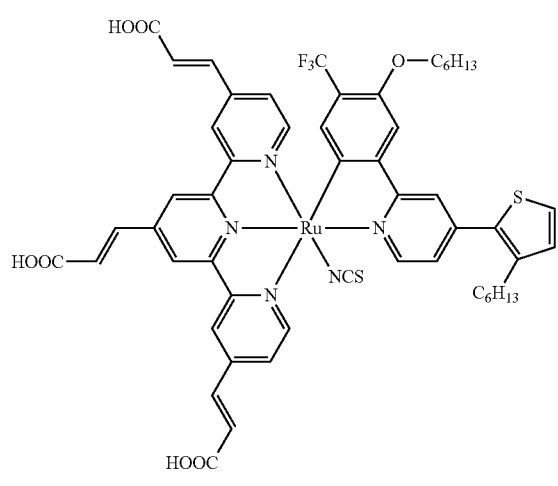
D-218
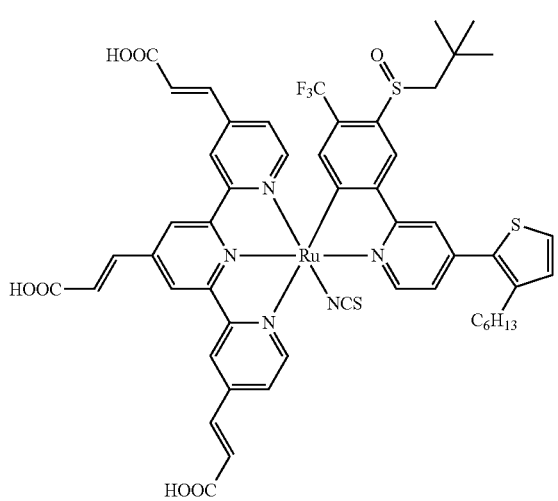

-continued
D-219
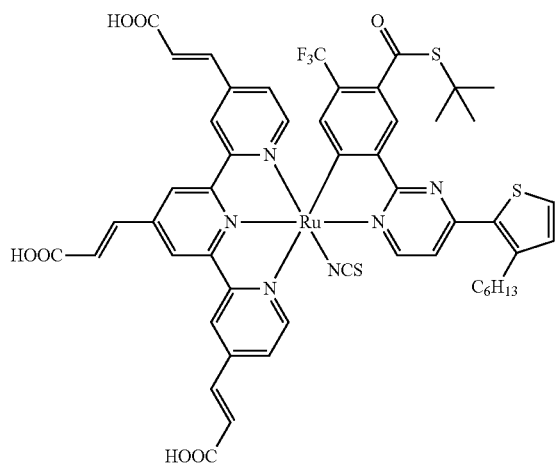
D-220
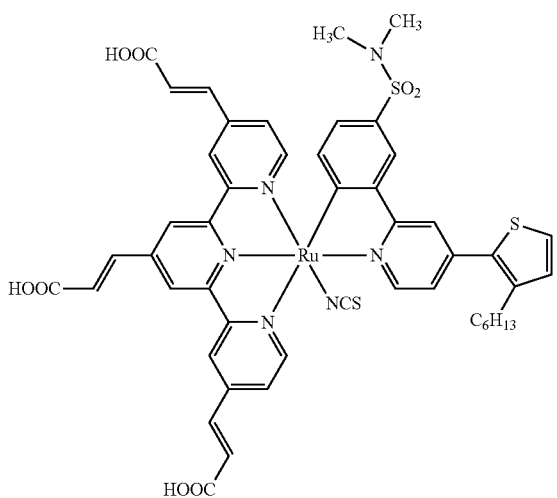
D-221
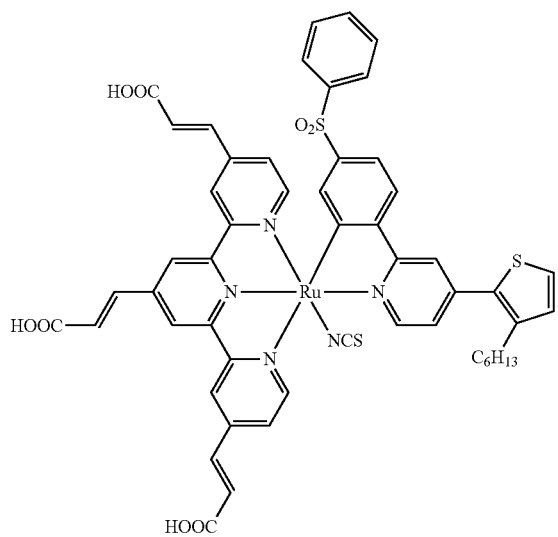
D-222
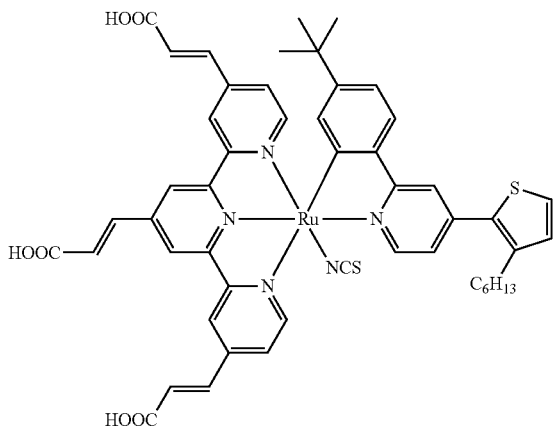
D-223
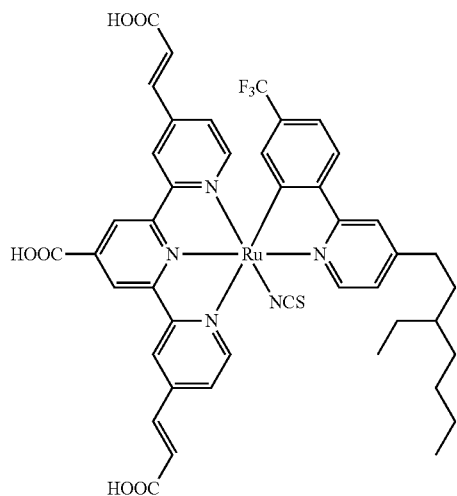
D-224
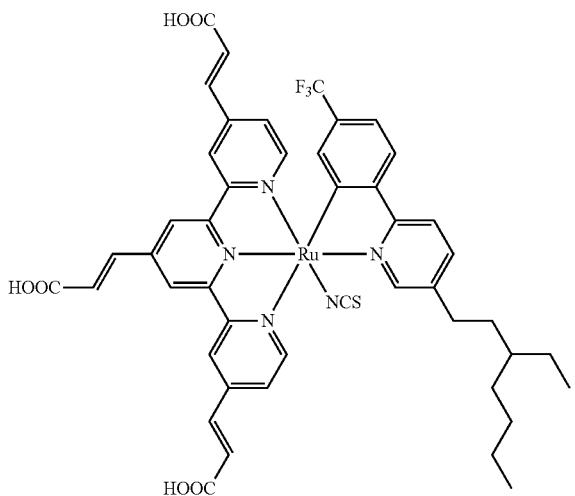

-continued
D-225
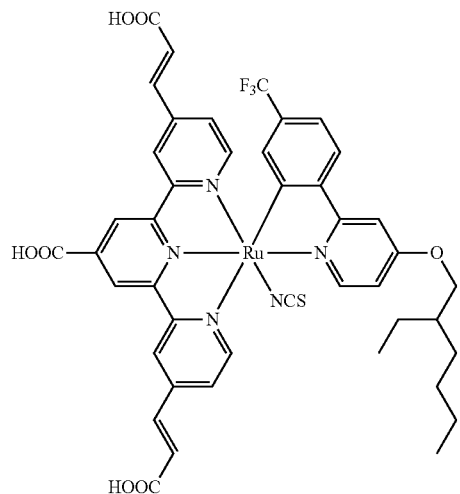
D-226
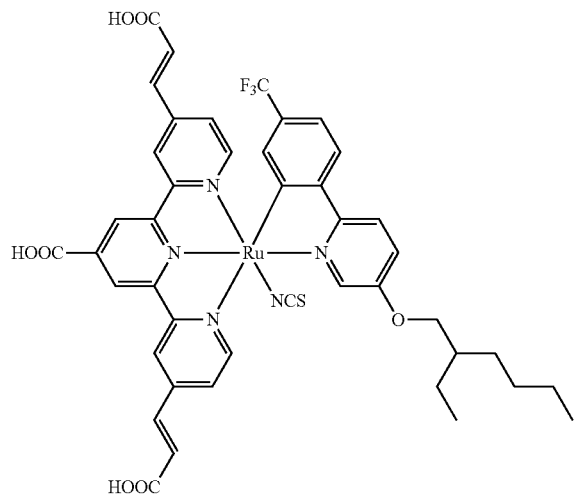
D-227
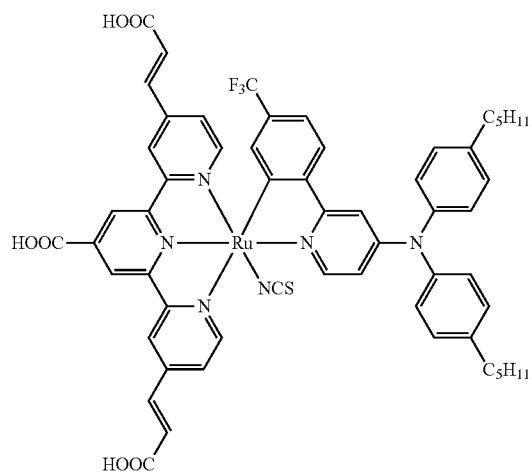
D-228
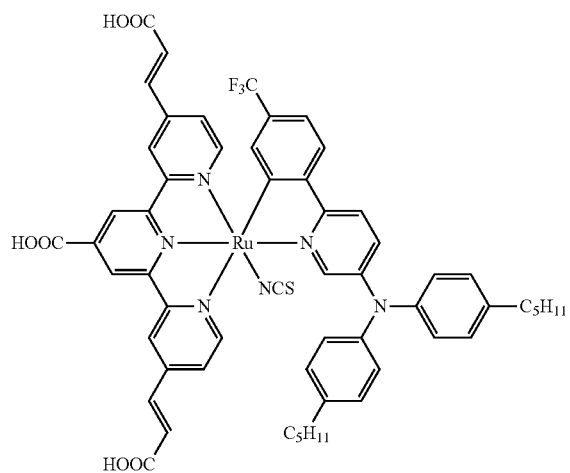
D-229
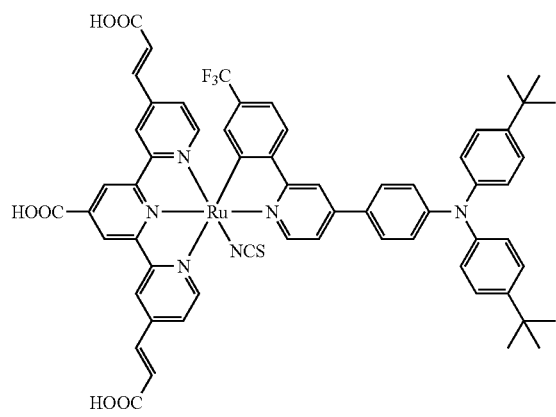
D-230
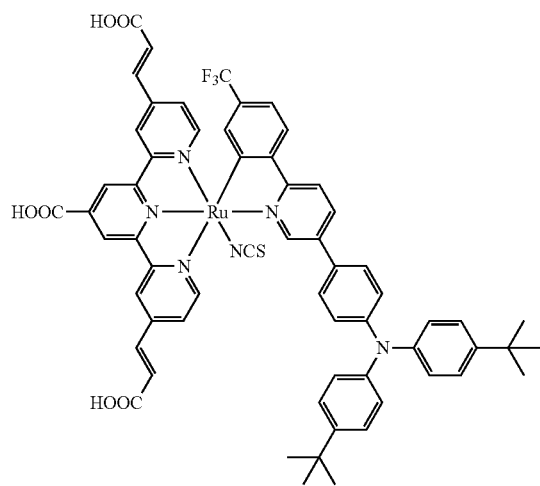

-continued
D-231
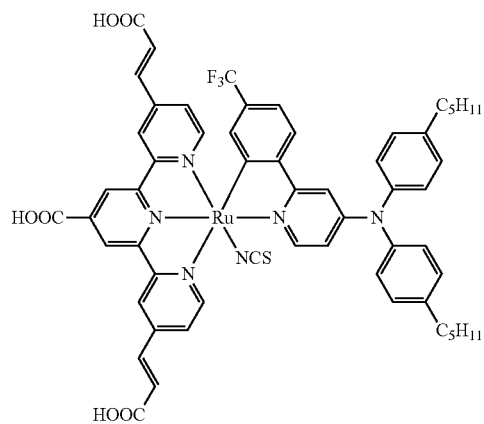
D-232
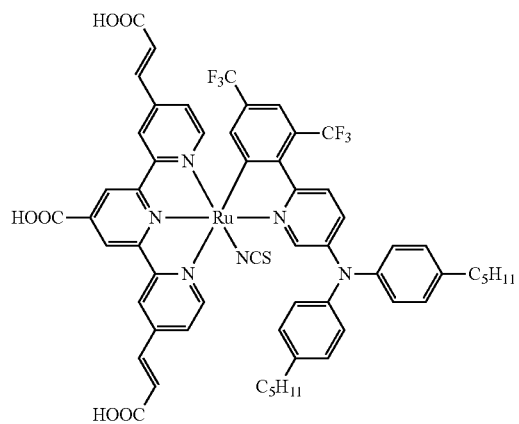
D-233
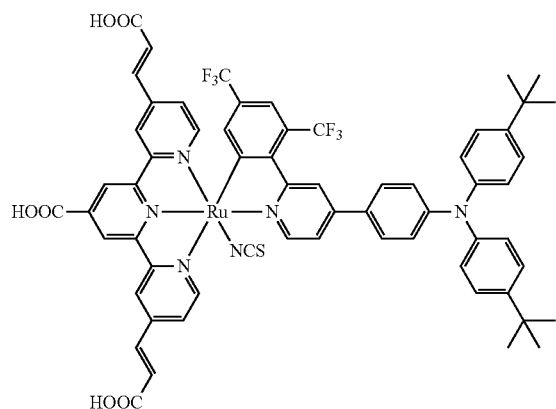
D-234
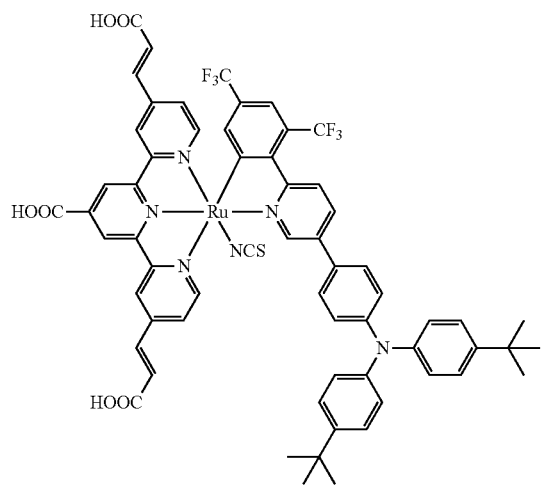
D-235
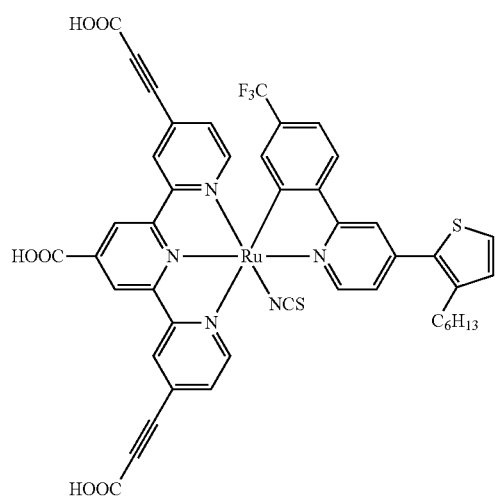
D-236
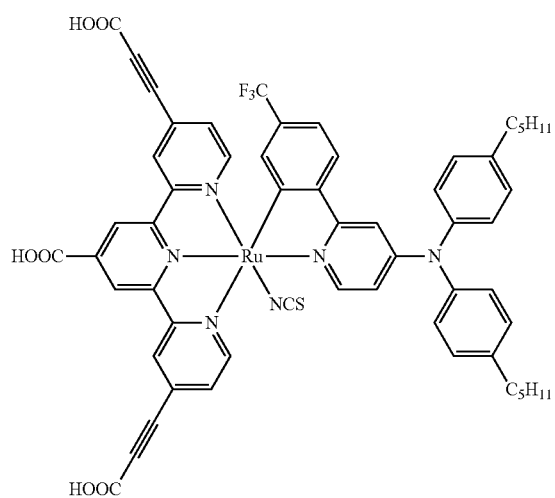

-continued
D-237
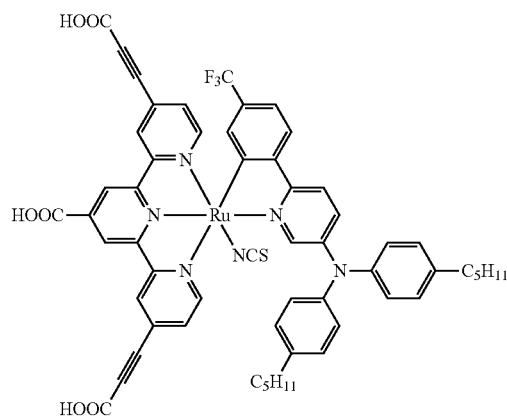
D-238
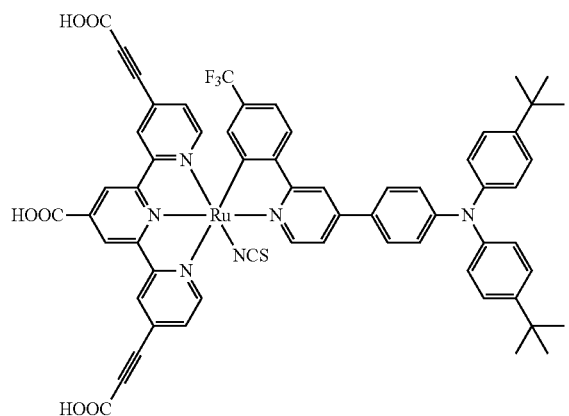
D-239
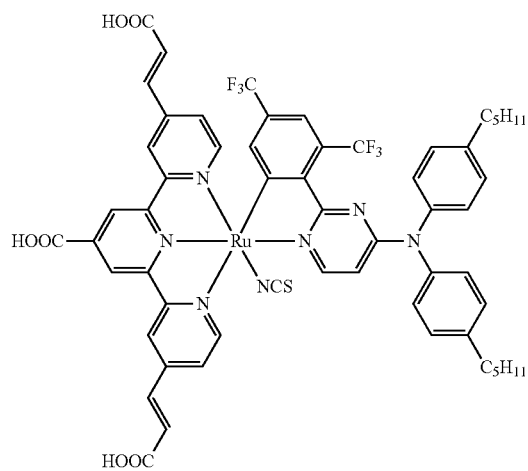
D-240
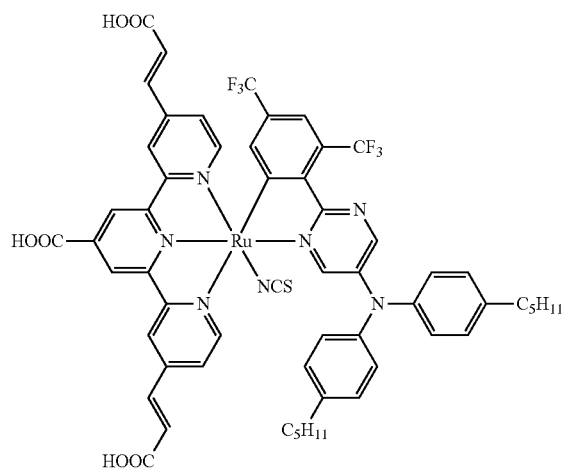
D-241
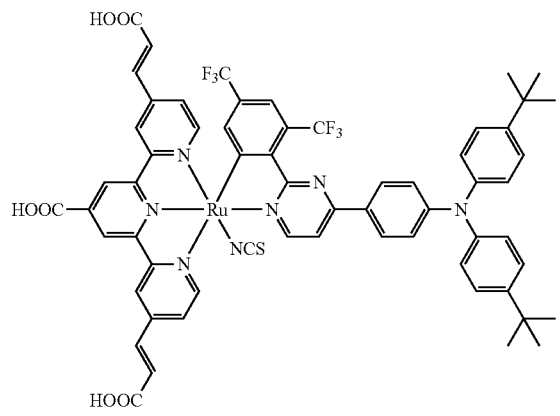
D-242
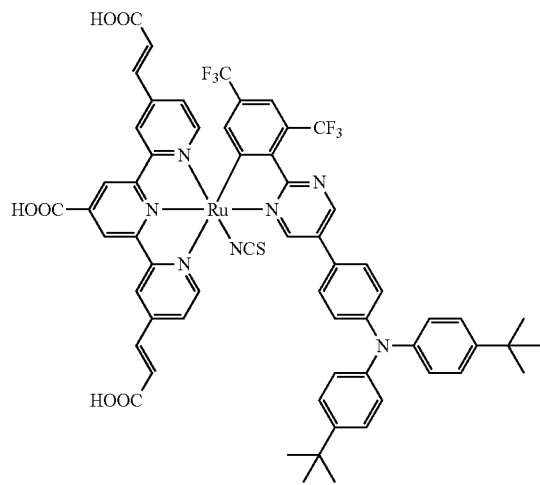

-continued
D-243
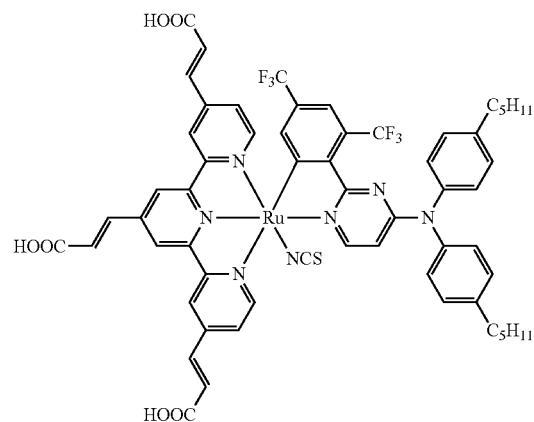
D-244
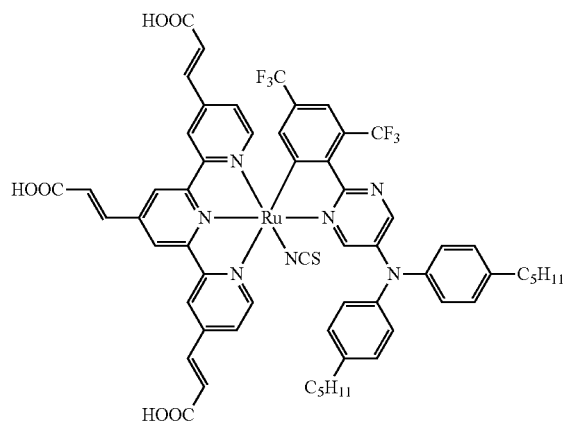
D-245
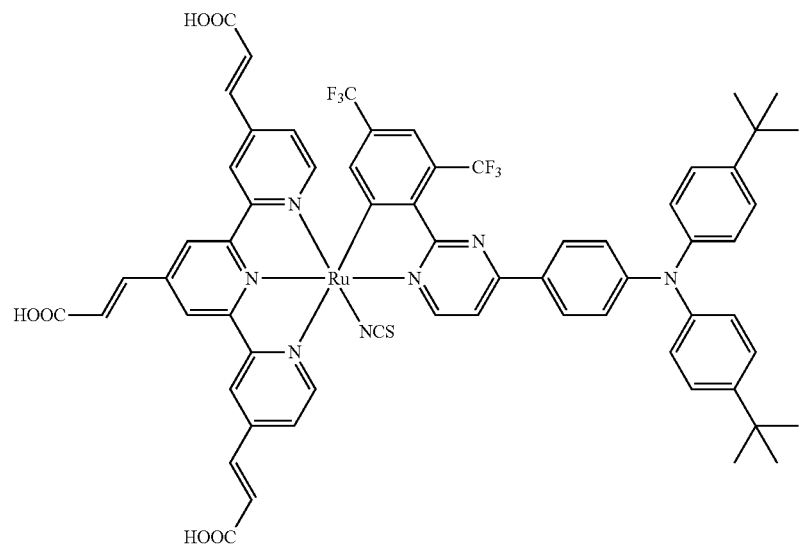
D-246
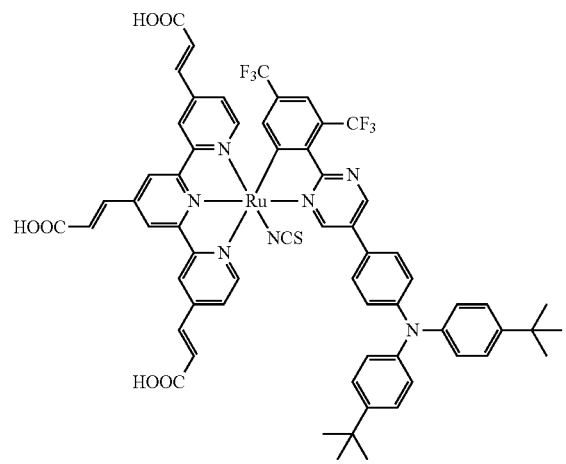
D-247
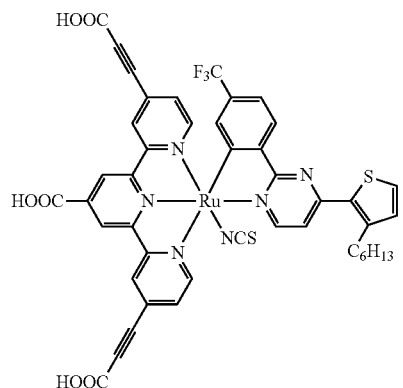

-continued
D-248
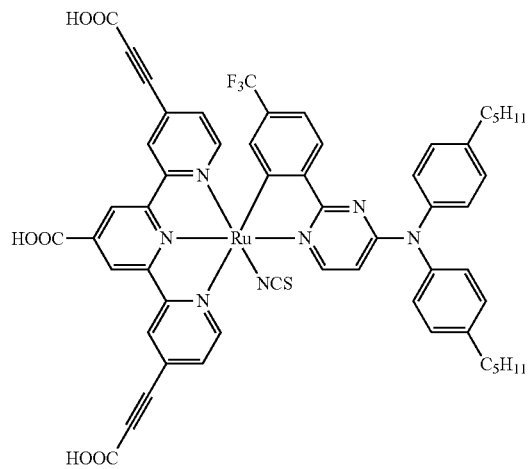
D-249
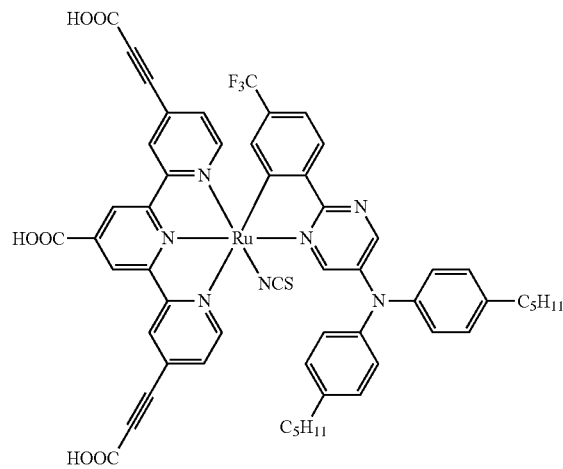
D-250
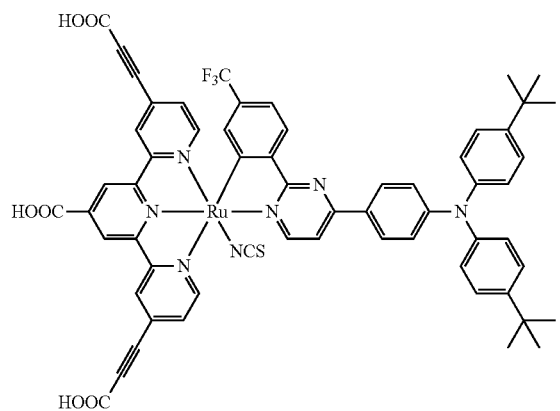
D-251
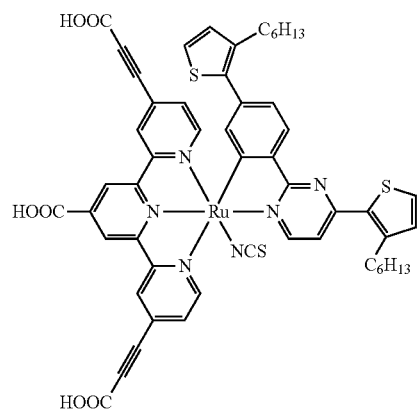
D-252
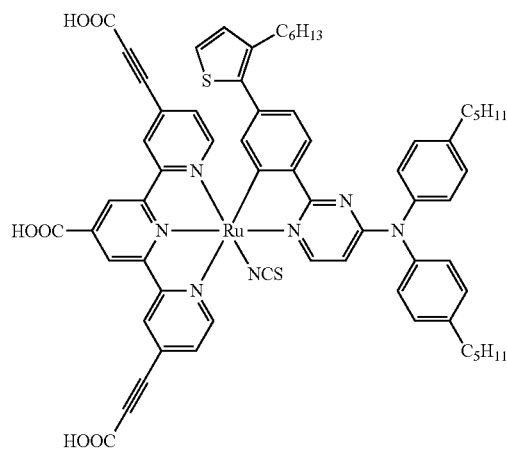
D-253
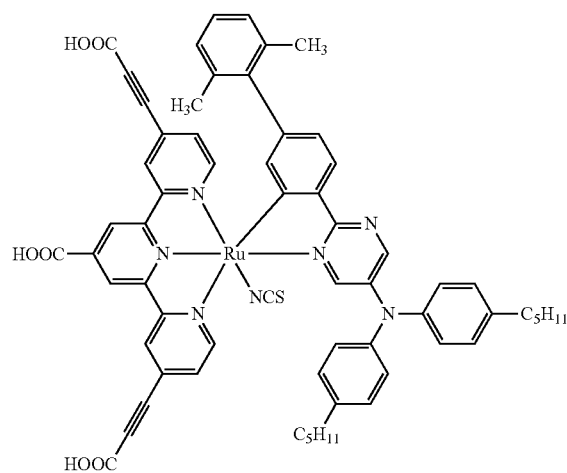

-continued
D-254
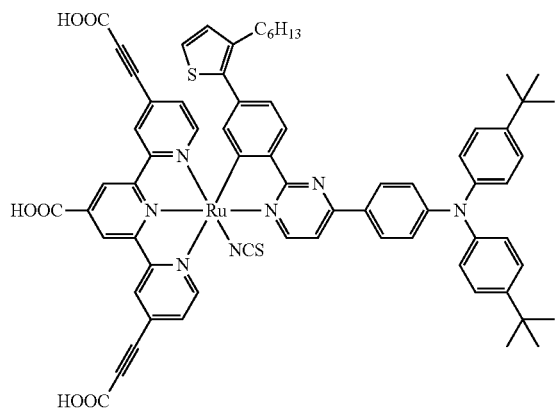
D-255
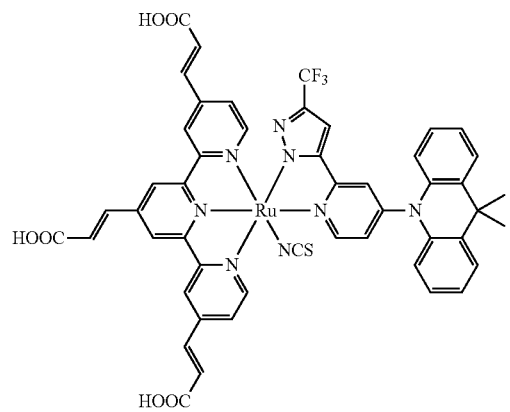
D-256
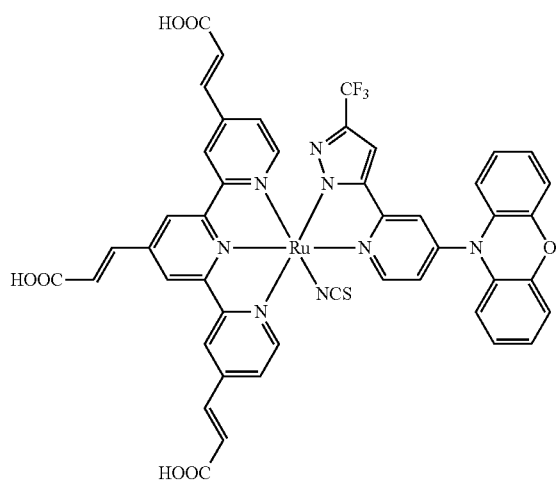
D-257
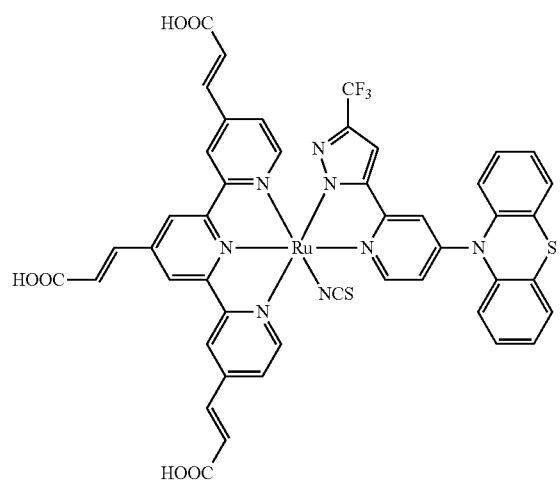
D-258
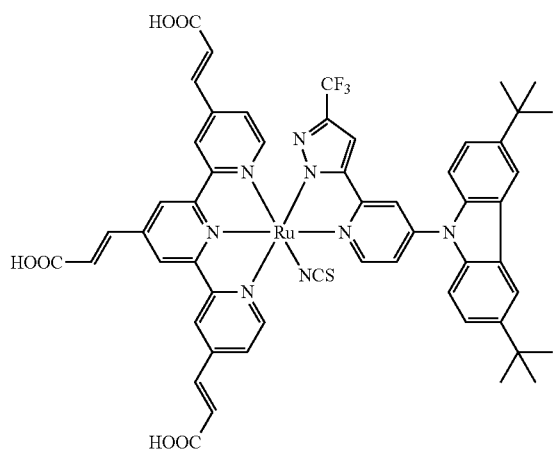
D-259
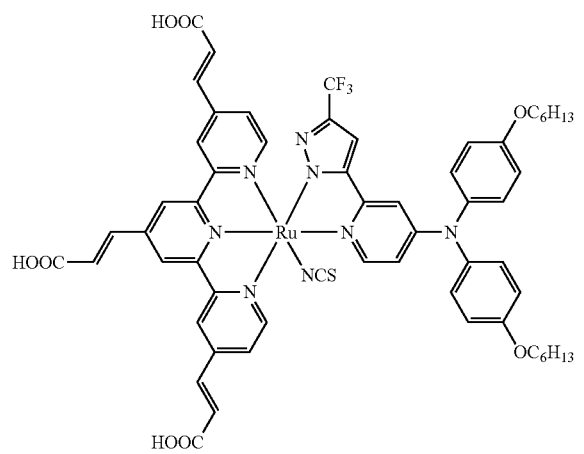

-continued
D-260
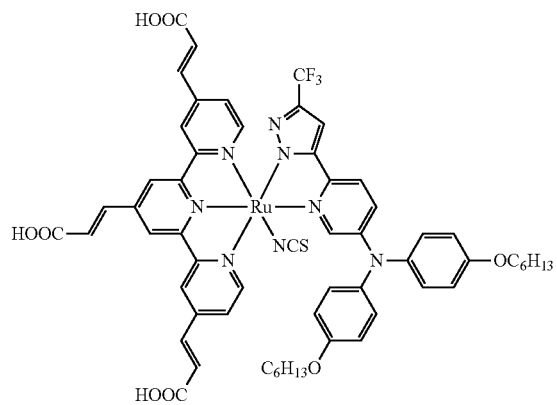
D-261
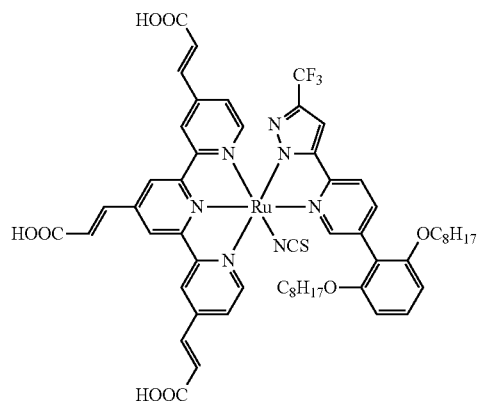
D-262
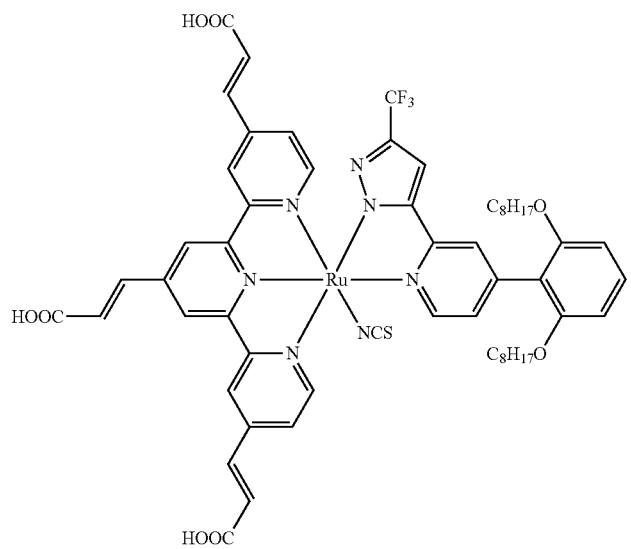
D-263
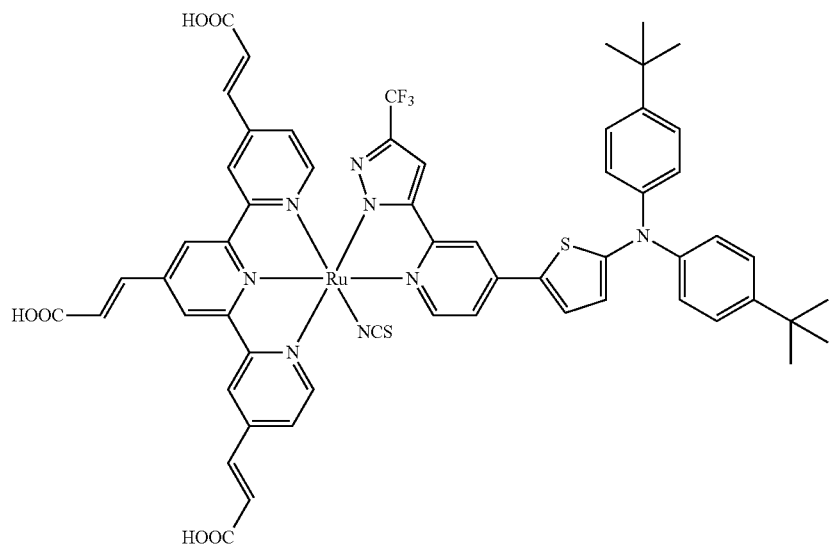

-continued
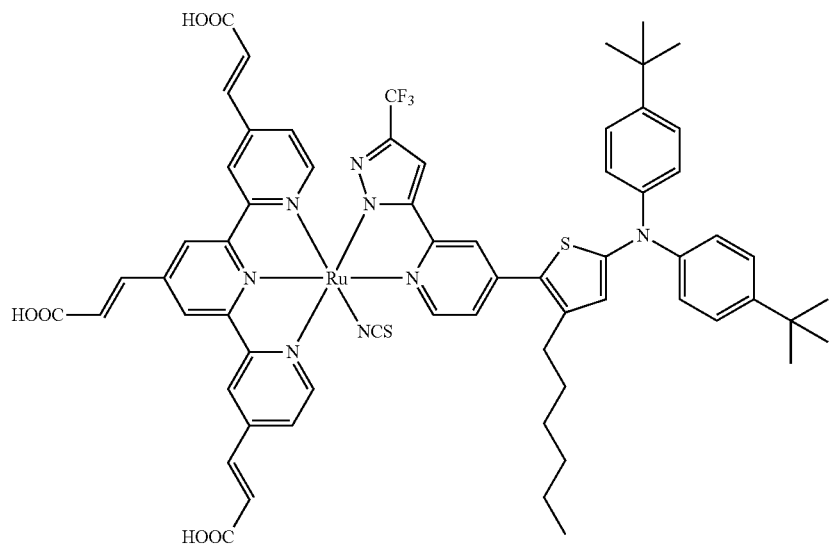
D-264
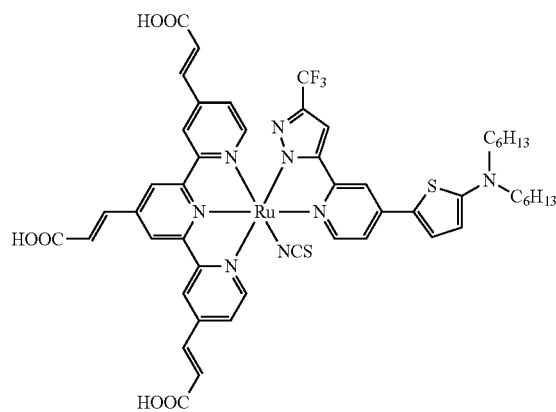
D-265
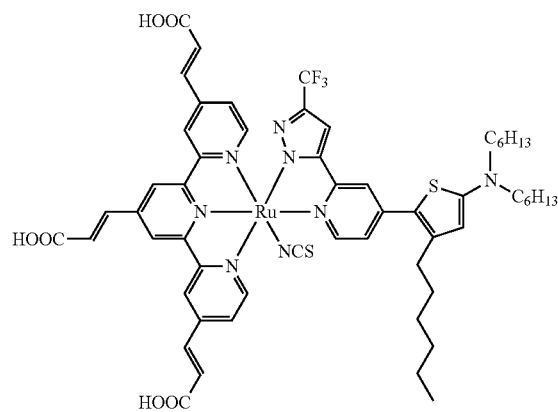
D-266
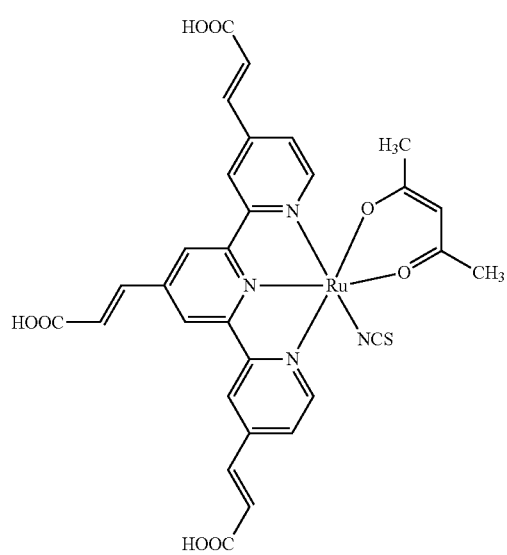
D-267
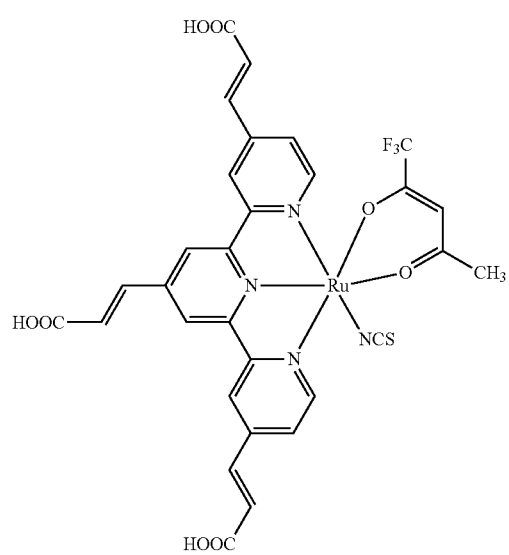
D-268

-continued
D-269
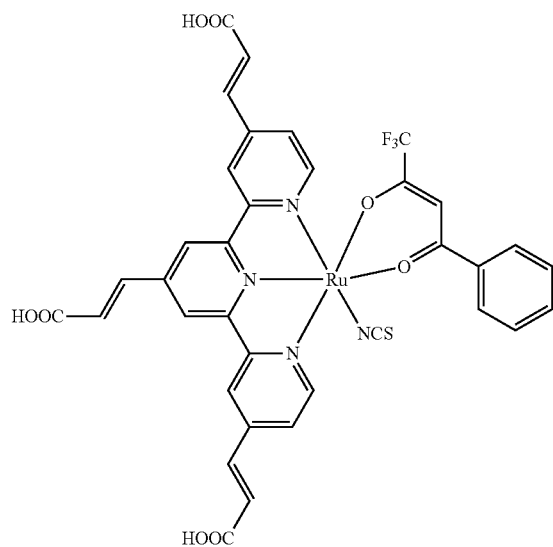
D-270
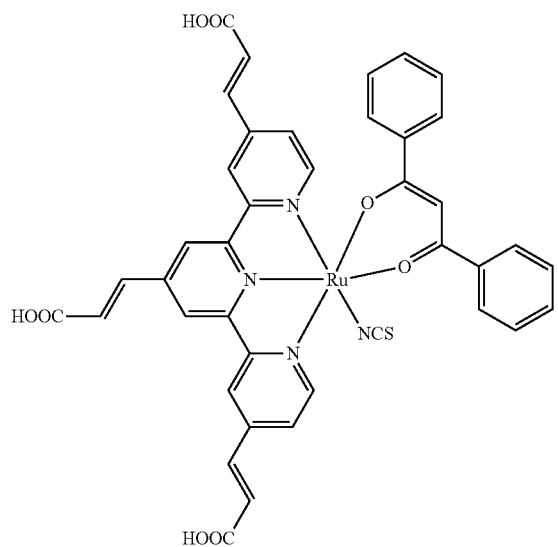
D-271
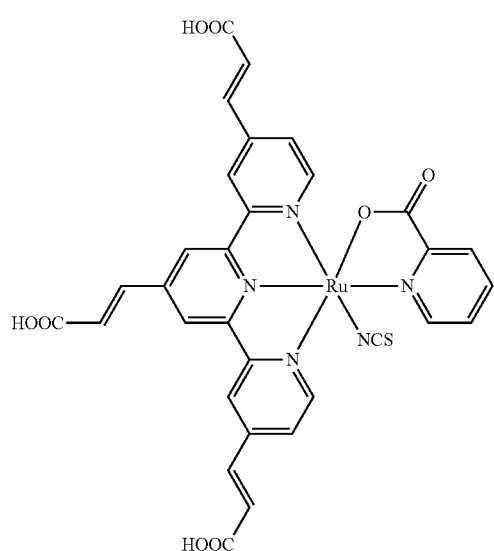
D-272
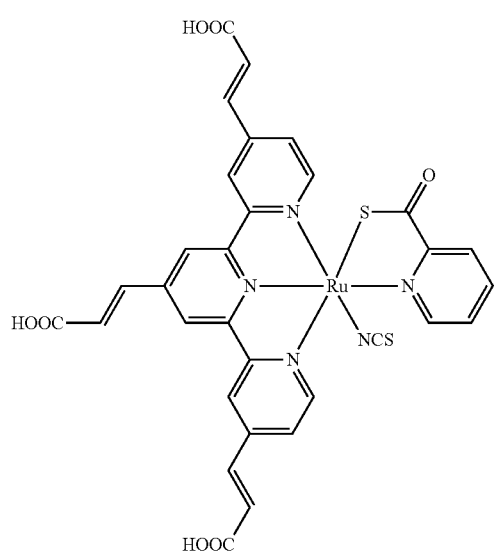
D-273
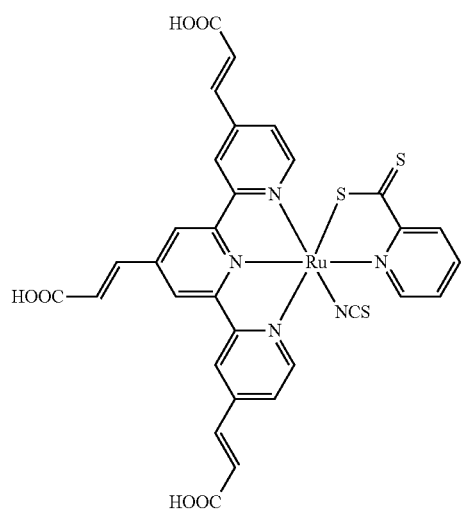
D-274
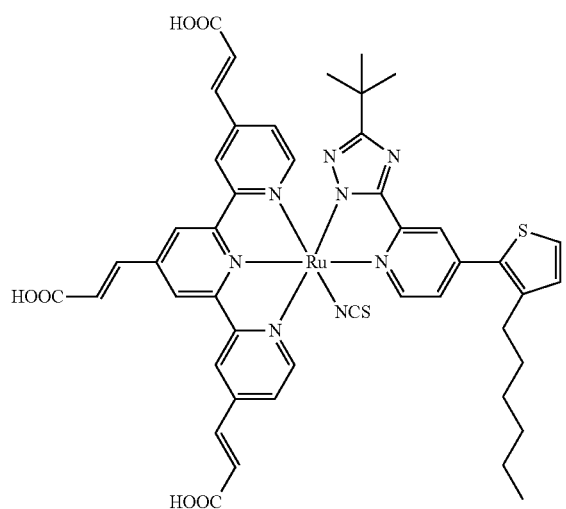

-continued
D-275
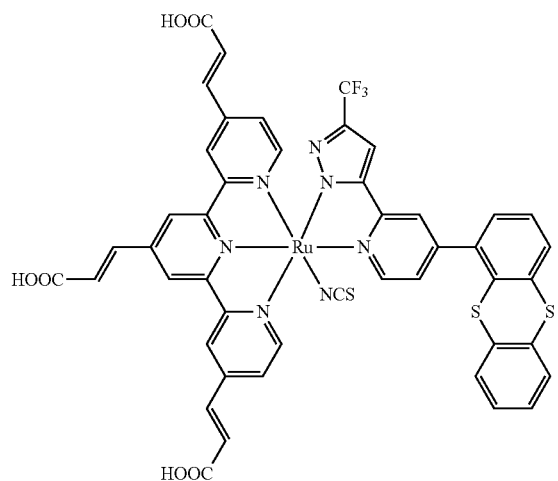
D-276
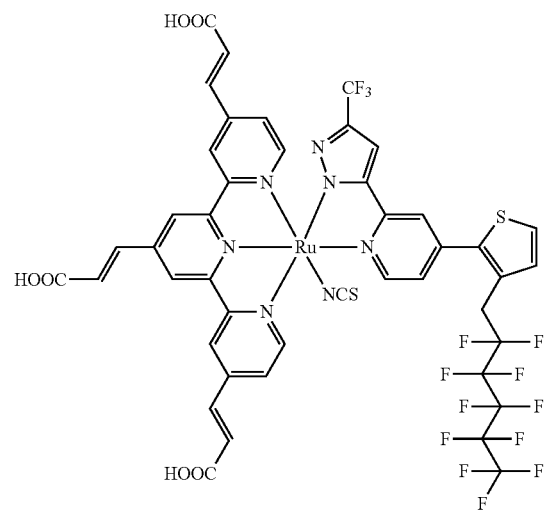
D-277
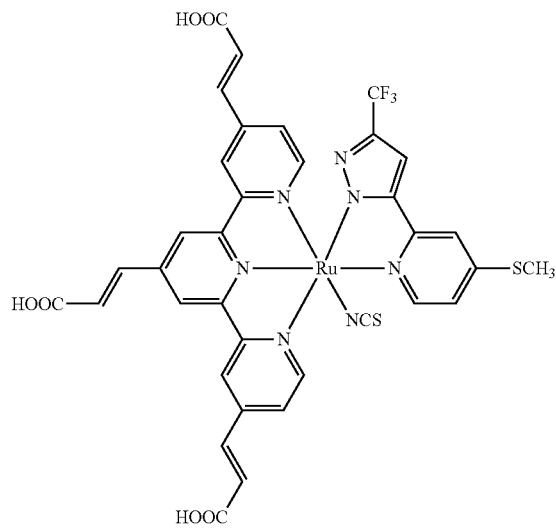
D-278
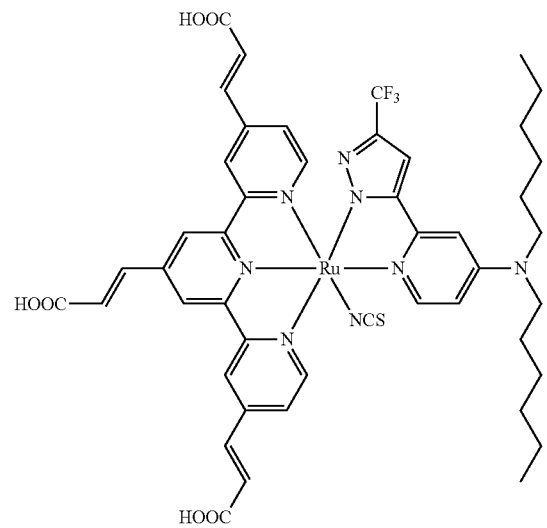

-continued
D-279
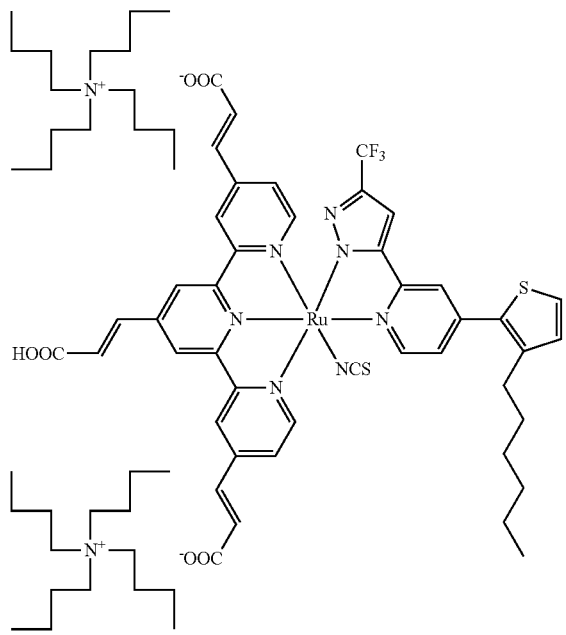
D-280
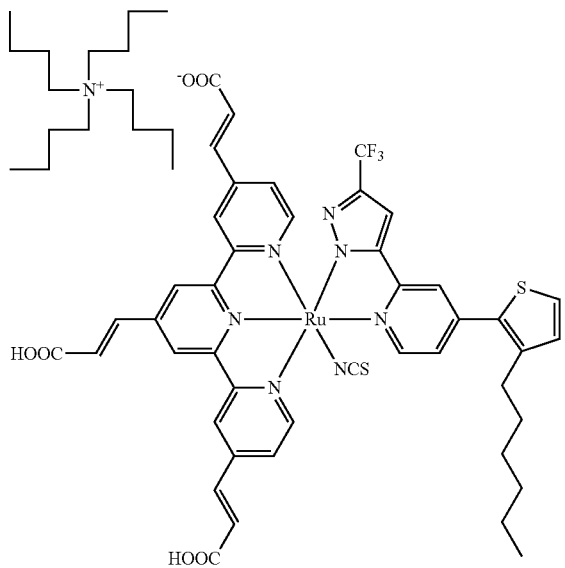
D-281
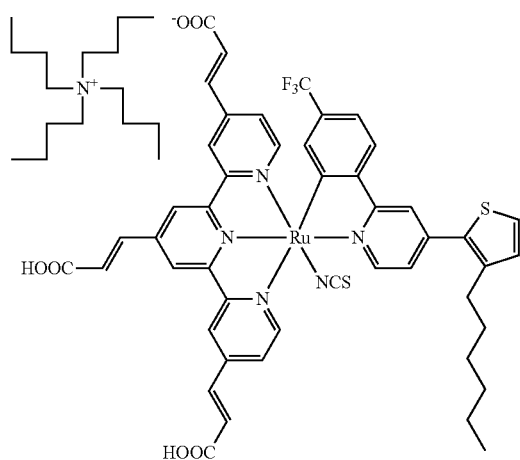
D-282
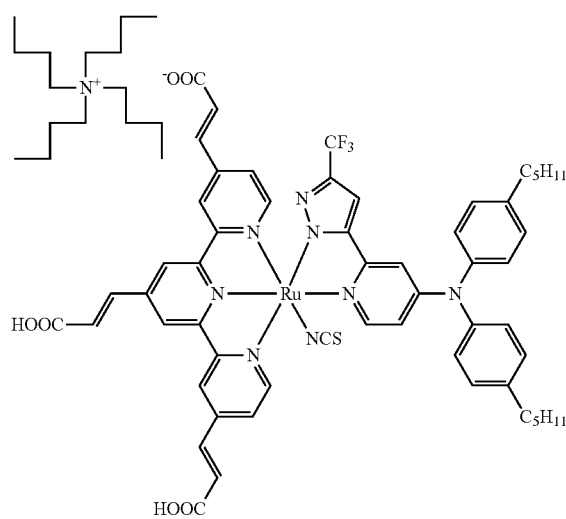

-continued
D-283
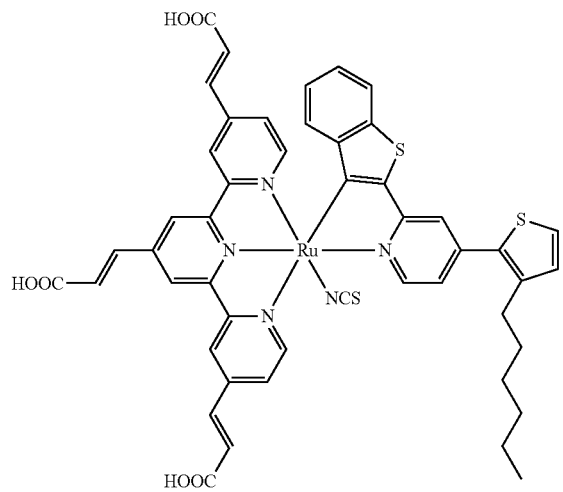
D-284
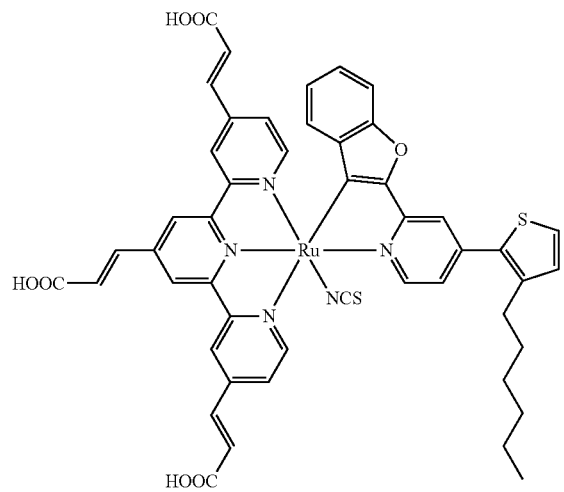
D-285
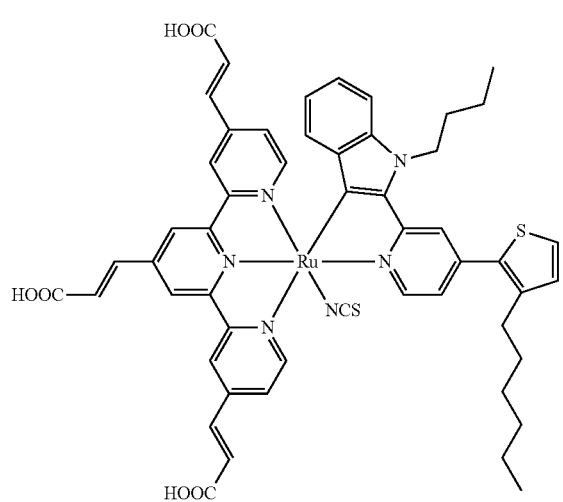
D-286
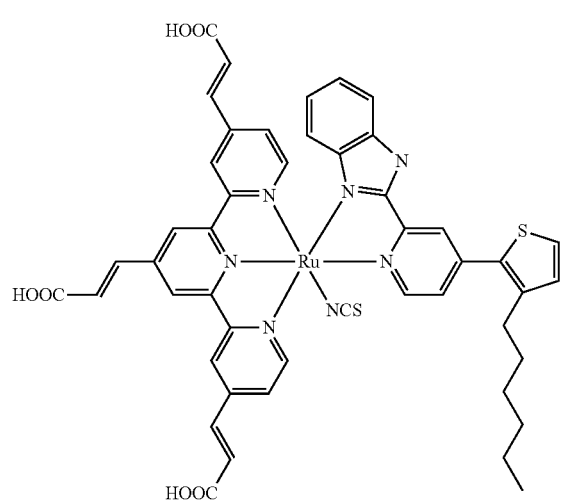
D-287
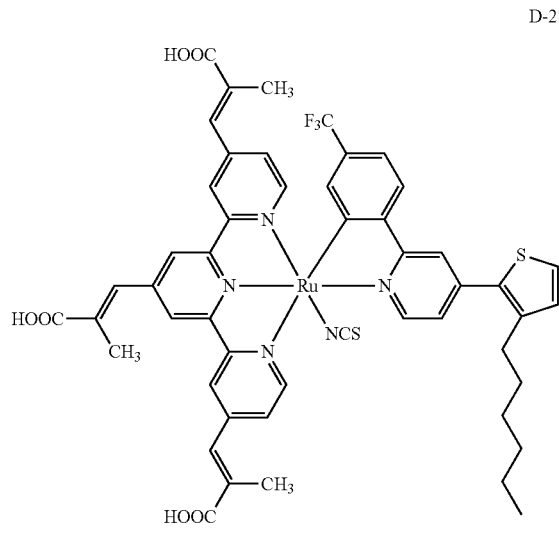
D-288
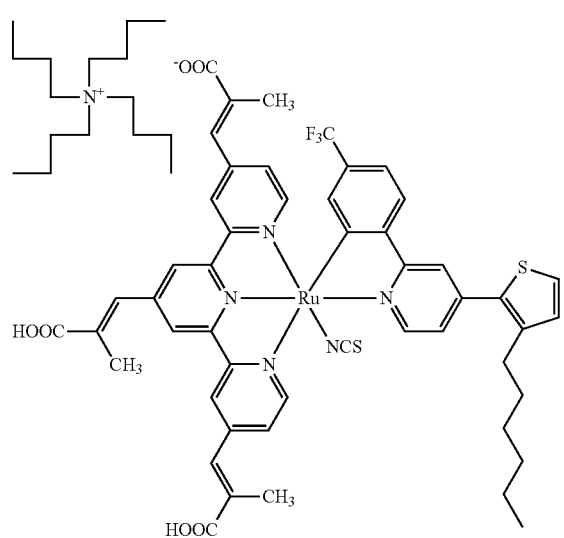

-continued
D-289
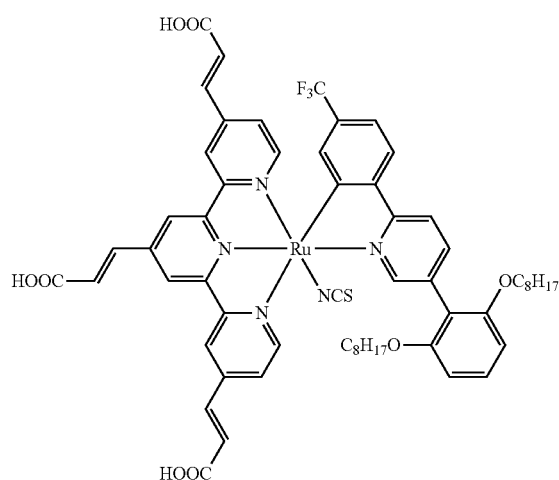
D-290
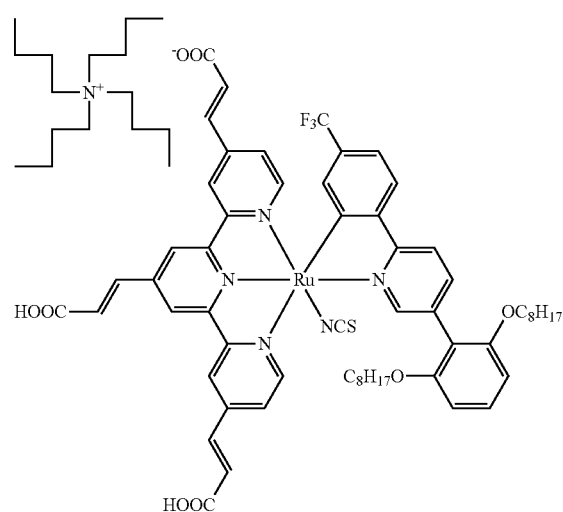
D-291
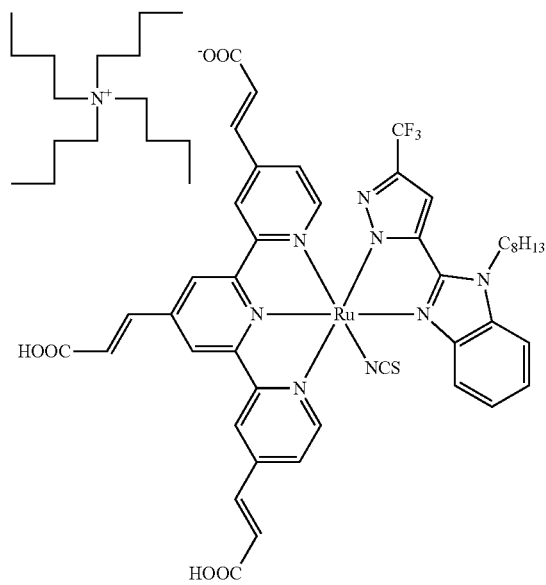
D-292
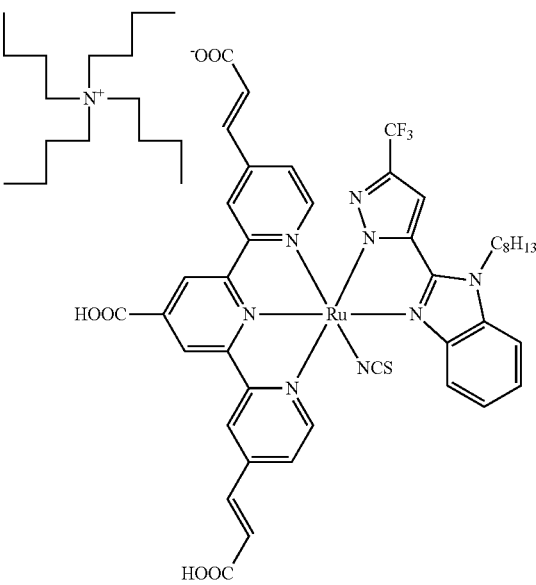

-continued
D-293
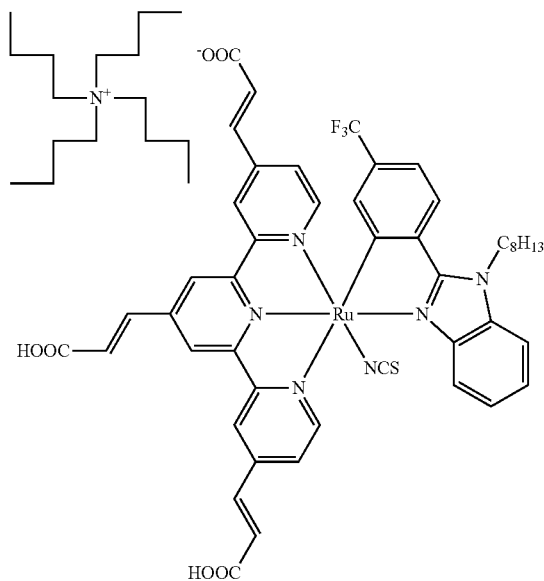
D-294
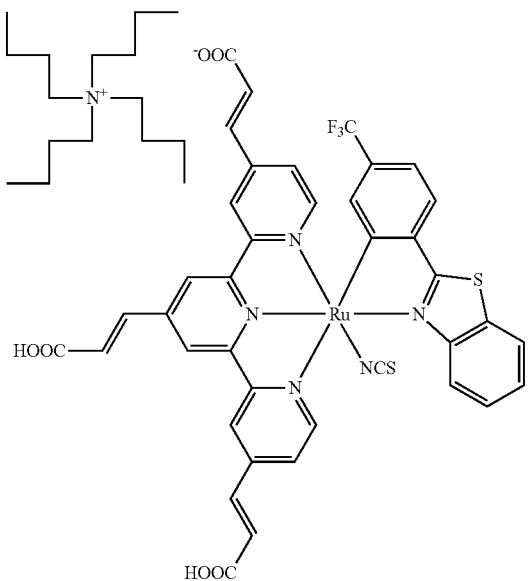
D-295
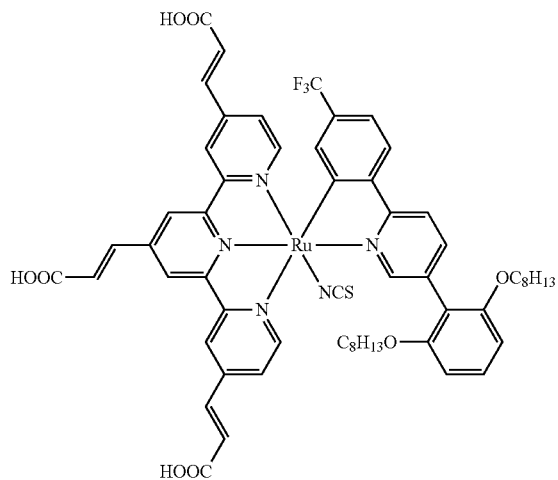
D-296
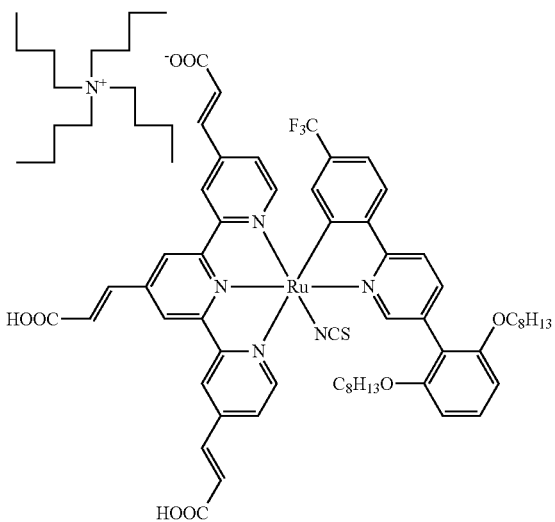

-continued
D-297
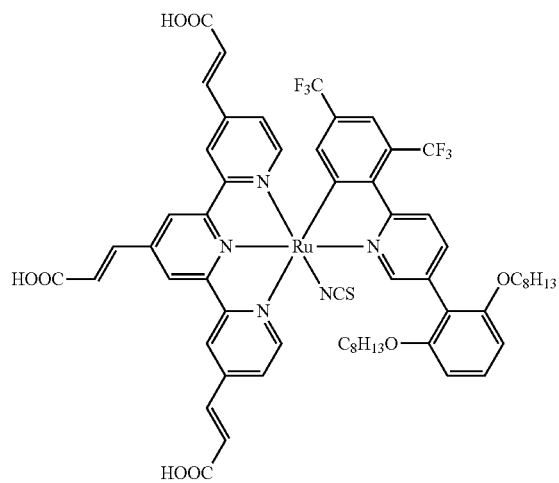
D-298
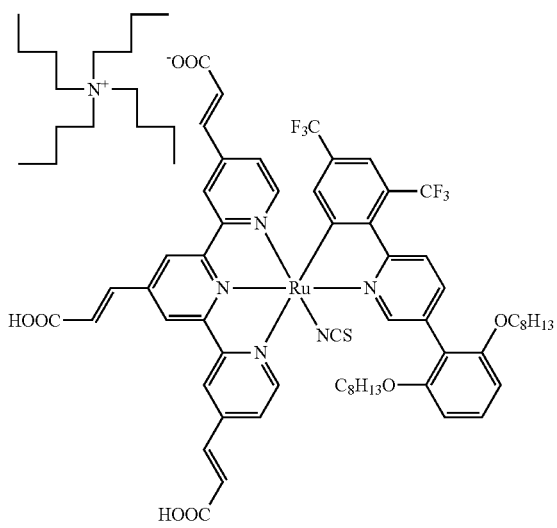
D-299
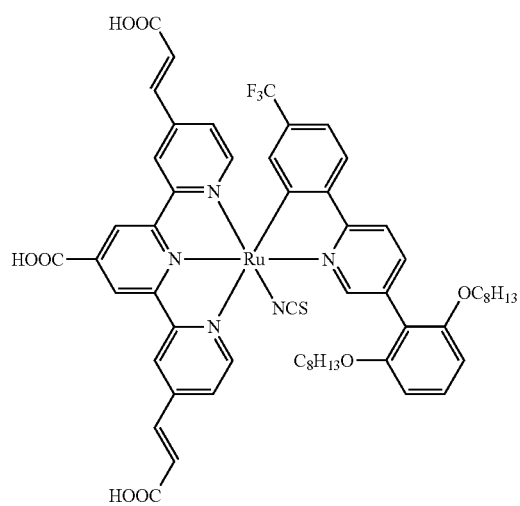
D-300
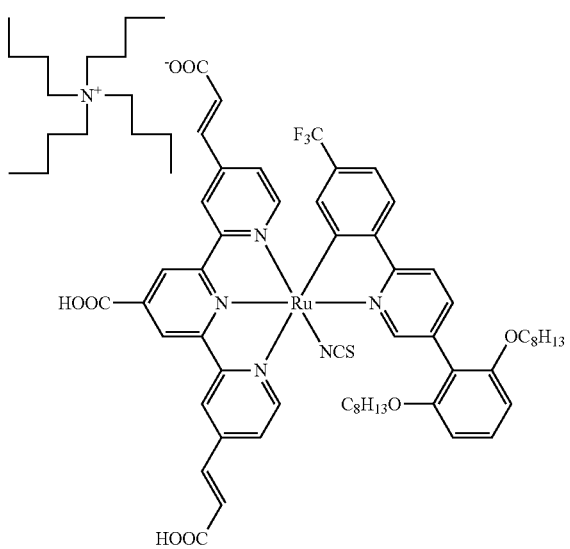
D-301
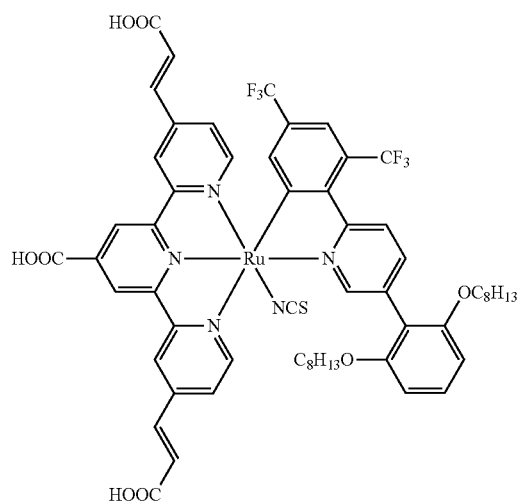
D-302
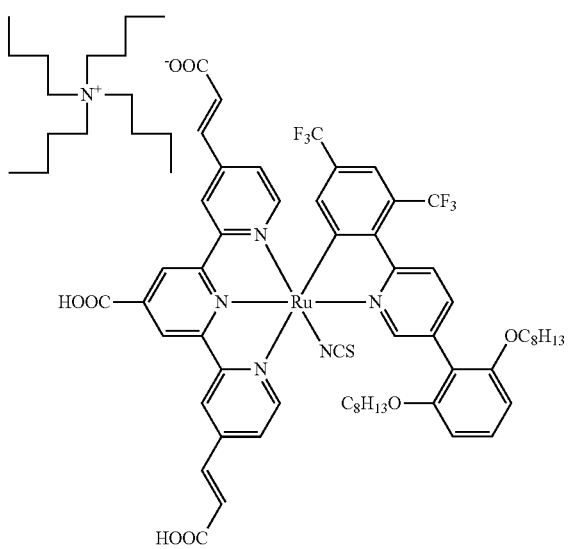

-continued
D-303
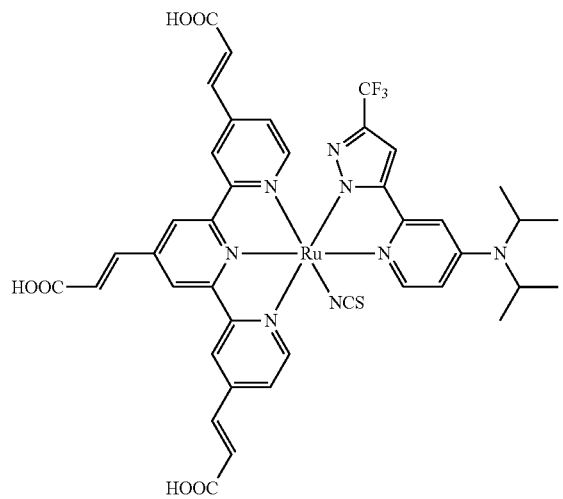
D-304
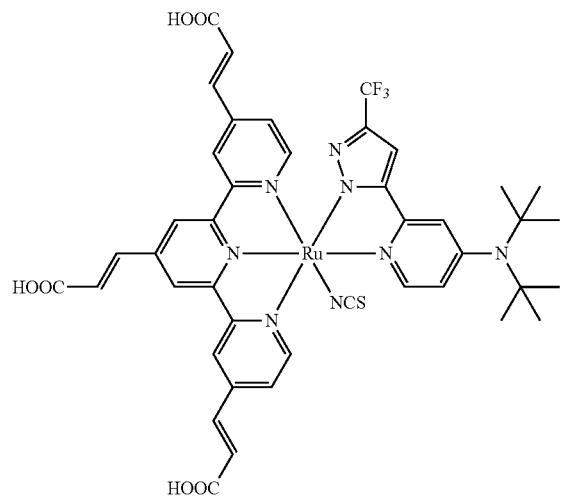
D-305
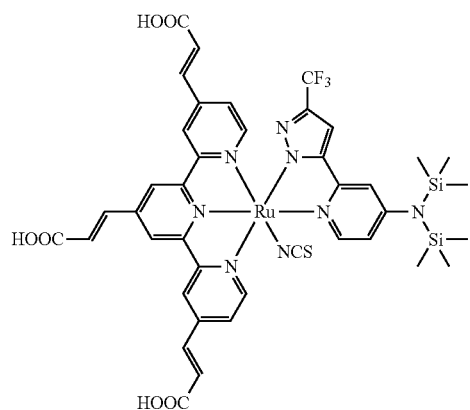
D-306
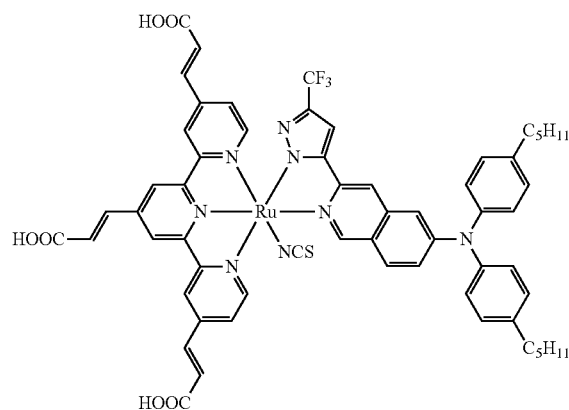
D-307
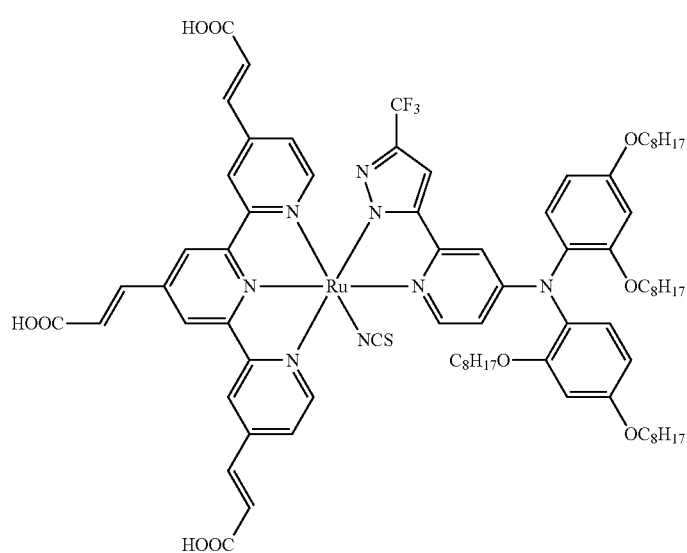

-continued
D-308
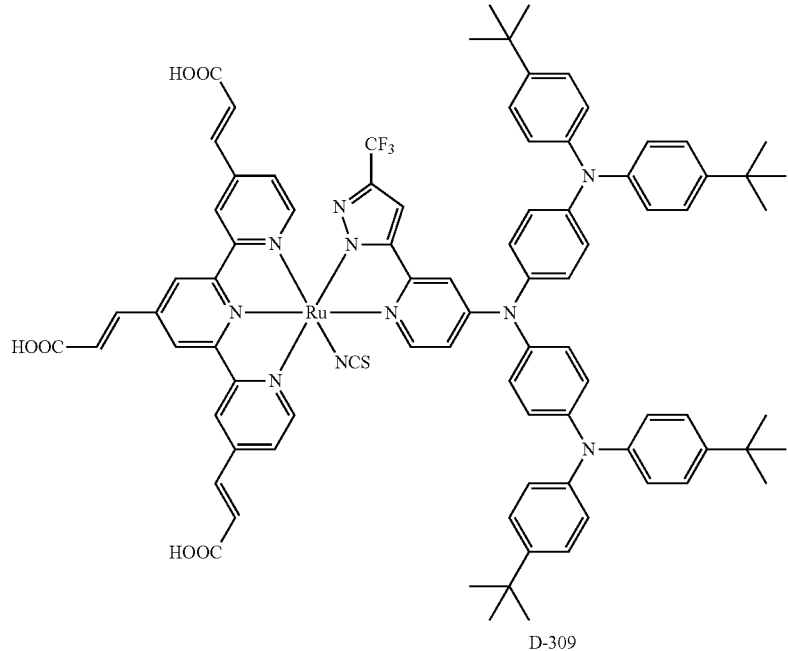
D-309
D-310
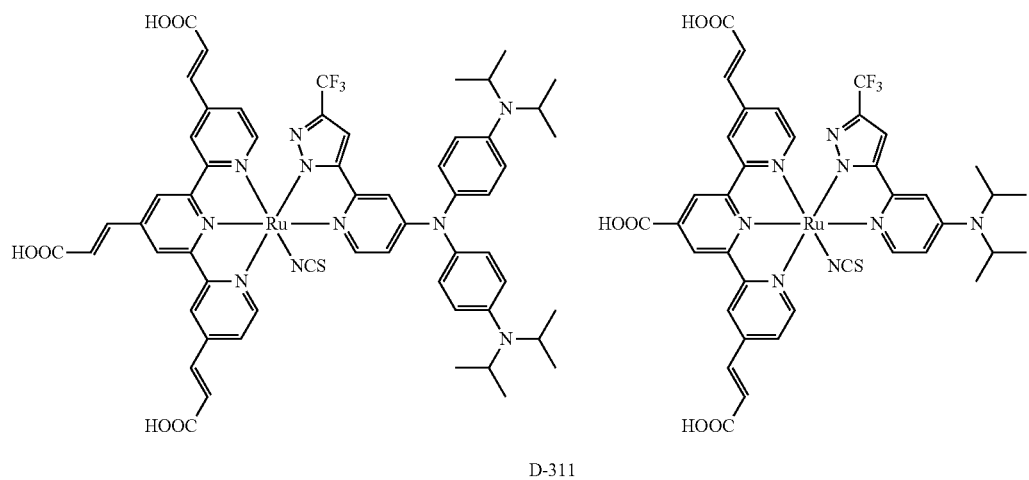
D-311
D-312
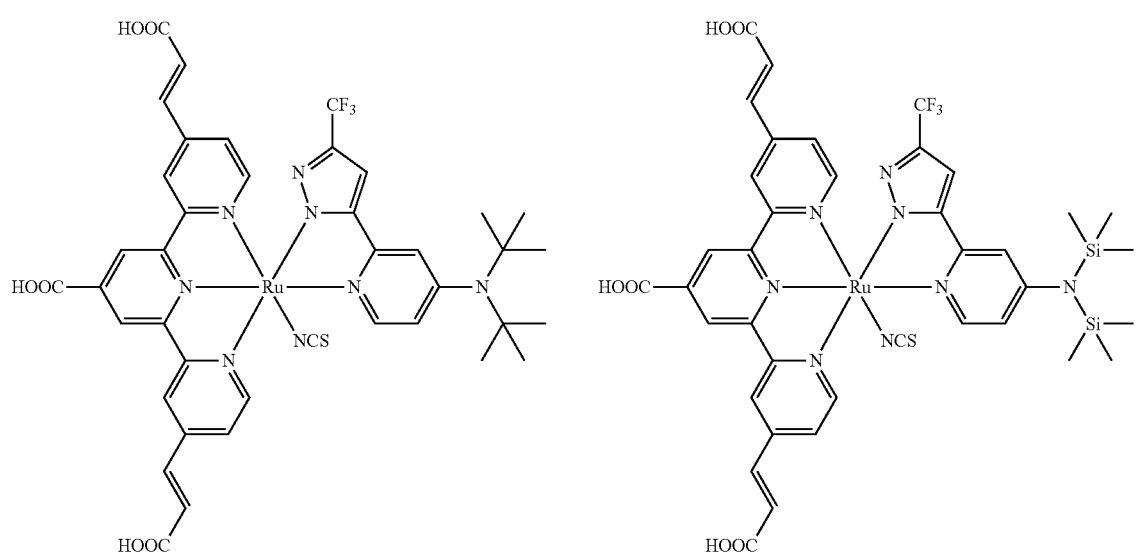

-continued
D-313
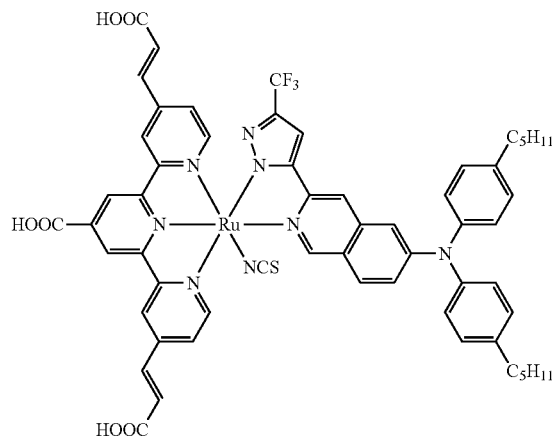
D-314
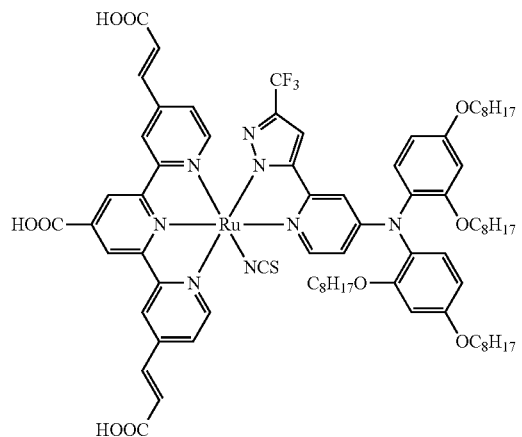
D-315
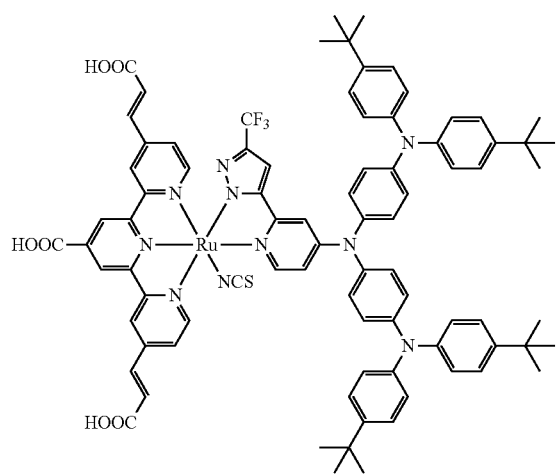
D-316
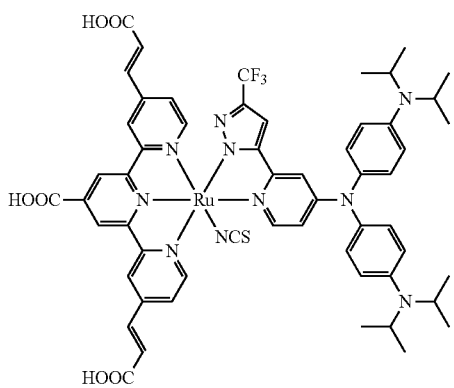

In addition to the above, it is possible to mention the following metal complex dyes.

In the following, the combinations of M, LA, LD, LX, CI, mX, and mY in Formula (I) are presented in a table (Table 1).

For example, the following D-317 indicates the metal complex dye having the following chemical structure.

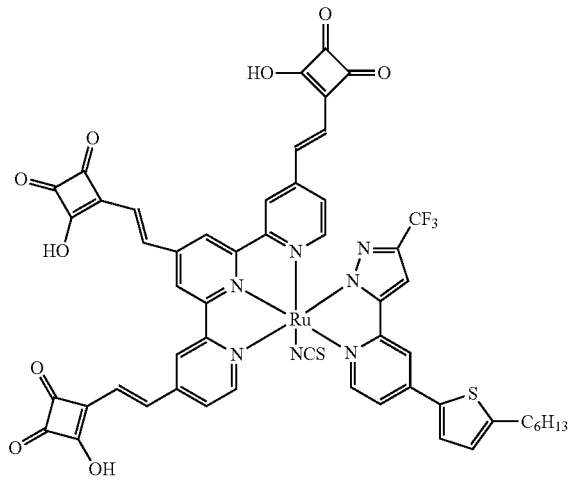

TABLE 1

| Metal complex dye No. | M | LA | LD | LX | mX | CI | mY |
|---|---|---|---|---|---|---|---|
| D-317 | Ru | LA-5-4 | LD-6-10 | ⊖NCS | 1 | — | — |
| D-318 | Ru | LA-5-4 | LD-6-5 | ⊖NCS | 1 | — | — |
| D-319 | Ru | LA-5-4 | LD-6-14 | ⊖NCS | 1 | — | — |
| D-320 | Ru | LA-5-4 | LD-2-7 | — | 0 | — | — |
| D-321 | Ru | LA-5-6 | LD-2-3 | — | 0 | — | — |
| D-322 | Ru | LA-5-8 | LD-6-10 | ⊖NCS | 1 | — | — |
| D-323 | Ru | LA-5-8 | LD-6-10 | ⊖NCS | 1 | Bu$_4$N$^+$ | 1 |
| D-324 | Ru | LA-5-8 | LD-6-95 | ⊖NCS | 1 | — | — |
| D-325 | Ru | LA-5-8 | LD-6-96 | ⊖NCS | 1 | — | — |
| D-326 | Ru | LA-5-8 | LD-6-97 | ⊖NCS | 1 | — | — |
| D-327 | Ru | LA-5-8 | LD-6-98 | ⊖NCS | 1 | — | — |
| D-328 | Ru | LA-5-8 | LD-2-3 | — | 0 | — | — |
| D-329 | Ru | LA-5-8 | LD-2-7 | — | 0 | — | — |
| D-330 | Ru | LA-5-8 | LD-3-17 | — | 0 | — | — |
| D-331 | Ru | LA-5-8 | LD-3-18 | — | 0 | — | — |
| D-332 | Ru | LA-5-8 | LD-3-19 | — | 0 | — | — |
| D-333 | Ru | LA-5-8 | LD-3-20 | — | 0 | — | — |
| D-334 | Ru | LA-5-8 | LD-3-21 | — | 0 | — | — |
| D-335 | Ru | LA-5-8 | LD-3-22 | — | 0 | — | — |
| D-336 | Ru | LA-5-8 | LD-3-23 | — | 0 | — | — |
| D-337 | Ru | LA-5-8 | LD-3-1 | — | 0 | — | — |
| D-338 | Ru | LA-5-8 | LD-3-24 | — | 0 | — | — |
| D-339 | Ru | LA-5-8 | LD-3-25 | — | 0 | — | — |
| D-340 | Ru | LA-5-8 | LD-3-26 | — | 0 | — | — |
| D-341 | Ru | LA-5-8 | LD-3-27 | — | 0 | — | — |
| D-342 | Ru | LA-5-8 | LD-3-28 | — | 0 | — | — |
| D-343 | Ru | LA-5-11 | LD-6-14 | ⊖NCS | 1 | — | — |
| D-344 | Ru | LA-5-11 | LD-2-3 | — | 0 | — | — |
| D-345 | Ru | LA-5-13 | LD-6-14 | ⊖NCS | 1 | — | — |
| D-346 | Ru | LA-5-13 | LD-2-3 | — | 0 | — | — |
| D-347 | Ru | LA-5-14 | LD-3-27 | — | 0 | — | — |
| D-848 | Ru | LA-5-15 | LD-3-29 | — | 0 | — | — |
| D-349 | Ru | LA-5-16 | LD-3-31 | — | 0 | — | — |
| D-350 | Ru | LA-5-17 | LD-3-32 | — | 0 | — | — |
| D-351 | Ru | LA-5-18 | LD-3-32 | — | 0 | — | — |
| D-352 | Ru | LA-5-19 | LD-3-30 | — | 0 | — | — |
| D-353 | Ru | LA-5-19 | LD-3-32 | — | 0 | — | — |

The metal complex dye represented by Formula (I) of the present invention can be synthesized by the methods described in US 2010/0258175 A1, Japanese Patent No. 4298799 and Angew. Chem. Int. Ed., 2011, 50, 2054-2058, the methods described in the references cited in the literatures or the methods according to these methods.

The maximum absorption wavelength in a solution of the metal complex dye of the present invention is preferably in a range from 300 to 1,000 nm, more preferably in a range from 350 to 950 nm, and particularly preferably in a range from 370 to 900 nm.

—Electrically-Conductive Support—

The electrically-conductive support is preferably a support having electroconductivity per se, such as a metal, or a glass or plastic support having an electrically-conductive film layer on the surface. As the plastic support, a transparent polymer film described in paragraph No. 0153 of JP-A-2001-291534 can be mentioned. As the support, in addition to the glass and plastic, ceramic (JP-A-2005-135902), an electrically-conductive resin (JP-A-2001-160425), or the like may be used. The electrically-conductive support may be provided with a light management function at the surface, and for example, the anti-reflective film having a high refractive index film and a low refractive index oxide film alternately laminated as described in JP-A-2003-123859, and the light guide function as described in JP-A-2002-260746 may be mentioned.

The thickness of the electrically-conductive film layer is preferably 0.01 to 30 μm, more preferably 0.03 to 25 μm, and particularly preferably 0.05 to 20 μm.

It is preferable that the electrically-conductive support is substantially transparent. The term "substantially transparent" means that the transmittance of light is 10% or more, preferably 50% or more, and particularly preferably 80% or more. As the transparent electrically-conductive support, a support formed from glass or plastic and coated with an electrically-conductive metal oxide is preferable. As the metal oxide, tin oxide is preferable, and indium-tin oxide and fluorine-doped oxide are particularly preferable. In this case, the coating amount of the electrically-conductive metal oxide is preferably 0.1 to 100 g, per square meter of the support made of glass or plastic. In the case of using a transparent electrically-conductive support, it is preferable that light is incident from the support side.

—Semiconductor Fine-Particles—

Regarding the semiconductor fine-particles, fine-particles of chalcogenides of metals (for example, oxides, sulfides and selenides), or fine-particles of perovskites may be used with preference. Preferred examples of the chalcogenides of metals include oxides of titanium, tin, zinc, tungsten, zirconium, hafnium, strontium, indium, cerium, yttrium, lanthanum, vanadium, niobium or tantalum, cadmium sulfide, and cadmium selenide. Preferred examples of the perovskites include strontium titanate, and calcium titanate. Among these, titanium oxide (titania), zinc oxide, tin oxide, and tungsten oxide are particularly preferred.

Examples of the crystal structure of titania include structures of anatase type, brookite type and rutile type, and anatase type and brookite type structures are preferred. A titania nanotube, nanowire, or nanorod may be mixed with titania fine-particles or may be used as a semiconductor electrode.

A particle size of the semiconductor fine-particles is expressed in terms of an average particle size using a diameter when a projected area is converted into a circle, and is preferably 0.001 to 1 μm as primary particles, and 0.01 to 100 μm as an average particle size of dispersions. Examples of the method for coating the semiconductor fine-particles on the electrically-conductive support include a wet method, a dry method or other methods.

It is preferable to form a short circuit-preventing layer between the transparent electrically-conductive film and the semiconductor layer ("photoconductor layer"), so as to prevent reverse current due to a direct contact between the electrolyte and the electrode. It is preferable to employ a spacer or a separator, so as to prevent contact between the photoelectrode and the counter electrode. It is preferable for the semiconductor fine-particles to have a large surface area, so that a large amount of dye can adsorb to the surface. For example, in a state of the semiconductor fine-particles being coated on the support, the surface area is preferably 10 times or more, and more preferably 100 times or more, relative to the projected surface area. The upper limit of this value is not particularly limited, and the upper limit is generally about 5,000 times. In general, as the thickness of the layer containing semiconductor fine particles increases, the amount of dye that can be supported (carried) per unit area increases, and therefore, the light absorption efficiency increases. However, since the diffusion distance of generated electrons increases along, the loss due to charge recombination also increases. Although a preferred thickness of the photoconductor layer being the semiconductor layer may vary depending on the utility of the element, the thickness is typically 0.1 to 100 µm. In the case of using the photoelectric conversion element for a dye-sensitized solar cell, the thickness of the photoconductor layer is preferably 1 to 50 µm, and more preferably 3 to 30 µm. The semiconductor fine-particles may be calcined after being applied on the support, at a temperature of 100 to 800° C. for 10 minutes to 10 hours, so as to bring about cohesion of the particles. When a glass support is used, the film-forming temperature is preferably 60 to 400° C.

The coating amount of the semiconductor fine-particles per square meter of the support is preferably 0.5 to 500 g, and more preferably 5 to 100 g. The overall amount of use of the dye is preferably 0.01 to 100 millimoles, more preferably 0.1 to 50 millimoles, and particularly preferably 0.1 to 10 millimoles, per square meter of the support. In this case, the amount of use of the metal complex dye of the present invention is preferably set to 5% by mole or more. The amount of the dye adsorbed to the semiconductor fine-particles is preferably 0.001 to 1 millimole, and more preferably 0.1 to 0.5 millimoles, based on 1 g of the semiconductor fine-particles. When the amount of the dye is set to such a range, the sensitization effect on the semiconductor fine-particles can be sufficiently obtained.

When the dye is a salt, a counter ion of the specific metal complex dye is not particularly limited. Examples thereof include an alkali metal ion and a quaternary ammonium ion.

After the dye has been adsorbed, the surface of the semiconductor fine-particles may be treated using amines Preferred examples of the amines include pyridines (e.g., 4-tert-butylpyridine, and polyvinylpyridine). These may be used directly when they are liquids, or may be used in a state of being dissolved in an organic solvent.

In the photoelectric conversion element (for example, photoelectric conversion element 10) and the dye-sensitized solar cell (for example, dye-sensitized solar cell 20) of the present invention, at least the metal complex dye of the present invention is used.

In the present invention, the metal complex dye of the present invention and another dye may be used in combination.

The dye to be used in combination includes: a Ru complex dye described in JP-T-7-500630 (in particular, dyes synthesized in Examples 1 to 19 described in from line 5 on left lower column on page 5 to line 7 on right upper column on page 7), a Ru complex dye described in JP-T-2002-512729 (in particular, dyes synthesized in Examples 1 to 16 described in line 3 from the bottom of page 20 to line 23 on page 29), a Ru complex dye described in JP-A-2001-59062 (in particular, dyes described in paragraph Nos. 0087 to 0104), a Ru complex dye described in JP-A-2001-6760 (in particular, dyes described in paragraph Nos. 0093 to 0102), a Ru complex dye described in JP-A-2001-253894 (in particular, dyes described in paragraph Nos. 0009 to 0010), a Ru complex dye described in JP-A-2003-212851 (in particular, dyes described in paragraph No. 0005), a Ru complex dye described in WO 2007/91525 pamphlet (in particular, dyes described in paragraph No. [0067]), a Ru complex dye described in JP-A-2001-291534 (in particular, dyes described in paragraph Nos. 0120 to 0144), a Ru complex dye described in JP-A-2012-012570 (in particular, dyes described in paragraph Nos. 0095 to 0103), a squarylium cyanine dye described in JP-A-11-214730 (in particular, dyes described in paragraph Nos. 0036 to 0047), a squarylium cyanine dye described in JP-A-2012-144688 (in particular, dyes described in paragraph Nos. 0039 to 0046 and 0054 to 0060), a squarylium cyanine dye described in JP-A-2012-84503 (in particular, dyes described in paragraph Nos. 0066 to 0076 and the like), an organic dye described in JP-A-2004-063274 (in particular, dyes described in paragraph Nos. 0017 to 0021), an organic dye described in JP-A-2005-123033 (in particular, dyes described in paragraph Nos. 0021 to 0028), an organic dye described in JP-A-2007-287694 (in particular, dyes described in paragraph Nos. 0091 to 0096), an organic dye described in JP-A-2008-71648 (in particular, dyes described in paragraph Nos. 0030 to 0034), an organic dye described in WO 2007/119525 pamphlet (in particular, dyes described in paragraph No. [0024]), a porphyrine dye described in Angew. Chem. Int. Ed., 49, 1 to 5 (2010), and a phthalocyanine dye described in Angew. Chem. Int. Ed., 46, 8358 (2007), or the like.

Preferable dyes to be used in combination include Ru complex dyes, squaryrium cyanine dyes, or organic dyes.

In the case where the metal complex dye of the present invention and another dye are used in combination, a ratio of mass of the metal complex dye of the present invention/mass of another dye is preferably from 95/5 to 10/90, more preferably from 95/5 to 50/50, still more preferably from 95/5 to 60/40, particularly preferably from 95/5 to 65/35, and most preferably from 95/5 to 70/30.

—Charge Transfer Layer—

The charge transfer layer for use in the photoelectric conversion element of the present invention is a layer having a function to replenish electrons to the oxidized form of the dye, and it is provided between the light-receiving electrode and the counter electrode (an opposite electrode). The charge-transfer layer contains an electrolyte. Examples of the electrolyte include a liquid electrolyte having a redox pair dissolved in an organic solvent, a so-called gel electrolyte in which a liquid having a redox pair dissolved in an organic solvent is impregnated in a polymer matrix, and a molten salt containing a redox pair. In order to enhance photoelectric conversion efficiency, a liquid electrolyte is preferred. As a solvent of the liquid electrolyte, a nitrile compound, an ether compound, an ester compound, or the like, is used, and a nitrile compound is preferred, and acetonitrile and methoxypropionitrile are particularly preferred.

Examples of the redox pair include a combination of iodine and an iodide (preferably an iodide salt, or an iodide ionic liquid; more preferably lithium iodide, tetrabutylammonium iodide, tetrapropylammonium iodide, or methylpropylimidazolium iodide), a combination of an alkylviologen (for example, methylviologen chloride, hexylviologen bromide, or benzylviologen tetrafluoroborate) and a reductant thereof, a combination of a polyhydroxybenzene (for example, hydroquinone, naphthohydroquinone, or the like) and an oxidized form thereof, a combination of a divalent iron complex and a trivalent iron complex (for example, a combination of potassium ferricyanide and potassium ferrocyanide), and a combination of a divalent cobalt complex and a trivalent cobalt complex. Among these, a combination of iodine and an iodide, and a combination of a divalent cobalt complex and a trivalent cobalt complex, are preferred.

The cobalt complex is preferably a complex represented by the following formula (CC).

$Co(LL)ma(X)mb\cdot CI$        Formula (CC)

In formula (CC), LL represents a bidentate or tridentate ligand. X represents a monodentate ligand. ma represents an integer of 0 to 3. mb represents an integer of 0 to 6. CI represents a counter ion in the case where the counter ion is necessary to neutralize a charge.

Examples of CI include those of CI in formula (I).

LL is preferably a ligand represented by the following formula (LC).

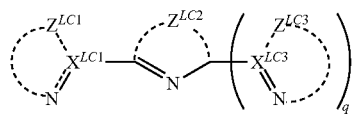

Formula (LC)

In Formula (LC), $X^{LC1}$ and $X^{LC3}$ each independently represent a carbon atom or a nitrogen atom. Herein, when $X^{LC1}$ is a carbon atom, the bond between $X^{LC1}$ and the N atom is a double bond ($X^{LC1}$=N). When $X^{LC3}$ is a carbon atom, the bond between $X^{LC3}$ and the N atom is a double bond ($X^{LC3}$=N). When $X^{LC1}$ is a nitrogen atom, the bond between $X^{LC1}$ and the N atom is a single bond ($X^{LC1}$—N). When $X^{LC3}$ is a nitrogen atom, the bond between $X^{LC3}$ and the N atom is a single bond ($X^{LC3}$—N).

$Z^{LC1}$, $Z^{LC2}$, and $Z^{LC3}$ each independently represent a group of nonmetallic atoms necessary to form a 5- or 6-membered ring. Each of $Z^{LC1}$, $Z^{LC2}$, and $Z^{LC3}$ may have a substituent, and may form a ring-closure together with an adjacent ring through a substituent. q represents 0 or 1. Examples of the substituent include the substituent T described later. Further, when q is 0, the carbon atom on a position at which $X^{LC3}$ bonds to a 5-membered ring or 6-membered ring formed by $Z^{LC2}$ bonds with a hydrogen atom or a substituent other than heterocyclic group formed by $Z^{LC3}$.

X is preferably a halogen ion.

The ligand represented by Formula (LC) is more preferably a ligand represented by any one of Formulas (LC-1) to (LC-4).

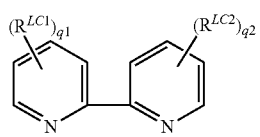
(LC-1)

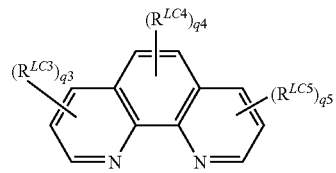
(LC-2)

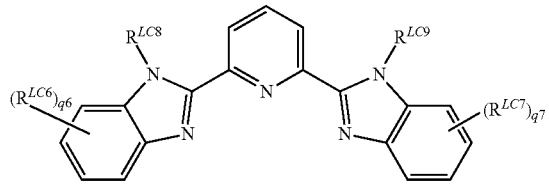
(LC-3)

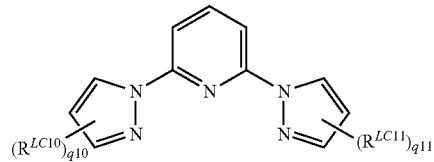
(LC-4)

$R^{LC1}$ to $R^{LC11}$ each independently represent a substituent. q1, q2, q6, and q7 each independently represent an integer of 0 to 4. q3, q5, q10, and q11 each independently represent an integer of 0 to 3. q4 represents an integer of 0 to 2.

In Formulas (LC-1) to (LC-4), examples of the substituent $R^{LC1}$ to $R^{LC11}$ include an aliphatic group, an aromatic group, a heterocyclic group or the like. Specific examples of the substituent include an alkyl group, an alkoxy group, an alkylthio group, an aryl group, an aryloxy group, an arylthio group, and a heterocycle. Preferred examples include an alkyl group (for example, methyl, ethyl, n-butyl, n-hexyl, isobutyl, sec-butyl, t-butyl, n-dodecyl, cyclohexyl, or benzyl), an aryl group (for example, phenyl, tolyl, or naphthyl), an alkoxy group (for example, methoxy, ethoxy, isopropoxy, or butoxy), an alkylthio group (for example, methylthio, n-butylthio, n-hexylthio, or 2-ethylhexylthio), an aryloxy group (for example, phenoxy, or naphthoxy), an arylthio group (for example, phenylthio, or naphthylthio), and a heterocyclic group (for example, 2-thienyl, or 2-furyl).

Specific examples of the cobalt complex having a ligand represented by Formula (LC) include the following complexes.

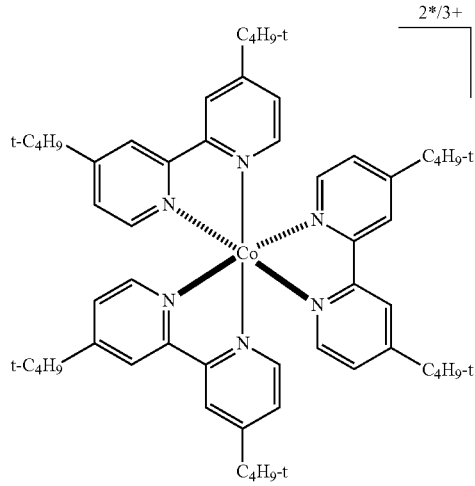
LL-1

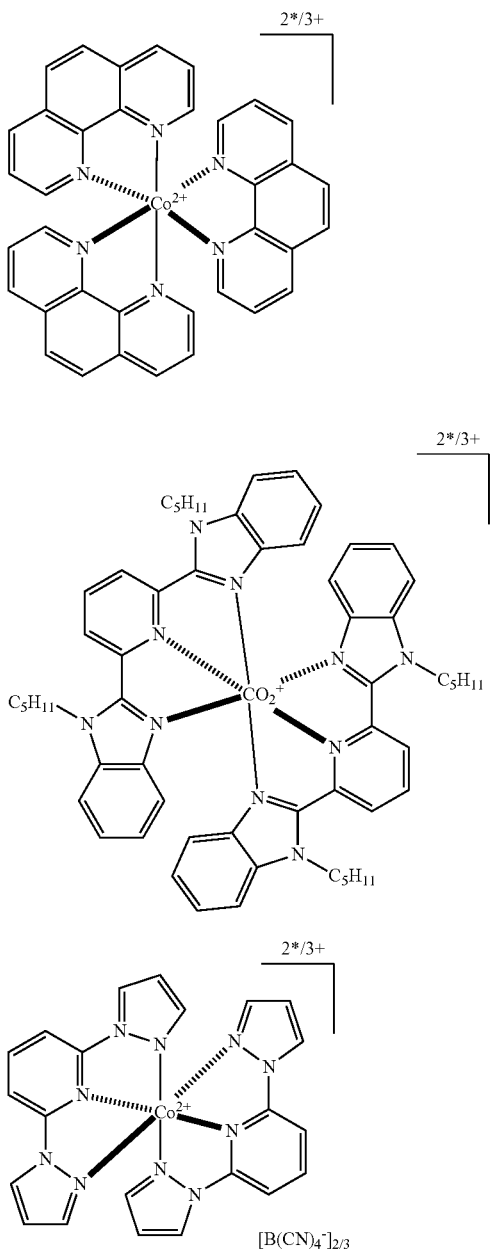

In the case where iodine and an iodide are used in combination, as an electrolyte, it is preferred that a 5- or 6-membered-ring nitrogen-containing aromatic cation iodide salt is additionally used in combination with them.

Preferred examples of the organic solvent that dissolves these redox pairs include aprotic polar solvents (for example, acetonitrile, propylene carbonate, ethylene carbonate, dimethylformamide, dimethylsulfoxide, sulfolane, 1,3-dimethylimidazolinone, and 3-methyloxazolidinone). Examples of the polymer used for a matrix of a gel electrolyte include polyacrylonitrile, polyvinylidene fluoride, and the like. Examples of the molten salts include, for example, a molten salt to which fluidity at room temperature has been imparted by mixing lithium iodide and at least one kind of other lithium salt (for example, lithium acetate or lithium perchlorate) with polyethylene oxide. The amount of addition of the polymer in this case is 1 to 50% by mass. Furthermore, the electrolyte liquid may contain γ-butyrolactone, and this increases the diffusion efficiency of iodide ions, and thereby the conversion efficiency is enhanced.

Examples of the additives to the electrolyte include 4-tert-butylpyridine mentioned above, as well as aminopyridine-based compounds, benzimidazole-based compounds, aminotriazole-based compounds, aminothiazole-based compounds, imidazole-based compounds, aminotriazine-based compounds, urea derivatives, amide compounds, pyrimidine-based compounds, and heterocycles that do not contain nitrogen.

It is also preferable to employ a method of controlling the water content of the electrolyte liquid, in order to enhance the photoelectric conversion efficiency. Preferred examples of the method of controlling the water content include a method of controlling the concentration, and a method of adding a dehydrating agent. In order to reduce the toxicity of iodine, a clathrate compound of iodine with cyclodextrin may be used. Alternatively, a method of supplying moisture on a steady basis may be used. Furthermore, a cyclic amidine may be used; or an oxidation inhibitor, a hydrolysis inhibitor, a decomposition inhibitor or zinc iodide may be added.

A molten salt may also be used as the electrolyte, and preferred examples of the molten salt include an ionic liquid containing an imidazolium or triazolium type cation, an oxazolium-based salt, a pyridinium-based salt, a guanidium-based salt, and combinations of these. These cations may be used in combination with particular anions. Additives may be added to these molten salts. The molten salt may have a substituent having liquid crystalline properties. Furthermore, the quaternary ammonium salt-based molten salt may also be used.

Molten salts other than those described above include, for example, a molten salt to which fluidity at room temperature has been imparted by mixing lithium iodide and at least one kind of other lithium salt (for example, lithium acetate or lithium perchlorate) with polyethylene oxide.

The electrolyte may be quasi-solidified by adding a gelling agent to an electrolyte liquid including an electrolyte and a solvent, and gelling the electrolyte liquid thereby. Examples of the gelling agent include an organic compound having a molecular weight of 1000 or less, an Si-containing compound having a molecular weight in the range of 500 to 5000, an organic salt obtained from a particular acidic compound and a particular basic compound, a sorbitol derivative, and polyvinylpyridine.

Furthermore, a method of confining a matrix polymer, a crosslinking type polymer compound or monomer, a crosslinking agent, an electrolyte, and a solvent, in a polymer may be used.

Preferred examples of the matrix polymer include a polymer having a nitrogen-containing heterocyclic ring in a repeating unit in the main chain or in a side chain, and a crosslinked structure formed by reacting the polymer with an electrophilic compound; a polymer having a triazine structure, a polymer having a ureide structure, a polymer containing a liquid crystalline compound, a polymer having an ether bond, a polyvinylidene fluoride-based polymer, a methacrylate or acrylate-based polymer, a thermosetting resin, crosslinked polysiloxane, polyvinyl alcohol (PVA), a clathrate compound of polyalkylene glycol and dextrin, a system incorporated with an oxygen-containing or sulfur-containing polymer, and a naturally occurring polymer. An alkali-swellable polymer, a polymer having a cation moiety and a component capable of forming a charge transfer complex with iodine within one polymer molecule, or the like may be added to those matrix polymers.

A system containing, as a matrix polymer, a crosslinked polymer formed by reacting a bifunctional or higher-functional isocyanate as one component with a functional group such as a hydroxyl group, an amino group or a carboxyl group, may also be used. Furthermore, a crosslinked polymer based on a hydrosilyl group and a double-bonded compound, a crosslinking method involving reacting polysulfonic acid, polycarboxylic acid or the like with a divalent or higher-valent metal ion compound, and the like may also be used.

Examples of the solvent that can be used with preference in combination with the quasi-solid electrolyte described above, include particular phosphates, a mixed solvent containing ethylene carbonate, a solvent having a particular relative permittivity, and the like. A liquid electrolyte solution may be retained in a solid electrolyte membrane or in pores, and preferred examples of the method include the usage of an electrically conductive polymer membrane, a fibrous solid, and a fabric-like solid such as filter.

A solid-state charge-transport layer, such as a p-type semiconductor or a hole-transporting material, for example, CuI or CuNCS, may also be used in place of a liquid electrolyte and a quasi-solid-state electrolyte as described above. Moreover, electrolytes described in Nature, vol. 486, p. 487 (2012) and the like may be used. For a solid charge-transport layer, an organic hole-transporting material may be used. Preferred examples of the hole-transport layer include electrically conductive polymers such as polythiophene, polyaniline, polypyrrole, and polysilane; a spiro compound in which two rings share a central element adopting a tetrahedral structure, such as C and Si; aromatic amine derivatives such as triarylamine; triphenylene derivatives; nitrogen-containing heterocycle derivatives; and liquid crystalline cyano derivatives.

The redox pair serves as an electron carrier, and thus it is required to have a certain concentration. The concentration is preferably 0.01 mol/L or more, more preferably 0.1 mol/L or more, and particularly preferably 0.3 mol/L or more, in total. The upper limit in this case is not particularly limited but is usually about 5 mol/L.

—Co-Adsorbent—

In the photoelectric conversion element of the present invention, a co-adsorbent is preferably used in combination with the metal complex dye of the present invention or another dye to be used if necessary. As such a co-adsorbent, a co-adsorbent having at least one acidic group (preferably a carboxy group or a salt thereof) is preferable, and examples of the co-adsorbent include a fatty acid and a compound having a steroid skeleton. The fatty acid may be a saturated fatty acid or an unsaturated fatty acid. Examples thereof include a butanoic acid, a hexanoic acid, an octanoic acid, a decanoic acid, a hexadecanoic acid, a dodecanoic acid, a palmitic acid, a stearic acid, an oleic acid, a linoleic acid, and a linolenic acid.

Examples of the compound having a steroid skeleton include a cholic acid, a glycocholic acid, a chenodeoxycholic acid, a hyocholic acid, a deoxycholic acid, a lithocholic acid, and ursodeoxycholic acid. Among these, a cholic acid, a deoxycholic acid, and a chenodeoxycholic acid are preferable; and a chenodeoxycholic acid is more preferable.

A preferred co-adsorbent is a compound represented by Formula (CA).

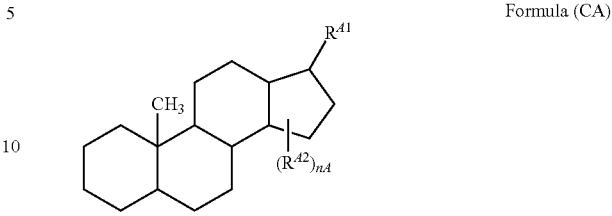

Formula (CA)

In the formula, $R^{41}$ represents a substituent having an acidic group. $R^{42}$ represents a substituent. nA represents an integer of 0 or more.

The acidic group has the same meaning as described above, and the preferable range is also the same.

Of these, $R^{41}$ is preferably an alkyl group substituted with any one of a carboxyl group, a sulfo group, and a salt thereof; and further preferably —CH(CH$_3$)CH$_2$CH$_2$CO$_2$H, or —CH(CH$_3$)CH$_2$CH$_2$CONHCH$_2$CH$_2$SO$_3$H.

Examples of $R^{42}$ include those exemplified as the substituent T described later. Of these, an alkyl group, a hydroxyl group, an acyloxy group, an alkylaminocarbonyloxy group, and an arylaminocarbonyloxy group are preferable; and an alkyl group, a hydroxyl group, and an acyloxy group are more preferable.

nA is preferably from 2 to 4.

Specific examples of these compounds include a compound that is exemplified as the compound having a steroid skeleton.

By adsorbing on the semiconductor fine-particles, the co-adsorbent that can be used in the present invention exhibits an effect of suppressing the inefficient association of the dye and an effect of preventing reverse electron transfer from the semiconductor fine-particle surface to the redox system in the electrolyte. The amount to be used of the co-adsorbent is not particularly limited, and from the viewpoint of exhibiting the above effects effectively, the amount is preferably from 1 to 200 moles, more preferably from 10 to 150 moles, and particularly preferably from 20 to 50 moles, with respect to 1 mole of the above described dye.

<Substituent T>

The specification uses an expression "compound" (including complex and dye) to mean, in addition to the compound itself, its salts, and its ion. Further, a substituent with which whether being substituted or unsubstituted is not explicitly described in the present specification (the same applies to a linking group and a ligand), means that the substituent may have an arbitrary substituent. This also applies to a compound with which whether being substituted or unsubstituted is not explicitly described. Preferable examples of the substituent include the following substituent T.

In the present specification, the simple description only as a "substituent" means to refer to this substituent T. Further, in the case where each of the substituents, for example, like an alkyl group, is described in a simplistic form, both a preferable range and specific examples for the corresponding group for the substituent T are applied to.

The substituent T includes the followings:

an alkyl group (preferably an alkyl group having 1 to 20 carbon atoms, e.g. methyl, ethyl, isopropyl, t-butyl, pentyl, heptyl, 1-ethylpentyl, benzyl, 2-ethoxyethyl, 1-carboxymethyl, or trifluoromethyl), an alkenyl group (preferably an alkenyl group having 2 to 20 carbon atoms, e.g. vinyl, allyl, or oleyl), an alkynyl group (preferably an alkynyl group having 2 to 20 carbon atoms, e.g. ethynyl, butadiynyl, or phenylethynyl), a cycloalkyl group (preferably a cycloalkyl group having 3 to 20 carbon atoms, e.g. cyclopropyl, cyclopentyl, cyclohexyl, or 4-methylcyclohexyl), an cycloalkenyl group (preferably a cycloalkenyl group having 5 to 20 carbon atoms, e.g. cyclopentenyl, or cyclohexenyl), an aryl group (preferably an aryl group having 6 to 26 carbon atoms, e.g. phenyl, 1-naphthyl, 4-methoxyphenyl, 2-chlorophenyl, or 3-methylphenyl), a heterocyclic group (preferably a 5- or 6-membered heterocyclic group having 2 to 20 carbon atoms and at least one oxygen atom, sulfur atom, or nitrogen atom, e.g. 2-pyridyl, 4-pyridyl, 2-imidazolyl, 2-benzimidazolyl, 2-thiazolyl, or 2-oxazolyl), an alkoxy group (preferably an alkoxy group having 1 to 20 carbon atoms, e.g. methoxy, ethoxy, isopropyloxy, or benzyloxy), an alkenyloxy group (preferably an alkenyloxy group having 2 to 20 carbon atoms, e.g. vinyloxy or allyloxy), an alkynyloxy group (preferably an alkynyloxy group having 2 to 20 carbon atoms, e.g. 2-propynyloxy or 4-butynyloxy), a cycloalkyloxy group (preferably a cycloalkyloxy group having 3 to 20 carbon atoms, e.g. cyclopropyloxy, cyclopentyloxy, cyclohexyloxy, or 4-methylcyclohexyloxy), an aryloxy group (preferably an aryloxy group having 6 to 26 carbon atoms, e.g. phenoxy, 1-naphthyloxy, 3-methylphenoxy, or 4-methoxyphenoxy), a heterocyclic oxy group (e.g. imidazolyloxy, benzoimidazolyloxy, thiazolyloxy, benzothiazolyloxy, triazinyloxy, or purinyloxy);

an alkoxycarbonyl group (preferably an alkoxycarbonyl group having 2 to 20 carbon atoms, e.g. ethoxycarbonyl, or 2-ethylhexyloxycarbonyl), a cycloalkoxycarbonyl group (preferably a cycloalkoxycarbonyl group having 4 to 20 carbon atoms, e.g. cyclopropyloxycarbonyl, cyclopentyloxycarbonyl, or cyclohexyloxycarbonyl), an aryloxycarbonyl group (preferably an aryloxycarbonyl group having 6 to 20 carbon atoms, e.g. phenyloxycarbonyl, or naphthyloxycarbonyl), an amino group (preferably an amino group having 0 to 20 carbon atoms including an alkylamino group, an alkenylamino group, an alkynylamino group, a cycloalkylamino group, a cycloalkenylamino group, an arylamino group, and a heterocyclic amino group, e.g. amino, N,N-dimethylamino, N,N-diethylamino, N-ethylamino, N-allylamino, N-(2-propinyl)amino, N-cyclohexylamino, N-cyclohexenylamino, anilino, pyridylamino, imidazolylamino, benzimidazolylamino, thiazolylamino, benzothiazolylamino, or triazinylamino), a sulfamoyl group (preferably a sulfamoyl group having 0 to 20 carbon atoms, preferably an alkyl-, cycloalkyl-, or aryl-sulfamoyl group, e.g. N,N-dimethylsulfamoyl, N-cyclohexylsulfamoyl, or N-phenylsulfamoyl), an acyl group (preferably an acyl group having 1 to 20 carbon atoms, e.g. acetyl, cyclohexylcarbonyl, or benzoyl), an acyloxy group (preferably an acyloxy group having 1 to 20 carbon atoms, e.g. acetyloxy, cyclohexylcarbonyloxy, or benzoyloxy), a carbamoyl group (preferably a carbamoyl group having 1 to 20 carbon atoms, preferably an alkyl-, cycloalkyl-, or aryl-carbamoyl group, e.g. N,N-dimethylcarbamoyl, N-cyclohexylcarbamoyl, or N-phenylcarbamoyl), an acylamino group (preferably an acylamino group having 1 to 20 carbon atoms, e.g. acetylamino, cyclohexylcarbonylamino, or benzoylamino), a sulfonamide group (preferably a sulfonamide group having 0 to 20 carbon atoms, preferably an alkyl-, cycloalkyl-, or aryl-sulfonamide group, e.g. methane sulfonamide, benzene sulfonamide, N-methyl methane sulfonamide, N-cyclohexyl sulfonamide, or N-ethyl benzene sulfonamide), an alkylthio group (preferably an alkylthio group having 1 to 20 carbon atoms, e.g. methylthio, ethylthio, isopropylthio, or benzylthio), a cycloalkylthio group (preferably a cycloalkylthio group having 3 to 20 carbon atoms, e.g. cyclopropylthio, cyclopentylthio, cyclohexylthio, or 4-methylcyclohexylthio), an arylthio group (preferably an arylthio group having 6 to 26 carbon atoms, e.g. phenylthio, 1-naphthylthio, 3-methylphenylthio, or 4-methoxyphenylthio), an alkyl-, cycloalkyl-, or aryl-sulfonyl group (preferably a sulfonyl group having 1 to 20 carbon atoms, e.g. methylsulfonyl, ethylsulfonyl, cyclohexylsulfonyl, or benzene sulfonyl), a silyl group (preferably a silyl group having 1 to 20 carbon atoms, preferably an alkyl-, aryl-, alkoxy-, or aryloxy-substituted silyl group, e.g. triethylsilyl, triphenylsilyl, diethylbenzylsilyl, or dimethylphenylsilyl), a silyloxy group (preferably a silyloxy group having 1 to 20 carbon atoms, preferably an alkyl-, aryl-, alkoxy-, or aryloxy-substituted silyloxy group, e.g. triethylsilyloxy, triphenylsilyloxy, diethylbenzylsilyloxy, or dimethylphenylsilyloxy), a hydroxyl group, a cyano group, a nitro group, a halogen atom (e.g. fluorine, chlorine, bromine, or iodine atom), a carboxyl group, a sulfo group, a phosphonyl group, a phosphoryl group, and a boric-acid group; more preferably an alkyl group, an alkenyl group, a cycloalkyl group, an aryl group, a heterocyclic group, an alkoxy group, a cycloalkoxy group, an aryloxy group, an alkoxycarbonyl group, a cycloalkoxycarbonyl group, the above-described amino group, an acyamino group, a cyano group, or a halogen atom; and particularly preferably an alkyl group, an alkenyl group, a heterocyclic group, an alkoxy group, an alkoxycarbonyl group, an amino group, an acylamino group, or a cyano group.

When the compound, the substituent or the like contains an alkyl group or an alkenyl group, these may be a straight chain or a branched chain, and these may be substituted or unsubstituted. Further, in the case of containing an aryl group, a heterocyclic group or the like, these may be a single ring or a fused ring, and may be substituted or unsubstituted.

<Counter Electrode (Opposite Electrode)>

The counter electrode is preferably an electrode working as a positive electrode in the dye-sensitized solar cell (photoelectrochemical cell). The counter electrode usually has the same meaning as the electrically-conductive support described above, but in a construction which is likely to maintain a sufficient strength, a support is not necessarily required. A preferred structure of the counter electrode is a structure having a high charge collecting effect. At least one of the electrically-conductive support and the counter electrode as mentioned above should be substantially transparent, in order for light to reach the photoconductor layer. In the dye-sensitized solar cell of the present invention, the electrically-conductive support is preferably transparent to allow sunlight to inject from the support side. In this case, the counter electrode further preferably has properties of reflecting light. As the counter electrode of the dye-sensitized solar cell, a glass or plastic plate on which a metal or an electrically-conductive oxide is deposited is preferable, and a glass plate on which platinum is deposited is particularly preferable. In the dye-sensitized solar cell, a lateral side of the cell is preferably sealed with a polymer, an adhesive, or the like, in order to prevent evaporation of components.

The present invention can be applied to the photoelectric conversion elements and the dye-sensitized solar cells described, for example, in Japanese Patent No. 4260494, JP-A-2004-146425, JP-A-2000-340269, JP-A-2002-289274, JP-A-2004-152613, and JP-A-9-27352. In addition, the present invention can be applied to the photoelectric conversion elements and the dye-sensitized solar cells described, for example, in JP-A-2004-152613, JP-A-2000-90989, JP-A-2003-217688, JP-A-2002-367686, JP-A-2003-323818, JP-A-2001-43907, JP-A-2000-340269, JP-A-2005-85500, JP-A-2004-273272, JP-A-2000-323190, JP-A-2000-228234, JP-A-2001-266963, JP-A-2001-185244, JP-T-2001-525108, JP-A-2001-203377, JP-A-2000-100483, JP-A-2001-210390, JP-A-2002-280587, JP-A-2001-273937, JP-A-2000-285977, and JP-A-2001-320068.

<<Dye Solution, Dye-Adsorbed Electrode Using the Same, and Production Method of Dye-Sensitized Solar Cell>>

In the present invention, the dye-adsorbed electrode is preferably produced using a dye solution containing the metal complex dye of the present invention.

The foregoing dye solution contains the metal complex dye of the present invention dissolved in a solvent, and may comprise a co-adsorbent and other ingredients as needed.

Examples of the solvent to be used include solvents described in JP-A-2001-291534, but the solvent is not particularly limited thereto. In the present invention, organic solvents are preferred. More preferred are alcohols, amides, nitriles, hydrocarbons, and a mixed solvent of two or more kinds of these solvents. As the mixed solvent, preferred are mixed solvents of alcohols and a solvent selected from amides, nitriles, and hydrocarbons. More preferred are mixed solvents of alcohols and amides and mixed solvents of alcohols and hydrocarbons, and particularly preferred are mixed solvents of alcohols and amides. In specific, methanol, ethanol, propanol, butanol, dimethylformamide, and dimethylacetamide are preferred.

The dye solution preferably contains a co-adsorbent, and the co-adsorbent is preferably the aforementioned ones. Among them, the compound represented by Formula (CA) is preferred.

The dye solution of the present invention is preferably one in which the concentrations of the metal complex dye and the co-adsorbent have been adjusted so that the dye solution can be used as it is at the time of preparation of a photoelectric conversion element or a dye-sensitized solar cell. In the present invention, the metal complex dye of the present invention is preferably contained in an amount of from 0.001 to 0.1% by mass.

In the dye solution, it is particularly preferable to adjust the water content, and thus in the present invention, it is preferred that the content (content rate) of water is adjusted to the range of from 0 to 0.1% by mass.

Similarly, it is also preferable to adjust the water content in the electrolyte in a photoelectric conversion element and a dye-sensitized solar cell, in order to achieve the effects of the present invention effectively. Thus, it is preferred that the content (content rate) of water in the electrolyte solution is adjusted to the range of from 0 to 0.1% by mass. The foregoing adjustment of the electrolyte is particularly preferably carried out with the dye solution.

In the present invention, a dye-adsorbed electrode is preferably a semiconductor electrode for dye-sensitized solar cell, which is prepared by allowing the surface of the semiconductor fine particles provided on the semiconductor electrode, to carry the metal complex dye, with using the above dye solution.

In other words, the dye-adsorbed electrode for dye-sensitized solar cell preferably has a photoconductor layer which is obtained by coating a composition obtained from the aforementioned dye solution, on an electrically-conductive support provided with semiconductor fine particles, and curing the composition after coating.

In the present invention, it is preferable that a dye-sensitized solar cell be produced by using the dye-adsorbed electrode for dye-sensitized solar cell, preparing an electrolyte and a counter electrode, and performing an assembly with using them.

EXAMPLES

The present invention will be described in more detail based on examples given below, but the invention is not meant to be limited by these.

Example 1

[Synthesis of Metal Complex Dye]

Hereinafter, the synthetic method of the metal complex dye of the present invention will be described in detail, but starting substances, dye intermediates and synthetic routes are not limited to these.

(Synthesis of metal complex dye D-1)

The metal complex dye D-1 was synthesized according to the following scheme.

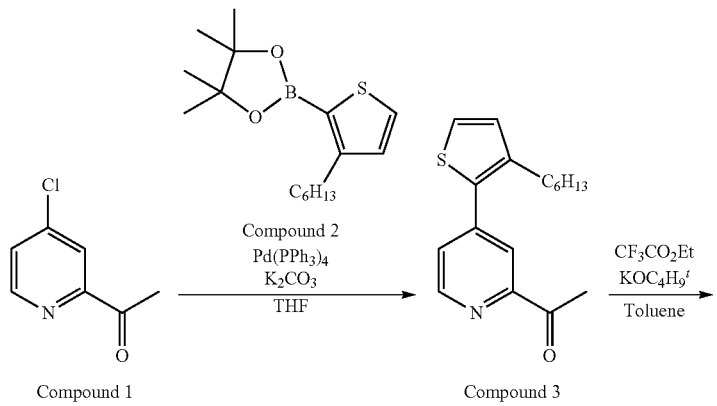

-continued
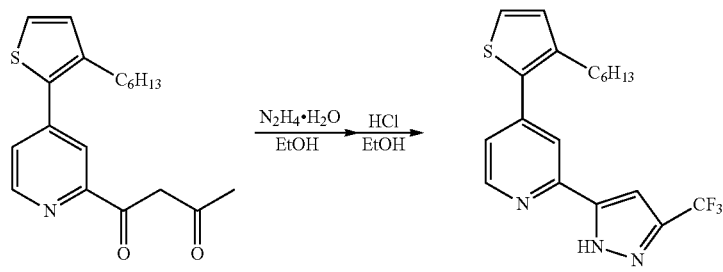
Compound 4 → Compound 5
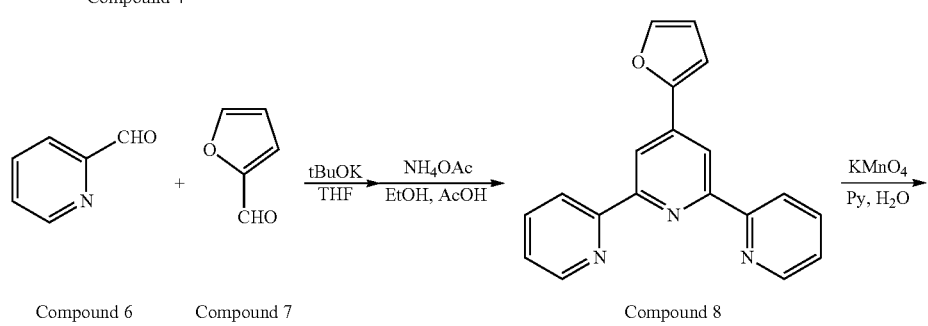
Compound 6 + Compound 7 → Compound 8
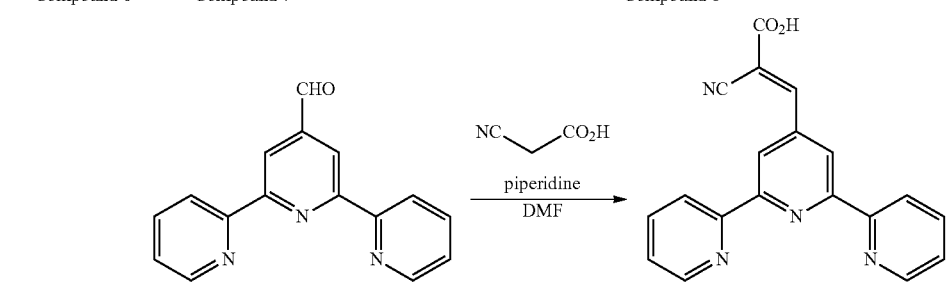
Compound 9 → Compound 10
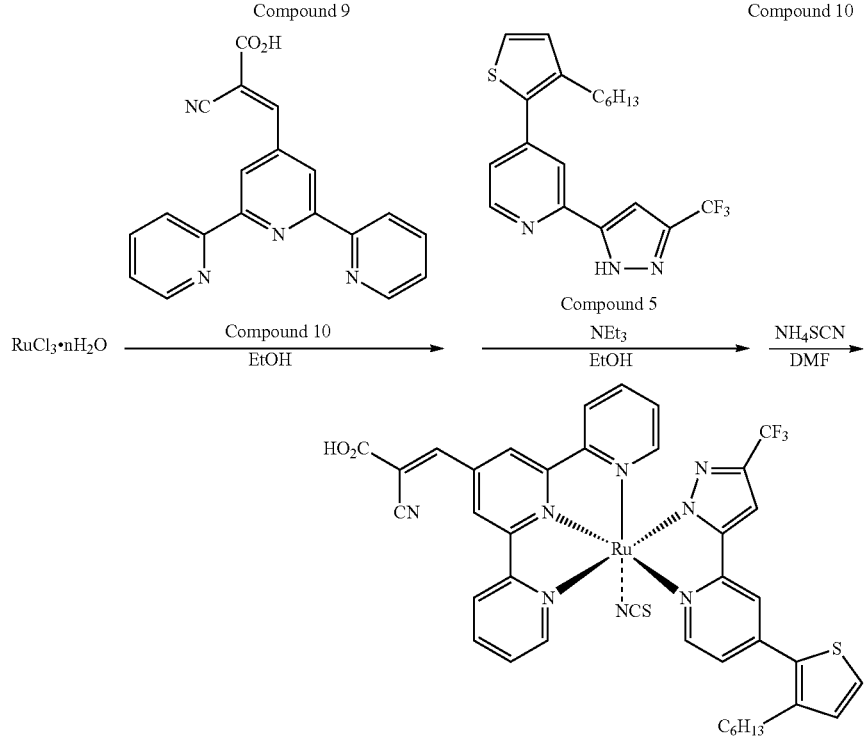
D-1

(i) Synthesis of Compound 3

In 62 ml of THF (tetrahydrofuran), 1 g of Compound 1 and 2.08 g of Compound 2 were dissolved. Thereto, 371 mg of Pd(PPh$_3$)$_4$ and 12.5 ml of a 2 N aqueous solution of potassium carbonate were added, and then the mixture was allowed to react at 80° C. over night. To the solution thus obtained, 100 ml of water, 40 ml of hexane, and 60 ml of ethyl acetate were added, and the liquid-liquid extraction was conducted. Thereafter, the organic layer was concentrated, and the crude product thus obtained was purified by silica gel column chromatography, thereby obtaining 1.59 g of Compound 3.

(ii) Synthesis of Compound 5

In 16 ml of toluene, 1.59 g of Compound 3 and ethyl trifluoroacetate were dissolved, and 1.27 g of potassium tert-butoxide was added under a nitrogen atmosphere while cooling on ice. The mixture was stirred for 30 minutes at room temperature. Thereto, 40 ml of a saturated aqueous solution of ammonium chloride and 40 ml of ethyl acetate were added, the liquid-liquid extraction thereof was conducted, and the organic layer was then concentrated. To the crude product thus obtained, 19 ml of ethanol and 305 mg of hydrazine monohydrate were added and stirred at 90° C. for 30 minutes, 310 µl of 12 N aqueous solution of hydrochloric acid was then added thereto and stirred for 30 minutes, and the resultant was concentrated under reduced pressure.

Thereafter, 20 ml of a saturated aqueous solution of sodium hydrogen carbonate and 20 ml of ethyl acetate were added thereto, the liquid-liquid extraction thereof were conducted, the organic layer was then concentrated, and the crude product thus obtained was purified by silica gel column chromatography, thereby obtaining 1.54 g of Compound 5.

(iii) Synthesis of Compound 8

In 200 ml of THF (tetrahydrofuran), 5 g of Compound 7, and Compound 6 in a 2 equivalent amount with respect to Compound 7 were dissolved. Under a nitrogen atmosphere, a 4 equivalent amount of potassium tert-butoxide was added thereto while stirring at 0° C., and the mixture was heated to 70° C. and stirred over night. To the solution thus obtained, excess amounts of acetic acid and ethanol were added dropwise, an excess amount of ammonium acetate was added, and the mixture was stirred at 70° C. over night. After concentrating the resultant under reduced pressure, 100 ml of a saturated aqueous solution of sodium hydrogen carbonate and 100 ml of methylene chloride were added thereto, and the liquid-liquid extraction thereof were conducted. Thereafter, the organic layer was concentrated, and the crude product thus obtained was recrystallized from methanol, thereby obtaining 1.01 g of Compound 8.

(iv) Synthesis of Compound 9

In 20 ml of pyridine and 10 ml of water, 1.0 g of Compound 8 was dissolved, potassium permanganate was added thereto under a nitrogen atmosphere, and the mixture was stirred at room temperature over night. To the solution thus obtained, an aqueous solution of sodium thiosulfate and an aqueous solution of sodium hydroxide were added, and the manganese dioxide thus produced was removed by filtration. The crude product obtained by concentrating the filtrate was recrystallized from acetonitrile, thereby obtaining 620 mg of Compound 9.

(v) Synthesis of Compound 10

In DMF (dimethylformamide), 600 mg of Compound 9, cyanoacetic acid in a 2 equivalent amount with respect to Compound 9, and piperidine in a 4 equivalent amount with respect to Compound 9 were dissolved, and the mixture was stirred at 60° C. over night. After concentrating the resultant under reduced pressure, the crude product thus obtained was recrystallized from methanol, thereby obtaining 460 mg of Compound 10.

Compound 10

MS data [M+H]$^+$=329

(vi) Synthesis of Metal Complex Dye D-1

In ethanol, 450 mg of Compound 10 and ruthenium chloride in a 1.0 equivalent amount with respect to Compound 10 were heated and refluxed for 5 hours, the resultant was then cooled to room temperature and filtered. To the residue thus obtained, 1 equivalent amount of Compound 5 and a 4 equivalent amount of triethylamine were added, and the mixture was stirred in 30 ml of diethylene glycol monoethyl ether at 110° C. for 2 hours. After concentrating the resultant under reduced pressure, the crude product thus obtained was recrystallized from acetonitrile. The crystal thus obtained was then heated and stirred in ammonium thiocyanate and DMF and concentrated under reduced pressure, thereby obtaining the crude product. This was dissolved in a methanol solution together with TBAOH (tetrabutylammonium hydroxide), and purified by SephadexLH-20 column. The fraction of the main layer was collected and concentrated, and then a solution of trifluoromethanesulfonic acid was added thereto so as to adjust the pH thereof to 3, and the precipitate was filtered, thereby obtaining 240 mg of the metal complex dye D-1.

(Synthesis of Metal Complex Dye D-14)

A ligand having a terpyridine skeleton was synthesized according to the following scheme, and the metal complex dye D-14 was synthesized in the same manner as the metal complex dye D-1.

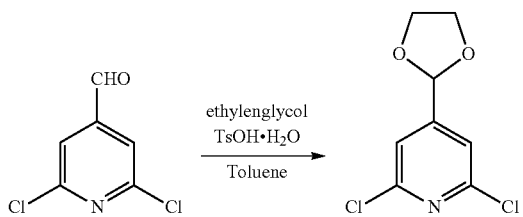

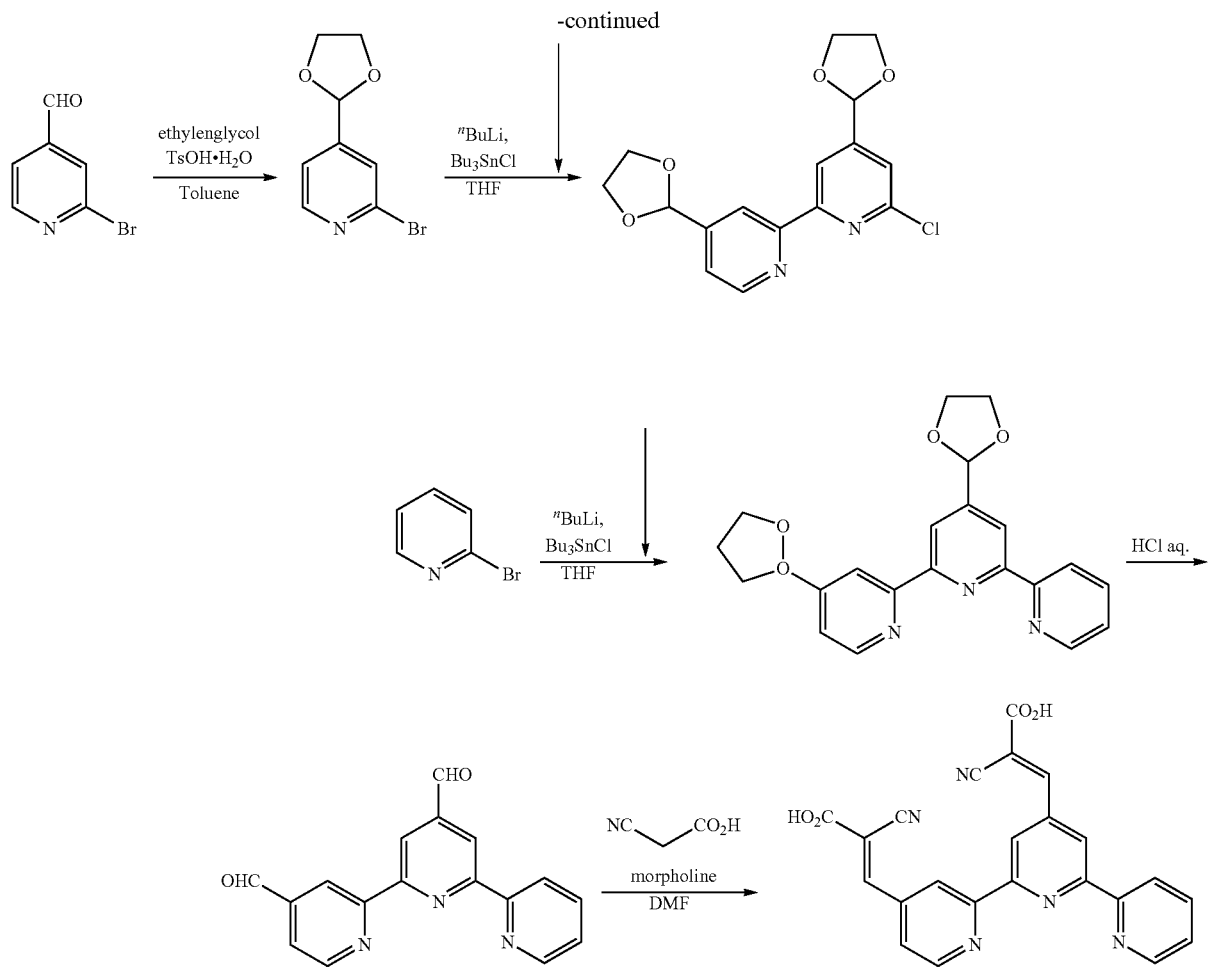
(Synthesis of Metal Complex Dye D-18)
A ligand having a terpyridine skeleton was synthesized according to the following scheme, and the metal complex dye D-18 was synthesized in the same manner as the metal complex dye D-1.
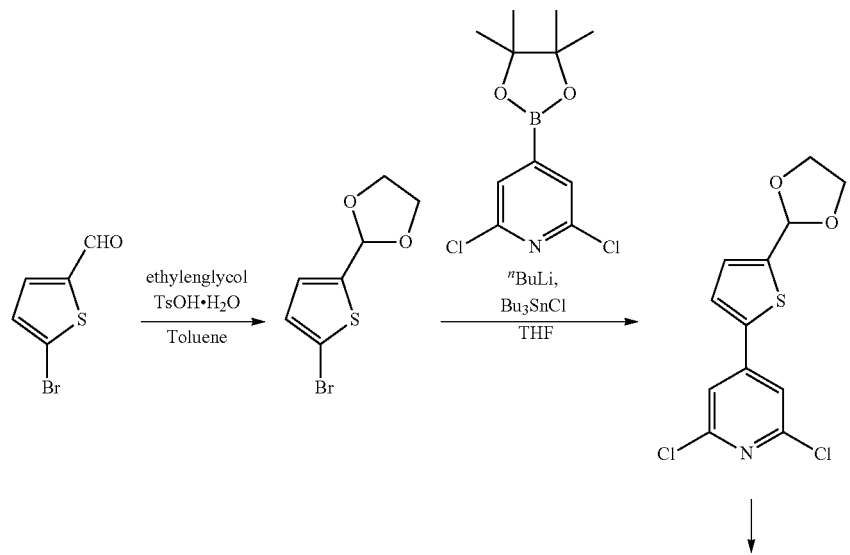

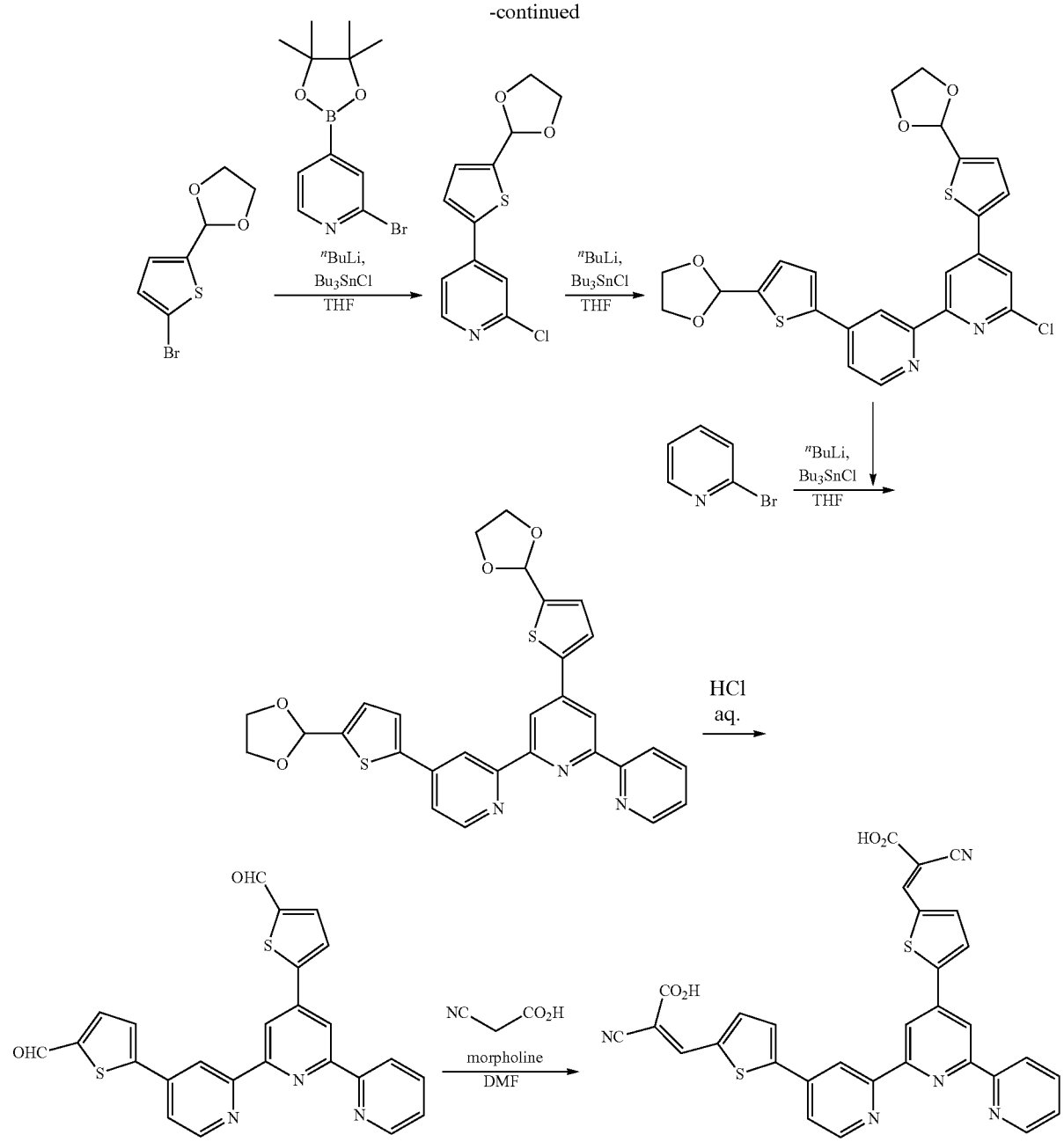
(Synthesis of Metal Complex Dye D-25)
The metal complex dye D-25 was synthesized according to the following scheme in the same manner as the metal complex dye D-1.
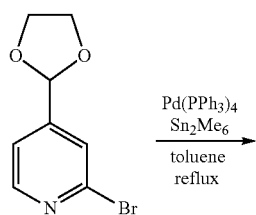
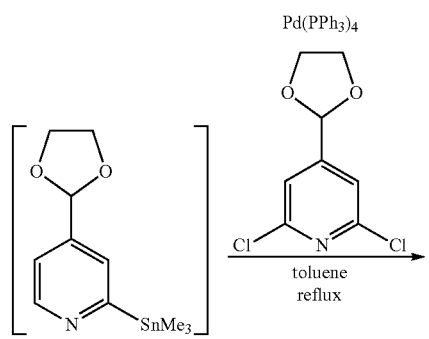

269
-continued

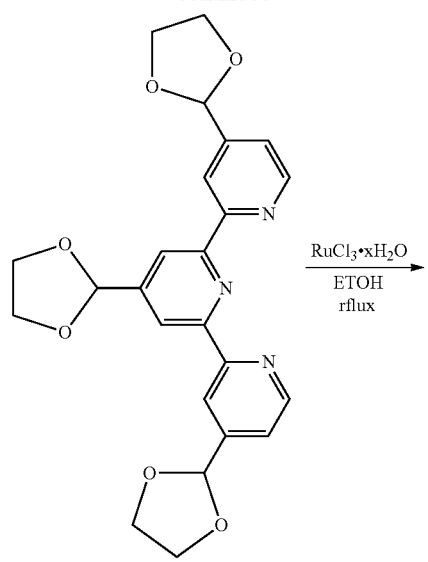

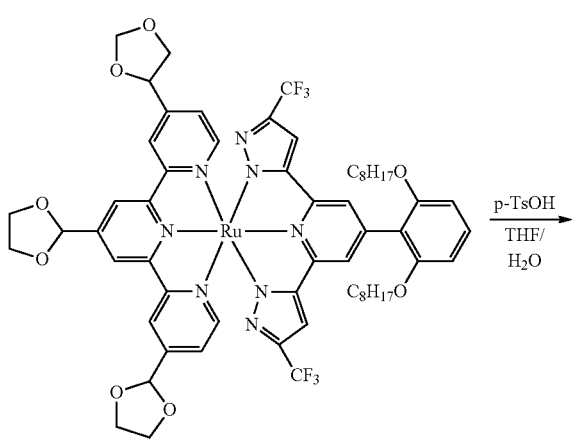

270
-continued

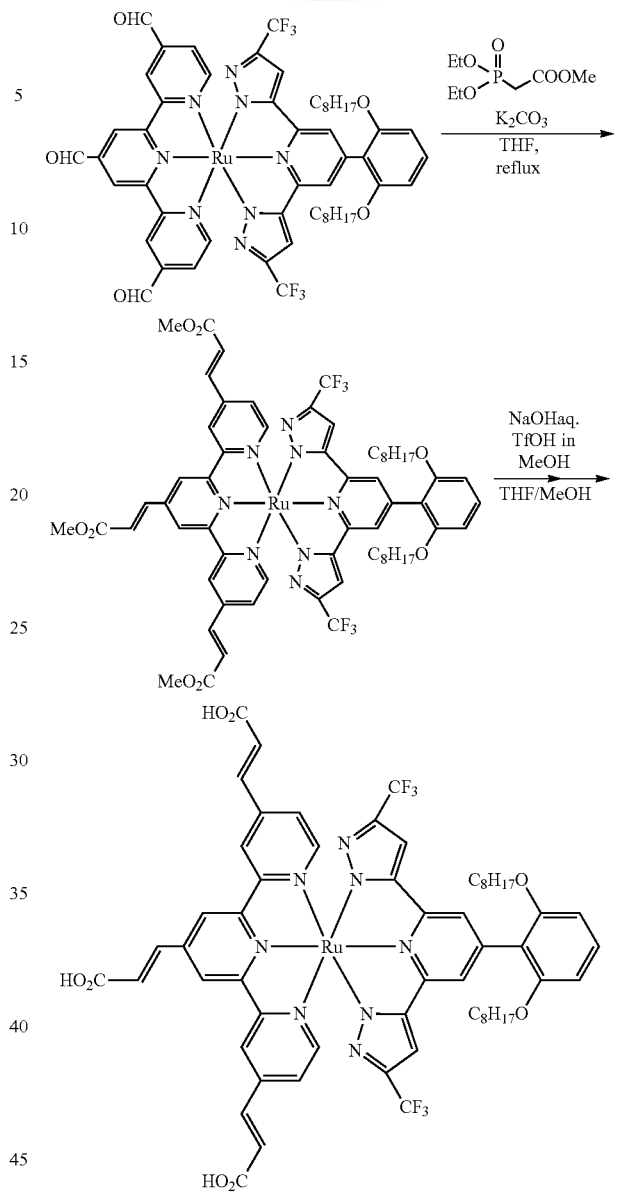

D-25

A visible absorption spectrum of the metal complex dye D-25 thus obtained is shown in FIG. 3.

The measurement was conducted at a concentration of 17 μmol/L using UV-3600 manufactured by Shimadzu Corporation.

FIG. 3 is a spectrum diagram when the solvent for measurement was N,N-dimethylformamide (DMF), and FIG. 4 is a spectrum diagram in a methanol solution containing tetrabutylammonium hydroxide (TBAOH) at 340 mmol/L. These spectrum diagrams are close to the visible absorption spectrum of the $TiO_2$ film on which the metal complex dye D-25 has been adsorbed.

(Synthesis of Metal Complex Dye D-26)

The metal complex dye D-26 was synthesized according to the following scheme in the same manner as the metal complex dyes D-1 and D-25.

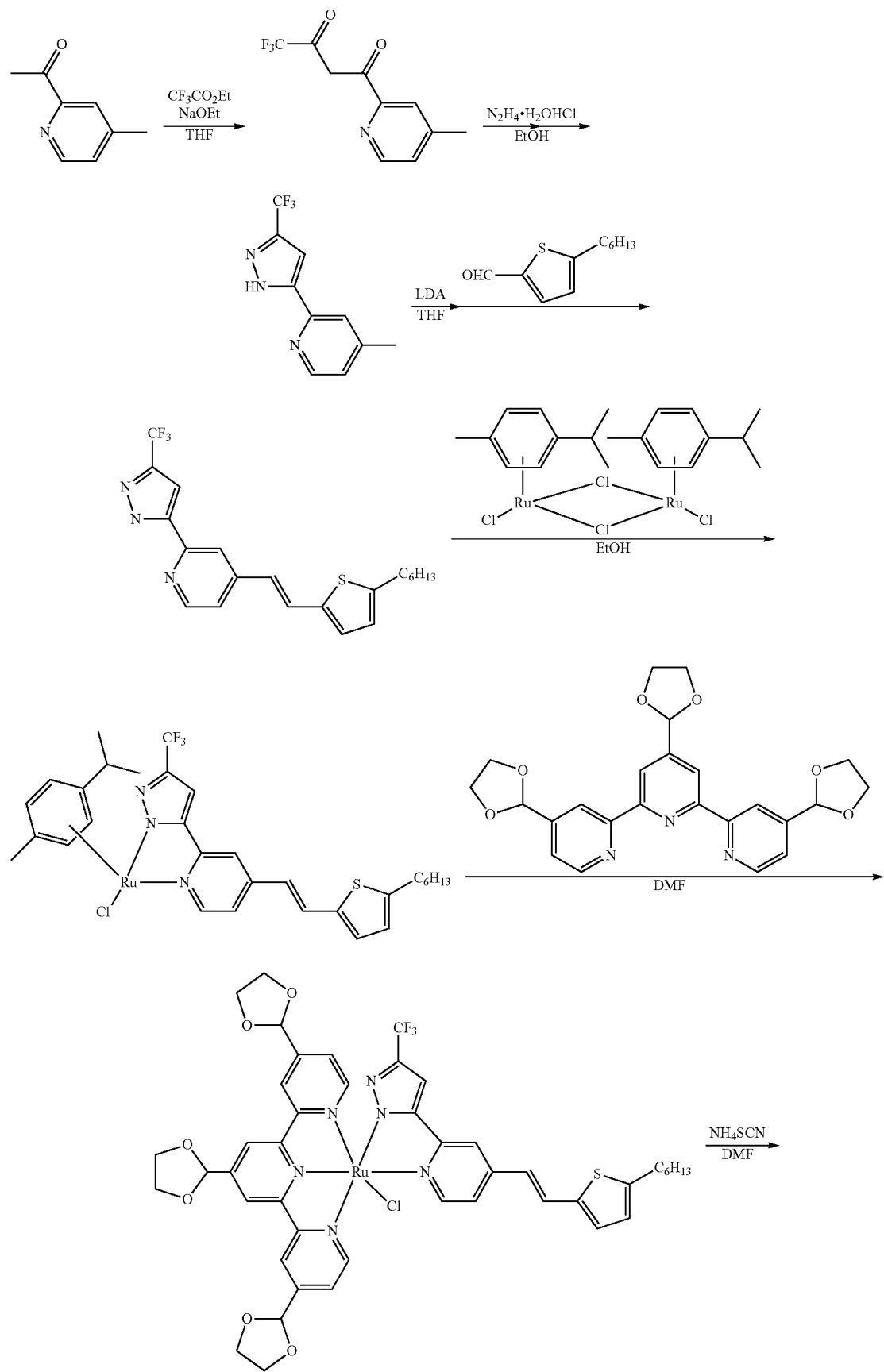

-continued
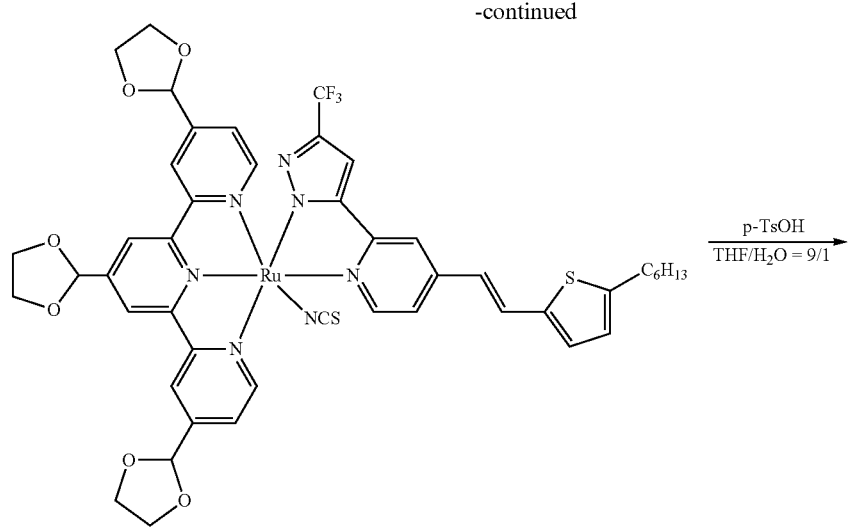
$\xrightarrow{\text{p-TsOH}}_{\text{THF/H}_2\text{O} = 9/1}$
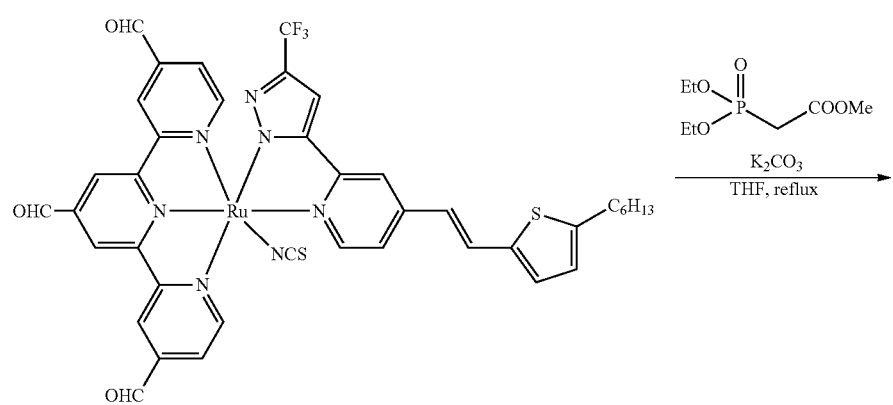
$\xrightarrow[\text{THF, reflux}]{\text{K}_2\text{CO}_3}$
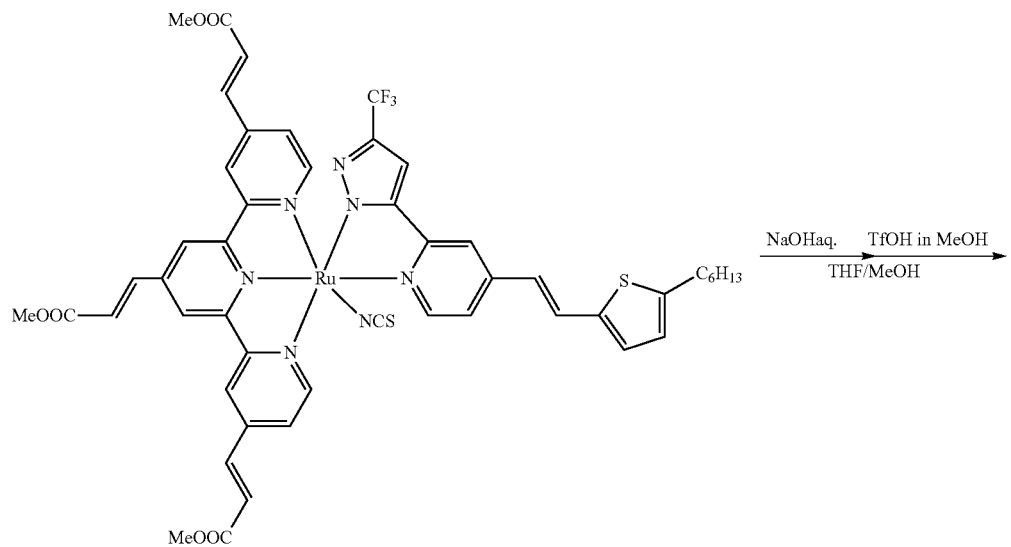
$\xrightarrow[\text{THF/MeOH}]{\text{NaOHaq.} \quad \text{TfOH in MeOH}}$ -continued
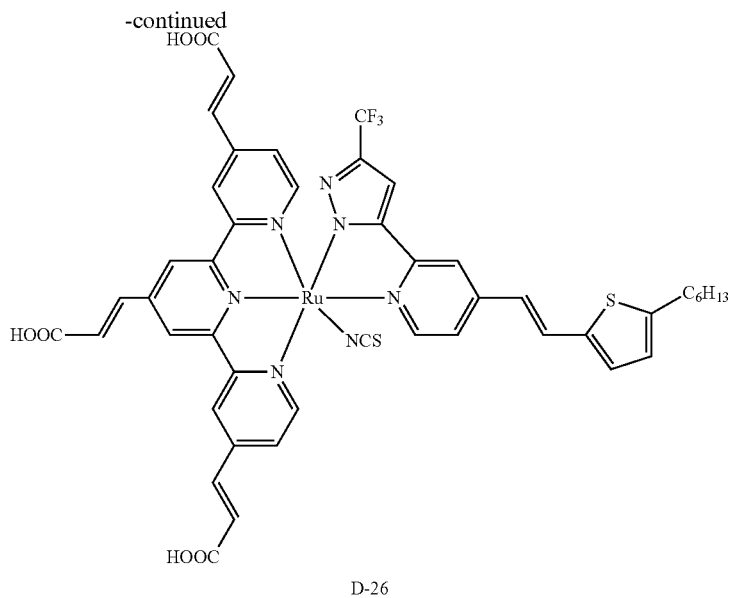
D-26
The synthesis of the metal complex dye D-26 was also conducted by the method according to the following scheme.
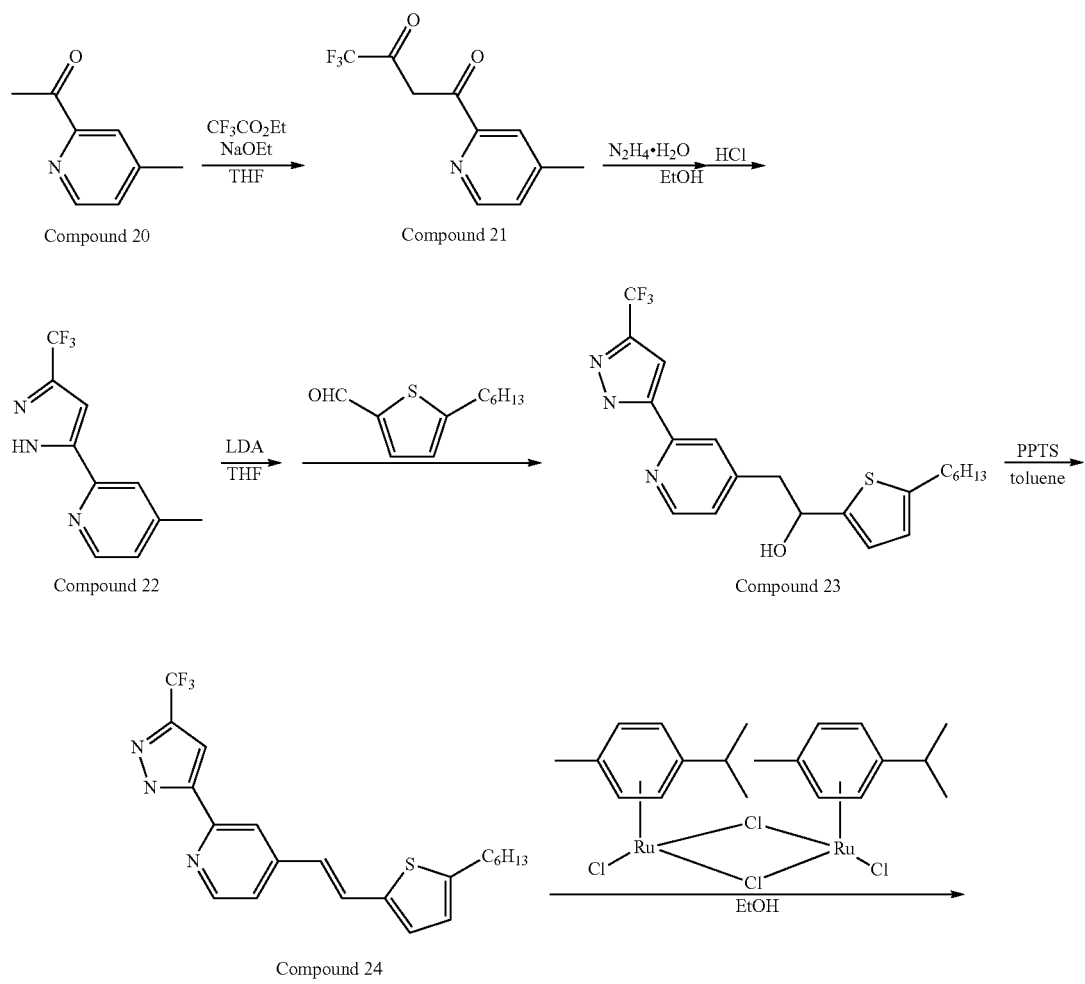

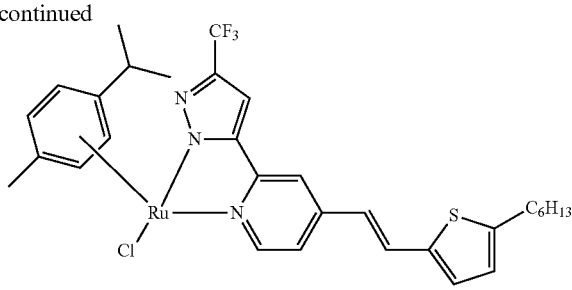

Compound 25

(i) Synthesis of Compound 21

In 200 ml of tetrahydrofuran (THF), 25 g of Compound 20 (2-acetyl-4-methylpyridine) was dissolved. Thereto, 18.9 g of sodium ethoxide was added under a nitrogen atmosphere while stirring at 0° C., and the mixture was stirred for 15 minutes. Thereafter, 28.9 g of ethyl trifluoroacetate was added thereto dropwise, and the resultant was stirred at an external temperature of 70° C. for 20 hours. After cooling the resultant to room temperature, an aqueous solution of ammonium chloride was added thereto dropwise, the liquid was separated, and the organic layer was concentrated, thereby obtaining 72.6 g of crude product of Compound 21.

(ii) Synthesis of Compound 22

In 220 ml of ethanol, 72.6 g of Compound 21 was dissolved. Thereto, 5.6 ml of hydrazine monohydrate was added under a nitrogen atmosphere while stirring at room temperature, and the mixture was heated at an external temperature 90° C. for 12 hours. Thereafter, 5 ml of concentrated hydrochloric acid was added thereto, and the mixture was stirred for 1 hour. After concentration, the resultant was then subjected to the liquid-liquid extraction using 150 ml of sodium bicarbonate water and 150 ml of ethyl acetate, and the organic layer was concentrated. The resultant was recrystallized from acetonitrile, thereby obtaining 31.5 g of Compound 22.

(iii) Synthesis of Compound 23

While stirring 4.1 g of diisopropyl amine and 30 ml of tetrahydrofuran at −40° C. under a nitrogen atmosphere, 23.1 ml of a 1.6 M solution of n-butyllithium hexane was added thereto dropwise and stirred for 2 hours. Thereafter, 4.0 g of Compound 22 was added thereto, and the mixture was stirred at 0° C. for 80 minutes, and then a solution prepared by dissolving 5.00 g of 2-hexylthiophene-5-carboxaldehyde in 15 ml of tetrahydrofuran was added thereto dropwise. Thereafter, the mixture was stirred at 0° C. for 80 minutes and at room temperature for 5 hours. Thereafter, a solution of ammonium chloride was added to the resultant, and the liquid-liquid extraction thereof was conducted using ethyl acetate. The organic layer was concentrated and purified by silica gel column chromatography, thereby obtaining 5.0 g of Compound 23.

(iv) Synthesis of Compound 24

To 50 ml of toluene, 4.9 g of Compound 23 and 4.1 g of PPTS (pyridinium p-toluenesulfonate) were added, and the mixture was heated and refluxed for 5 hours under a nitrogen atmosphere. After concentration, the resultant was then subjected to the liquid separation using saturated sodium bicarbonate water and methylene chloride, and the organic layer was concentrated. The crystal thus obtained was recrystallized from methanol and methylene chloride, thereby obtaining 3.2 g of Compound 24.

(v) Synthesis of Compound 25

In 150 ml of ethanol, 1.22 g of dichloro(p-cymene) ruthenium(II) dimer and 1.62 g of Compound 24 were added, and the mixture was stirred at 70° C. for 3 hours under a nitrogen atmosphere. Thereafter, the resultant was cooled to room temperature, and sodium bicarbonate water and ethyl acetate were added thereto so as to conduct the liquid separation operation thereof, and the organic layer was concentrated under reduced pressure. Acetonitrile was added to the crude product thus obtained, and the recrystallization thereof was conducted, the recrystallized product was filtered and dried, thereby obtaining 1.5 g of Compound 25.

Compound 28 was synthesized using Compound 25 synthesized in this manner and Compound 27, as a ligand, according to the following reaction scheme, and the metal complex D-26 was synthesized via Compound 29.

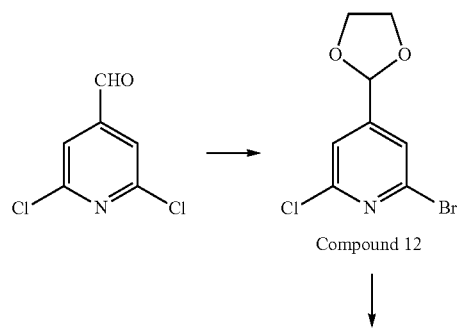

Compound 12

-continued
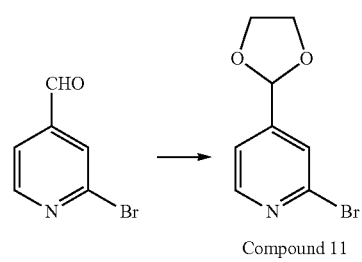 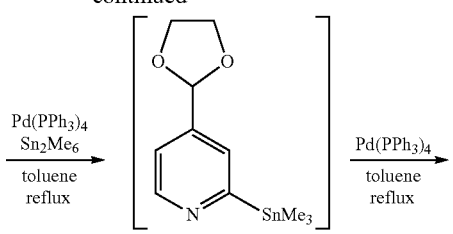
Compound 11
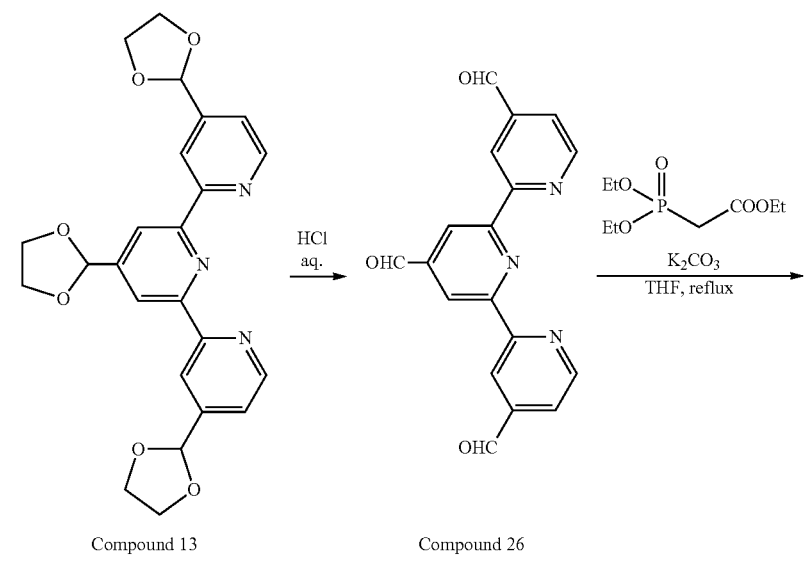
Compound 13     Compound 26
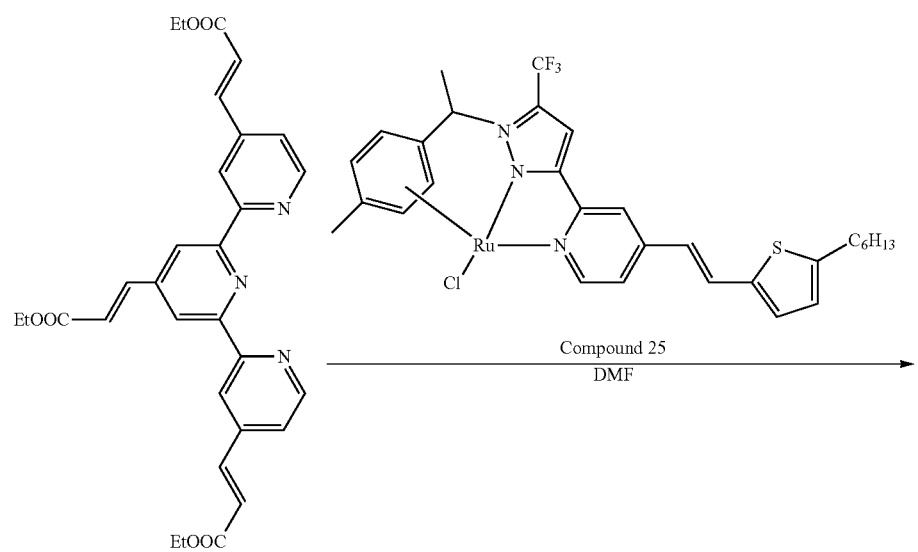
Compound 27

-continued
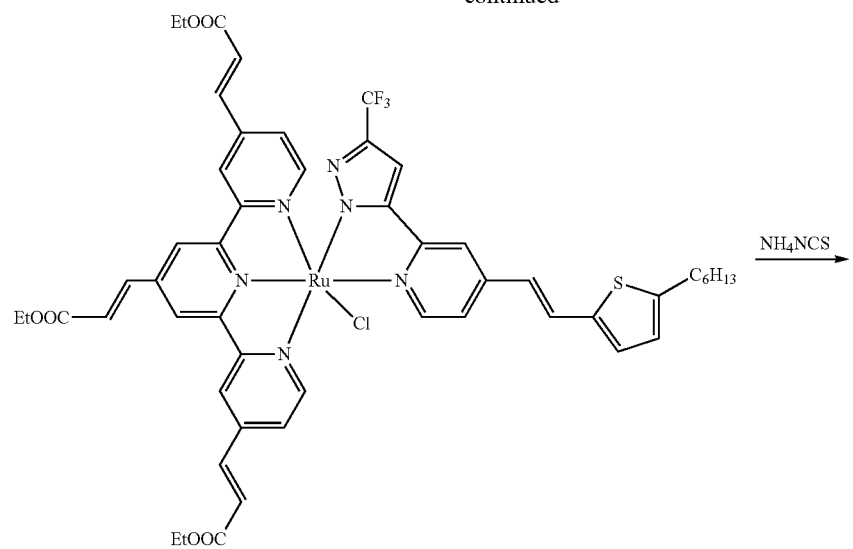
Compound 28
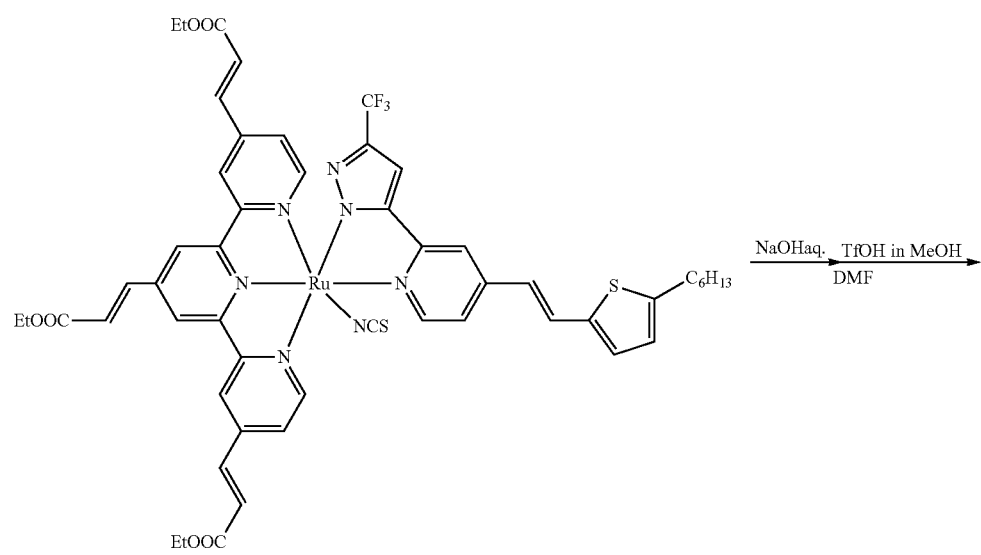
Compound 29

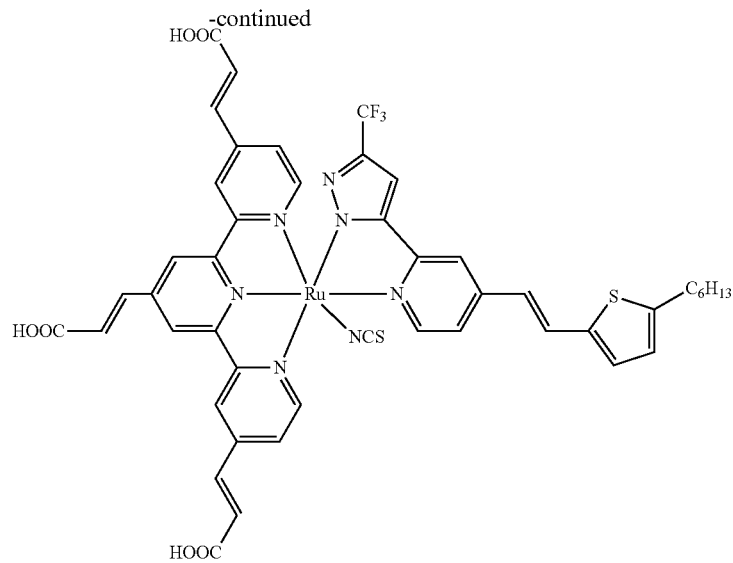

D-26

(vi) Synthesis of Compound 12

Into a three-necked flask, 4.30 g of 2,6-dichloro-4-pyridine carboxaldehyde, 1.49 g of p-toluenesulfonic acid, and 50 ml of dehydrated toluene were introduced and stirred. Thereto, 3.0 ml of ethylene glycol was added, and Dean-Stark was installed to the flask, and the mixture was heated and refluxed in an oil bath at 140° C. for 6 hours. The flask was cooled to room temperature, 50 ml of 5% sodium bicarbonate water was gradually added thereto dropwise, and the organic layer was extracted by the liquid separation operation. The operation of adding 50 ml of toluene to the aqueous layer and the conducting extraction was repeated twice, and the organic layer was summed with the extracted liquid and concentrated under reduced pressure. The resultant was purified by silica gel column chromatography using hexane/ethyl acetate as the eluent, thereby obtaining 4.91 g of Compound 12. Furthermore, the reaction was conducted by increasing the scale, and 30 g of Compound 12 was synthesized.

(vii) Synthesis of Compound 11

Using 50 g of 2-bromo-4-pyridine carboxaldehyde, 58.0 g of Compound 11 was synthesized by the same synthetic method as Compound 12.

(viii) Synthesis of Compound 13

Into a three-necked flask, 20.71 g of Compound 11, 400 ml of dehydrated toluene, and 30.96 g of hexamethylditin were introduced and subjected to the nitrogen purge while stirring. Thereto, 10.4 g of tetrakis(triphenylphosphine)palladium was added, and the mixture was heated and refluxed in an oil bath at 140° C. for 2 hours. Thereafter, 8.21 g of Compound 12 was added thereto and subjected to the nitrogen purge again, 10.4 g of tetrakis(triphenylphosphine)palladium was added thereto, and the mixture was heated and refluxed in an oil bath at 140° C. for 12 hours. The resultant was cooled to room temperature, 200 ml of chloroform was added thereto. The mixture was subjected to the ultrasonic treatment and filtered through Celite and concentrated under reduced pressure. This was purified by alumina column chromatography using toluene/ethyl acetate as the eluent, thereby obtaining 9.09 g of Compound 13. The identification of the compound thus obtained was performed by $^1$H-NMR and MS spectra.

Compound 13
  MS data [M+H]$^+$=450
  The $^1$H-NMR spectrum is shown in FIG. 29.

(ix) Synthesis of Compound 26

Into a three-necked flask, 6.0 g of Compound 13 and 120 ml of concentrated hydrochloric acid were introduced, and heated and stirred in an oil bath at 70° C. for 2 hours. Thereafter, 180 ml of distilled water was added thereto and heated and stirred for 1 hour. The resultant was cooled to room temperature. Thereto, 1200 ml of sodium bicarbonate water was added dropwise, and the crystal thus produced was filtrated, washed with water, and dried, thereby obtaining 4.18 g of Compound 26. The identification of the compound thus obtained was performed by $^1$H-NMR and MS spectra.

Compound 26
  MS data [M+H]$^+$=318
  The $^1$H-NMR spectrum is shown in FIG. 30.

(x) Synthesis of Compound 27

Into a three-necked flask, 2 g of Compound 26 and 200 ml of dehydrated tetrahydrofuran were introduced and heated and stirred in an oil bath at 95° C. After completely dissolving Compound 26, 8.72 g of potassium carbonate and 7.07 g of ethyl diethylphosphonoacetate were added thereto, and the mixture was heated and refluxed for 2 hours under nitrogen. The resultant was cooled to room temperature, 600 ml of distilled water was added thereto, and the precipitate thus produced was filtered, washed with water and dried, thereby obtaining 2.6 g of Compound 27. The identification of the compound thus obtained was performed by $^1$H-NMR and MS spectra.

Compound 27
  MS data [M+H]$^+$=528
  The $^1$H-NMR spectrum is shown in FIG. 31.

(xi) Synthesis of Compound 28

Into a three-necked flask, 640 mg of Compound 25, 500 mg of Compound 27, and 10 ml of N, N-dimethylformamide were introduced, and heated and stirred at 130° C. for 3 hours. The resultant was cooled to room temperature. Thereto, saturated saline solution and ethyl acetate were added thereto, the liquid separation operation thereof was conducted. The organic layer was then concentrated under reduced pressure and purified by silica gel column chromatography, thereby obtaining 300 mg of Compound 28.

(xii) Synthesis of Compound 29

Into a three-necked flask, 200 mg of Compound 28, 142 mg of ammonium thiocyanate, and 4 ml of N, N-dimethylformamide were introduced and heated and stirred at 130° C. for 2 hours. The resultant was cooled to room temperature, saturated saline solution and ethyl acetate were added thereto, the liquid separation operation thereof was conducted. The organic layer was then concentrated under reduced pressure and purified by silica gel column chromatography, thereby obtaining 110 mg of Compound 29.

(xiii) Synthesis of Metal Complex Dye D-26

Into a three-necked flask, 97 mg of Compound 29 and 6 ml of N, N-dimethylformamide were introduced and cooled to 0° C. An excess amount of 3 N aqueous solution of sodium hydroxide was added thereto while stirring, and the mixture was stirred for 6 hours. Next, a 1 N aqueous solution of trifluoromethanesulfonic acid prepared in advance was added to the mixture so as to make the mixture acidic. The precipitate thus produced was filtered, washed with water and dried, thereby obtaining 87 mg of the metal complex dye D-26.

The visible absorption spectra of the metal complex dye D-26 thus obtained are shown in FIGS. 5 and 6.

A visible absorption spectrum is shown in FIG. 5, which was measured at a concentration of 17 µmol/L in a methanol solution containing tetrabutylammonium hydroxide (TBAOH) at 340 mmol/L, using UV-3600 manufactured by Shimadzu Corporation, in the same manner as the metal complex dye D-25. In addition, a visible absorption spectrum in a model semiconductor film (a titanium oxide film on which metal complex dye D-26 had been adsorbed), in accordance with the sample No. 102 in Example 4 described later is shown in FIG. 6.

It can be seen that the visible absorption spectrum in the methanol solution containing tetrabutylammonium hydroxide (TBAOH) at 340 mmol/L (FIG. 5) is similar to the visible absorption spectrum in the titanium oxide film on which metal complex dye D-26 had been adsorbed (FIG. 6).

(Synthesis of Metal Complex Dye D-28)

The metal complex dye D-28 was synthesized in the same manner as the metal complex dyes D-1, D-25, and D-26.

D-28

(Synthesis of Metal Complex Dye D-45)

The metal complex dye D-45 was synthesized in the same manner as the metal complex dyes D-1, D-25, and D-26.

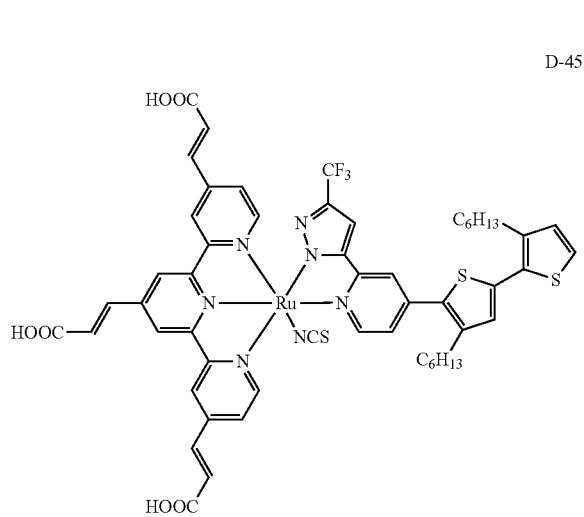

D-45

(Synthesis of Metal Complex Dye D-57)

Into a 50 ml eggplant-type flask, 100 mg of the metal complex dye D-28 synthesized as described above and 10 ml of THF were added. Thereto, tetrabutylammonium hydroxide in a 1 equivalent amount with respect to the metal complex dye D-28 was added while stirring, and the mixture was stirred for 30 minutes at room temperature. Thereafter, the solvent was distilled off under reduced pressure, and the residue was dried, thereby obtaining the metal complex dye D-57. The identification of the compound was performed by MALDI-MS.

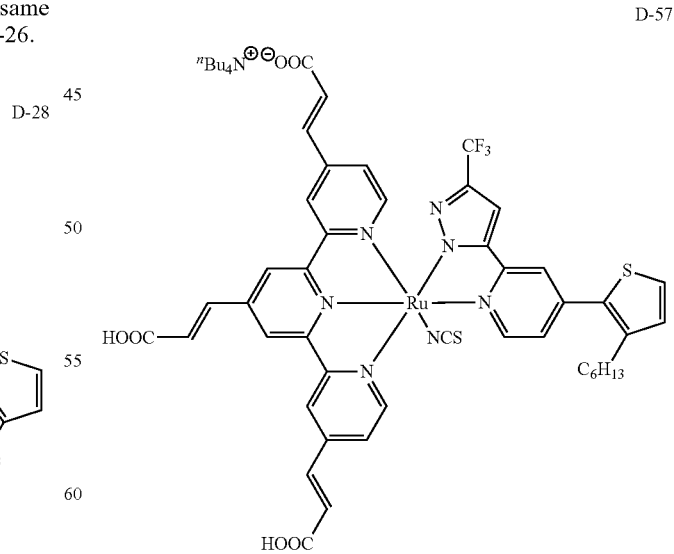

D-57

(Synthesis of Metal Complex Dye D-59)

The metal complex dye D-59 was synthesized in the same manner as the metal complex dyes D-1, D-25, and D-26.

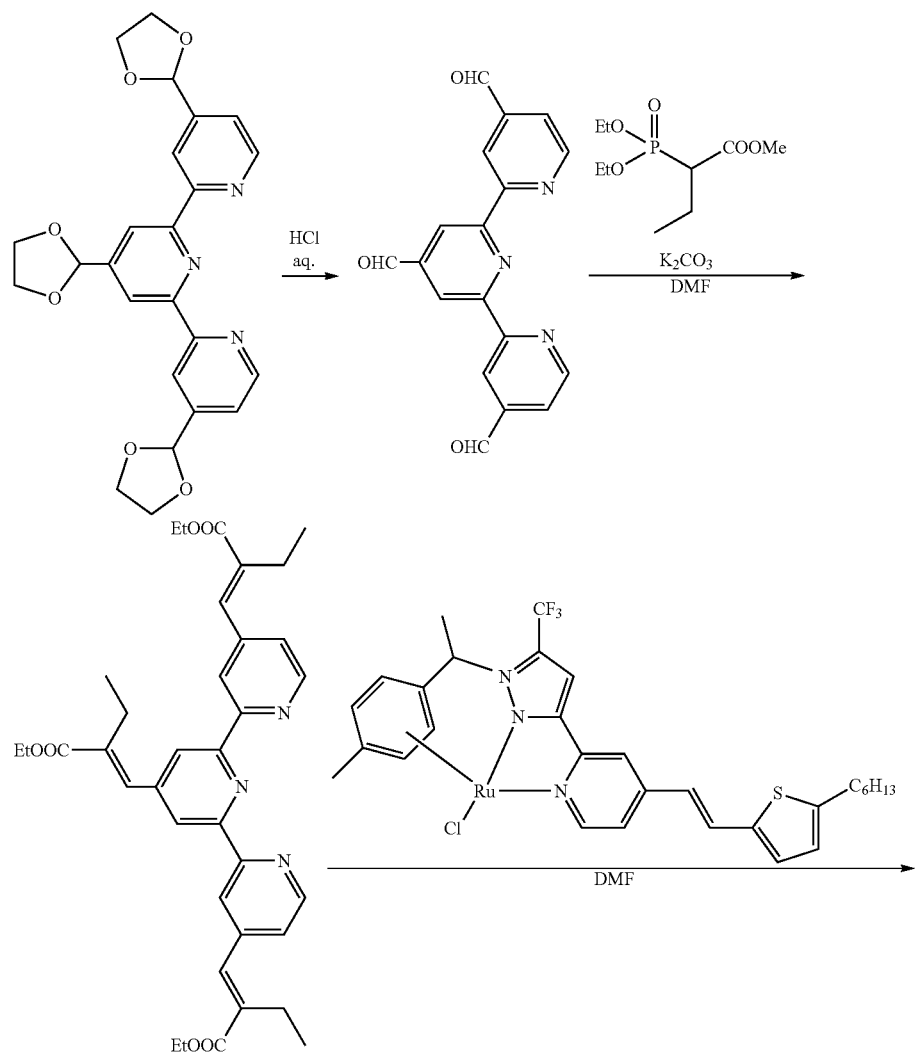
Compound 14
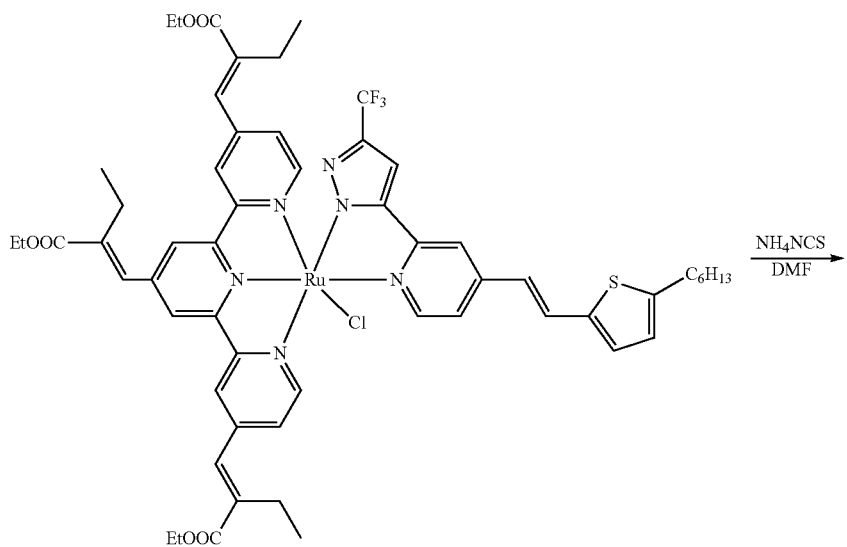

289
-continued
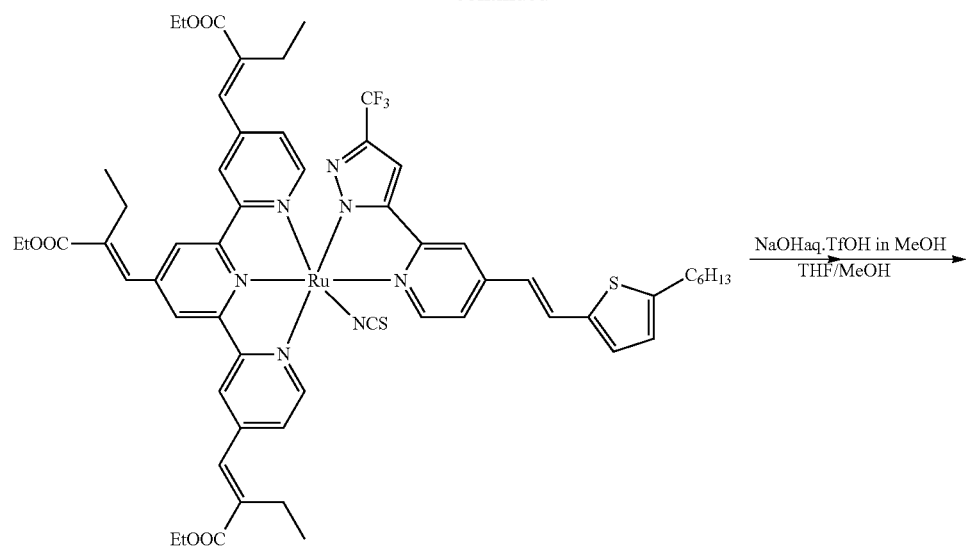
NaOHaq.TfOH in MeOH
THF/MeOH
→
290
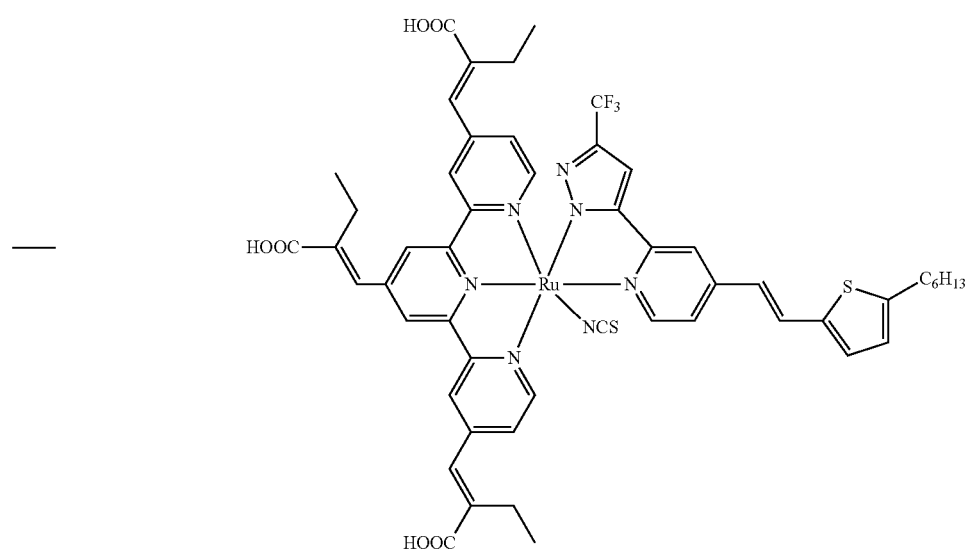
D-59

The MS spectrum of Compound 14 is shown below.
Compound 14
MS data [M+H]$^+$=612
(Synthesis of Metal Complex Dye D-62)
According to the following scheme, Compound 34 was synthesized, and the metal complex dye D-62 was synthesized in the same manner as the metal complex dyes D-26 and D-59.
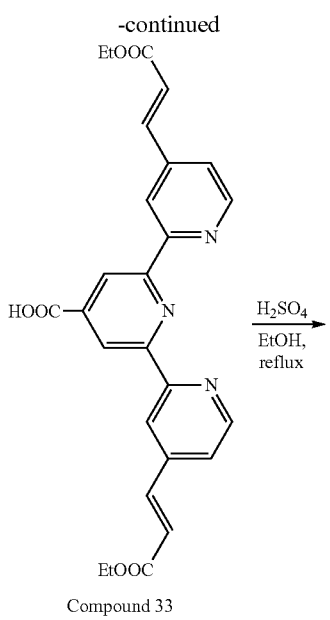
Compound 33
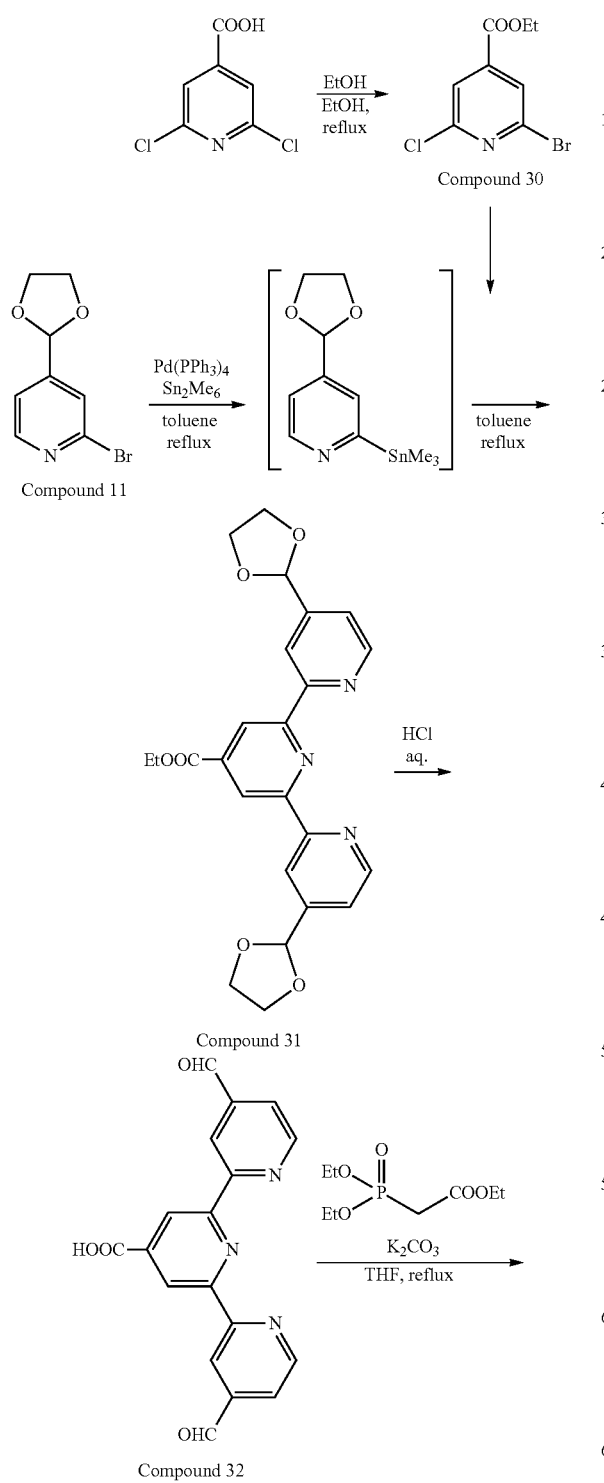
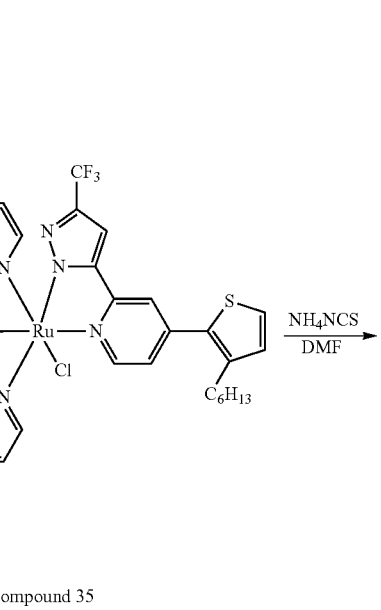
Compound 34
Compound 35

-continued

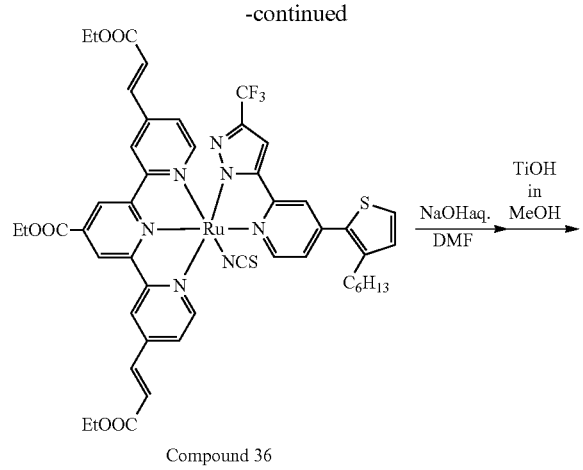

Compound 36

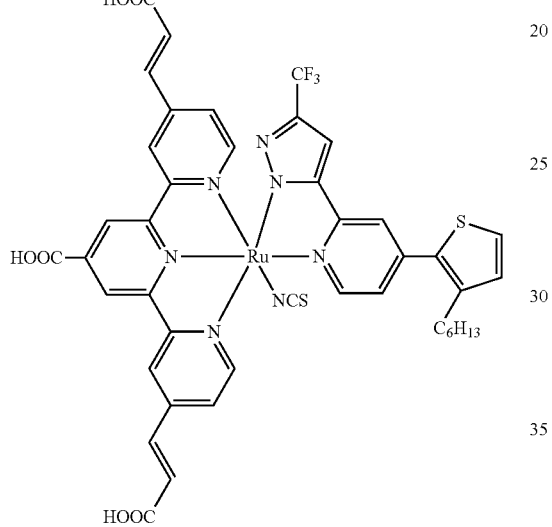

D-62

MS spectra of Compounds 31 to 34 are shown below.
Compound 31
  MS data [M+H]$^+$=450
Compound 32
  MS data [M+H]$^+$=334
Compound 33
  MS data [M+H]$^+$=474
Compound 34
  MS data [M+H]$^+$=502
The $^1$H-NMR spectrum is shown in FIG. 32.

(Synthesis of Metal Complex Dye D-78)

Compounds 51 to 53 were synthesized, using Compound 50 as the starting substance, by the same method as the method described in J. Heterocycl. Chem. 2008, 45, 91-96, and subsequently Compounds 54 was obtained by performing the Stille coupling using Compound 53 and Compound 30. The identification of the compounds thus obtained was performed by ESI-MS. The metal complex dye D-78 was synthesized using Compound 54, in the same manner as the metal complex dye D-141 described later. The identification of the compound was performed by ESI-MS.

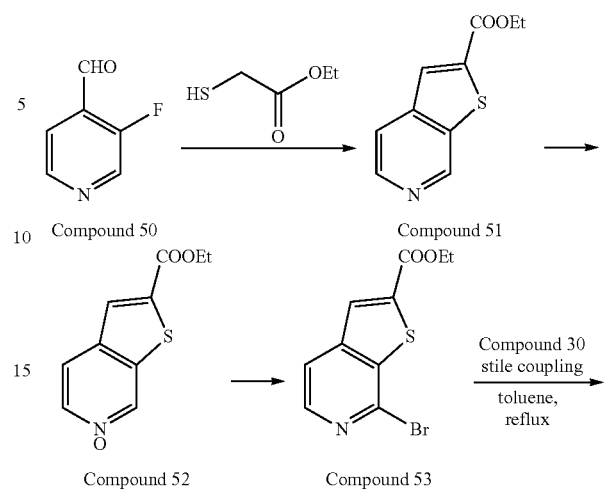

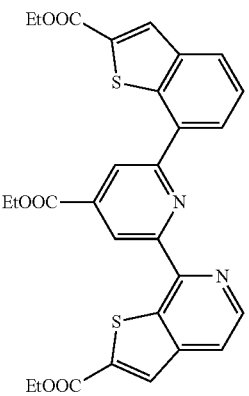

Compound 54

D-78

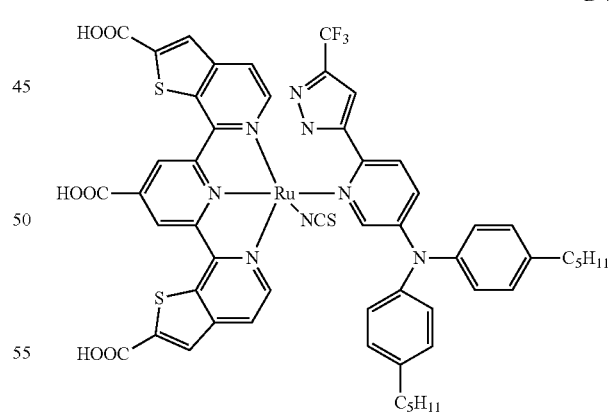

The MS spectrum of Compound 54 is shown below.
Compound 54
  MS data [M+H]$^+$=562

(Synthesis of Metal Complex Dye D-97)

The metal complex dye D-97 was synthesized according to the following scheme in the same manner as the metal complex dyes D-26 and D-59.

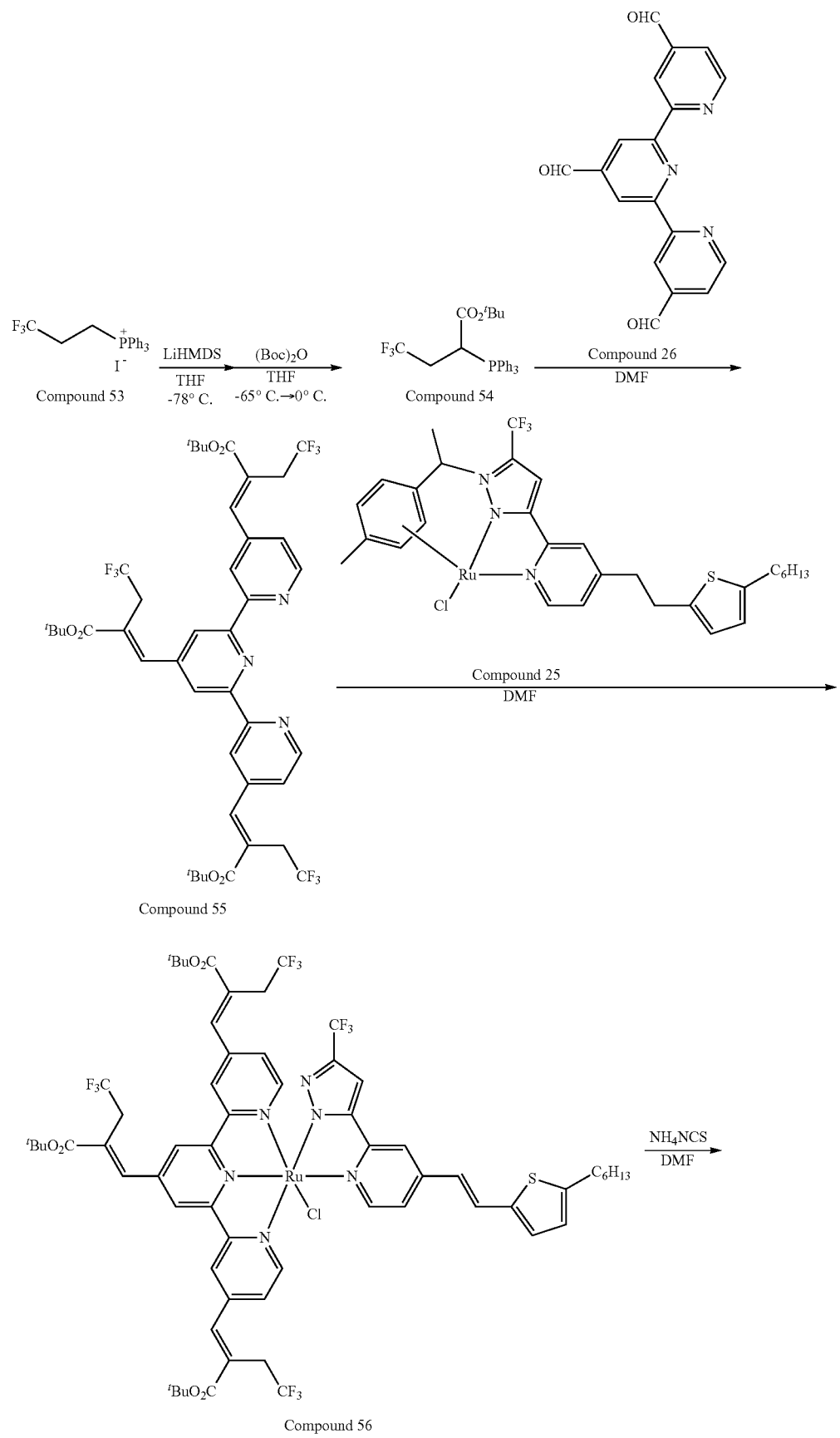

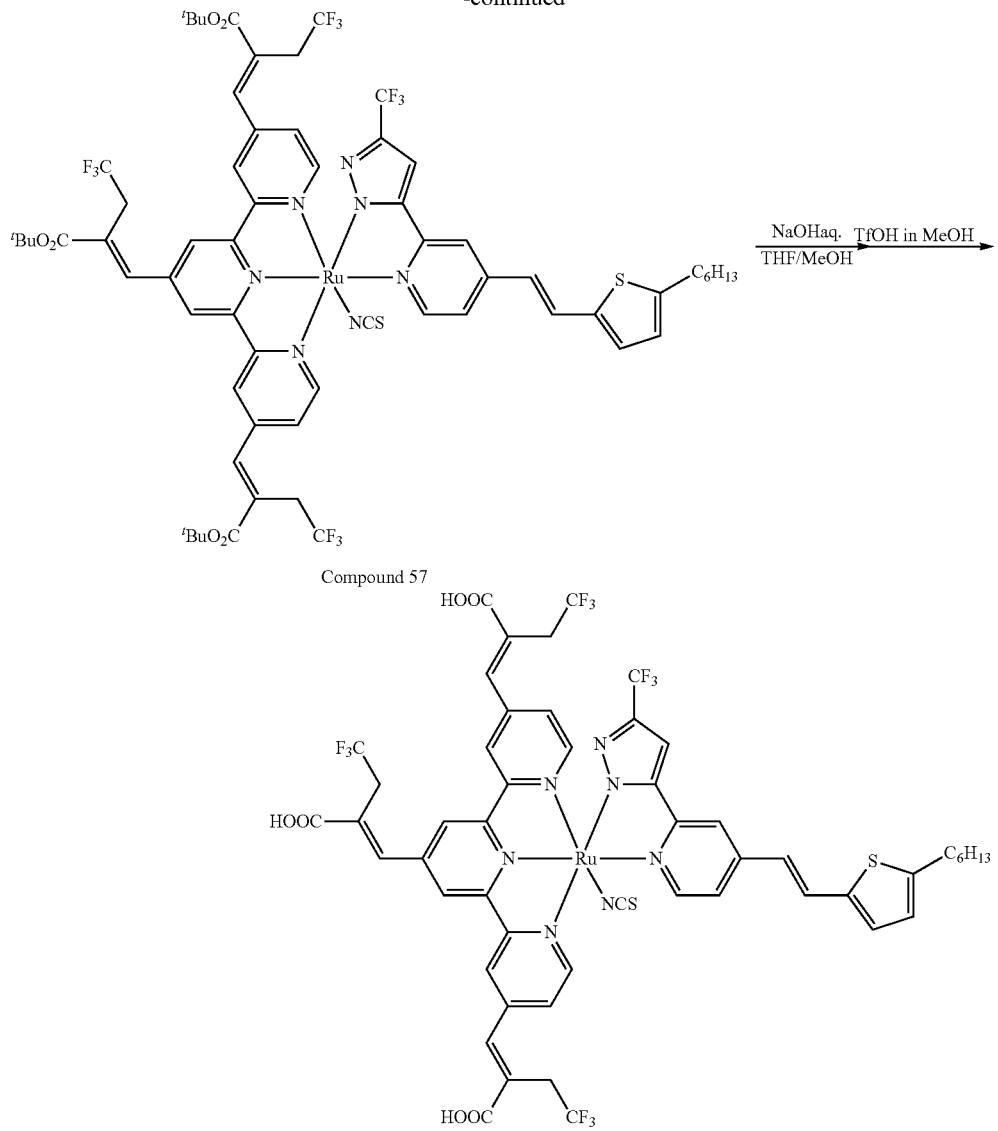

Compound 57

D-97

(i) Synthesis of Compound 53
Compound 53 was synthesized according to the method described in Bioorg. Med. Chem. Lett., 17, 2401-2403 (2007).

(ii) Synthesis of Compound 54
Compound 54 was synthesized using Compound 53 and di-tert-butyl dicarbonate, by the same method as the method described in Bioorg. Med. Chem. Lett., 17, 2401-2403 (2007).

(iii) Synthesis of Compound 55
Into a 20 ml eggplant-flask, 1 g of Compound 26, 7.22 g of Compound 54, and 8 ml of N,N-dimethylformamide (dehydrated) were introduced, and heated and stirred in an oil bath at 140° C. for 1.5 hours. The resultant was cooled to room temperature, the solvent was distilled off under reduced pressure, and the residue was purified by silica gel column chromatography and further purified by GPC, thereby obtaining 800 mg of Compound 55.

Here, the MS spectrum of Compound 55 is presented below.

Compound 55
MS data [M+H]$^+$=858

(iv) Synthesis of Metal Complex Dye D-97
Compound 57 was synthesized using Compound 55 in the same manner as D-26. Into a 100-ml three-necked flask, 370 mg of Compound 57, 50 ml of methylene chloride, and 2 ml of trifluoroacetic acid were introduced and stirred for 2.5 hours. Thereafter, 25 ml of methylene chloride and 3 ml of trifluoroacetic acid were added to the mixture and stirred for 1.5 hours. Then, 100 ml of methylene chloride and 10 ml of trifluoroacetic acid were added thereto and stirred at 30° C. for 2 hours, further 8 ml of trifluoroacetic acid was added thereto and stirred at 30° C. for 2 hours. The resultant was cooled to room temperature, the solvent was distilled off under reduced pressure, the residue was dispersed in methanol, and the precipitate was filtered, washed with methanol and water, and dried, thereby obtaining 283 mg of D-97.

(Synthesis of Metal Complex Dye D-101)

The metal complex dye D-101 was synthesized in the same manner as the metal complex dyes D-26, D-59 and D-97.

D-101

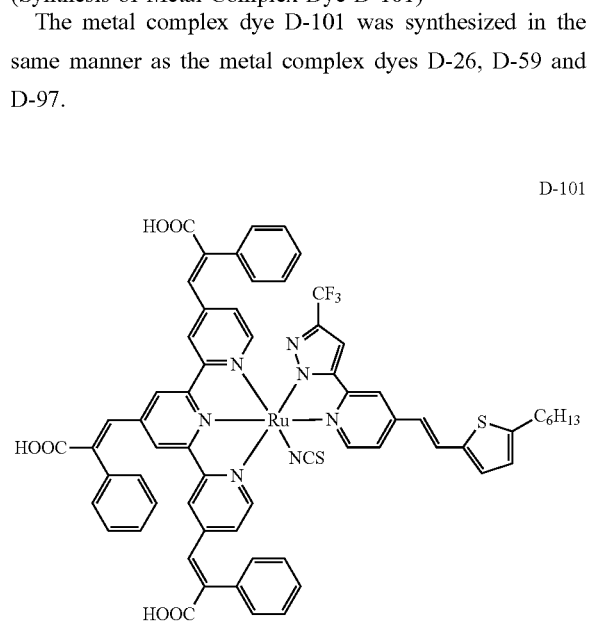

In this connection, the MS spectrum of the following Compound 15, which is an intermediate raw material of the metal complex dye D-101, is presented below. Herein, Compound 15 was synthesized by a method in accordance with Compound 55.

Compound 15

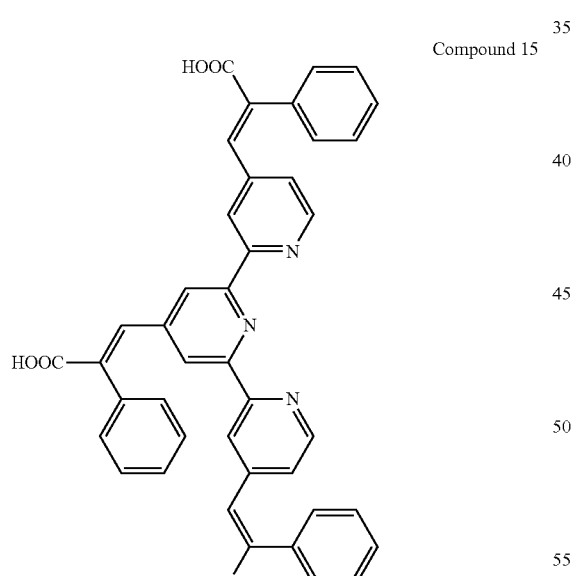

Compound 15
MS data [M+H]$^+$=756

(Synthesis of Metal Complex Dye D-136)

Compound 41 was synthesized according to the following scheme, and the metal complex dye D-136 was synthesized in the same manner as the metal complex dyes D-26 and D-59.

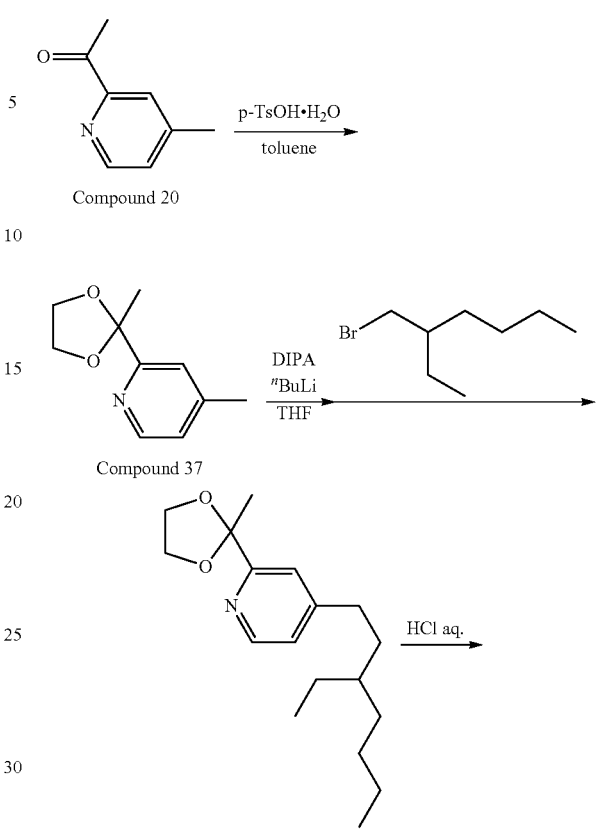

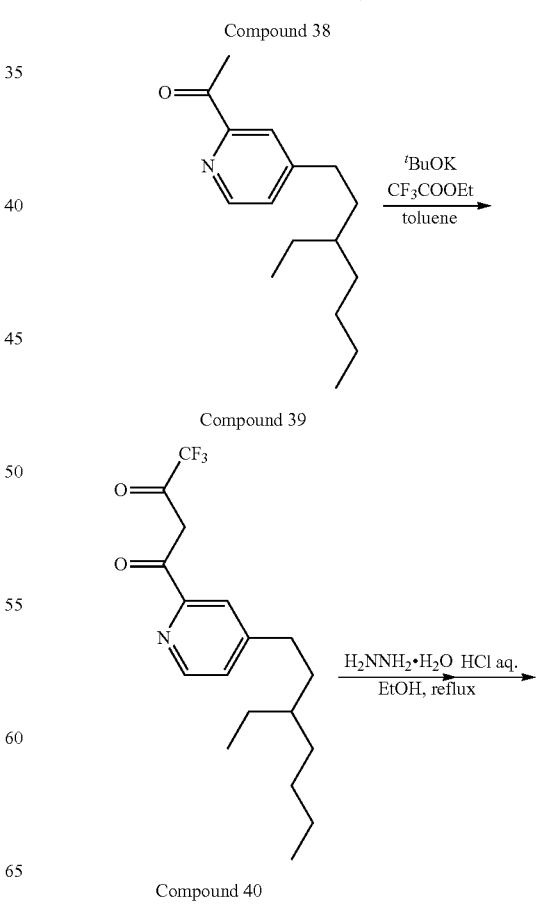

-continued

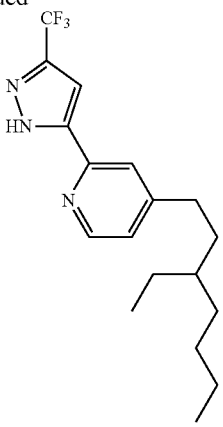

Compound 41

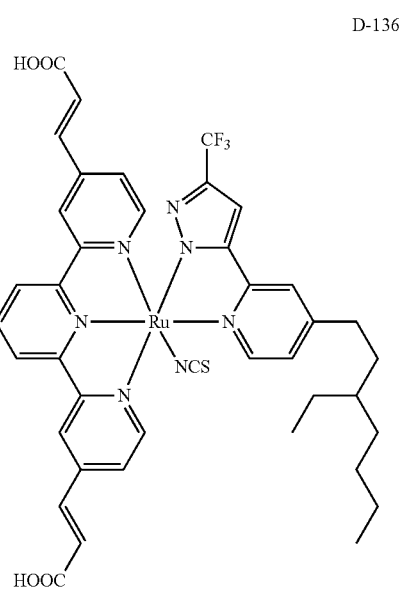

D-136

(i) Synthesis of Compound 37

Into a three-necked flask, 10 g of Compound 20, 8.24 ml of ethylene glycol, 4.22 g of p-toluenesulfonic acid monohydrate, and 200 ml of dehydrated toluene were introduced, and heated and stirred at 140° C. for 5 hours. The resultant was cooled to room temperature, sodium bicarbonate water and toluene were added thereto, the mixture was subjected to the liquid separation operation, and the organic layer was concentrated under reduced pressure. The resultant was purified by silica gel column chromatography using hexane/ethyl acetate as the eluent, thereby obtaining 11.78 g of Compound 37.

(ii) Synthesis of Compound 38

Into a three-necked flask which had been purged with nitrogen, 12.89 g of diisopropylamine and 60 ml of dehydrated tetrahydrofuran (THF) were introduced, and cooled to −60° C. Thereto, 72 ml of n-butyllithium was gradually added dropwise, and the mixture was stirred for 30 minutes. After gradually adding 188 ml of diisopropylamine thereto dropwise, the temperature thereof was raised to −50° C., and a solution of 9.85 g of Compound 37 dissolved in 5 ml of tetrahydrofuran was added thereto dropwise. Thereafter, the temperature of the mixture was raised to 0° C., a solution of 23.4 g of 1-bromo-2-ethylhexane dissolved in 45 ml of tetrahydrofuran was added thereto dropwise, and the mixture was stirred for 2 hours. Thereto, 100 ml of an aqueous solution of ammonium chloride was added, the resultant was subjected to the liquid separation operation, and the organic layer was concentrated under reduced pressure. The resultant was purified by silica gel column chromatography using hexane/ethyl acetate as the eluent, thereby obtaining 7.3 g of Compound 38.

(iii) Synthesis of Compound 39

Into a three-necked flask, 6.60 g of Compound 38 and 25 ml of concentrated hydrochloric acid were introduced, and heated and stirred at 90° C. for 30 minutes. The reaction mixture was cooled to room temperature, and gradually added to sodium bicarbonate water dropwise, and 200 ml of ethyl acetate was added thereto. The organic layer was concentrated under reduced pressure, thereby obtaining 5.73 g of Compound 39.

(iv) Synthesis of Compound 41

Into a three-necked flask, 5.73 g of Compound 39, 7.61 g of ethyl trifluoroacetate, and 100 ml of dehydrated toluene were introduced. Thereto, 5.44 g of potassium t-butoxide was added while stirring at room temperature, and the mixture was stirred for 1 hour. Thereto, 100 ml of a saturated aqueous solution of ammonium chloride and 20 ml of ethyl acetate were added, the resultant was subjected to the liquid separation operation, and the organic layer was concentrated. Thereto, ethanol and 1.50 g of hydrazine monohydrate were added, and the mixture was heated and refluxed at 90° C. for 1 hour. Thereto, 7 ml of hydrochloric acid, 200 ml of distilled water, and 200 ml of ethyl acetate were added, and the mixture was subjected to the liquid separation operation, and the organic layer was gradually added to 200 ml of sodium bicarbonate water dropwise. The resultant was subjected to the liquid separation operation, and purified by silica gel column chromatography using hexane/ethyl acetate as the eluent, thereby obtaining 6.04 g of Compound 41.

(Synthesis of Metal Complex Dye D-140)

According to the following scheme, Compound 45 was synthesized, and the metal complex dye D-140 was synthesized in the same manner as the metal complex dyes D-26 and D-59.

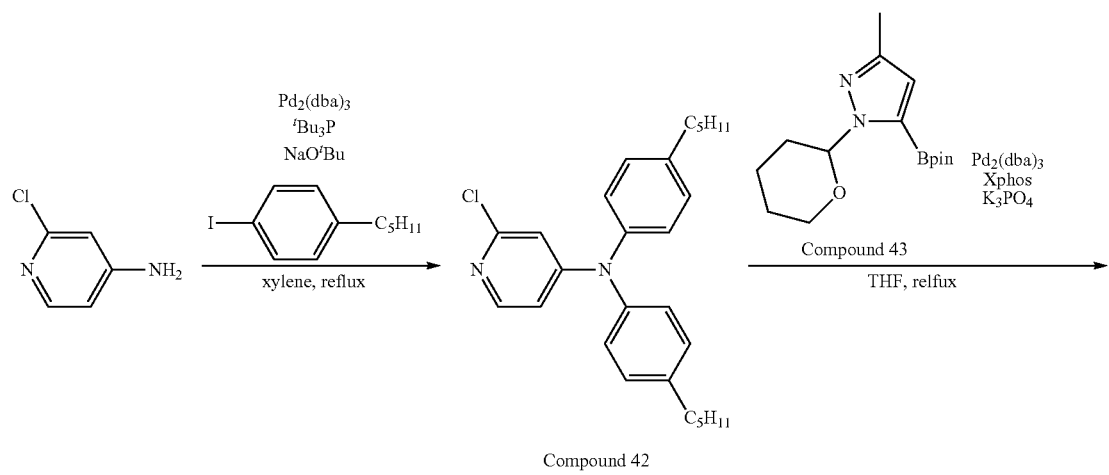
Compound 42
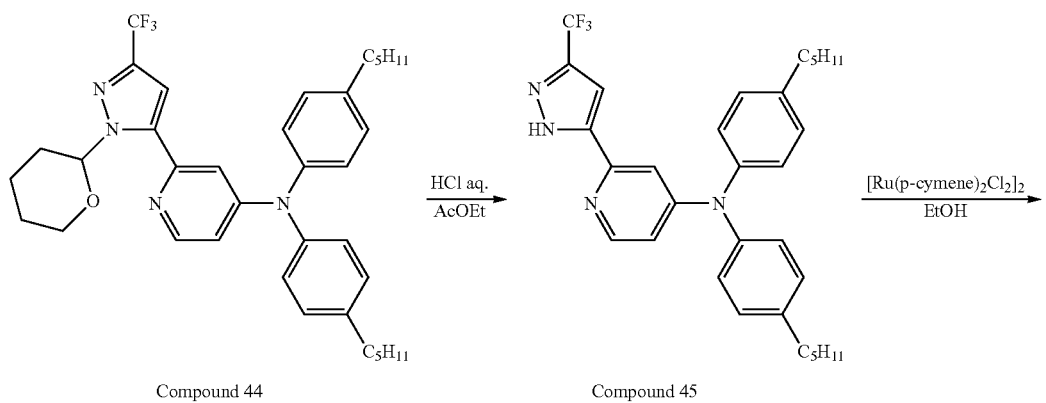
Compound 44     Compound 45
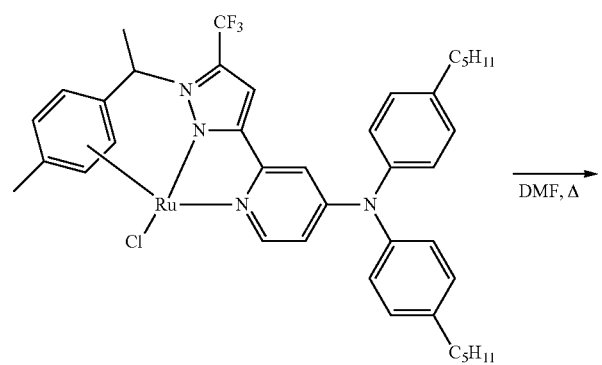

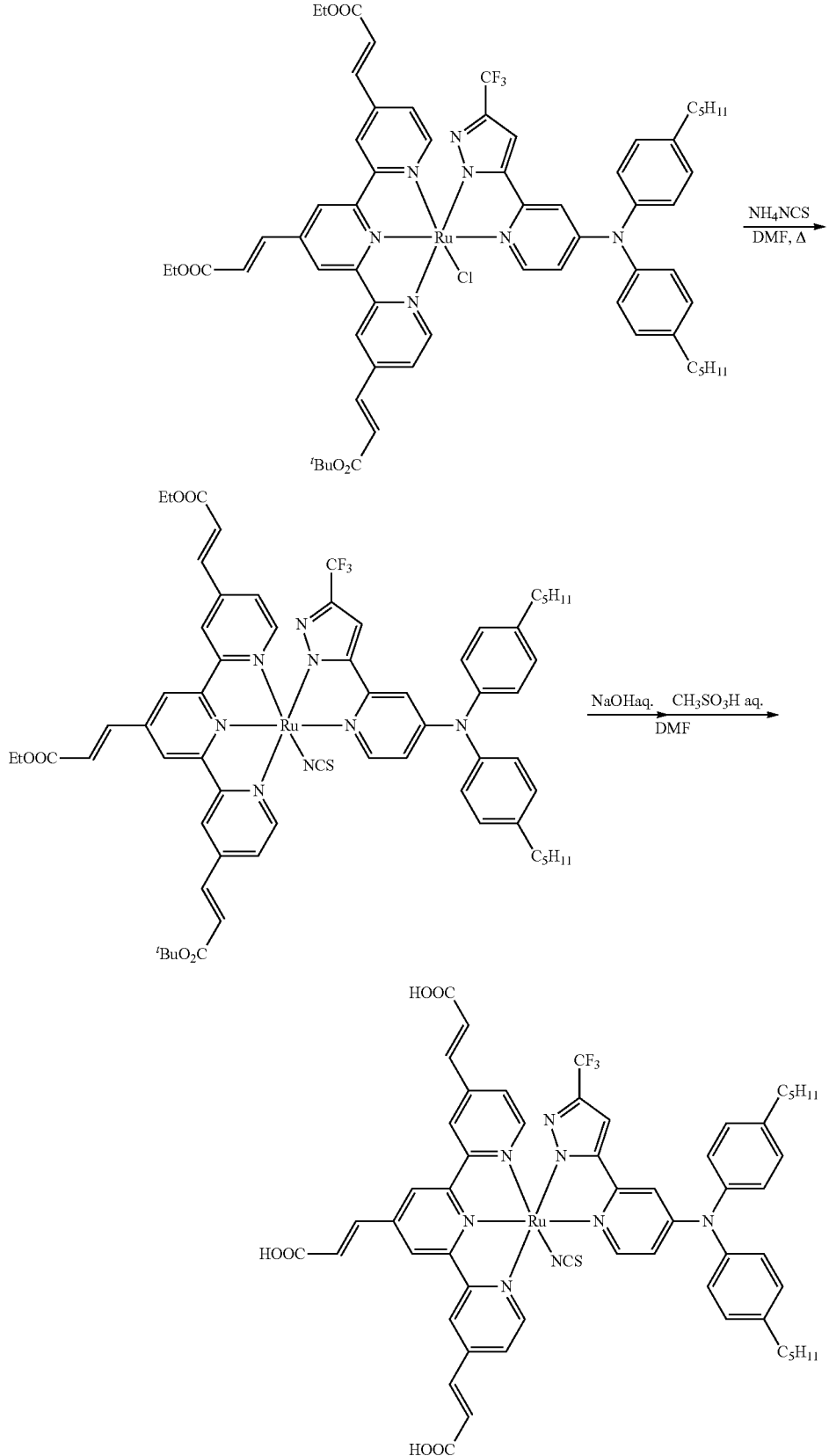
D-140

307

(i) Synthesis of Compound 42

Into a three-necked flask, 2.47 g of sodium tert-butoxide, 25 ml of xylene, 1.5 g of 4-amino-2-chloropyridine and 9.60 g of 4-iodopentylbenzene were introduced, and the flask was purged with nitrogen. Thereto, 0.534 g of tris(dibenzylideneacetone)dipalladium(0) and 0.472 g of tri-tert-butylphosphine were added while stirring, and the mixture was heated and refluxed for 2 hours. The resultant was cooled to room temperature, iced water and ethyl acetate were added thereto, and the organic layer was concentrated under reduced pressure. The resultant was purified by silica gel column chromatography, using hexane/ethyl acetate as the eluent, thereby obtaining 3.7 g of Compound 42.

(ii) Synthesis of Compound 44

Into a three-necked flask, 2.66 g of Compound 43 synthesized according to the method described in J. Org. Chem., 2008, 73, p. 4309-4312, 2.70 g of Compound 42, 5.45 g of tripotassium phosphate, and 54 ml of 1,2-dimethoxyethane were introduced, and the flask was purged with nitrogen. Thereto, 0.54 g of Xphos GIII was added while stirring, and the mixture was heated and refluxed for 3 hours. The resultant was cooled to room temperature, and filtered through Celite; the solvent was distilled off under reduced pressure, and the residue was purified by silica gel column chromatography using hexane/ethyl acetate as the eluent, thereby obtaining 1.82 g of Compound 44.

(iii) Synthesis of Compound 45

Into a three-necked flask, 1.70 g of Compound 44 and 28 ml of a solution of hydrochloric acid/ethyl acetate were introduced, and stirred for 1 hour. Thereafter, sodium bicarbonate water was added thereto, the mixture was subjected to the liquid separation operation, and the organic layer was concentrated. The pressure thereof was reduced at 140° C., thereby obtaining 3.7 g of Compound 45.

(Synthesis of Metal Complex Dye D-141)

Compounds 49 was synthesized according to the following scheme in the same manner as D-45, and the metal complex dye D-141 was synthesized in the same manner as the metal complex dye D-140.

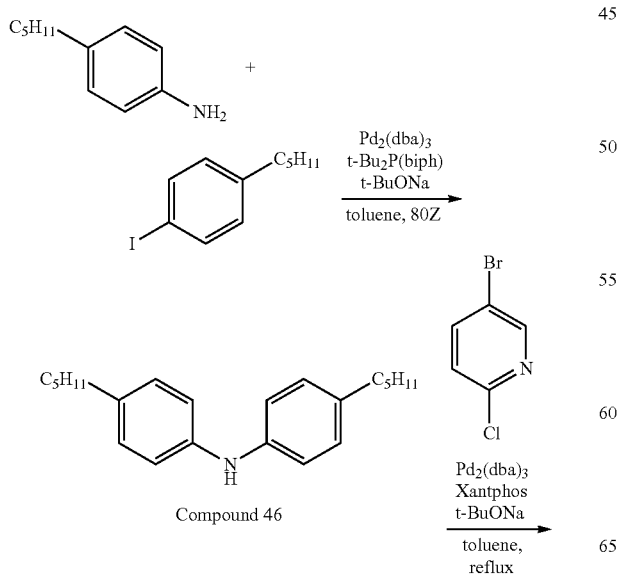

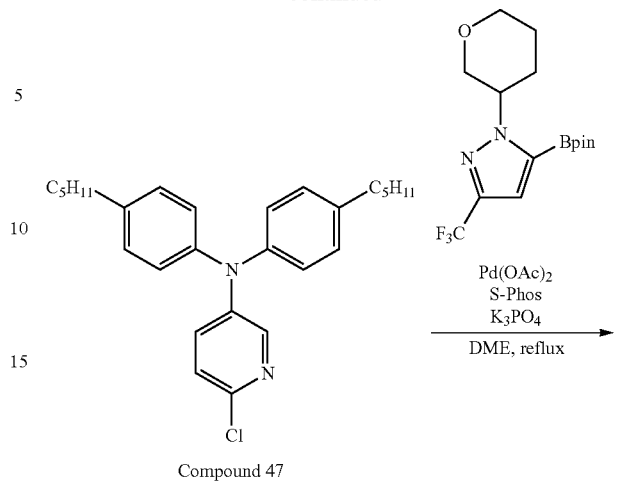

Compound 47

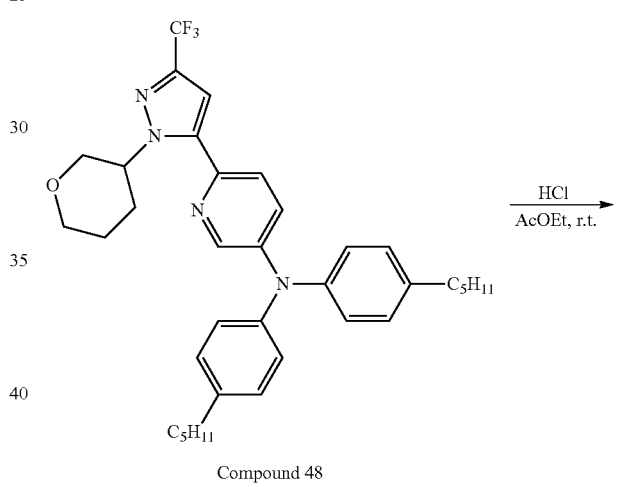

Compound 48

Compound 49

D-141
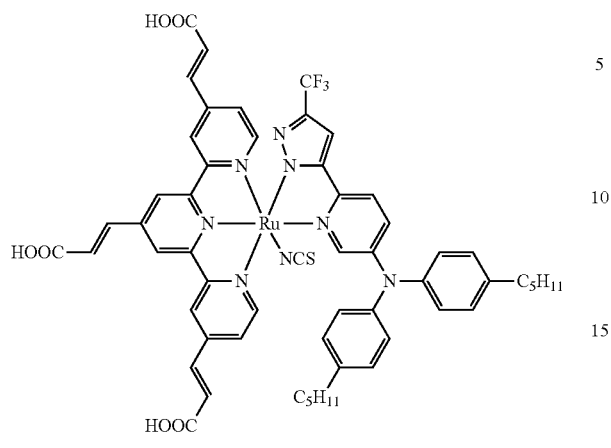
(Synthesis of Metal Complex Dye D-188)
The metal complex dye D-188 was synthesized according to the following scheme in the same manner as the metal complex dye D-140.
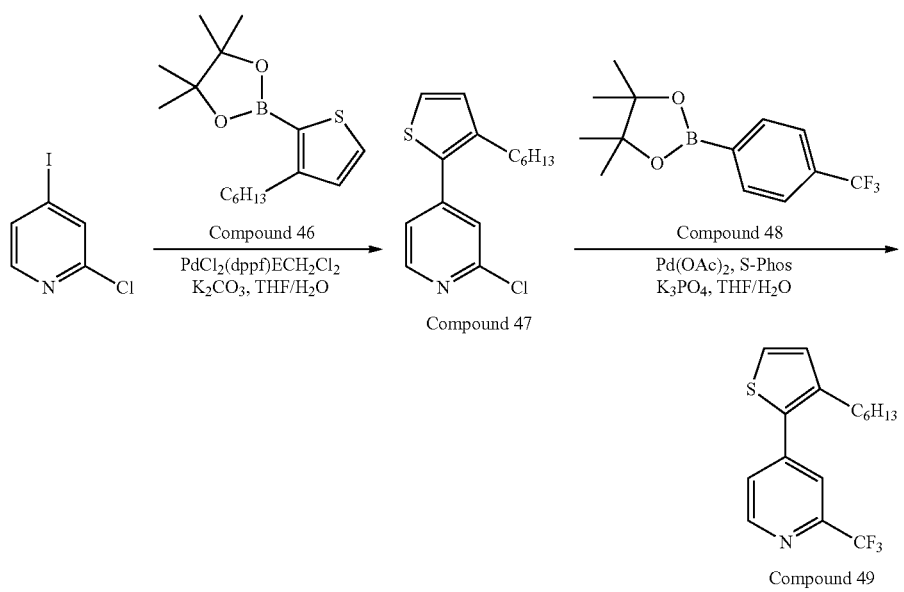
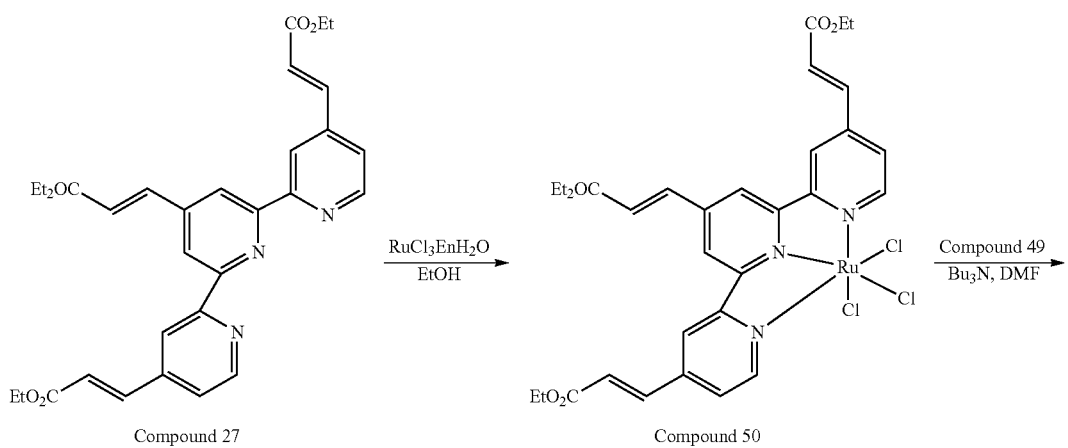

-continued
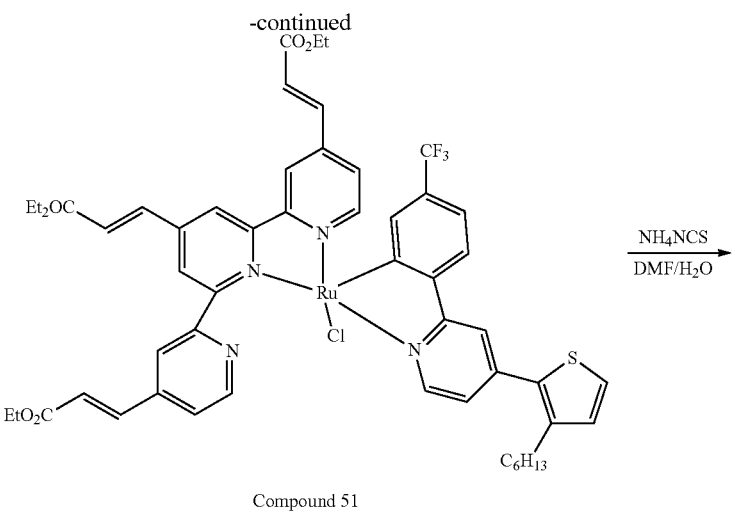
Compound 51
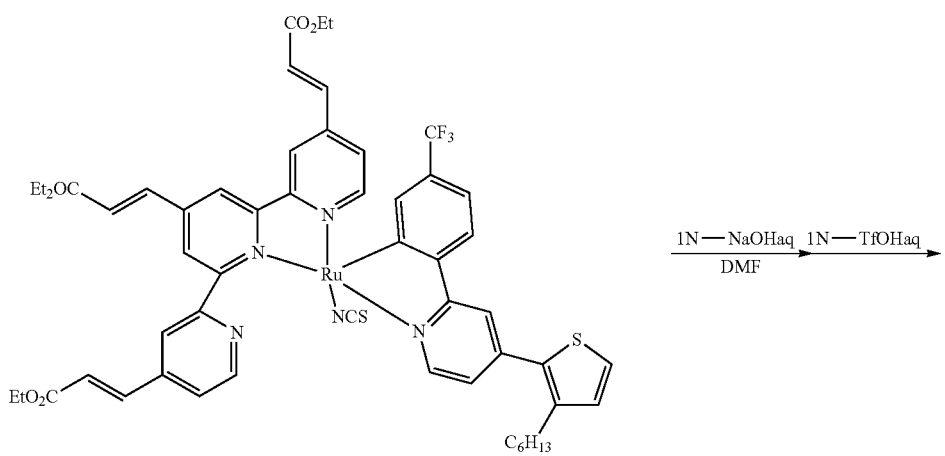
Compound 52
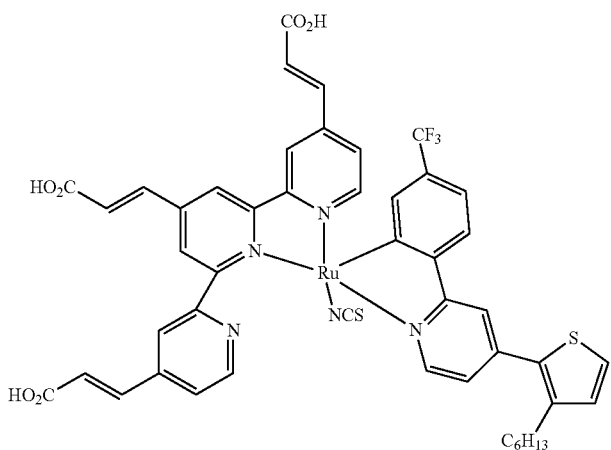
D-188

313

(i) Synthesis of Compound 47

Into a 500-mL three-necked flask, 15.0 g of 2-chloro-4-iodopyridine, 20.5 mL of Compound 46, 26.0 g of potassium carbonate, 5.1 g of 1,1'-bis(diphenylphosphino)ferrocene-palladium(II)dichloride-dichloromethane complex, 150 mL of THF, and 150 mL of pure water were introduced, and heated and refluxed for 3 hours under a nitrogen atmosphere. The solution thus obtained was cooled to room temperature, neutralized with ammonium chloride, and extracted using ethyl acetate. The organic layer was concentrated, and purified by silica gel column chromatography, thereby obtaining 13 g of Compound 47.

(ii) Synthesis of Compound 49

Into a 200-mL three-necked flask, 5.0 g of Compound 47, 15.2 g of potassium phosphate, 45 mL of THF, 45 mL of pure water, 0.2 g of palladium acetate, 0.88 g of S-Phos, and 5.83 g of Compound 48 were introduced, and heated and refluxed for 3 hours under a nitrogen atmosphere. The solution thus obtained was cooled to room temperature, neutralized with ammonium chloride, and extracted using ethyl acetate.

The organic layer was concentrated, and purified by silica gel column chromatography, thereby obtaining 3.8 g of Compound 49.

(iii) Synthesis of Compound 50

Into a 100-mL three-necked flask, 0.73 g of Compound 27, 0.38 g of ruthenium chloride, and 15 mL of ethanol were introduced, and heated and refluxed for 4 hours under a nitrogen atmosphere. The precipitate thus obtained was filtered and washed with ethanol, thereby obtaining 0.96 g of Compound 50.

(iv) Synthesis of Compound 51

Into a three-necked flask, 0.2 g of Compound 50, 0.11 g of Compound 46, 20 mL of N,N-dimethylformamide, and 0.25 g of tributylamine were introduced, and heated at 100° C. for 1 hour under a nitrogen atmosphere. The resultant was cooled to room temperature, then concentrated, and purified by silica gel column chromatography, thereby obtaining 0.18 g of Compound 51.

(v) Synthesis of Compound 52

A mixture of 0.17 g of Compound 51, 16 mg of ammonium thiocyanate, 14.5 mL of DMF, and 1.5 mL of pure water was introduced into a 5-mL glass container, and heated at 160° C. for 10 minutes by microwave. The solution thus obtained was concentrated, and purified by silica gel column chromatography, thereby obtaining 0.1 g of Compound 52.

(vi) Synthesis of Metal Complex Dye D-188

Into a 10-mL eggplant flask, 80 mg of Compound 52, 3 mL of DMF, and 0.1 mL of a 0.3 N aqueous solution of NaOH were introduced, and allowed to react in an ice bath. The solution thus obtained was adjusted to have a pH of 2.9 with TfOH, filtered, and washed with ultrapure water, thereby obtaining 60 mg of the metal complex dye D-188. The identification of the compound was performed by MALDI-MS.

(Synthesis of Metal Complex Dye D-280)

Into a 50-ml eggplant-type flask, 100 mg of metal complex dye D-62 and 10 ml of THF were introduced, and tetrabutylammonium hydroxide in a 1 equivalent amount with respect to D-62 was added thereto while stirring, and the mixture was stirred for 30 minutes at room temperature. Thereafter, the solvent was distilled off under reduced pressure, and the residue was dried, thereby obtaining the metal complex dye D-280. The identification of the compound was performed by MALDI-MS.

314

Metal complex dye D-280
MS data [M+H]$^+$=956

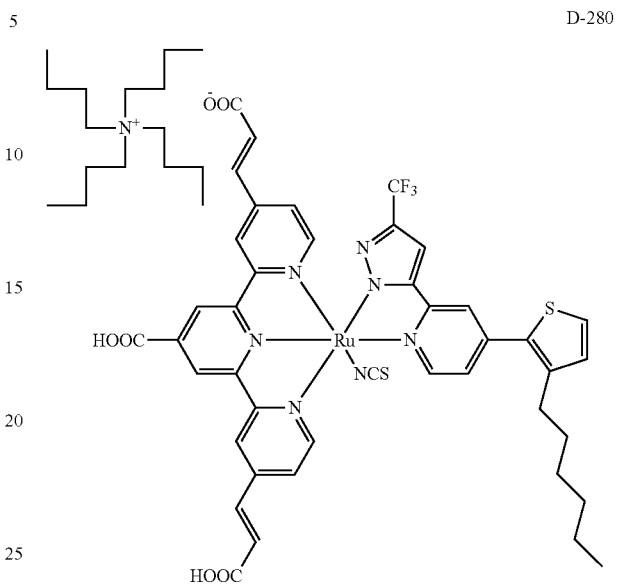

D-280

Among the metal complex dyes synthesized as described above, the visible absorption spectra of the metal complex dyes D-28, D-45, D-57, D-59, D-62, D-97, D-101, D-136, D-140, D-141, D-187, D-188, and D-280 are shown in FIGS. 7 to 28.

The measurement was conducted using UV-3600 manufactured by Shimadzu Corporation, in the same manner as the metal complex dyes D-25 and D-26.

FIG. 7 illustrates the visible absorption spectrum of the metal complex dye D-28 in a DMF solution, and FIG. 8 illustrates the visible absorption spectrum of the metal complex dye D-28 in a model semiconductor film. FIG. 9 illustrates the visible absorption spectrum of the metal complex dye D-45 at a concentration of 17 µmol/L in a methanol solution containing tetrabutylammonium hydroxide (TBAOH) at 340 mmol/L, and FIG. 10 illustrates the visible absorption spectrum of the metal complex dye D-59 at a concentration of 17 µmol/L in a methanol solution containing tetrabutylammonium hydroxide (TBAOH) at 340 mmol/L, respectively. FIG. 11 illustrates the visible absorption spectrum of the metal complex dye D-62 in a DMF solution, FIG. 12 illustrates the visible absorption spectrum of the metal complex dye D-62 in a model semiconductor film, FIG. 13 illustrates the visible absorption spectrum of the metal complex dye D-97 in a DMF solution, FIG. 14 illustrates the visible absorption spectrum of the metal complex dye D-97 in a model semiconductor film, FIG. 15 illustrates the visible absorption spectrum of the metal complex dye D-101 in a DMF solution, FIG. 16 illustrates the visible absorption spectrum of the metal complex dye D-101 in a model semiconductor film, FIG. 17 illustrates the visible absorption spectrum of the metal complex dye D-136 in a DMF solution, FIG. 18 illustrates the visible absorption spectrum of the metal complex dye D-136 in a model semiconductor film, FIG. 19 illustrates the visible absorption spectrum of the metal complex dye D-140 in a DMF solution, FIG. 20 illustrates the visible absorption spectrum of the metal complex dye D-140 in a model semiconductor film, FIG. 21 illustrates the visible absorption spectrum of the metal complex dye D-141 in a DMF solution, FIG. 22 illustrates the visible absorption spectrum of the metal complex dye D-141 in a model semiconductor film, FIG. 23 illustrates the visible absorption spectrum of the metal complex dye D-187 in a DMF solution, FIG. 24 illustrates the visible absorption spectrum of the metal complex dye D-187 in a model semiconductor film, FIG. 25 illustrates the visible absorption spectrum of the metal complex dye D-188 in a DMF solution, FIG. 26 illustrates the visible absorption spectrum of the metal complex dye D-188 in a model semiconductor film, FIG. 27 illustrates the visible absorption spectrum of the metal complex dye D-57 in a model semiconductor film, and FIG. 28 illustrates the visible absorption spectrum of the metal complex dye D-280 in a model semiconductor film.

The metal complex dyes D-2 to D-4, D-7, D-9, D-12, D-16, D-17, D-24, D-27, D-29, D-35, D-48, D-61, D-91, D-96, D-121, D-132, D-142 to D-150, D-155, D-187, D-189, D-200, D-241, D-242, and D-297 were synthesized in the same manner as the metal complex dyes D-25, D-26, and D-59.

The structures of the illustrative metal complex dyes thus obtained were confirmed by MS (mass spectrum) measurement.

The measurement results of mass spectra (MS) are presented in the following Table 2.

TABLE 2

| Metal complex dye | ESI-MS or MALDI-MS |
|---|---|
| D-1 | ESI-MS m/z = 867(M—H)$^+$ |
| D-2 | ESI-MS m/z = 867(M—H)$^+$ |
| D-3 | ESI-MS m/z = 877(M—H)$^+$ |
| D-4 | ESI-MS m/z = 893(M—H)$^+$ |
| D-7 | ESI-MS m/z = 845(M—H)$^+$ |
| D-9 | ESI-MS m/z = 942(M—H)$^+$ |
| D-12 | ESI-MS m/z = 944(M—H)$^+$ |
| D-14 | ESI-MS m/z = 962(M—H)$^+$ |
| D-16 | ESI-MS m/z = 1115(M—H)$^+$ |
| D-17 | ESI-MS m/z = 1037(M—H)$^+$ |
| D-18 | ESI-MS m/z = 1201 (M—H)$^+$ |
| D-24 | ESI-MS m/z = 1056(M—H)$^+$ |
| D-25 | ESI-MS m/z = 1223(M—H)$^+$ |
| D-26 | ESI-MS m/z = 1008(M—H)$^+$ |
| D-27 | ESI-MS m/z = 982(M—H)$^+$ |
| D-28 | ESI-MS m/z = 982(M—H)$^+$ |
| D-29 | ESI-MS m/z =1082(M—H)$^+$ |
| D-35 | ESI-MS m/z = 1033(M—H)$^+$ |
| D-45 | ESI-MS m/z = 1148(M—H)$^+$ |
| D-48 | ESI-MS m/z = 1044(M—H)$^+$ |
| D-57 | MALDI-MS m/z = 982(M—H)$^+$, 242(M$^+$) |
| D-59 | ESI-MS m/z = 1092(M—H)$^+$ |
| D-61 | ESI-MS m/z = 982(M—H)$^+$ |
| D-62 | ESI-MS m/z = 956(M—H)$^+$ |
| D-78 | ESI-MS m/z = 1157(M—H)$^+$ |
| D-91 | MALDI-MS m/z = 1061(M—H)$^+$ |
| D-96 | ESI-MS m/z = 961(M—H)$^+$ |
| D-97 | ESI-MS m/z = 1054(M—H)$^+$ |
| D-101 | ESI-MS m/z = 1236(M—H)$^+$ |
| D-121 | ESI-MS m/z = 1145(M—H)$^+$ |
| D-132 | ESI-MS m/z = 1034(M—H)$^+$ |
| D-136 | ESI-MS m/z = 942(M—H)$^+$ |
| D-140 | ESI-MS m/z = 1123(M—H)$^+$ |
| D-141 | ESI-MS m/z = 1123 (M—H)$^+$ |
| D-142 | ESI-MS m/z = 1171(M—H)$^+$ |
| D-143 | ESI-MS m/z = 1171(M—H)$^+$ |
| D-144 | ESI-MS m/z = 1097(M—H)$^+$ |
| D-145 | ESI-MS m/z = 1097(M—H)$^+$ |
| D-146 | ESI-MS m/z = 1145(M—H)$^+$ |
| D-147 | ESI-MS m/z = 1145(M—H)$^+$ |
| D-148 | ESI-MS m/z = 1093(M—H)$^+$ |
| D-149 | ESI-MS m/z = 1093(M—H)$^+$ |
| D-150 | ESI-MS m/z = 1141(M—H)$^+$ |
| D-155 | ESI-MS m/z = 999(M—H)$^+$ |
| D-187 | MALDI-MS m/z = 1060(M—H)$^+$ |
| D-188 | MALDI-MS m/z = 992(M—H)$^+$ |
| D-189 | ESI-MS m/z = 993(M—H)$^+$, 242(M$^+$) |
| D-200 | MALDI-MS m/z = 966(M—H)$^+$ |
| D-241 | MALDI-MS m/z = 1224(M—H)$^+$ |
| D-242 | MALDI-MS m/z = 1224(M—H)$^+$ |
| D-280 | MALDI-MS m/z = 956(M—H)$^+$, 242(M$^+$) |
| D-297 | MALDI-MS m/z = 1050(M—H)$^+$ |

The metal complex dyes other than the above and used below were also synthesized by the same methods as these.

Example 2

[Dye-Sensitized Solar Cell]

The dye-sensitized solar cell was fabricated in the following manner, and subjected to the measurement of IPCE (quantum yield) at 900 nm.

According to the procedure described below, a photoelectrode having the same configuration as that of the photoelectrode 12 shown in FIG. 5 of JP-A-2002-289274 was produced, and using the photoelectrode, a dye-sensitized solar cell 20 of a scale of 10 mm×10 mm having the same configuration as that of the dye-sensitized solar cell 20 shown in FIG. 3 of JP-A-2002-289274 except for the photoelectrode, was produced. The specific configuration thereof is shown in FIG. 2 attached to the present application.

In FIG. 2 of the present application, 41 denotes a transparent electrode, 42 denotes a semiconductor electrode, 43 denotes a transparent electrically-conductive film, 44 denotes a substrate, 45 denotes a semiconductor layer, 46 denotes a light-scattering layer, 40 denotes a photoelectrode, 20 denotes a dye-sensitized solar cell, CE denotes a counter electrode, E denotes an electrolyte, and S denotes a spacer.

(Preparation of Paste)

(Paste A) Spherical $TiO_2$ particles (anatase, a mean particle diameter; 25 nm, hereinafter, referred to as spherical $TiO_2$ particles A) were put into a nitric acid solution, and the resultant mixture was stirred to prepare a titania slurry. Next, a cellulose-based binder was added to the titania slurry as a thickening agent, and the resultant mixture was kneaded to prepare a paste.

(Paste 1) Spherical $TiO_2$ particles A and spherical $TiO_2$ particles (anatase, a mean particle diameter: 200 nm, hereinafter, referred to as spherical $TiO_2$ particles B) were put into a nitric acid solution, and the resultant mixture was stirred to prepare a titania slurry. Next, a cellulose-based binder was added to the titania slurry as a thickening agent, and the resultant mixture was kneaded to prepare a paste ((mass of $TiO_2$ particles A):(mass of $TiO_2$ particles B)=30:70).

(Paste 2) Rod-shaped $TiO_2$ particles (anatase, diameter: 100 nm, aspect ratio: 5, hereinafter, referred to as rod-shaped $TiO_2$ particles C) were mixed with the paste A, to prepare a paste having (mass of rod-shaped $TiO_2$ particles C):(mass of the paste A)=30:70.

(Production of Photoelectrode)

A transparent electrode 41 was prepared in which a fluorine-doped $SnO_2$ electrically-conductive film 43 (thickness: 500 nm) was formed on a glass substrate (44). On this $SnO_2$ electrically-conductive film, the paste 1 was applied to by screen printing, followed by drying. Then, the paste was calcined under the conditions of 450° C. in the air. Further, by repeating this screen printing and calcination with using the paste 2, a semiconductor electrode having the same configuration as that of the semiconductor electrode 42 shown in FIG. 2 of the present application (the area of the light-receiving face: 10 mm×10 mm; the layer thickness: 15 µm; the layer thickness of the semiconductor layer: 10 µm; the layer thickness of the light-scattering layer: 5 µm; and the content of the rod-shaped $TiO_2$ particles C contained in the light-scattering layer: 30% by mass) was formed on the $SnO_2$ electrically-conductive film. Thus, the photoelectrode, which did not contain the metal complex dye, was prepared.

(Adsorption of Dye)

Next, a metal complex dye was adsorbed onto the thus-prepared photoelectrode as follows.

First, using anhydrous ethanol dehydrated over magnesium ethoxide as a solvent, each of the metal complex dyes described in Table 3 below was dissolved to be $3\times10^{-4}$ mol/L. Further, as a co-adsorbent, 20 mol of an equimolar mixture of chenodeoxycholic acid and cholic acid was added per 1 mol of metal complex dye, to prepare each dye solution. The measurement of the moisture content in each of the dye solution based on Karl Fisher titration showed that water was less than 0.01% by mass. Next, the semiconductor electrode prepared above was immersed into this solution, to complete a photoelectrode (40) in which about $1.5\times10^{-7}$ mol/cm² of metal complex dye was adsorbed onto the semiconductor electrode 42.

Then, prepared were, as a counter electrode CE, a platinum electrode (thickness of Pt thin film, 100 nm) having the same shape and size as those of the photoelectrode (40), and, as an electrolyte E, an iodine-based redox solution containing iodine and lithium iodide. Further, a spacer-S (trade name: "Surlyn") manufactured by DuPont, which had a shape matching to the size of the semiconductor electrode 42, was prepared. As shown in FIG. 3 described in JP-A-2002-289274, the photoelectrode (40) and the counter electrode CE were arranged to face each other, with the spacer-S interposed therebetween, and followed by filling the above described electrolyte in the inside thereof. Thus, a dye-sensitized solar cell utilizing the photoelectrode was completed.

The IPCE (quantum yield) at from 300 to 1000 nm of each of the dye-sensitized solar cells fabricated in this manner was measured using an IPCE measurement device manufactured by Peccell.

Among these, the IPCE at 900 nm is presented in the following Table 3.

Evaluation Criteria

A: IPCE at 900 nm is 1.1 times or more that of Comparative Compound (3)

B: IPCE at 900 nm is greater than 1.0 time and less than 1.1 times that of Comparative Compound (3)

C: IPCE at 900 nm is 1.0 time that of Comparative Compound (3)

D: IPCE at 900 nm is less than 1.0 time that of Comparative Compound (3)

Example 3

The adsorption stability of metal complex dye was evaluated in the following manner.

For evaluation of the adsorption stability (adsorptive power) of the metal complex dye onto the surface of semiconductor fine particles, titanium dioxide was used as the semiconductor fine particles, and the desorption rate of the metal complex dye from the surface of the titanium dioxide was used as an index.

The desorption rate of the metal complex dye was calculated by means of a Quartz Crystal microbalance with Dissipation monitoring (QCM-D) intermolecular interaction measuring apparatus E1 (manufactured by Meiwafosis).

Paste A (anatase, average particle size: 25 nm) was printed by screen printing (film thickness: 20 µm) on a gold sensor (manufactured by Meiwafosis) for use for the QCM-D. By calcining the thus-printed gold sensor at 450° C. for 1 hour in the air, a gold sensor having a semiconductor layer adsorbed thereon was prepared.

The thus-prepared sensor was installed into the QCM-D intermolecular interaction measuring apparatus, and a dye solution of 0.2 mM (DMF/t-BuOH=1/1) was flowed therein, to make the dye adsorb on the semiconductor layer in a dye adsorption amount of a predetermined value (200 µg/cm²). The dye adsorption amount was calculated from a resonance frequency shift (ΔF) of a quartz oscillator according to the following Sauerbrey equation.

$$\Delta F = -2\times F_0^2 \times \Delta m / A(\mu\times P)^{1/2}$$

Herein, $F_0$ represents a frequency of a quartz oscillator alone, Δm represents a mass change, A represents a piezo-electrically active area of the Au electrode, and µ and P represent quartz density and modulus of rigidity, respectively.

Then, by flowing the above-described electrolyte E at 75° C. for 1 hour, the desorption amount of the dye was measured. The desorption amount of the dye was also calculated according to the Sauerbrey equation. The value obtained was evaluated based on the following criteria.

Evaluation Criteria

A: desorption rate is less than 10 µg/cm²·hr

B: desorption rate is 10 µg/cm²·hr or more and less than 15 µg/cm²·hr

C: desorption rate is 15 µg/cm²·hr or more and less than 20 µg/cm²·hr

D: desorption rate is 20 µg/cm²·hr or more and less than 25 µg/cm²·hr

E: desorption rate is 25 µg/cm²·hr or more and less than 30 µg/cm²·hr

F: desorption rate is 30 µg/cm²·hr or more and less than 35 µg/cm²·hr

G: desorption rate is 35 µg/cm²·hr or more Herein, the evaluation criteria A to E are the acceptable level.

In the following Table 3, the above results are collectively presented together with the results of Example 2.

TABLE 3

| Metal complex dye | IPCE at 900 nm | Adsorption stability |
| --- | --- | --- |
| D-1 | A | D |
| D-2 | A | D |
| D-3 | A | D |
| D-4 | A | D |
| D-7 | A | D |
| D-9 | A | D |
| D-12 | A | D |
| D-14 | A | B |
| D-16 | A | C |
| D-17 | A | B |
| D-18 | A | C |
| D-24 | A | A |
| Comparative compound (1) | D | F |
| Comparative compound (2) | D | G |
| Comparative compound (3) | C (reference) | G |
| Comparative compound (4) | D | G |

Comparitive Compound (1)

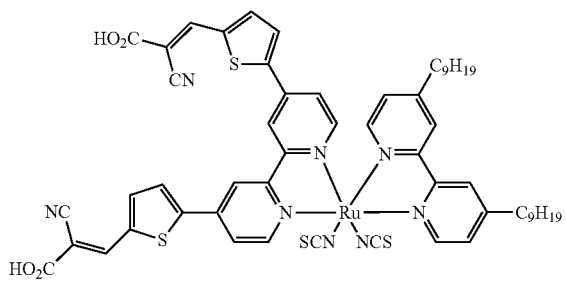

Comparitive Compound (2)

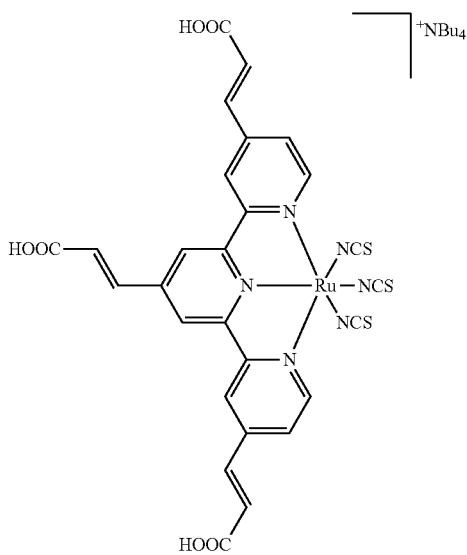

Comparitive Compound (3)

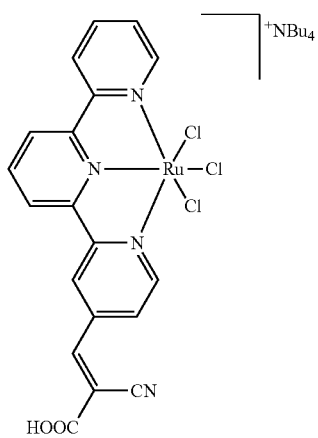

Comparitive Compound (4)

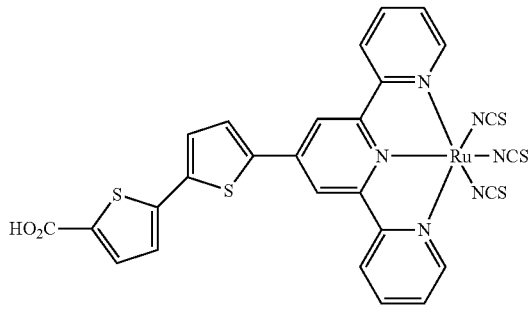

Herein, Comparative compound (3) is a metal complex dye of the evaluation reference, and was synthesized in the same manner as the metal complex dyes of the present invention described above.

Comparative compound (1) is Compound 9 described in JP-T-2011-502187, Comparative compound (2) is Compound D-11 described in JP-A-2002-105346, and Comparative compound (4) is a compound described in JP-T-2011-502965.

As it is apparent from Table 3, it can be seen that all of the metal complex dyes of the present invention are dyes that exhibit a high IPCE at a long wavelength of 900 nm and moreover are compatible with adsorption stability.

Example 4

[Dye-Sensitized Solar Cell]

A dye-sensitized solar cell was fabricated in the following manner, and evaluated for photoelectric conversion efficiency and durability in terms of the thermal deterioration at a constant temperature and the heat cycle test.

A dye-sensitized solar cell 1 having the configuration presented in FIG. 2 attached to the present specification and a scale of 10 mm×10 mm was fabricated according to the same procedure as in Example 2.

In addition, the pastes used were those which were prepared in Example 2.

(Production of Photoelectrode)

A transparent electrode was prepared in which a fluorine-doped $SnO_2$ electrically-conductive film (thickness: 500 nm) was formed on a glass substrate. On this $SnO_2$ electrically-conductive film, the paste 1 described above was applied to by screen printing, followed by drying. Then, the paste was calcined under the conditions of 450° C. in the air. Further, by repeating this screen printing and calcination using the paste 2, a semiconductor electrode having the same configuration as that of the semiconductor electrode 42 shown in FIG. 2 (the area of the light-receiving face: 10 mm×10 mm; the layer thickness: 10 μm; the layer thickness of the semiconductor layer: 6 μm; the layer thickness of the light-scattering layer: 4 μm; and the content of the rod-shaped $TiO_2$ particles C contained in the light-scattering layer: 30% by mass) was formed on the $SnO_2$ electrically-conductive film. In this manner, the photoelectrode, which did not contain the dye, was prepared.

(Adsorption of Dye)

Next, a metal complex dye was adsorbed onto the semiconductor electrode (precursor of a dye-adsorbed electrode) as follows. First, using a 1:1 (volume ratio) mixture of anhydrous t-butanol and dimethyl formamide, dehydrated over magnesium ethoxide, as a solvent, each of the metal complex dyes described in Table 4 below was dissolved to be $3\times10^{-4}$ mol/L. Further, as a co-adsorbent, 20 mol of equimolar mixture of chenodeoxycholic acid and cholic acid was added per 1 mol of metal complex dye, to prepare each dye solution. The measurement of the moisture content in the dye solutions based on Karl Fisher titration showed that water was less than 0.01% by mass. Next, the semiconductor electrodes were immersed into this solution for 10 hours at 40° C. and dried at 50° C. after pulling out from this solution, to complete photoelectrodes 40 in which about $2\times10^{-7}$ mol/cm$^2$ of dye was adsorbed onto the semiconductor electrode.

(Assembly of Dye-Sensitized Solar Cell)

Then, prepared were, as a counter electrode, a platinum electrode (thickness of Pt thin film, 100 nm) having the same shape and size as those of the photoelectrode described above, and, as an electrolyte, an iodine-based redox acetonitrile solution containing 0.1 M of iodine, 0.05 M of lithium iodide, and 0.25 M of 4-t-butylpyridine. Further, a spacer-S (trade name: "Surlyn") manufactured by DuPont, which had a shape matching to the size of the semiconductor electrode, was prepared. The photoelectrode 40 and the counter electrode CE were arranged to face each other, with the spacer-S interposed therebetween, thermally compressed, and followed by filling the above-described electrolyte in the inside thereof. The outer periphery and inlet for electrolytic solution of the prepared cell were sealed and cured with using Resin XNR-5516 manufactured by Nagase ChemteX Corporation. Thus, each dye-sensitized solar cell (sample numbers 101 to 136, and c11 to c14) was completed.

The performance evaluation of the dye-sensitized solar cells was conducted as described below.

<Evaluation of Photoelectric Conversion Efficiency>

The cell characteristic test was conducted by irradiating artificial sunlight of 1000 W/m$^2$ from a xenon lamp passed through an AM 1.5 filter, using a solar simulator (WXS-85H manufactured by WACOM). The current-voltage characteristic was measured using an I-V tester, to determine the photoelectric conversion efficiency. The photoelectric conversion efficiency thus determined was evaluated according to the following criteria in comparison with that of Comparative compound (2).

A: 1.5 times or more
B: 1.1 times or more and less than 1.5 times
B': greater than 1.0 time and less than 1.1 times
C: 1.0 time or less It is presented as the conversion efficiency in the following Table 4.

<Evaluation of Thermal Deterioration>

The heat resistance test was conducted by introducing the dye-sensitized solar cell fabricated, into a thermostatic chamber at 40° C. The current was evaluated for the dye-sensitized solar cell before being subjected to the heat resistance test and the dye-sensitized solar cell after being subjected to the heat resistance test for 12 hours. The value obtained by dividing a decrease of the current value after the heat resistance test by the current value before the heat resistance test, was adopted as the thermal deterioration rate. The thermal deterioration rate obtained in this manner was evaluated according to the following criteria in comparison with that of Comparative compound (2).

A: less than 0.9 time
B: 0.9 time or more and less than 1.0 time
C: 1.0 time or more It is presented as the thermal deterioration in the following Table 4.

<Heat Cycle Test>

The heat cycle test was conducted by alternately introducing the dye-sensitized solar cell fabricated into a freezer at −10° C. and a thermostatic chamber at 40° C. every 2 hours so as to repeat cooling and heating. The current was evaluated for the dye-sensitized solar cell before being subjected to the heat cycle test and the dye-sensitized solar cell after being subjected to the heat cycle test for 24 hours. The value obtained by dividing a decrease of the current value after the heat resistance test by the current value before the heat cycle test was adopted as the deterioration rate. The deterioration rate obtained in this manner was evaluated according to the following criteria in comparison with that of Comparative compound (1).

A: less than 0.9 time
B: 0.9 time or more and less than 1.0 time
C: 1.0 time or more It is presented as the heat cycle in the following Table 4.

In this connection, Comparative compounds (1) to (4) were compounds used in Examples 2 and 3.

TABLE 4

| Sample No. | Metal complex dye | Conversion efficiency | Thermal deterioration | Heat cycle | Remarks |
|---|---|---|---|---|---|
| 101 | D-25 | A | B | B | This invention |
| 102 | D-26 | A | A | A | This invention |
| 103 | D-27 | A | A | A | This invention |
| 104 | D-28 | A | A | A | This invention |
| 105 | D-29 | A | A | A | This invention |
| 106 | D-45 | A | A | A | This invention |
| 107 | D-48 | A | A | A | This invention |
| 108 | D-57 | A | B | B | This invention |
| 109 | D-59 | A | A | A | This invention |
| 110 | D-61 | A | A | A | This invention |
| 111 | D-62 | A | A | A | This invention |
| 112 | D-91 | A | A | A | This invention |
| 113 | D-96 | B | A | A | This invention |
| 114 | D-97 | B | A | A | This invention |
| 115 | D-101 | B | A | A | This invention |
| 116 | D-121 | A | A | A | This invention |
| 117 | D-132 | B | B | B | This invention |
| 118 | D-136 | A | A | A | This invention |
| 119 | D-140 | A | A | A | This invention |
| 120 | D-141 | A | A | A | This invention |
| 121 | D-142 | A | A | A | This invention |
| 122 | D-143 | A | A | A | This invention |

TABLE 4-continued

| Sample No. | Metal complex dye | Conversion efficiency | Thermal deterioration | Heat cycle | Remarks |
|---|---|---|---|---|---|
| 123 | D-144 | A | A | A | This invention |
| 124 | D-145 | A | A | A | This invention |
| 125 | D-146 | A | A | A | This invention |
| 126 | D-147 | A | A | A | This invention |
| 127 | D-148 | A | A | A | This invention |
| 128 | D-149 | A | A | A | This invention |
| 129 | D-150 | A | A | A | This invention |
| 130 | D-155 | B | B | B | This invention |
| 131 | D-187 | B | A | B | This invention |
| 132 | D-188 | B | A | B | This invention |
| 133 | D-189 | B | B | B | This invention |
| 134 | D-200 | B | A | B | This invention |
| 135 | D-241 | A | A | A | This invention |
| 136 | D-242 | A | A | A | This invention |
| 137 | D-280 | A | B | B | This invention |
| 138 | D-297 | B | A | A | This invention |
| c11 | Comparative compound (1) | C | C | C (Reference) | Comparative example |
| c12 | Comparative compound (2) | C (Reference) | C (Reference) | C | Comparative example |
| c13 | Comparative compound (3) | C | C | C | Comparative example |
| c14 | Comparative compound (4) | C | C | C | Comparative example |

As it is apparent from Table 4, it can be seen that all of the dye-sensitized solar cells of the photoelectric conversion elements fabricated using the metal complex dyes of the present invention exhibit high photoelectric conversion efficiency and moreover excellent durability to the thermal deterioration and the deterioration by the heat cycle test.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Electrically conductive support
2 Photoconductor layer
21 Dye
22 Semiconductor fine particles
3 Charge transfer layer
4 Counter electrode
5 Light-receiving electrode
6 Circuit
10 Photoelectric conversion element
100 System utilizing a dye-sensitized solar cell
M Electric motor (Electric fan)
20 Dye-sensitized solar cell
40 Photoelectrode
41 Transparent electrode
42 Semiconductor electrode
43 Transparent electrically-conductive film
44 Substrate
45 Semiconductor layer
46 Light-scattering layer
CE Counter electrode
E Electrolyte
S Spacer

The invention claimed is:

1. A photoelectric conversion element, comprising an electrically conductive support, a photoconductor layer containing an electrolyte, a charge transfer layer containing an electrolyte, and a counter electrode, wherein the photoconductor layer contains semiconductor fine particles carrying a metal complex dye represented by the following Formula (I):

$$M(LA)(LD)(LX)_{mX}(CI)_{mY} \quad \text{formula (I)}$$

wherein, in the formula, M represents a metal ion,
LA represents a tridentate ligand represented by the following Formula (AL),
LD represents a bidentate ligand or a tridentate ligand different from LA, in which, at least one of coordinating atoms which bond to the metal ion M in the bidentate ligand or the tridentate ligand is an anion,
LX represents a monodentate ligand; mX is 1 when LD is the bidentate ligand and mX is 0 when LD is the tridentate ligand;
CI represents a counter ion necessary for neutralizing an electric charge;
mY represents an integer of 0 to 3;

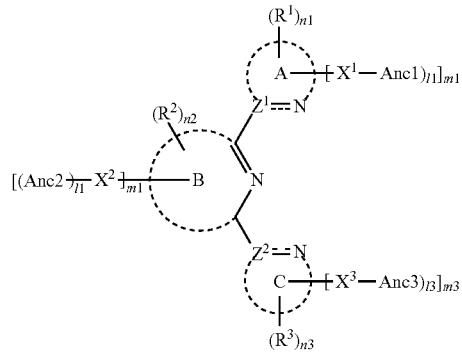

Formula (AL)

wherein, in the formula, the ring A, the ring B, and the ring C each independently represent a nitrogen-containing aromatic heterocyclic ring, herein, the bond between $Z^1$ and the N atom and the bond between $Z^2$ and the N atom may be a single bond or a double bond; $Z^1$ and $Z^2$ each independently represent a carbon atom or a nitrogen atom;

Anc1 to Anc3 each independently represent an acidic group; l1 and l3 each independently are an integer of 1 to 4, and l2 is an integer of 1 to 5, respectively;

$X^1$ and $X^3$ each independently represent a single bond or a linking group; each combinations of $X^1$ and the ring A, and $X^3$ and the ring C may bond to each other to form a fused ring; m1 and m3 each independently represent an integer of 0 to 4, and m2 represents an integer of 1 to 3;

$X^2$ represents the following Formula (X-1):

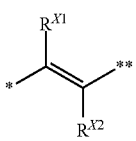

Formula (X-1)

wherein, in Formula (X-1), $R^{X1}$ and $R^{X2}$ are both a hydrogen atom; * represents a bonding position with the ring B, and ** represents a bonding position with Anc2;

$R^1$ to $R^3$ each independently represent a substituent that does not have any of Anc1 to Anc3; n1 and n2 each independently represent an integer of 0 to 3, and n3 represents an integer of 0 to 4; when a plurality of $R^1$s, a plurality of $R^2$s, or a plurality of $R^3$ exist, each of these may bond with each other to form a ring.

2. The photoelectric conversion element according to claim 1, wherein M is $Os^{2+}$ or $Ru^{2+}$.

3. The photoelectric conversion element according to claim 1, wherein at least one of $X^1$ and $X^3$ is each independently any one of the following Formulas (X-1) to (X-6) or a group of any combination of these:

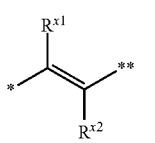

Formula (X-1)

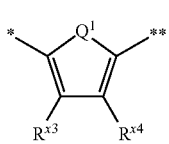

Formula (X-2)

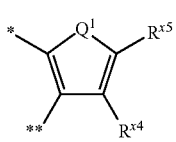

Formula (X-3)

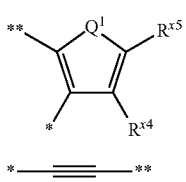

Formula (X-4)

Formula (X-5)

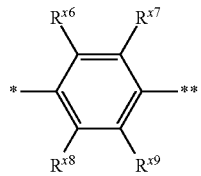

Formula (X-6)

wherein, in the formulas, $Q^1$ represents a group selected from —S—, —O—, —N($R^{XA}$)—, —C(R)($R^{XC}$)—, and —Si(R)($R^{XC}$)—, in which $R^{XA}$ to $R^{XC}$ each independently represent a hydrogen atom or a substituent, and $R^{XB}$ and $R^{XC}$ may bond with each other to form a ring; $R^{X1}$ to $R^{X9}$ each independently represent a hydrogen atom or a substituent; herein, each combination of $R^{X1}$ and $R^{X2}$, $R^{X3}$ and $R^{X4}$, $R^{X4}$ and $R^{X5}$, $R^{X5}$ and $R^{X4}$, $R^{X5}$ and $R^{XB}$, $R^{X6}$ and $R^{X7}$, and $R^{X8}$ and $R^{X9}$ may bond with each other to form a ring; $R^{X1}$ to $R^{X4}$ and $R^{X6}$ to $R^{X9}$ may bond to the ring A or the ring C to form a fused ring; * represents a bonding position with the ring A or the ring C, and ** represents a bonding position with Anc1 or Anc3.

4. The photoelectric conversion element according to claim 1, wherein $X^1$ and $X^3$ each independently are a linking group represented by $X^2$.

5. The photoelectric conversion element according to claim 1, wherein the ring B is a pyridine ring.

6. The photoelectric conversion element according to claim 1, wherein the ring A and the ring C each independently are a ring selected from a pyridine ring, a quinoline ring, a pyrimidine ring, a triazine ring, an imidazole ring, a benzimidazole ring, an oxazole ring, a thiazole ring, a benzothiazole ring, an oxadiazole ring, a thiadiazole ring, an isoxazole ring, an isothiazole ring, a triazole ring, and a pyrazole ring.

7. The photoelectric conversion element according to claim 1, wherein the ring A to the ring C are a pyridine ring.

8. The photoelectric conversion element according to claim 1, wherein at least one of m1 and m3 is 1 and m2 is 1.

9. The photoelectric conversion element according to claim 1, wherein m1 to m3 are all 1.

10. The photoelectric conversion element according to claim 1, wherein m1 to m3 are all 1 and $X^2$ is a single bond.

11. The photoelectric conversion element according to claim 1, wherein LD is a bidentate ligand represented by any one of the following Formulas (2L-1) to (2L-5):

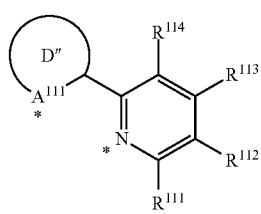

Formula (2L-1)

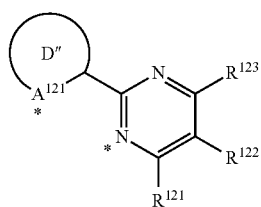

Formula (2L-2)

Formula (2L-3)

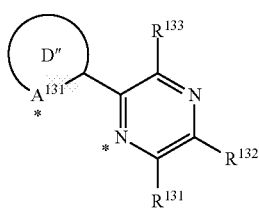

Formula (2L-4)

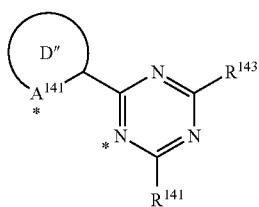

Formula (2L-5)

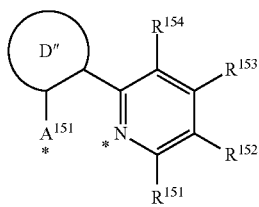

wherein, in the formulas, the ring D″ represents an aromatic ring; $A^{111}$ to $A^{141}$ each independently represent a nitrogen atom anion or a carbon atom anion, $A^{151}$ represents a nitrogen atom anion, an oxygen atom anion, or a sulfur atom anion; $R^{111}$ to $R^{154}$ each independently represent a hydrogen atom or a substituent that does not have any of Anc1, Anc2, and Anc3; and * represents a bonding position to the metal ion M.

12. The photoelectric conversion element according to claim 1, wherein LD is a tridentate ligand represented by any one of the following Formulas (3L-1) to (3L-4):

Formula (3L-1)

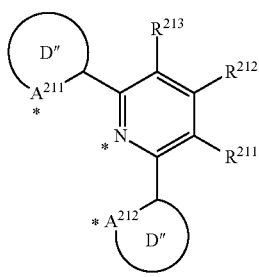

Formula (3L-2)

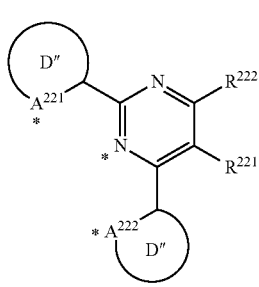

Formula (3L-3)

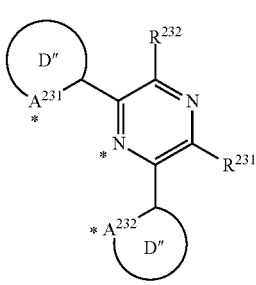

Formula (3L-4)

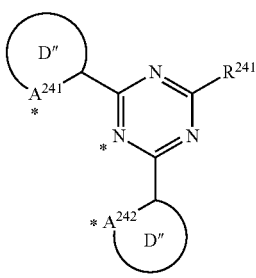

wherein, in the formulas, the ring D″ represents an aromatic ring; $A^{211}$ to $A^{242}$ each independently represent a nitrogen atom or a carbon atom; at least one of $A^{211}$ and $A^{212}$, of $A^{221}$ and $A^{222}$, of $A^{231}$ and $A^{232}$, and of $A^{241}$ and $A^{242}$ is an anion, respectively; $R^{211}$ to $R^{241}$ each independently represent a hydrogen atom or a substituent that does not have any of Anc1, Anc2, and Anc3; and * represents a bonding position to the metal ion M.

13. The photoelectric conversion element according to claim 1, wherein the bidentate or tridentate ligand in LD has a nitrogen anion or a carbon anion as an atom coordinating to the metal ion M and the following Formula (SA) as a partial structure:

Formula (SA)

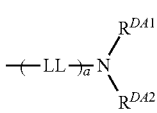

wherein, in the formula, $R^{DA1}$ represents an aryl group, and $R^{DA2}$ represents an alkyl group or an aryl group; $R^{DA1}$ and $R^{DA2}$ may bond with each other to form a ring; LL represents an ethenyl group, an ethynyl group, an arylene group, or a heteroarylene group; a represents an integer of 0 to 5.

14. The photoelectric conversion element according to claim 1, wherein Formula (I) is represented by the following Formula (I-1) or (I-2):

Formula (I-1)

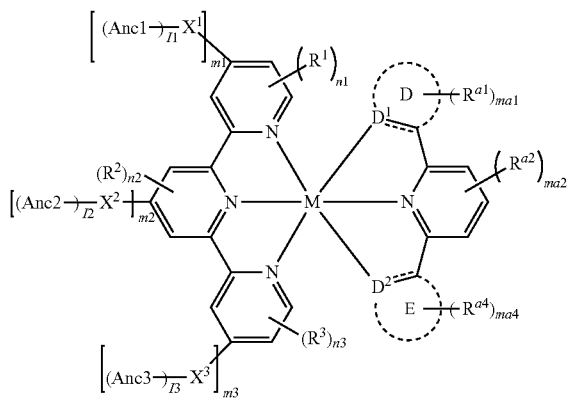

Formula (I-2)

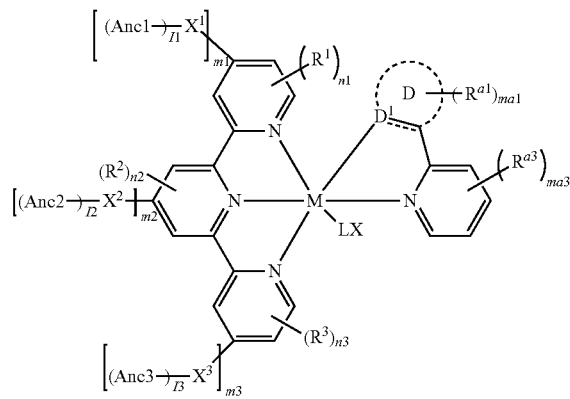

wherein, in the formulas, M and LX have the same meaning as M and LX in Formula (I); and Anc1 to Anc3, $X^1$ to $X^3$, l1 to l3, m1 to m3, $R^1$ to $R^3$, and n1 to n3 have the same meaning as Anc1 to Anc3, $X^1$ to $X^3$, l1 to l3, m1 to m3, $R^1$ to $R^3$, and n1 to n3 in Formula (AL);

the ring D and the ring E each independently represent a 5- or 6-membered aromatic ring; $D^1$ and $D^2$ each independently represent a carbon atom that bonds to M by dissociation of a hydrogen atom or a nitrogen atom that bonds to M by dissociation of a hydrogen atom; herein the bond linking $D^1$ in the ring D with the carbon atom bonding to the pyridine ring and the bond linking $D^2$ in the ring E with the carbon atom bonding to the pyridine ring each may be a single bond or a double bond;

$R^{a1}$ to $R^{a4}$ each independently represent a substituent; ma1, ma2, and ma4 each independently represent an integer of 0 to 3; ma3 represents an integer of 0 to 4;

when each of ma1 to ma4 is an integer of 2 or more, each of a plurality of $R^{a1}$s to a plurality of $R^{a4}$s may bond with each other to form a ring.

15. The photoelectric conversion element according to claim 14, wherein the ring D and the ring E in Formula (I-1) or (I-2) each independently are a pyrazole ring, a triazole ring or a benzene ring.

16. The photoelectric conversion element according to claim 1, wherein the semiconductor fine particles further carry a co-adsorbent having one or more acidic groups.

17. The photoelectric conversion element according to claim 16, wherein the co-adsorbent is represented by the following Formula (CA):

Formula (CA)

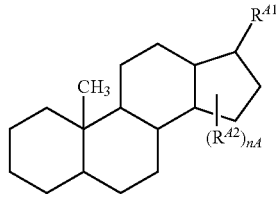

wherein, in formula, $R^{41}$ represents a substituent having an acidic group; $R^{42}$ represents a substituent; nA represents an integer of 0 or more.

18. A dye-sensitized solar cell including the photoelectric conversion element according to claim 1.

19. A metal complex dye represented by the following Formula (I):

$$M(LA)(LD)(LX)_{mX}(CI)_{mY}$$ Formula (I)

wherein, in the formula, M represents a metal ion,

LA represents a tridentate ligand represented by the following Formula (AL),

LD represents a bidentate ligand or a tridentate ligand different from LA, herein, at least one of coordinating atoms which bond to the metal ion M in the bidentate ligand or the tridentate ligand is an anion, LX represents a monodentate ligand; mX is 1 when LD is the bidentate ligand and mX is 0 when LD is the tridentate ligand;

CI represents a counter ion necessary for neutralizing an electric charge;

mY represents an integer of 0 to 3;

Formula (AL)

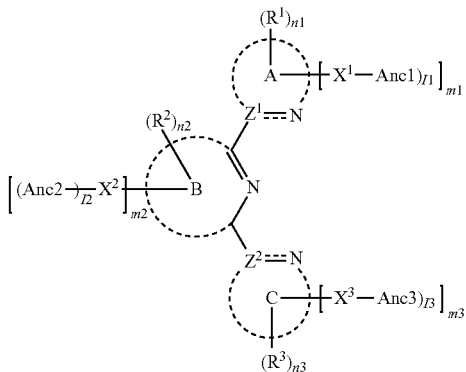

wherein, in the formula, the ring A, the ring B, and the ring C each independently represent a nitrogen-containing aromatic heterocyclic ring, herein, the bond between $Z^1$ and the N atom and the bond between $Z^2$ and the N atom may be a single bond or a double bond; $Z^1$ and $Z^2$ each independently represent a carbon atom or a nitrogen atom;

Anc1 to Anc3 each independently represent an acidic group; l1 and l3 each independently are an integer of 1 to 4, and l2 is an integer of 1 to 5, respectively;

$X^1$ and $X^3$ each independently represent a single bond or a linking group; each combination of $X^1$ and the ring A, and $X^3$ and the ring C may bond to each other to form a fused ring; m1 and m3 each independently represent an integer of 0 to 4, and m2 represents an integer of 1 to 3;

$X^2$ represents the following Formula (X-1):

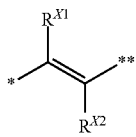

Formula (X-1)

wherein, in Formula (X-1), $R^{X1}$ and $R^{X2}$ are both a hydrogen atom; * represents a bonding position with the ring B, and ** represents a bonding position with Anc2;

$R^1$ to $R^3$ each independently represent a substituent that does not have any of Anc1 to Anc3; n1 and n2 each independently represent an integer of 0 to 3, and n3 represents an integer of 0 to 4; when a plurality of $R^1$s, a plurality of $R^2$s, or a plurality of $R^3$ exist, each of these may bond with each other to form a ring.

20. The metal complex dye according to claim 19, wherein LD is a bidentate ligand represented by any one of the following Formulas (2L-1) to (2L-5):

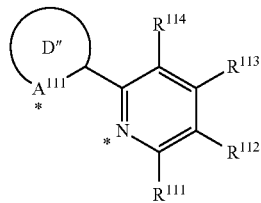

Formula (2L-1)

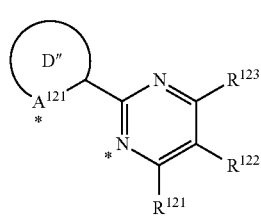

Formula (2L-2)

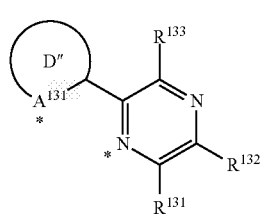

Formula (2L-3)

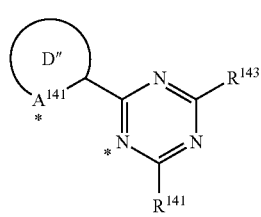

Formula (2L-4)

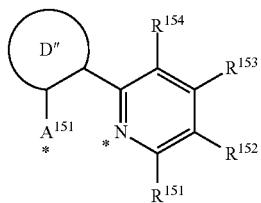

Formula (2L-5)

wherein, in the formulas, the ring D″ represents an aromatic ring; $A^{111}$ to $A^{141}$ each independently represent a nitrogen atom anion or a carbon atom anion, $A^{151}$ represents a nitrogen atom anion, an oxygen atom anion, or a sulfur atom anion; $R^{111}$ to $R^{154}$ each independently represent a hydrogen atom or a substituent that does not have any of Anc1, Anc2, and Anc3; and * represents a bonding position to the metal ion M.

21. The metal complex dye according to claim 19, wherein LD is a tridentate ligand represented by any one of the following Formulas (3L-1) to (3L-4):

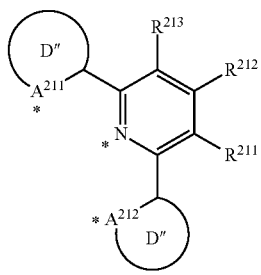

Formula (3L-1)

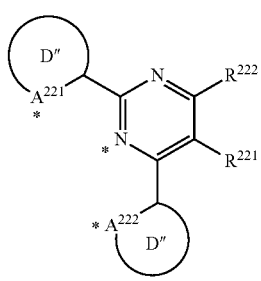

Formula (3L-2)

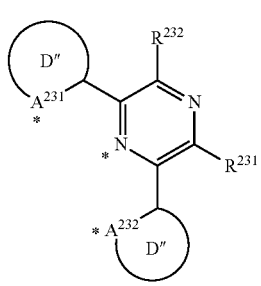

Formula (3L-3)

333

-continued

Formula (3L-4)

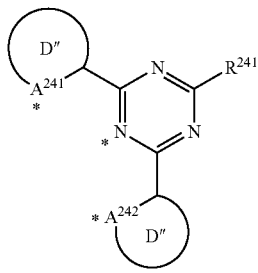

wherein, in the formulas, the ring D" represents an aromatic ring; $A^{211}$ to $A^{242}$ each independently represent a nitrogen atom or a carbon atom; at least one of $A^{211}$ and $A^{212}$, of $A^{221}$ and $A^{222}$, of $A^{231}$ and $A^{232}$, and of $A^{241}$ and $A^{242}$ is an anion, respectively; $R^{211}$ to $R^{241}$ each independently represent a hydrogen atom or a substituent that does not have any of Anc1, Anc2 and Anc3; and * represents a bonding position to the metal ion M.

22. The metal complex dye according to claim 19, wherein the bidentate or tridentate ligand in LD has a nitrogen anion or a carbon anion as an atom coordinating to the metal ion M and the following Formula (SA) as a partial structure:

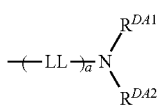

Formula (SA)

wherein, in the formula, $R^{DA1}$ represents an aryl group, and $R^{DA2}$ represents an alkyl group or an aryl group; $R^{DA1}$ and $R^{DA2}$ may bond with each other to form a ring; LL represents an ethenyl group, an ethynyl group, an arylene group, or a heteroarylene group; a represents an integer of 0 to 5.

23. A dye solution formed by dissolving the metal complex dye according to claim 19.

24. The dye solution according to claim 23, containing, in an organic solvent, the metal complex dye in an amount of 0.001 to 0.1% by mass and water in an amount controlled to 0.1% by mass or less.

25. A dye-adsorbed electrode for dye-sensitized solar cell, wherein an electrically conductive support provided with semiconductor fine particles is coated with the dye solution according to claim 23 and cured by reaction to form a photoconductor layer.

26. A method for producing dye-sensitized solar cell, including assembling a dye-sensitized solar cell using the dye-adsorbed electrode for dye-sensitized solar cell according to claim 25, and respective materials to be an electrolyte and a counter electrode.

334

27. A compound represented by the following Formula (AL):

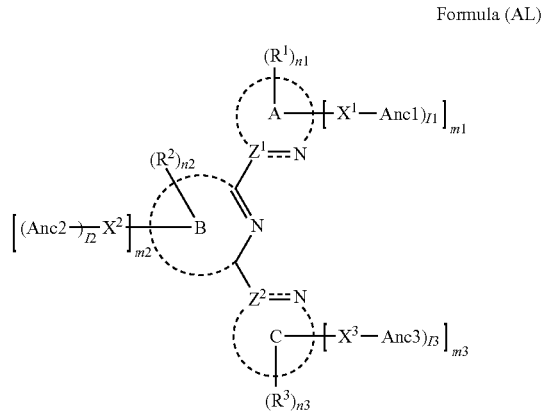

Formula (AL)

wherein, in the formula, the ring A, the ring B, and the ring C each independently represent a nitrogen-containing aromatic heterocyclic ring, herein, the bond between $Z^1$ and the N atom and the bond between $Z^2$ and the N atom may be a single bond or a double bond; $Z^1$ and $Z^2$ each independently represent a carbon atom or a nitrogen atom;

Anc1 to Anc3 each independently represent an acidic group; l1 and l3 each independently are an integer of 1 to 4, and l2 is an integer of 1 to 5, respectively;

$X^1$ and $X^3$ each independently represent a single bond or a linking group; each combination of $X^1$ and the ring A, and $X^3$ and the ring C may bond to each other to form a fused ring; m1 and m3 each independently represent an integer of 1 to 4, and m2 represents an integer of 1 to 3;

$X^2$ represents the following Formula (X-1):

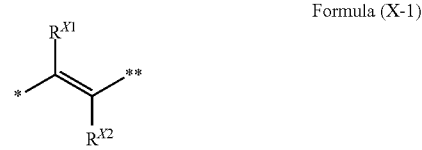

Formula (X-1)

wherein in Formula (X-1), $R^{X1}$ and $R^{X2}$ are both a hydrogen atom; * represents a bonding position with the ring B, and ** represents a bonding position with Anc2;

$R^1$ to $R^3$ each independently represent a substituent that does not have any of Anc1 to Anc3; n1 and n2 each independently represent an integer of 0 to 3, and n3 represents an integer of 0 to 4; when a plurality of $R^1$s, a plurality of $R^2$s, or a plurality of $R^3$ exist, each of these may bond with each other to form a ring.

* * * * *